(12) United States Patent
Hester, Jr. et al.

(10) Patent No.: US 6,537,986 B2
(45) Date of Patent: Mar. 25, 2003

(54) OXAZOLIDINONE ANTIBACTERIAL AGENTS HAVING A THIOCARBONYL FUNTIONALITY

(75) Inventors: Jackson B. Hester, Jr., Galesburg; Eldon George Nidy, Kalamazoo; Salvatore Charles Perricone, Delton; Toni-Jo Poel, Wayland, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/822,072

(22) Filed: Mar. 30, 2001

(65) Prior Publication Data

US 2001/0041728 A1 Nov. 15, 2001

Related U.S. Application Data

(60) Division of application No. 09/200,904, filed on Nov. 27, 1998, now Pat. No. 6,255,304, which is a continuation-in-part of application No. 09/080,751, filed on May 18, 1998, now Pat. No. 6,218,413.
(60) Provisional application No. 60/048,342, filed on May 30, 1997.

(51) Int. Cl.⁷ .................. A61K 31/55; C07D 267/02
(52) U.S. Cl. .................. 514/211.01; 540/544
(58) Field of Search .................. 514/211.01; 540/544

(56) References Cited

U.S. PATENT DOCUMENTS 5,627,181 A  5/1997  Riedl et al.
5,880,118 A  * 3/1999  Barbachycn et al.

FOREIGN PATENT DOCUMENTS

| DE | 19601264 | 7/1997 |
|----|----------|--------|
| EP | 0127 902 | 12/1984 |
| EP | 0184 170 | 6/1986 |
| EP | 0352 781 | 1/1990 |
| EP | 0359 418 | 3/1990 |
| EP | 0789 025 | 8/1997 |
| WO | WO95/07271 | 3/1995 |
| WO | WO97/14690 | 4/1997 |
| WO | WO98/07708 | 2/1998 |

* cited by examiner

Primary Examiner—Deborah C. Lambkin
(74) Attorney, Agent, or Firm—Lucy X. Yang

(57) ABSTRACT

The present invention provides compounds of Formula 1

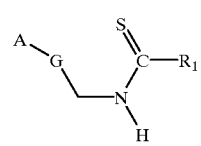

or pharmaceutical acceptable salts thereof wherein A, G and $R_1$ are as defined in the claims which are antibacterial agents.

11 Claims, No Drawings

OXAZOLIDINONE ANTIBACTERIAL AGENTS HAVING A THIOCARBONYL FUNTIONALITY

CROSS-REFERENCE TO RELATED APPLICATIONS

This application is a divisional application of U.S. patent application Ser. No: 09/200,904, filed Nov. 27, 1998 U.S. Pat. No. 6,255,304; which is a continuation-in-part of co-pending application U.S. Ser. No. 09/080,751, filed May 18, 1998U.S. Pat. No. 6,218,413, which claims the benefit of provisional application U.S. Serial No. 60/048,342, filed May 30, 1997, under 35 USC 119(e)(i).

BACKGROUND OF THE INVENTION

The present invention relates to new and useful oxazolidinone compounds and their preparations, and more particularly to oxazolidinone compounds in which the carbonyl functionality of —NH—C(O)—R is converted to a thiocarbonyl functionality, such as a thiourea —NH—C(S)—NH$_2$, an alkyl thiourea —NH—C(S)—NH—(C$_{1-4}$ alkyl), thioamide —NH—C(S)—(C$_{1-4}$ alkyl) or —NH—C(S)—H.

Replacement of the oxygen atom with a sulfur atom has unexpectedly improved the antimicrobial properties of the compounds. The compounds are useful antimicrobial agents, effective against a number of human and veterinary pathogens, including Gram-positive aerobic bacteria such as multiply-resistant staphylococci and streptococci, Gram-negative organisms such as *H. influenzae* and *M. catarrahlis* as well as anaerobic organisms such as bacteroides and clostridia species, and acid-fast organisms such as *Mycobacterium tuberculosis* and *Mycobacterium avium*. The compounds are particularly useful because they are effective against the latter organisms which are known to be responsible for infection in persons with AIDS.

SUMMARY OF THE INVENTION

In one aspect the subject invention is a compound of the Formula I

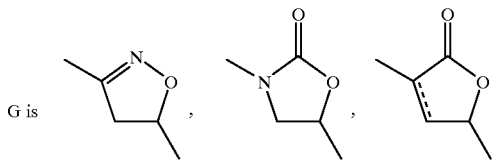

I or pharmaceutical acceptable salts thereof wherein:

G is 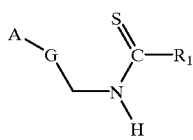

R$_1$ is
a) H,
b) NH$_2$,
c) NH—C$_{1-4}$ alkyl,
d) C$_{1-4}$ alkyl,
e) —OC$_{1-4}$ alkyl,
f) —S C$_{1-4}$ alkyl,
g) C$_{1-4}$ alkyl substituted with 1–3 F, 1–2 Cl, CN or —COOC$_{1-4}$ alkyl,
h) C$_{3-6}$ cycloalkyl,
i) N(C$_{1-4}$ alkyl)$_2$ or
j) N(CH$_2$)$_{2-5}$;

A is

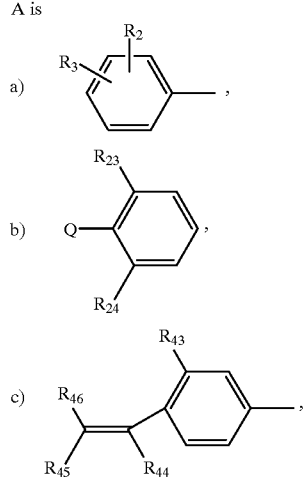

d) a 5-membered heteroaromatic moiety having one to three atoms selected from the group consisting of S, N, and O,
   wherein the 5-membered heteroaromatic moiety is bonded via a carbon atom,
   wherein the 5-membered heteroaromatic moiety can additionally have a fused-on benzene or naphthyl ring,
   wherein the heteroaromatic moiety is optionally substituted with one to three R$_{48}$,
e) a 6-membered heteroaromatic moiety having at least one nitrogen atom,
   wherein the heteroaromatic moiety is bonded via a carbon atom,
   wherein the 6-membered heteroaromatic moiety can additionally have fused-on benzene or naphthyl ring,
   wherein the heteroaromatic moiety is optionally substituted with one to three R$_{55}$,
f) a β-carbolin-3-yl, or indolizinyl bonded via the 6-membered ring, optionally substituted with one to three R$_{55}$,

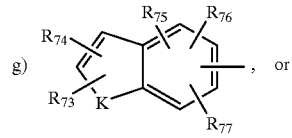, or

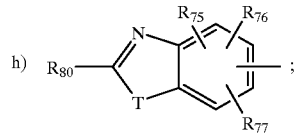;

wherein R$_2$ is
a) H,
b) F,
c) Cl,
d) Br,
e) C$_{1-3}$ alkyl,
f) NO$_2$, or
g) R$_2$ and R$_3$ taken together are —O—(CH$_2$)$_n$—O—;

$R_3$ is
- a) —S(=O)$_i$R$_4$,
- b) —S(=O)$_2$—N=S(O)$_j$R$_5$R$_6$,
- c) —SC(=O)R$_7$,
- d) —C(=O)R$_8$,
- e) —C(=O)R$_9$,
- f) —C(=O)NR$_{10}$R$_{11}$,
- g) —C(=NR$_{12}$)R$_8$,
- h) —C(R$_8$)(R$_{11}$)—OR$_{13}$,
- i) —C(R$_9$)(R$_{11}$)—OR$_{13}$,
- j) —C(R$_8$)(R$_1$l)—OC(=O)R$_{13}$,
- k) —C(R$_9$)(R$_{11}$)—OC(=O)R$_{13}$,
- l) —NR$_{10}$R$_{11}$,
- m) —N(R$_{10}$)—C(=O)R$_7$,
- n) —N(R$_{10}$)—S(=O)$_i$R$_7$,
- o) —C(OR$_{14}$)(OR$_{15}$)R$_8$,
- p) —C(R$_8$)(R$_{16}$)—NR$_{10}$R$_{11}$, or
- q) C$_{1-8}$ alkyl substituted with one or more =O other than at alpha position, —S(=O)$_i$R$_{17}$, —NR$_{10}$R$_{11}$, C$_{2-5}$ alkenyl, or C$_{2-5}$ alkynyl;

$R_4$ is
- a) C$_{1-4}$ alkyl optionally substituted with one or more halos, OH, CN, NR$_{10}$R$_{11}$, or —CO$_2$R$_{13}$,
- b) C$_{2-4}$ alkenyl,
- c) —NR$_{16}$R$_{18}$,
- d) —N$_3$,
- e) —NHC(=O)R$_7$,
- f) —NR$_{20}$(=O)R$_7$,
- g) —N(R$_{19}$)$_2$,
- h) —NR$_{16}$R$_{19}$, or
- i) —NR$_{19}$R$_{20}$, $R_5$ and $R_6$ at each occurrence are the same or different and are
- a) C$_{1-2}$ alkyl, or
- b) R$_5$ and R$_6$ taken together are —(CH$_2$)$_k$—;

$R_7$ is C$_{1-4}$ alkyl optionally substituted with one or more halos;

$R_8$ is
- a) H, or
- b) C$_{1-8}$ alkyl optionally substituted with one or more halos, or C$_{3-8}$ cycloalkyl;

$R_9$ is C$_{1-4}$ alkyl substituted with one or more
- a) —S(=O)R$_{17}$,
- b) —OR$_{13}$,
- c) —OC(=O)R$_{13}$,
- d) —NR$_{10}$R$_{11}$, or
- e) C$_{1-5}$ alkenyl optionally substituted with CHO;

$R_{10}$ and $R_{11}$ at each occurrence are the same or different and are
- a) H,
- b) C$_{1-4}$ alkyl, or
- c) C$_{3-8}$ cycloalkyl;

$R_{12}$ is
- a) —NR$_{10}$R$_{11}$,
- b) —OR$_{10}$; or
- c) —NHC(=O)R$_{10}$;

$R_{13}$ is
- a) H, or
- b) C$_{1-4}$ alkyl;

$R_{14}$ and $R_{15}$ at each occurrence are the same or different and are
- a) C$_{1-4}$ alky, or
- b) R$_{14}$ and R$_{15}$ taken together are —(CH)$_l$—;

$R_{16}$ is
- a) H,
- b) C$_{1-4}$ alkyl, or
- c) C$_{3-8}$ cycloalkyl;

$R_{17}$ is
- a) C$_{1-4}$ alkyl, or
- b) C$_{3-8}$ cycloalkyl;

$R_{18}$ is
- a) H,
- b) C$_{1-4}$ alkyl,
- c) C$_{2-4}$ alkenyl,
- d) C$_{3-4}$ cycloalkyl,
- e) —OR$_{13}$ or
- f) —NR$_{21}$R$_{22}$;

$R_{19}$, is
- a) Cl,
- b) Br, or
- c) I;

$R_{20}$ is a physiologically acceptable cation;

$R_{21}$ and $R_{22}$ at each occurrence are the same or different and are
- a) H,
- b) C$_{1-4}$ alkyl, or
- c) —NR$_{21}$R$_{22}$ taken together are —(CH$_2$)$_m$—;

wherein $R_{23}$ and $R_{24}$ at each occurrence are the same or different and are
- a) H,
- b) F,
- c) Cl,
- d) C$_{1-2}$ alkyl,
- e) CN
- f) OH,
- g) C$_{1-2}$ alkoxy,
- h) nitro, or
- i) amino;

Q is a) 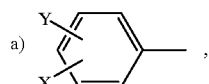, b) 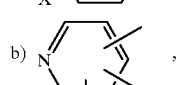, c) 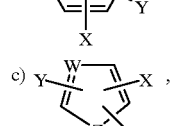, d) 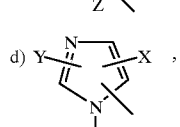, e) 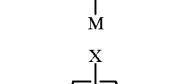, f) 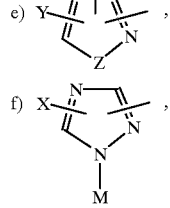, g) 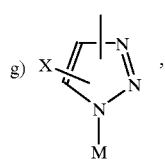

h) 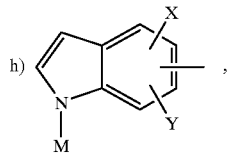

i) 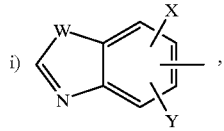

j) 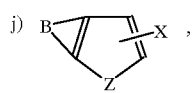

k) 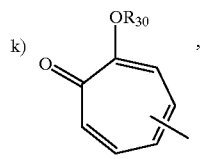

l) 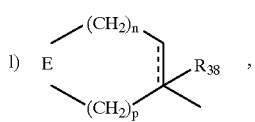

m) a diazinyl group optionally substituted with X and Y,
n) a triazinyl group optionally substituted with X and Y,
o) a quinolinyl group optionally substituted with X and Y,
p) a quinoxalinyl group optionally substituted with X and Y,
q) a naphthyridinyl group optionally substituted with X and Y, r) 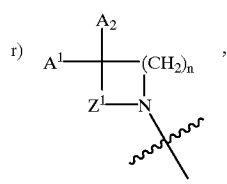

s) 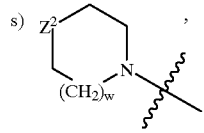

t) 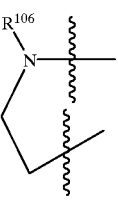

u) 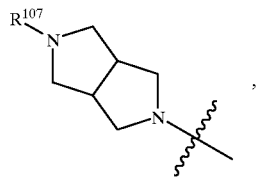

v) 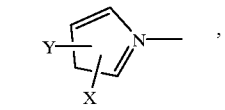

w) 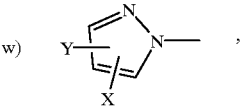

x) 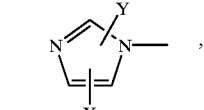

y) 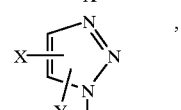

z) 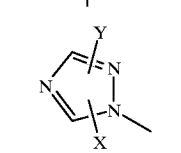

aa) 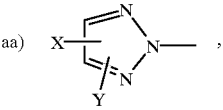

bb) 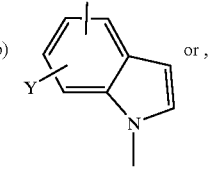 or,

Q and $R_{24}$ taken together are

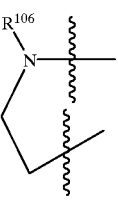

wherein $Z^1$ is
a) —CH$_2$—,
b) —CH(R$^{104}$)—CH$_2$—,
c) —C(O)—, or
d) —CH$_2$CH$_2$CH$_2$—;
wherein $Z^2$ is
a) —O$_2$S—,
b) —O—,
c) —N(R$^{107}$)—, d) —OS—, or
e) —S—;
wherein $Z^3$ is
   a) —O$_2$S—,
   b) —O—,
   c) —OS—, or
   d) —S—;
wherein $A^1$ is
   a) H—, or
   b) CH$_3$;
wherein $A^2$ is
   a) H—,
   b) HO—,
   c) CH$_3$—,
   d) CH$_3$O—,
   e) $R^{102}$O—CH$_2$—C(O)—NH—
   f) $R^{103}$O—C(O)—NH—,
   g) (C$_1$–C$_2$)alkyl-O—C(O)—,
   h) HO—CH$_2$—,
   i) CH$_3$O—NH—,
   j) (C$_1$–C$_3$)alkyl-O$_2$C—,
   k) CH$_3$—C(O)—,
   l) CH$_3$—C(O)—CH$_2$—, m) 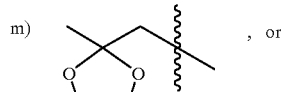, or n) 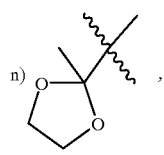, $A^1$ and $A^2$ taken together are:

a) 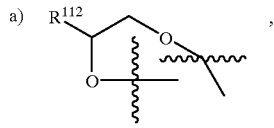, b) 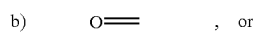, or c) 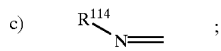;

wherein $R^{102}$ is
   a) H—,
   b) CH$_3$—,
   c) phenyl-CH$_2$—, or
   d) CH$_3$C(O)—;
wherein $R^{103}$ is
   a) (C$_1$–C$_3$)alkyl-, or
   b) phenyl-;
wherein $R^{104}$ is
   a) H—, or
   b) HO—;
wherein $R^{105}$ is
   a) H—,
   b) (C$_1$–C$_3$)alkyl-,
   c) CH$_2$=CH—CH$_2$—, or
   d) CH$_3$—O—(CH$_2$)$_2$—;

wherein $R^{106}$ is
   a) CH$_3$—C(O)—,
   b) H—C(O)—,
   c) Cl$_2$CH—C(O)—,
   d) HOCH$_2$—C(O)—,
   e) CH$_3$SO$_2$—, f) 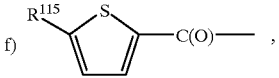, g) F$_2$CHC(O)—, h) 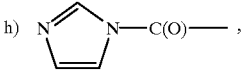, i) H$_3$C—C(O)—O—CH$_2$—C(O)—,
j) H—C(O)—O—CH$_2$—C(O)—, k) 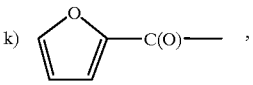, l) HC≡C—CH$_2$—O—CH$_2$—C(O)—, or
m) phenyl-CH$_2$—O—CH$_2$—C(O)—;
wherein $R^{107}$ is
   a) $R^{102}$O—C($R^{110}$)($R^{111}$)—C(O)—,
   b) $R^{103}$O—C(O)—,
   c) $R^{108}$—C(O)—, d) 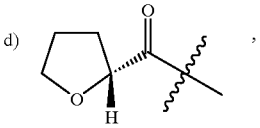, e) 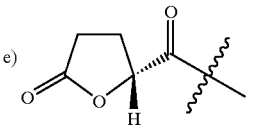, f) H$_3$C—C(O)—(CH$_2$)$_2$—C(O)—,
g) $R^{109}$—SO$_2$—, h) 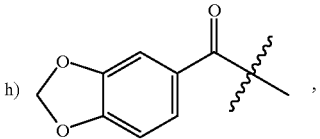, i) HO—CH$_2$—C(O)—,
j) $R^{116}$—(CH$_2$)$_2$—,
k) $R^{113}$—C(O)—O—CH$_2$—C(O)—,
l) (CH$_3$)$_2$N—CH$_2$—C(O)—NH—,
m) NC—CH$_2$—,
n) F$_2$—CH—CH$_2$—, or
o) $R^{150}R^{151}$NSO$_2$;
wherein $R^{108}$ is
   a) H—,
   b) (C$_1$–C$_4$)alkyl,
   c) aryl —(CH$_2$)$_p$,
   d) ClH$_2$C—,
   e) Cl$_2$HC—,
   f) FH$_2$C—, g) $F_2HC-$,
h) $(C_3-C_6)$cycloalkyl, or
i) $CNCH_2-$.

wherein $R^{109}$ is
a) alkyl$C_1-C_4$,
b) $-CH_2Cl$
c) $-CH_2CH=CH_2$,
d) aryl, or
e) $-CH_2CN$;

wherein $R^{110}$ and $R^{111}$ are independently
a) $H-$,
b) $CH_3-$; or wherein $R^{112}$ is
a) $H-$,
b) $CH_3O-CH_2O-CH_2-$, or
c) $HOCH_2-$;

wherein $R^{113}$ is
a) $CH_3-$,
b) $HOCH_2-$,
c) $(CH_3)_2N$-phenyl, or
d) $(CH_3)_2N-CH_2-$;

wherein $R^{114}$ is
a) $HO-$,
b) $CH_3O-$,
c) $H_2N-$,
d) $CH_3O-C(O)-O-$,
e) $CH_3-C(O)-O-CH_2-C(O)-O-$,
f) phenyl-$CH_2-O-CH_2-C(O)-O-$,
g) $HO-(CH_2)_2-O-$,
h) $CH_3O-CH_2-O-(CH_2)_2-O-$, or
i) $CH_3O-CH_2-O-$;

wherein $R^{113}$ is
a) $CH_3-$,
b) $HOCH_2-$,
c) $(CH_3)_2N$-phenyl, or
d) $(CH_3)_2N-CH_2-$;

wherein $R^{115}$ is
a) $H-$, or
b) $Cl-$;

wherein $R^{116}$ is
a) $HO-$
b) $CH_3O-$, or
c) $F$;

wherein $R^{150}$ and $R^{151}$ are each H or alkyl $C_1-C_4$ or $R^{150}$ and $R^{151}$ taken together with the nitrogen atom to which each is attached form a monocyclic heterocyclic ring having from 3 to 6 carbon atoms;

B is an unsaturated 4-atom liner having one nitrogen and three carbons;

M is
a) H,
b) $C_{1-8}$ alkyl,
c) $C_{3-8}$ cycloalkyl,
d) $-(CH_2)_mOR_{13}$, or
e) $-(CH_2)_h-NR_{21}R_{22}$;

Z is
a) O,
b) S, or
c) NM;

W is
a) CH,
b) N, or
c) S or O when Z is NM;

Y is
a) H,
b) F,
c) Cl,
d) Br,
e) $C_{1-3}$ alkyl, or
f) $NO_2$;

X is
a) H,
b) $-CN$,
c) $OR_{27}$,
d) halo,
e) $NO_2$,
f) tetrazoyl,
g) $-SH$,
h) $-S(=O)_iR_4$,
i) $-S(=O)_2-N=S(O)_jR_5R_6$,
j) $-SC(=O)R_7$,
k) $-C(=O)R_{25}$,
l) $-C(=O)NR_{27}R_{28}$,
m) $-C(=NR_{29})R_{25}$,
n) $-C(R_{25})(R_{28})-OR_{13}$,
o) $-C(R_{25})(R_{28})-OC(=O)R_{13}$,
p) $-C(R_{28})(OR_{13})-(CH_2)_h-NR_{27}R_{28}$,
q) $-NR_{27}R_{28}$,
r) $-N(R_{27})C(=O)R_7$,
s) $-N(R_{27})-S(=O)_iR_7$,
t) $-C(OR_{14})(OR_{15})R_{28}$,
u) $-C(R_{25})(R_{16})-NR_{27}R_{26}$, or
v) $C_{1-8}$ alkyl substituted with one or more halos, OH, $=O$ other than at alpha position, $-S(=O)_iR_{17}$, $-NR_{27}R_{28}$, $C_{2-5}$ alkenyl, $C_{2-5}$ alkynyl, or $C_{3-8}$ cycloalkyl;

$R_4$, $R_5$, $R_6$, $R_7$, $R_{13}$, $R_{14}$, $R_{15}$, $R_{16}$, and $R_{17}$ are the same as defined above;

$R_{25}$ is
a) H,
b) $C_{1-8}$ alkyl optionally substituted with one or more halos, $C_{3-8}$ cycloalkyl, $C_{1-4}$ alkyl substituted with one or more of $-S(=O)_iR_{17}$, $-OR_{13}$, or $OC(=O)R_{13}$, $N_{27}R_{28}$, or
c) $C_{2-5}$ alkenyl optionally substituted with CHO, or $CO_2R_{13}$;

$R_{26}$ is
a) $R_{28}$, or
b) $NR_{27}N_{28}$;

$R_{27}$ and $R_{28}$ at each occurrence are the same or different and are
a) H,
b) $C_{1-8}$ alkyl,
c) $C_{3-8}$ cycloalkyl,
d) $-(CH_2)_mOR_{13}$,
e) $-(CH_2)_h-NR_{21}R_{22}$, or
f) $R_{27}$ and $R_{28}$ taken together are $-(CH_2)_2O(CH_2)_2-$, $-(CH_2)_hCH(COR_7)-$, or $-(CH_2)_2N(CH_2)_2(R_7)$;

$R_{29}$ is
a) $-NR_{27}R_{28}$,
b) $-OR_{27}$, or
c) $-NHC(=O)R_{28}$;

wherein $R_{30}$ is
a) H,
b) $C_{1-8}$ alkyl optionally substituted with one or more halos, or
c) $C_{1-8}$ alkyl optionally substituted with one or more OH, or $C_{1-6}$ alkoxy;

wherein E is
- a) $NR_{39}$,
- b) —$S(=O)_i$, or
- c) O;

$R_{38}$ is
- a) H,
- b) $C_{1-6}$ alkyl,
- c) —$(CH_2)_q$-aryl, or
- d) halo;

$R_{39}$ is
- a) H,
- b) $C_{1-6}$ alkyl optionally substituted with one or more OH, halo, or —CN,
- c) —$(CH_2)_q$-aryl,
- d) —$CO_2R_{40}$,
- e) —$COR_{41}$,
- f) $C(=O)$—$(CH_2)_q$—$C(=O)R_{40}$,
- g) —$S(=O)_2$—$C_{1-6}$ alkyl,
- h) —$S(=O)_2$—$(CH_2)_q$-aryl, or
- i) —$(C=O)_j$-Het;

$R_{40}$ is
- a) H,
- b) $C_{1-6}$ alkyl optionally substituted with one or more OH, halo, or —CN,
- c) —$(CH_2)_q$-aryl, or
- d) —$(CH_2)_q$—$OR_{42}$;

$R_{41}$ is
- a) $C_{1-6}$ alkyl optionally substituted with one or more OH, halo, or —CN,
- b) —$(CH_2)_q$-aryl, or
- c) —$(CH_2)_q$—$OR_{42}$;

$R_{42}$ is
- a) H,
- b) $C_{1-6}$ alkyl,
- c) —$(CH_2)_q$-aryl, or
- d) —$C(=O)$—$C_{1-6}$ alkyl;

aryl is
- a) phenyl,
- b) pyridyl, or
- c) napthyl; a to c optionally substituted with one or more halo, —CN, OH, SH, $C_{1-6}$ alkyl, $C_{1-6}$ alkoxy, or $C_{1-6}$ alkylthio;

wherein $R_{43}$ is
- a) H,
- b) $C_{1-2}$ alkyl,
- c) F, or
- d) OH;

$R_{44}$ is
- a) H,
- b) $CF_3$,
- c) $C_{1-3}$ alkyl optionally substituted with one or more halo,
- d) phenyl optionally substituted with one or more halo,
- e) $R_{44}$ and $R_{45}$ taken together are a 5-, 6-, or 7-membered ring of the formula, or 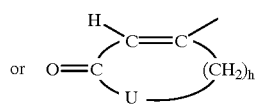

- f) $R_{44}$ and $R_{45}$ taken together are —$(CH_2)_k$—, when $R_{46}$ is an electron-withdrawing group;

$R_{45}$ and $R_{46}$ at each occurrence are the same or different and are
- a) an electron-withdrawing group,
- b) H,
- c) $CF_3$,
- d) $C_{1-3}$ alkyl optionally substituted with one halo,
- e) phenyl, provided at least one of $R_{45}$ or $R_{46}$ is an electron-withdrawing group, or
- f) $R_{45}$ and $R_{46}$ taken together are a 5-, 6-, 7-membered ring of the formula

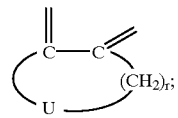

U is
- a) $CH_2$,
- b) O,
- c) S, or
- d) $NR_{47}$;

$R_{47}$ is
- a) H, or
- b) $C_{1-5}$ alkyl;

wherein $R_{48}$ is
- a) carboxyl,
- b) halo,
- c) —CN,
- d) mercapto,
- e) formyl,
- f) $CF_3$,
- g) —$NO_2$,
- h) $C_{1-6}$ alkoxy,
- i) $C_{1-6}$ alkoxycarbonyl,
- j) $C_{1-6}$ alkythio,
- k) $C_{1-6}$ acyl,
- l) —$NR_{49}R_{50}$,
- m) $C_{1-6}$ alkyl optionally substituted with OH, $C_{1-5}$ alkoxy, $C_{1-5}$ acyl, or —$NR_{49}R_{50}$,
- n) $C_{2-8}$ alkenylphenyl optionally substituted with one or two $R_{51}$,
- o) phenyl optionally substituted with one or two $R_{51}$,
- p) a 5-, or 6-membered (un)saturated heterocyclic moiety having one to three atoms selected from the group consisting of S, N, and O, optionally substituted with one or two $R_{51}$, or q) 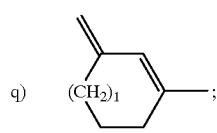

$R_{49}$ and $R_{50}$ at each occurrence are the same or different and are
- a) H,
- b) $C_{1-4}$ alkyl,
- c) $C_{5-6}$ cycloalkyl, or
- d) $R_{49}$ and $R_{50}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, $C_{1-3}$ alkyl, or $C_{1-3}$ acyl;

$R_{51}$ is
- a) carboxyl,
- b) halo, c) —CN,
d) mercapto,
e) formyl,
f) $CF_3$,
g) —$NO_2$,
h) $C_{1-6}$ alkoxy,
i) $C_{1-6}$ alkoxycarbonyl,
j) $C_{1-6}$ alkythio,
k) $C_{1-6}$ acyl,
l) $C_{1-6}$ alkyl optionally substituted with OH, $C_{1-5}$ alkoxy, $C_{1-5}$ acyl, or —$NR_{49}R_{50}$,
m) phenyl,
n) —C(=O)$NR_{52}R_{53}$,
o) —$NR_{49}R_{50}$,
p) —$N(R_{52})$(—$SO_2R_{54}$),
q) —$SO_2$—$NR_{52}R_{53}$, or
r) —S(=O)$_iR_{54}$;

$R_{52}$ and $R_{53}$ at each occurrence are the same or different and are
a) H,
b) $C_{1-6}$ alkyl, or
c) phenyl;

$R_{54}$ is
a) $C_{1-4}$ alkyl, or
b) phenyl optionally substituted with $C_{1-4}$ alkyl;

wherein $R_{55}$ is
a) carboxyl,
b) halo,
c) —CN,
d) mercapto,
e) formyl,
f) $CF_3$,
g) —$NO_2$,
h) $C_{1-6}$ alkoxy,
i) $C_{1-6}$ alkoxycarbonyl,
j) $C_{1-6}$ alkythio
k) $C_{1-6}$ acyl,
l) —$NR_{56}R_{57}$,
m) $C_{1-6}$ alkyl optionally substituted with OH, $C_{1-5}$ alkoxy, $C_{1-5}$ acyl, or —$NR_{56}R_{57}$,
n) $C_{2-8}$ alkenylphenyl optionally substituted with one or two $R_{58}$,
o) phenyl optionally substituted with one or two $R_{58}$,
p) a 5- or 6-membered (un)saturated heterocyclic moiety having one to three atoms selected from the group consisting of S, N, and O, optionally substituted with one or two $R_{58}$, or q) 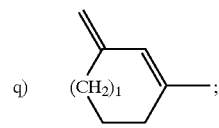;

$R_{56}$ and $R_{57}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl, or
g) $R_{56}$ and $R_{57}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, phenyl, pyrimidyl, $C_{1-3}$ alkyl, or $C_{1-3}$ acyl;

$R_{58}$ is
a) carboxyl,
b) halo,
c) —CN,
d) mercapto,
e) formyl,
f) $CF_3$,
g) —$NO_2$,
h) $C_{1-6}$ alkoxy,
i) $C_{1-6}$ alkoxycarbonyl,
j) $C_{1-6}$ alkythio,
k) $C_{1-6}$ acyl,
l) phenyl,
m) $C_{1-6}$ alkyl optionally substituted with OH, azido, $C_{1-5}$ alkoxy, $C_{1-5}$ acyl, —$NR_{65}R_{66}$, —$SR_{67}$, —O—$SO_2R_{68}$, or

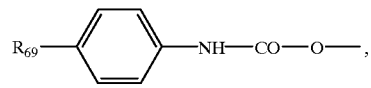, n) —C(=O)$NR_{59}R_{60}$,
o) —$NR_{56}R_{57}$,
p) —$N(R_{59})$(—$SO_2R_{54}$),
q) —$SO_2$—$NR_{59}R_{60}$,
r) —S(=O)$_iR_{54}$,
s) —CH=N—$R_{61}$, or
t) —CH(OH)—$SO_3R_{64}$;

$R_{54}$ is the same as defined above;

$R_{59}$ and $R_{60}$ at each occurrence are the same or different and are
a) H,
b) $C_{1-6}$ alkyl,
c) phenyl, or
d) tolyl;

$R_{61}$ is
a) OH,
b) benzyloxy,
c) —NH—C(=O)—$NH_2$,
d) —NH—C(=S)—$NH_2$, or
e) —NH—C(=NH)—$NR_{62}R_{63}$;

$R_{62}$ and $R_{63}$ at each occurrence are the same or different and are
a) H, or
b) $C_{1-4}$ alkyl optionally substituted with phenyl or pyridyl;

$R_{64}$ is
a) H, or
b) a sodium ion;

$R_{65}$ and $R_{66}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl,
g) $R_{65}$ and $R_{66}$ taken together are a 5-, 6-membered saturated heterocyclic moiety having one to three atoms selected from the group consisting of S, N, and O, optionally substituted with, including on the nitrogen atom, phenyl, pyrimidyl, $C_{1-3}$ alkyl, or $C_{1-3}$ acyl, h) —P(O)(OR$_{70}$O)(OR$_{71}$), or
i) —SO$_2$—R$_{72}$;

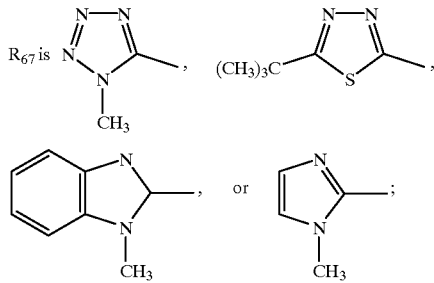

R$_{68}$ is C$_{1-3}$ alkyl;
R$_{69}$ is
  a) C$_{1-6}$ alkoxycarbonyl, or
  b) carboxyl;
R$_{70}$ and R$_{71}$ at each occurrence are the same or different and are
  a) H, or
  b) C$_{1-3}$ alkyl;
R$_{72}$ is
  a) methyl,
  b) phenyl, or
  c) tolyl;
wherein K is
  a) O, or
  b) S;
R$_{73}$, R$_{74}$, R$_{75}$, R$_{76}$, and R$_{77}$ at each occurrence are the same or different and are
  a) H,
  b) carboxyl,
  c) halo,
  d) —CN,
  e) mercapto,
  f) formyl,
  g) CF$_3$,
  h) —NO$_2$,
  i) C$_{1-6}$ alkoxy,
  j) C$_{1-6}$ alkoxycarbonyl,
  k) C$_{1-6}$ alkythio,
  l) C$_{1-6}$ acyl,
  m) —NR$_{78}$R$_{79}$,
  n) C$_{1-6}$ alkyl optionally substituted with OH, C$_{1-5}$ alkoxy, C$_{1-5}$ acyl, —NR$_{78}$R$_{79}$, —N(phenyl)(CH$_2$—CH$_2$—OH), —O—CH(CH$_3$)(OCH$_2$CH$_3$), or —O-phenyl-[para-NHC(=O)CH$_3$],
  o) C$_{2-8}$ alkenylphenyl optionally substituted with R$_{51}$,
  p) phenyl optionally substituted with R$_{51}$, or
  q) a 5-, or 6-membered (un)saturated heterocyclic moiety having one to three atoms selected from the group consisting of S, N, and O, optionally substituted with R$_{51}$;
R$_{51}$ is the same as defined above;
R$_{78}$ and R$_{79}$ at each occurrence are the same or different and are
  a) H,
  b) C$_{1-4}$ allyl,
  c) phenyl, or
  d) R$_{78}$ and R$_{79}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, C$_{1-3}$ alkyl, or C$_{1-3}$ acyl;

wherein T is
  a) O,
  b) S, or
  c) SO$_2$;
R$_{75}$, R$_{76}$, and R$_{77}$ are the same as defined above;
R$_{80}$ is
  a) H,
  b) formyl,
  c) carboxyl,
  d) C$_{1-6}$ alkoxycarbonyl,
  e) C$_{1-8}$ alkyl,
  i) C$_{2-8}$ alkenyl, wherein the substituents (e) and (f) can be optionally substituted with OH, halo, C$_{1-6}$ alkoxy, C$_{1-6}$ acyl, C$_{1-6}$ alkylthio or C$_{1-6}$ alkoxycarbonyl, or phenyl optionally substituted with halo,
  g) an aromatic moiety having 6 to 10 carbon atoms optionally substituted with carboxyl, halo, —CN, formyl, CF$_3$, —NO$_2$, C$_{1-6}$ alkyl, C$_{1-6}$ alkoxy, C$_{1-6}$ acyl, C$_{1-6}$ alkylthio, or C$_{1-6}$ alkoxycarbonyl;
  h) —NR$_{81}$R$_{82}$,
  i) —OR$_{90}$,
  j) —S(=O)$_i$—R$_{91}$,
  k) —SO$_2$—N(R$_{92}$)(R$_{93}$), or
  l) a radical of the following formulas:
R$_{81}$ and R$_{82}$ at each occurrence are the same or different and are
  a) H,
  b) C$_{3-6}$ cycloalkyl,
  c) phenyl,
  d) C$_{1-6}$ acyl,
  e) C$_{1-8}$ alkyl optionally substituted with OH, C$_{1-6}$ alkoxy which can be substituted with OH, a 5-, or 6-membered aromatic heterocyclic moiety having one to three atoms selected from the group consisting of S, N, and O, phenyl optionally substituted with OH, CF$_3$, halo, —NO$_2$, C$_{1-4}$ alkoxy, —NR$_{83}$R$_{84}$, or

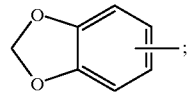

f) 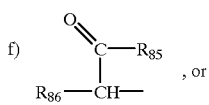, or g) 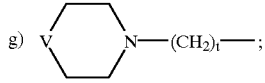;

b) CH$_2$, or
  c) NR$_{87}$;
R$_{83}$ and R$_{84}$ at each occurrence are the same or different and are
  a) H, or
  b) C$_{1-4}$ alkyl;
R$_{85}$ is
  a) OH,
  b) C$_{1-4}$ alkoxy, or
  c) —NR$_{88}$R$_{89}$;
R$_{86}$ is
  a) H, or
  b) C$_{1-7}$ alkyl optionally substituted with indolyl, OH, mercaptyl, imidazoly, methylthio, amino, phenyl optionally substituted with OH, —C(=O)—NH$_2$, —CO$_2$H, or —C(=NH)—NH$_2$;

$R_{87}$ is
a) H,
b) phenyl, or
c) $C_{1-6}$ alkyl optionally substituted by OH;

$R_{88}$ and $R_{89}$ at each occurrence are the same or different and are
a) H,
b) $C_{1-5}$ alkyl
c) $C_{3-6}$ cycloalky, or
d) phenyl;

$R_{90}$ is
a) $C_{1-8}$ alkyl optionally substituted with $C_{1-6}$ alkoxy or $C_{1-6}$ hydroxy, $C_{3-6}$ cycloalkyl, a 6-membered aromatic optionally benzo-fused heterocyclic moiety having one to three nitrogen atoms, which can in turn be substituted with one or two —$NO_2$, $CF_3$, halo, —CN, OH, $C_{1-5}$ alkyl, $C_{1-5}$ alkoxy, or $C_{1-5}$ acyl;

b) 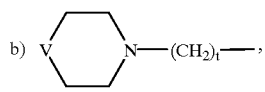

c) phenyl, or
d) pyridyl;

$R_{91}$ is
a) $C_{1-16}$ alkyl,
b) $C_{2-16}$ alkenyl, wherein the substituents (a) and (b) can be optionally substituted with $C_{1-6}$ alkoxycarbonyl, or a 5-, 6-, 7-membered aromatic heterocyclic moiety having one to three atoms selected from the group consisting of S, N, and O,
c) an aromatic moiety having 6 to 10 carbon atoms, or
d) a 5-, 6-, 7-membered aromatic heterocyclic moiety having one to three atoms selected from the group consisting of S, N, and O, wherein the substituents (c) and (d) can be optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$alkylthio, or $C_{1-6}$ alkoxycarbonyl;

$R_{92}$ and $R_{93}$ at each occurrence are the same or different and are
a) H,
b) phenyl,
c) $C_{1-6}$ alkyl, or
d) benzyl;

$R_{94}$ and $R_{95}$ at each occurrence are the same or different and are
a) H,
b) OH,
c) $C_{1-6}$ alkyl optionally substituted with —$NR_{83}R_{84}$, or
d) $R_{94}$ and $R_{95}$ taken together are =O;

$R_{96}$ is
a) an aromatic moiety having 6 to 10 carbon atoms,
b) a 5-, or 6-membered aromatic optionally benzo-fused heterocyclic moiety having one to three atoms selected from the group consisting of S, N, and O, wherein the substituents (a) and (b) which can in turn be substituted with one or three —$NO_2$, $CF_3$, halo, —CN, OH, phenyl, $C_{1-5}$ alkyl, $C_{1-5}$ alkoxy, or $C_{1-5}$ acyl,
c) morpholinyl,
d) OH,
e) $C_{1-6}$ alkoxy,
f) —$NR_{83}R_{84}$,
g) —C(=O)—$R_{97}$, or h) 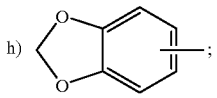

$R_{97}$ is
a) morpholinyl,
b) OH, or
c) $C_{1-6}$ alkoxy;

h is 1, 2, or 3;
i is 0, 1, or 2;
j is 0 or 1;
k is 3, 4, or 5;
l is 2 or 3;
m is 4 or 5;
n is 0, 1, 2, 3, 4, or 5;
p is 0, 1, 2, 3, 4, or 5; with the proviso that n and p together are 1, 2, 3, 4, or 5;
q is 1, 2, 3, or 4;
r is 2, 3, or 4;
t is 0, 1, 2, 3, 4, 5, or 6;
u is 1 or 2;
w is 0, 1, 2, or 3.

DETAILED DESCRIPTION OF THE INVENTION

The new compounds of the invention can be prepared using known compounds and intermediates of oxzolidinones, isoxazolines and butyolactones as intermediates and synthetic methods known in the art. Thioamides of the invention can typically be prepared by the reaction of the corresponding amide with Lawesson's reagent.

Compounds disclosed in the following publications are suitable intermediates for preparation of the compounds of this invention and are hereby incorporated by reference for their disclosure of suitable compounds that can be converted to the subject thiocarbonyl derivatives.

U.S. Pat. Nos. 5,225,565; 5,182,403; 5,164,510; 5,247,090; 5,231,188; 5,565,571; 5,547,950; and 5,523,403.

PCT Application and publications PCT/US93/04850, WO94/01110; PCT/US94/08904, WO95/07271; PCT/US95/02972, WO95/25106; PCT/US95/10992, WO96/13502; PCT/US96/05202, WO96/35691; PCT/US96/12766; PCT/US96/13726; PCT/US96/14135; PCT/US96/17120; PCT/US96/19149; PCT/US97/01970; PCT/US95/12751, WO96/15130; and PCT/US96/00718, WO96/23788.

Chemical conversion techniques for converting various intermediates having a $CH_2NH_2$ on the oxazolidinone ring to $CH_2NH$—C(S)—$CH_3$ is disclosed by Hartke, K, Barrmeyer, S., J. prakt. Chem. 1996, 338, 251–6. Similarly, conversion of $CH_2NHC(=O)CH_3$ to $CH_2NHC(S)NHCH_3$ is reported by Cava, M. P.; Levinson, M. I., Thionation Reactions of Lawesson's Reagents, Tetrahedron 1985, 41, 5061–87.

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of 1–4 carbon atoms, inclusive, or methyl, ethyl, propyl, butyl and isomeric forms thereof.

The terms "$C_{1-2}$ alkyl", "$C_{1-3}$ alkyl", "$C_{1-4}$ alkyl", "$C_{1-5}$ alkyl", "$C_{1-6}$ alkyl", "$C_{1-8}$ alkyl", and "$C_{1-6}$ alkyl" refer to an alkyl group having one to two, one to three, one to four, one to five, one to six, one to eight, or one to sixteen carbon atoms respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "$C_{2-4}$ alkenyl", "$C_{2-5}$ alkenyl", "$C_{2-8}$ alkenyl", $C_{2-14}$ alkenyl" and "$C_{2-16}$ alkenyl" refer to at least one double bond alkenyl group having two to four, two to five, two to eight, two to fourteen, or two to sixteen carbon atoms, respectively such as, for example, ethenyl, propenyl, butenyl, pentenyl, pentdienyl, hexenyl, hexdienyl, heptenyl, heptdienyl, octenyl, octdienyl, octatrienyl, nonenyl, nonedienyl, nonatrienyl, undecenyl, undecdienyl, dodecenyl, tridecenyl, tetradecenyl and their isomeric forms thereof.

The terms "$C_{2-5}$ alkynyl", "$C_{2-8}$ alkynyl", and "$C_{2-10}$ alkynyl" refer to at least one triple bond alkynyl group having two to five, two to eight, or two to ten carbon atoms respectively such as, for example, ethynyl, propynyl, butynyl, pentynyl, pentdiynyl, hexynyl, hexdiynyl, heptynyl, heptdiynyl, octynyl, octdiynyl, octatriynyl, nonynyl, nonediynyl, nonatriynyl and their isomeric forms thereof.

The terms "$C_{3-4}$ cycloalkyl", "$C_{3-6}$ cycloalkyl", "$C_{5-6}$ cycloalkyl", and "$C_{3-8}$ cycloalkyl" refer to a cycloalkyl having three to four, three to six, five to six, or threE to eight carbon atoms respectively such as, for example, cyclopropyl, cyclobutyl, cyclopentyl, cyclohexyl, cycloheptyl, cyclooctyl, and their isomeric forms thereof.

The terms "$C_{1-4}$ alkoxy", "$C_{1-6}$ alkoxy", and "$C_{1-8}$ alkoxy" refer to an alkyl group having one to four, one to six, or one to eight carbon atoms respectively attached to an oxygen atom such as, for example, methoxy, ethoxy, propyloxy, butyloxy, pentyloxy, hexyloxy, heptyloxy, or octyloxy and their isomeric forms thereof The terms "$C_{1-6}$ alkylamino", and "$C_{1-8}$ alkylamino" refer to an alkyl group having one to six, or one to eight carbon atoms respectively attached to an amino moiety such as, for example, methylamino, ethylamino, propylamino, butylamino, pentylamino, hexylamino, heptylamino, or octoylamino and their isomeric forms thereof.

The terms "$C_{1-6}$ dialkylamino", and "$C_{1-8}$ dialkylamino" refer to two alkyl groups having one to six, or one to eight carbon atoms respectively attached to an amino moiety such as, for example, dimethylamino, methylethylamino, diethylamino, dipropylamino, methypropylamino, ethylpropylamino, dibutylamino, dipentylamino, dihexylamino, methylhecylamino, diheptylamino, or dioctoylamino and their isomeric forms thereof The terms "$C_{1-3}$ acyl", "$C_{1-4}$ acyl", "$C_{1-5}$ acyl", "$C_{1-6}$ acyl", "$C_{1-8}$ acyl", and "$C_{2-8}$ acyl" refer to a carbonyl group having an alkyl group of one to three, one to four, one to five, one to six, one to eight, or two to eight carbon atoms.

The terms "$C_{1-4}$ alkoxyearbonyl", "$C_{1-6}$ alkoxyearbonyl", and "$C_{1-8}$ alkoxycarbonyl" refer to an ester group having an alkyl group of one to four, one to six, or one to eight carbon atoms.

The term "$C_{1-8}$ alkyl phenyl" refers to an alkyl group having one to eight carbon atoms and isomeric forms thereof which is substituted with at least one phenyl radical.

The term "$C_{2-8}$ alkenyl phenyl" refers to a at least one double bond alkenyl group having one to eight carbon atoms and isomeric forms thereof which is substituted with at least one phenyl radical.

The term "$C_{1-8}$ alkyl pyridyl" refers to an alkyl group having one to eight carbon atoms and isomeric forms thereof which is substituted with at least one pyridyl radical.

The term "$C_{1-8}$ hydroxyl" refers to an alkyl group having one to eight carbon atoms and isomeric forms thereof attached to a hydroxy group.

The term "$C_{1-8}$ alkylsulfonyl" refers to an alkyl group having one to eight carbon atoms and isomeric forms thereof attached to a $SO_2$ moiety.

The term "$C_{1-6}$ alkylthio" refers to an alkyl group having one to six carbon atoms and isomeric forms thereof attached to a sulfur atom.

The term "Het" refers to 5 to 10 membered saturated, unsaturated or aromatic heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2, 4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl,1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The term halo refers to fluoro, chloro, bromo, or iodo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

When Q is the structure of

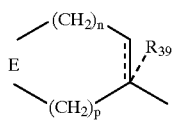

the dotted line in the heterocyclic ring means that this bond can be either single or double. In the case where the dotted line is a double bond, the $R_{39}$ group will not be present.

The compounds of Formula I of this invention contain a chiral center at C5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in any of A or $R_1$ group, and this invention embraces all possible stereoisomers and geometric forms in these groups.

The compounds of this invention are useful for treatment of microbial infections in humans and other warm blooded animals, under both parenteral and oral administration.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day.

It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

When the compounds according to this invention are administered parenterally, i.e., by injection, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

MIC Test Method

The in vitro MICs of test compounds were determined by a standard agar dilution method. A stock drug solution of each analog is prepared in the preferred solvent, usually DMSO:$H_2O$ (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC $\mu$g/ml), the lowest concentration of drug that inhibits visible growth of the organism, is read and recorded. The data is shown in Tables I and II.

TABLE 1

| Structure | Oxazolidinone MIC Values (Gram+) | | | | |
|---|---|---|---|---|---|
| | SAUR 9213 | SEPI 12084 | EFAE 9217 | SPNE 9912 | SPYO 152 |
| Comparison* | 16 | 4 | 8 | .5 | 1 |
| *(structure: spiro hydantoin-piperidine linked to fluorophenyl-oxazolidinone-acetamide)* | | | | | |
| Example 3 | 4 | 1 | 2 | .25 | .5 |
| *(structure: spiro hydantoin-piperidine linked to fluorophenyl-oxazolidinone-thioacetamide)* | | | | | |
| Comparison* | 2 | 1 | 2 | .5 | 1 |
| *(structure: morpholine-fluorophenyl-oxazolidinone-acetamide)* | | | | | |
| Example 1 | 1 | .25 | .5 | .13 | .13 |
| *(structure: morpholine-fluorophenyl-oxazolidinone-thioacetamide)* | | | | | |
| Example 5 | 1 | .25 | .5 | <.125 | .25 |
| *(structure: morpholine-fluorophenyl-oxazolidinone-thiourea)* | | | | | |

TABLE 1-continued
| Structure | Oxazolidinone MIC Values (Gram+) | | | | |
|---|---|---|---|---|---|
| | SAUR 9213 | SEPI 12084 | EFAE 9217 | SPNE 9912 | SPYO 152 |
| Example 6 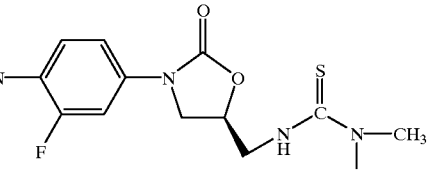 | 2 | 1 | 2 | .5 | 1 |
| Comparison* 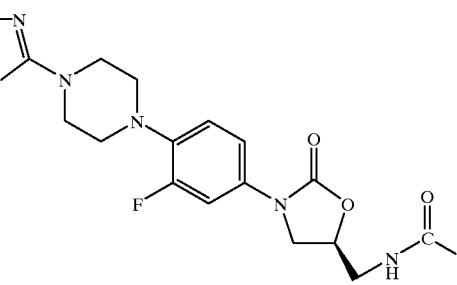 | .5 | .25 | 1 | .13 | .25 |
| Example 2 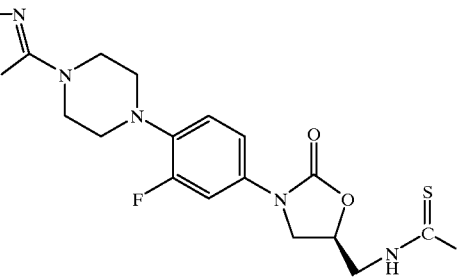 | 8 | 2 | 4 | 2 | 4 |
SAUR: *S. aureus*
SEPI: *S. epidermidis*
EFAE: *E. faecalis*
SPNE: *S. pneumoniae*
SPYO: *S. pyogenes*
*not a compound of the subject invention
TABLE II
| Example No. | SAUR 9213 MIC | SEPI 30593 MIC | EFAE 12712 MIC | SPNE 9912 MIC | SPYO 152 MIC | HINF 30063 MIC | MCAT 30610 MIC | EFAE 9217 MIC |
|---|---|---|---|---|---|---|---|---|
| 1 | 1 | 0.25 | 0.5 | <0.125 | <0.125 | 8 | 1 | 0.5 |
| 2 | 8 | 4 | 8 | 2 | 4 | >16 | >16 | 4 |
| 3 | 4 | 1 | 1 | 0.25 | 0.5 | 16 | 4 | 2 |
| 5 | 1 | 0.5 | 0.5 | <0.125 | 0.25 | 4 | 2 | 0.5 |
| 6 | 2 | 2 | 2 | 0.5 | 1 | 16 | 8 | 2 |
| 7 | 0.5 | 0.25 | 0.5 | <0.125 | 0.25 | 4 | 1 | 0.5 |
| 8 | 2 | 1 | 0.5 | <0.125 | 0.25 | 4 | 2 | 1 |
| 9 | 0.5 | 0.25 | 0.25 | <0.125 | <0.125 | 2 | 0.5 | 0.25 |
| 10 | 2 | 1 | 0.5 | <0.125 | 0.25 | 2 | 1 | 1 |
| 11 | 0.25 | 0.25 | 0.25 | <0.125 | 0.25 | 2 | 1 | 0.25 |
| 12 | 1 | 0.5 | 0.25 | <0.125 | <0.125 | 1 | 0.5 | 0.5 |
| 13 | 1 | 1 | 2 | 0.5 | 1 | >16 | 8 | 2 |
| 14 | 1 | 0.5 | 1 | 0.25 | 0.5 | 8 | 1 | 1 |

TABLE II-continued

| Example No. | SAUR 9213 MIC | SEPI 30593 MIC | EFAE 12712 MIC | SPNE 9912 MIC | SPYO 152 MIC | HINF 30063 MIC | MCAT 30610 MIC | EFAE 9217 MIC |
|---|---|---|---|---|---|---|---|---|
| 15 | 32 | 16 | 32 | 4 | 8 | >64 | 64 | 32 |
| 16 | 8 | 8 | 16 | 2 | 8 | >64 | 32 | 16 |
| 17 | 2 | 2 | 4 | 1 | 2 | 64 | 16 | 4 |
| 18 | 2 | 1 | 2 | <0.5 | 1 | 32 | 4 | 2 |
| 19 | 32 | 16 | 32 | 16 | 16 | 64 | 32 | 32 |
| 21 | 4 | 4 | 8 | 2 | 4 | 64 | 16 | 8 |
| 22, 23 | 0.5 | 0.5 | 1 | <0.125 | 0.25 | 4 | 2 | 1 |
| 24 | 1 | 0.25 | 0.5 | <0.125 | 0.25 | 4 | 2 | 0.5 |
| 25 | 0.5 | 0.25 | 0.5 | <0.125 | <0.125 | 2 | 2 | 0.5 |
| 26 | 1 | 0.5 | 1 | 0.25 | 0.5 | 16 | 2 | 1 |
| 27 | 0.5 | 0.5 | 0.5 | <0.125 | 0.25 | 4 | 2 | 1 |
| 28 | 0.5 | 0.25 | 0.5 | 0.25 | 0.25 | 2 | 1 | 0.5 |
| 29 | 0.25 | 0.25 | 0.25 | <0.125 | <0.125 | 2 | 0.5 | 0.25 |
| 30 | 4 | 1 | 0.5 | <0.125 | 0.25 | 8 | 2 | 1 |
| 31 | 2 | 1 | 1 | <0.125 | 0.25 | 4 | 1 | 1 |
| 32 | 16 | 2 | 2 | 0.25 | 0.25 | 8 | 2 | 4 |
| 33 | 4 | 2 | 1 | 0.25 | 0.25 | 4 | 2 | 4 |
| 34 | 2 | 1 | 2 | 0.5 | 1 | >16 | 4 | 2 |
| 35 | 1 | 0.5 | 1 | 0.25 | 0.5 | 16 | 2 | 1 |

Key:
SAUR 9213: *S. aureus*
SEPI 30593: *S. epidermidis*
EFAE 12712: *E. Faecium*
SPNE 9912: *S. pneumoniae*
SPYO 152: *S. pyogenes*
HINF 30063: *Haemophilus influenzae*
MCAT 30610: *Moraxella catarrhalis*
EFAE 9217: *Enterococcus faecalis*

As shown in Scheme 1, the intermediates II for the compounds of this invention are also intermediates disclosed in the oxazolidinone patents and published applications hereinabove incorporated by reference. The intermediates IV for this invention are final products (Examples) from the oxazolidinone patents and published applications hereinabove incorporated by reference.

As shown in Scheme 1, Step 1, and illustrated in Example 5, the isothiocyanates III can be conveniently prepared by allowing the amine intermediates (II) to react with 1,1'-thiocarbonyldi-2(1H)-pyridone in solvents such as methylene chloride at 0 to 25° C. The thioureas (Ia, R'=H, alkyl$_{1-4}$) can then be prepared as shown in Step 2 by the reaction of III with ammonia or the appropriate primary amines in solvents such as 1,4-dioxane or tetrahydrofuran at 0–50° C. Alternatively, as illustrated in Example 6 and shown in Step 3, the thioureas can be prepared by allowing II to react with an appropriate isothiocyanate (R'—N=C=S) in solvents such as tetrahydrofuran at 0–50° C. Thioamides (Ib, R''=H, alkyl$_{1-4}$) are prepared by allowing II to react with an appropriate dithioester (R'''S—C(=S)—R'', Step 4 as illustrated in Example 4. This reaction is carried out in aqueous-alcoholic solvents at 0–50° C. in the presence of an equivalent of an alkali metal hydroxide. This reaction, especially when R''' is methyl or ethyl, can be catalyzed by an alkali metal fluoride.

The reaction of II with R'''—S—C(S)—R''' (R'''=CH$_3$, C$_2$H$_5$) to give Ib (Step 4) can also be carried out in the presence of a tertiary amine base such as triethylamine in solvents such as THF, dioxane or methylene chloride at 10–50° C. for 3–48 hr.

When the reaction conditions are tolerated by the substituents on R (see, for example, Examples 1–3) the thioamides (Ib, R''=H, alkyl$_{1-4}$) can also be conveniently prepared (Step 5) by allowing the appropriate amide intermediates (IV) to react with reagents such as 2,4-bis(p-methoxyphenyl)-1,3-dithiadiphosphetane-2,4-disulfide (Lawesson's Reagent) in 1,4dioxane, benzene, toluene or tetrahydrofuran at 60–110° C.; phosphorus decasulfide and sodium carbonate in tetrahydrofuran at 20–50° C. [Brillon, D., Synthetic Communications, 20, 3085 (1990)] or phosphorus decasulfide and sodium fluoride in 1,2-dimethoxyethane at 20–50° C. [Hartke, K, Gerber, H.-D., J. Prakt. Chem., 338, 763 (1996)].

Compounds Ic are prepared (Step 6) by allowing II to react first with carbon disulfide and a tertiary amine base such as triethylamine in solvent mixtures containing water and methanol, ethanol or isopropanol at 10–50° C. for 5–24 hours. The resulting intermediate is treated with an alkylating agent (R'''' X where X represents bromo, iodo, alkylsulfonyloxy or arylsulfonyloxy) at 0–30° C. to give compounds Ic. In Step 7, compounds Ic are allowed to react with alkali metal alkoxide such as sodium methoxide or potassium ethoxide in the corresponding alkanol as solvent. This reaction is conveniently carried out at the reflux temperature of the alkanol for 1–24 hr.

SCHEME 1

-continued

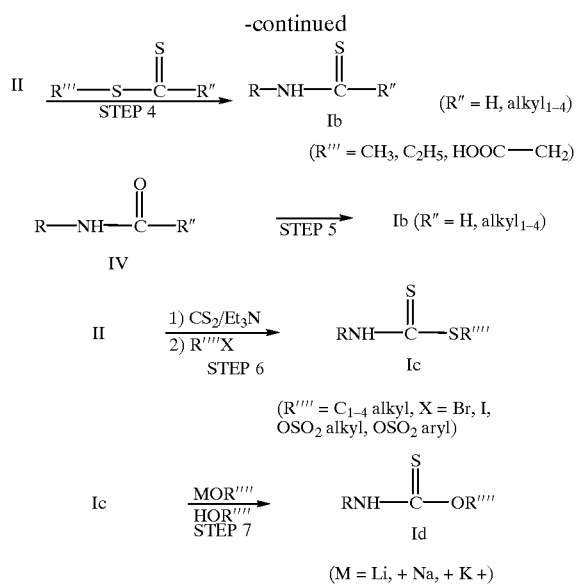

(R'''' = C₁₋₄ alkyl, X = Br, I, OSO₂ alkyl, OSO₂ aryl)

(M = Li, + Na, + K +)

In order to more fully illustrate the nature of the invention and the manner of practicing the same, the following experimental examples are presented.

EXAMPLE 1

(S)-N-[[3-[3-Fluoro-4-(4-morpholinyl)phenyl]-2-oxo-5-oxazolidinyl]methyl]thioacetamide (I)

A stirred mixture of II (PCT/US94/08904, 3.37 g, 10.0 mmol) in dry dioxane (100 mL), under nitrogen was treated with Lawesson's Reagent (4.04 g, 10.0 mml), warmed to reflux during 1 h and refluxed for 1.5 h. The reaction was complete by TLC on silica gel with 10% MeOH—CHCl₃. It was kept at ambient temperature for 18 h and concentrated in vacuo. Chromatography of the residue on silica gel with mixtures of acetone-methylene chloride containing 10–15% acetone gave the product which was crystallized from acetone-hexane to give 1: mp 157.5–158.5° C.; HRMS theory for $C_{16}H_{20}FN_3O_3S$ (M⁺): 353.1209; found: 353.1212. Anal. calcd for $C_{16}H_{20}FN_3O_3S$: C, 54.38; H, 5.38; N, 11.89; S, 9.07. Found: C, 54.21; H, 5.58; N, 11.78; S, 8.93.

EXAMPLE 2

(S)-N-[[3-[3-Fluoro-4-[4-(5-methyl-1,3,4-thiadiazol-2-yl)-1-piperazinyl]phenyl]-2-oxo-5-oxazolidinyl]methyl]thioacetamide (2)

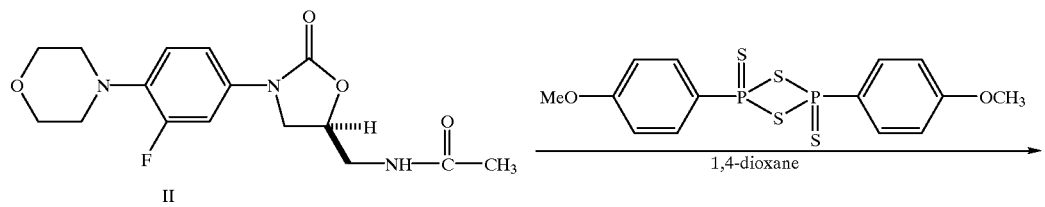

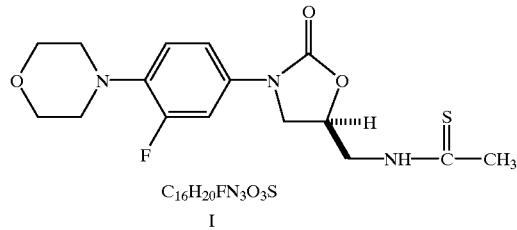

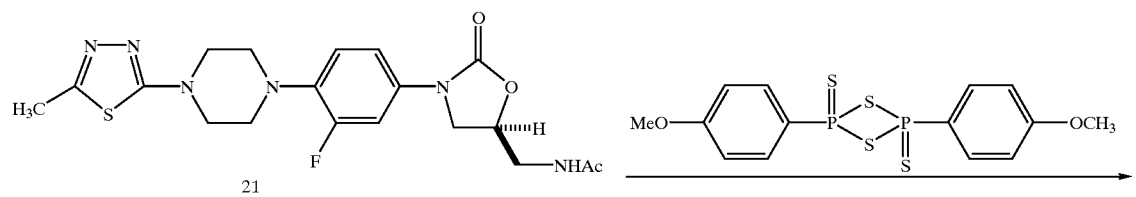

-continued

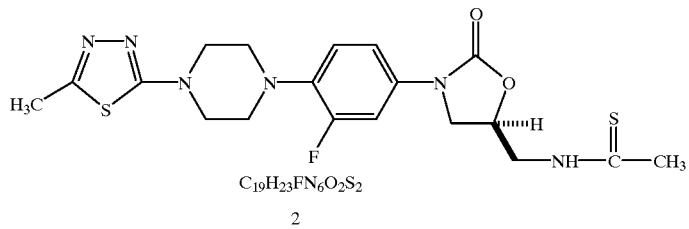

According to Example 1, for the preparation of 1, 21 (PCT/US97/01970) was allowed to react with Lawesson's Reagent in refluxing dioxane to give 2: mp 222–223° C.; HRMS theory for $C_{19}H_{24}FN_6O_2S_2$ (M+H$^+$): 451.1386; found 451.1381.

EXAMPLE 3

(S)-N-[[3-[3-Fluoro-4-[2',5'-dioxospiro[piperidine-4,4'-imidazolidine]-1-yl]phenyl]-2-oxo-5-oxazolidinyl]methyl]thioacetamide (3)

STEP A: (S)-N-[[3-[3-Fluoro-4-[2',5'-dioxospiro[piperidine-4,4'-imidazolidine]-1-yl]phenyl]-2-oxo-5-oxazolidinyl]methyl]acetamide (32).

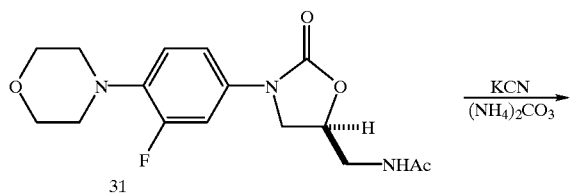

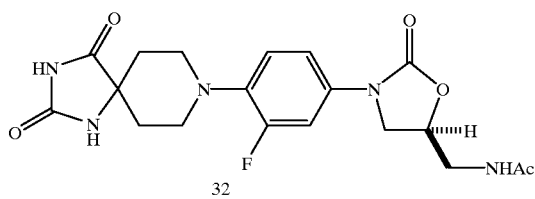

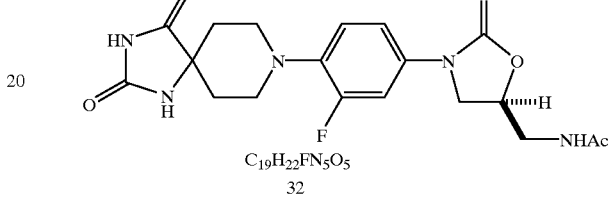

A stirred suspension of 31 (WO95/25106, 0.349 g, 1.00 mmol) in 1:1 EtOH:H$_2$O (5 mL), under nitrogen, was treated with potassium cyanide (0.130 g, 2.00 mmol) and ammonium carbonate (0.701 g, 7.30 mmol), warmed at 55–60° C. for 5 h 15 min and kept at ambient temperature for 17 h 15 min. It was then chromatographed on silica gel with mixtures of MeOH—NH$_4$OH—GHCl$_3$ containing 5–20% MeOH and 0.5% NH$_4$OH to give 0.280 g of 32: HRMS calcd for $C_{19}H_{22}FN_5O_5$: 419.1605 (M$^+$); found 419.1613; Anal. calcd for $C_{19}H_{22}FN_5O_5 \cdot 1\ H_2O$: C, 52.17; H. 5.53; N. 16.01. Found: C, 52.44; H, 5.30; N. 16.11.

STEP B: (S)-N-[[3-[3-Fluoro-4-[2',5'-dioxospiro[piperidine-4,4'-imidazolidine]-1-yl]phenyl]-2-oxo-5-oxazolidinyl]methyl]thioacetamide (3).

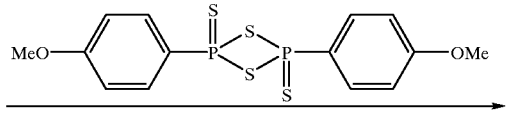

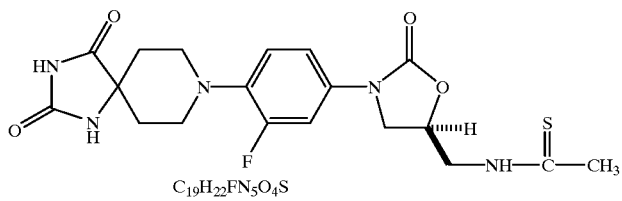

A stirred suspension of 32 (0.210 g, 0.500 mmol) in dioxane (5.0 mL), under nitrogen was treated with Lawesson's Reagent (0.202 g, 0.500 mmol), refluxed for 4 h and concentrated in vacuo. The residue was chromatographed on silica gel with mixctures of MeOH—NH$_4$OH—CHCl$_3$ containing 1–10% MeOH and 0.1–0.5% NH$_4$OH and the resulting product was crystallized from MeOH—CHCl$_3$—EtOAc to give 0.0491 g of 3: mlp 218.5° C.; HR FAB MS theory for C$_{19}$H$_{22}$FN$_5$O$_4$S (M$^+$): 435.1376; found 435.1370. Anal. calcd for C$_{19}$H$_{22}$FN$_5$O$_4$S. 0.5 H$_2$O: C, 51.34; H, 5.21; N. 15.76. Found: C, 51.69; H, 5.00; N, 15.25.

EXAMPLE 4

(S)-N-[[3-[3-Fluoro-4-(4-morpholinyl)phenyl]-2-oxo-5-oxazolidinyl]methyl]thioacetamide (4)

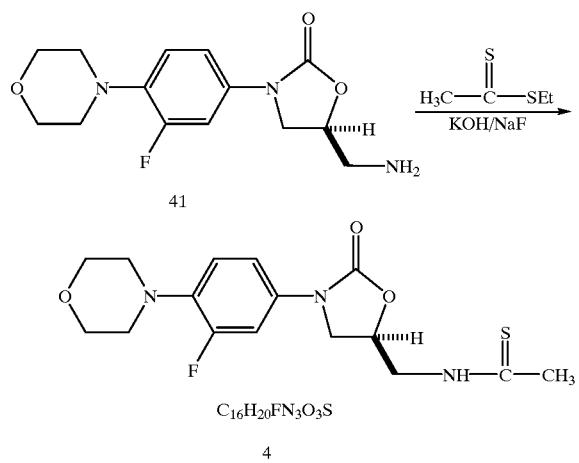

A solution of 41 (148 mg, 0.500 mmol) and 0.97 M KOH (0.515 mL) in absolute EtOH (5 mL) was added to a solution of ethyl dithioacetate (57 µL, 0.50 mmol) and sodium fluoride (20 mg, 0.47 mmol) in absolute EtOH (5 mL) and the mixture was kept at ambient temperature for 3 h 40 min. Additional ethyl dithioacetate (5 µL) was added after 1 h 55 min and additional 0.97 M KOH (40 mL) and sodium fluoride (6 mg) were added to the mixture after 3h 5 min. The reaction was followed by TLC on silica gel with 10% MeOH—CHCl$_3$ and 30% acetone-CH$_2$Cl$_2$. The major product had an R$_f$ on TLC that was the same as that of 4.

EXAMPLE 5

(S)-N-[[3-[3-Fluoro-4-(4-morpholinyl)phenyl]-2-oxo-5-oxazolidinyl]methyl]thiourea (5)

STEP A:

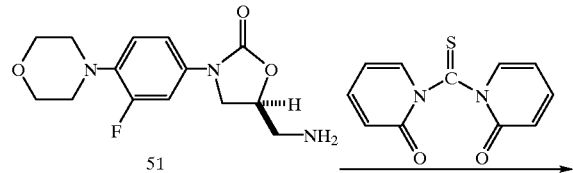

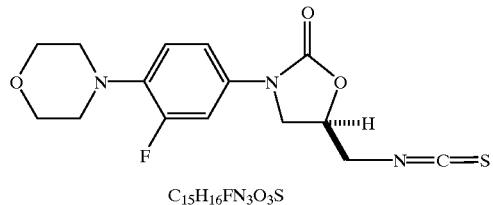

A solution of 51 (PCT/US94/08904, 2.07 g, 7.00 mmol) in CH$_2$Cl$_2$ was added, dropwise during 30 min, under nitrogen to an ice cold, stirred solution of 1,1'-thiocarbonyldi-2(1H)-pyridone (1.95 g, 8.40 mmol) in CH$_2$Cl$_2$ (70 mL). The mixture was warmed slowly to ambient temperature and kept for 18 h. It was then diluted with CH$_2$Cl$_2$, washed with water and aqueous NaCl, dried (Na$_2$SO$_4$) and concentrated. Chromatography of the residue on silica gel with 10% acetonitrile-CH$_2$Cl$_2$ gave 1.60 g of the isothiocyanate: HRMS theory for C$_{15}$H$_{16}$FN$_3$O$_3$S (M$^+$): 337.0896; found 337.0888.

STEP B:

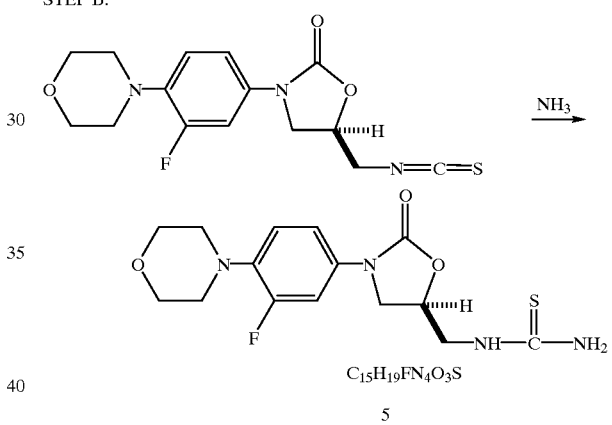

Anhydrous ammonia was bubbled for 7 min through a stirred solution of the product from Step I (1.00 g, 2.96 mmol) in [HF (10 mL) and the mixture was k ep t at ambient temperature for 3 h 25 min and concentrated in vacuo. Crystallization of the residue from acetone-hexane gave 0.861 g of 5: mp 199–199.5° C.; MS m/z 354 (M$^+$). Anal. calcd for C$_{15}$H$_{19}$FN$_4$O$_3$S: C, 50.84; H, 5.40; N, 15.81. Found: C, 50.87; H, 5.39; N, 15.72.

EXAMPLE 6

(S)-N-[[3-[3-Fluoro-4-(4-morpholinyl)phenyl]-2-oxo-5-oxazolidinyl]methyl]-N'-methylthiourea (6)

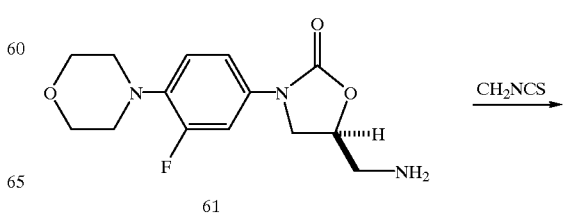

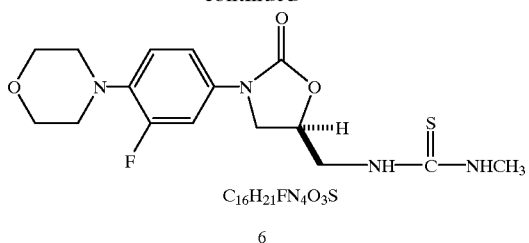

C₁₆H₂₁FN₄O₃S

6

A stirred solution of methyl isothiocyanate (93 mg, 1.27 mmol) in THF, was treated with 61 (295 mg, 1.00 mmol), kept at ambient temperature for 18 h and concentrated in vacuo. The residue was recrystallized from EtOAc-hexane to give 246 mg of 6: mp 158–160° C.; MS m/z 368 (M⁺). Anal. calcd for $C_{16}H_{21}FN_4O_3S$: C, 52.16; H, 5.74; N, 15.21. Found: C, 52.20; H, 5.85; N, 15.17.

EXAMPLE 7

(S)-cis-N-[[3-[3-Fluoro-4-(tetrahydro-1-oxido-2H-thiopyran-4-yl)phenyl]-2-oxo-5-oxazolidinyl]methyl]ethanethioamide

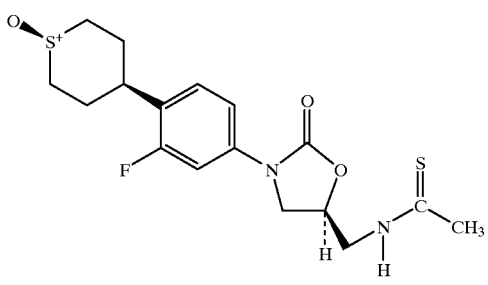

Step 1: A mixture of (S)-(−)-N-[[3-[3-fluoro-4-(3,6-dihydro-2H-thiopyran-4-yl)phenyl]-2-oxo-5-oxazolidinyl]methyl]acetamide S-oxide (4.50 g, can be obtained according to the procedures disclosed in International Publication No. WO 97/09328) and platinum oxide (697 mg) in methanol (164 mL) is shaken on the Parr apparatus under a hydrogen atmosphere at 40 psi for 18 hours. The catalyst is then removed by filtration through Celite, and the filtrate is concentrated under reduced pressure and the residue chromatographed on silica gel (230–400 mesh, 350 g), eluting with a gradient of methanol/methylene chloride (3/97–7/93). Pooling and concentration of those fractions with an $R_f=0.44$ by TLC (methanol/chloroform, 10/90) gives (S)-cis-)-N-[[3-[3-Fluoro-4-(tetrahydro-1-oxddo-2H-thiopyran-4-yl)phenyl]-2-oxo-5-oxazolidinyl]methyl]acetamide, mp 203–204° C.

Step 2: A mixture of the compound prepared in Step 1 (2.50 g) and hydroxylamine hydrochloride (2.36 g) in pyridine (30.6 mL) and ethanol (3.4 mL) is stirred in a screw-cap vial at 100° C. for 22 hrs and at ambient temperature for 16 hrs, during which additional hydroxylamine hydrochloride (944 mg) and pyridine (4 mL) is added. The reaction mixture is then concentrated under reduced pressure, diluted with saturated aqueous sodium bicarbonate (100 mL) and saline (50 mL), adjusted to pH 11 with solid sodium carbonate and extracted with methanol/methylene chloride (10/90, 5×100 mL). The combined organic phase is concentrated under reduced pressure, and the crude product is chromatographed on silica gel (230–400 mesh, 150 g), eluting with a gradient of methanol/methylene chloride (6/94–10/90). Pooling and concentration of those fractions with an $R_f=0.14$ by TLC (methanol/chloroform, 10/90) gives (S)-cis-3-[3-fluoro-4-(tetrahydro-1-oxido-2H-thiopyran-4-yl)phenyl]-5-aminomethyl-2-oxazolidinone, mp 159–161° C.

Step 3: A solution of ethyl dithioacetate (105 mL, 0.919 mmol) and sodium fluoride (39 mg, 0.919 mmol) in ethanol (9.2 mL) under a nitrogen atmosphere was treated with a mixture of (S)-cis-3-[3-fluoro4-(tetrahydro-1-oxido-2H-thiopyran-4-yl)phenyl]-5-aminomethyl-2-oxazolidinone, as prepared in Step 2,(300 mg, 0.919 mmol) and aqueous potassium hydroxide (1M, 0.92 mL) in ethanol (46 mL). The resulting solution was stirred at ambient temperature for 4 hours and was then diluted with methylene chloride (150 mL) and washed with water (50 mL), aqueous potassium hydrogen sulfate (1M, 50 mL) and brine (25 mL). The organic phase was dried over anhydrous sodium sulfate and concentrated in vacuo, and the crude product was triturated with methylene chloride/diethyl ether and filtered to give the title compound, mp 176–177° C. (dec.).

EXAMPLE 8

(S)-cis-[[3-[3-Fluoro-4-(tetrahydro-1-oxido-2H-thiopyran-4-yl)phenyl]-2-oxo-5-oxazolidinyl]methyl]thiourea

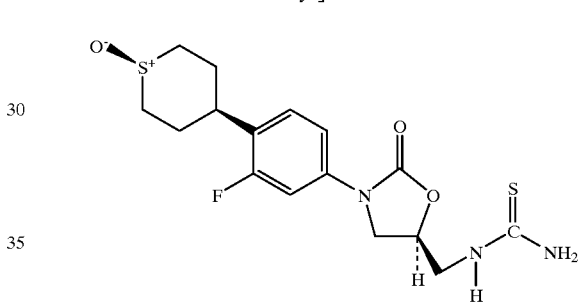

Step 1: A solution of 1,1'-thiocarbonyldi-2(1H)-pyridone (235 mg, 1.01 mmol) in anhydrous methylene chloride (10 mL) at 0° C. under a nitrogen atmosphere was treated with a solution of (S)-cis-3-[3-fluoro-4-(tetrahydro-1-oxido-2H-thiopyran4-yl)phenyl]-5-aminomethyl-2-oxazolidinone, as prepared in Example 7, Step 2, (275 mg, 0.843 mmol) in anhydrous methylene chloride (34 mL) over 30 minutes. The resulting mixture was stirred at 0° C. for 30 minutes and at ambient temperature for 1 hour and was then diluted with methylene chloride (40 mL), washed with water (25 mL) and brine (25 mL), dried over anhydrous sodium sulfate and concentrated in vacuo. The crude product was chromatographed on silica gel (70–230 mesh, 20 g), eluting with acetonitrile/methylene chloride (40/60), and those fractions with an $R_f=0.07$ by TLC (acetonitrile/methylene chloride, 30/70) were pooled and concentrated to give (S)-cis-3-[3-Fluoro-4-(tetrahydro-1-oxido-2H-thiopyran-4-yl)phenyl]-5-isothiocyanatomethyl-2-oxazolidinone, mp 187–190° C. (dec.).

Step 2: A solution of (S)-cis-3-[3-fluoro-4-(tetrahydro-1-oxido-2H-thiopyran-4-yl)phenyl]-5-isothiocyanatomethyl-2-oxazolidinone (Step 1, 290 mg, 0.787 mmol) in anhydrous tetrahydrofuran (39 mL) at 0° C. under a nitrogen atmosphere was treated (bubbled) with a stream of ammonia gas for 5 minutes. The reaction pot was sealed, and the resulting mixture was stirred at 0° C. for 1 hour. The excess ammonia was then removed under a stream of nitrogen, and the reaction mixture was concentrated in uacuo to give the crude

37 product. Recrystallization from methanol/methylene chloride/diethyl ether gave the title compound, mp 206–208° C. (dec.).

EXAMPLE 9

(S)-trans-N-[[3-[3-Fluoro-4-(tetrahydro-1-oxido-2H-thiopyran-4-yl)phenyl]-2-oxo-5-oxazolidinyl]methyl]ethanethioamide

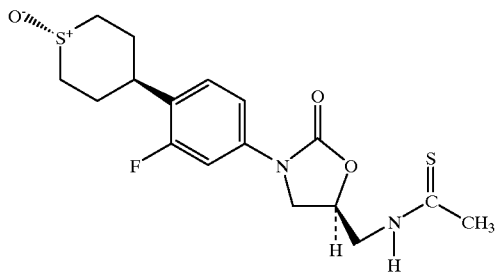

Step 1: (S)-(–)-N-[[3-[3-fluoro-4-(3,6-dihydro-2H-thiopyran-4-yl)phenyl]-2-oxo-5-ox azolidinyl]methyl] acetamide S-oxide (disclosed in International Publication No. WO 97/09328) may be reduced to the corresponding cis- and trans-sulfoxides by catalytic hydrogenation in the presence of a catalyst and solvent. Alternatively, the sulfide by product of this reduction reaction can be oxidized with an oxidizing agent such $NaIO_4$ or meta-chloroperoxybenzoic acid in solvent to provide the cis- and trans-sulfoxides. Alternatively, the sulfide byproduct acn be oxidized selectively to the trans isomer using t-butyl hydroperoxide and a catalyst such as Ti(OiPr)4 and D-diisopropyl tartrate in a suitable solvent. The isomeric mixture can then be separated by chromatography to isolate the trans-sulfoxide, mp 211–212° C. (dec.). A mixture of the trans-sulfoxide, (S)trans-(–)-N-[[3-[3-fluoro-4-(tetrahydro-1-oido-2H-thiopyran-4-yl)phenyl]-2-oxo-5-oxazolidinyl]methyl] acetamide, (0.90 g) and hydroxylamine hydrochloride (0.85 g) in pyridine (11.0 mL) and ethanol (1.2 mL) is stirred in a screw-cap vial at 100° C. for 23 hrs and at ambient temperature for 19 hrs, during which additional hydroxylamine hydrochloride (340 mg) and pyridine (1 mL) is added. The reaction mixture is then concentrated under reduced pressure, diluted with saturated aqueous sodium carbonate (50 mL) and saline (50 mL) and extracted with methanolmethylene chloride (10/90, 6×100 mL). The combined organic phase is concentrated under reduced pressure, and the crude product is chromatographed on silica gel (230–400 mesh, 45 g), eluting with a gradient of methanol/methylene chloride (7.5/92.5–10/90). Pooling and concentration of those fractions with an $R_{f=0.14}$ by TLC (methanol/chloroform, 10/90) gives (S)-trans-3-[3-fluoro-4-(tetrahydro-1-oxido-2H-thiopyran-4-yl)phenyl]-5-aminomethyl-2-5 oxazolidinone, mp 138–140° C.

Step 2: A solution of ethyl dithioacetate (105 mL, 0.919 mmol) and sodium fluoride (39 mg, 0.919 mmol) in ethanol (9.2 mL) under a nitrogen atmosphere was treated with a mixture of (S)-trans-3-[3-fluoro-4-(tetrahydro-1-oxido-2H-thiopyran-4-yl)phenyl]-5-aminomethyl-2-oxazolidinone, as

38 prepare in Step 1, (300 mg, 0.919 mmol) and aqueous potassium hydroxide (1M, 0.92 mL) in ethanol (46 mL). The resulting solution was stirred at ambient temperature for 17 hours and was then diluted with methylene chloride (150 mL), washed with water (2×50 mL) and brine (25 mL), dried over anhydrous sodium sulfate and concentrated in vacuo. The crude product was chromatographed on silica gel (230–400 mesh, 35 g), eluting with methanol/methylene chloride (3/97), and those fractions with an $R_f$=0.56 by TLC (methanolchloroform, 10/90) were pooled and concentrated and the residue recrystallized from methylene chloride/diethyl ether to give the title compound, mp 193–194° C. (dec.).

EXAMPLE 10

(S)-trans-[[3-[3-Fluoro-4-(tetrahydro-1-oxido-2H-thiopyran4-yl)phenyl]-2-oxo-5-oxazolidinyl]methyl]thiourea

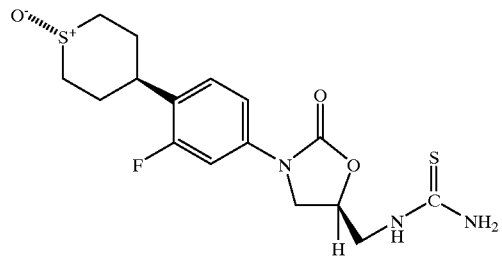

Step 1: A solution of 1,1'-thiocarbonyldi-2(1H)-pyridone (192 mg, 0.827 mmol) in anhydrous methylene chloride (8.3 mL) at 0° C. under a nitrogen atmosphere was treated with a solution of (S)-trans-3-[3-fluoro-4-(tetrahydro-1-oxido-2H-thiopyran4-yl)phenyl]-5-aminomethyl-2-oxazolidinone, as prepared in Example 9, Step 1, (225 mg, 0.689 mmol) in anhydrous methylene chloride (28 mL) over 30 minutes. The resulting mixture was stirred at 0° C. for 30 minutes and at ambient temperature for 40 minutes and was then diluted with methylene chloride (20 mL), washed with water (15 mL) and brine (15 mL), dried over anhydrous sodium sulfate and concentrated in uacuo. The crude product was chromatographed on silica gel (32–63 mm, 40 g), eluting with a gradient of acetonitrile/methylene chloride (30/70–60/40) under 15 psi $N_2$, and those fractions with an $R_f$=0.12 by TLC (acetonitrile/methylene chloride, 30/70) were pooled and concentrated to give (S)-trans-3-[3-Fluoro-4-(tetrahydro-1-oxido-2H-thiopyran-4-yl)phenyl]-5-isothiocyanatomethyl-2-oxazolidinone, mp 165–167° C.

Step 2: A solution of (S)-trans-3-[3-fluoro-4-(tetrahydro-1-oxido-2H-thiopyran-4-yl)phenyl]-5-isothiocyanatomethyl-2-oxazolidinone (Step 1, 230 mg, 0.624 mmol) in anhydrous tetrahydrofuran (31.2 mL) at 0° C. under a nitrogen atmosphere was treated (bubbled) with a stream of ammonia gas for 5 minutes. The reaction pot was sealed, and the resulting mixture was stirred at 0° C. for 1 hour. The excess ammonia was then removed under a stream of nitrogen, and the reaction mixture was concentrated in vacuo to give the crude product. Trituration with methanol/methylene chloride/diethyl ether gave the title compound, mp 209–210° C. (dec.).

EXAMPLE 11

(S)-N-[[3-[3-Fluoro-4-(tetrahydro-1,1-dioxido-2H-thiopyran-4-yl)phenyl]-2-oxo-5-oxazolidinyl]methyl]ethanethioamide

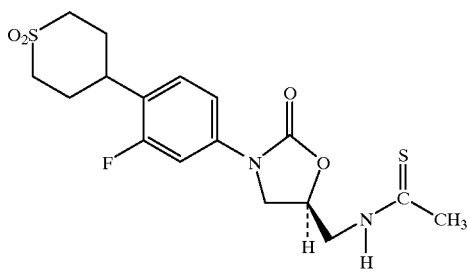

Step 1: Starting with (S)-cis-(–)-N-[[3-[3-Fluoro-4-(tetrahydro-1-oxido-2H-thiopyran-4-yl)phenyl]-2-oxo-5-oxazolidinyl]methyl]acetamide as prepared in Example 7, Step 1, and following the general procedure of Step 2, and making non-critical variations by substituting (S)-(–)-N-[[3-[3-fluoro-4-(tetrahydro-2H-thiopyran-4-yl)phenyl]-2-oxo-5-oxazolidinyl]methyl]acetamide S,S-dioxide (disclosed in International Publication No. WO 97/09328) for (S)cis-(–)-N-[[3-[3-fluoro-4-(tetrahydro-1-oxido-2H-thiopyran-4-yl)phenyl]-2-oxo-5-oxazolidinyl]methyl]acetamide, the product (S)-(–)-3-[3-Fluoro-4-(tetrahydro-1,1-dioxddo-2H-thiopyran-4-yl)phenyl]-5-aminomethyl-2-oxazolidinone is obtained, mp 194° C. (dec.).

Step 2: A solution of ethyl dithioacetate (100 mL, 0.876 mmol) and sodium fluoride (37 mg, 0.876 mmol) in ethanol (8.8 mL) under a nitrogen atmosphere was treated with a mixture of (S)-(–)-3-[3-fluoro-4-(tetrahydro-1,1-dioxido-2H-thiopyran-4-yl)phenyl]-5-aminomethyl-2-oxazolidinone, as prepared in Step 1, (300 mg, 0.876 mmol) and aqueous potassium hydroxide (1M, 0.88 mL) in ethanol (43.8 mL). The resulting mixture was stirred at ambient temperature for 26 hours, during which additional ethyl dithioacetate (50 mL, 0.438 mmol), sodium fluoride (19 mg, 0.438 mmol), aqueous potassium hydroxide (1M, 0.44 mL) and ethanol (3.0 mL) was added, and was then diluted with methylene chloride (150 mL), washed with water (50 mL), aqueous potassium hydrogen sulfate (1M, 50 mL) and brine (25 mL), dried over anhydrous sodium sulfate and concentrated in vacuo. The crude product was recrystallized from methylene chlorideldiethyl ether to give the title compound, mp 186–187° C. (dec.).

EXAMPLE 12

(S)-N-[[3-[3-Fluoro-4-(tetrahydro-1,1-dioxido-2H-thiopyran-4-yl)phenyl]-2-oxo-5-oxazolidinyl]methyl]thiourea

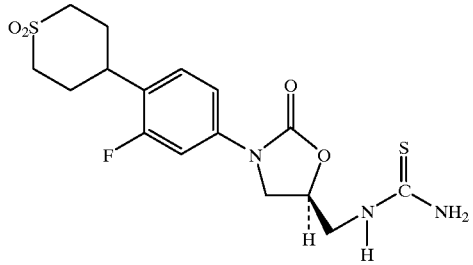

Step 1: A solution of 1,1'-thiocarbonyldi-2(1H)-pyridone (304 mg, 1.31 mmol) in anhydrous methylene chloride (13 mL) at 0° C. under a nitrogen atmosphere was treated with a solution of (S)-(–)-3-[3-fluoro-4-(tetrahydro-1,1-dioxido-2H-thiopyran-4-yl)phenyl]-5-aminomethyl-2-oxazolidinone, as prepared in Example 11, Step 1, (375 mg, 1.09 mmol) in anhydrous methylene chloride (88 mL) over 30 minutes. The resulting mixture was stirred at 0° C. for 30 minutes and at ambient temperature for 30 minutes and was then diluted with methylene chloride (40 mL), washed with water (25 mL) and brine (25 mL), dried over anhydrous sodium sulfate and concentrated in vacuo. The crude product was chromatographed on silica gel (230–400 mesh, 45 g), eluting with acetonitrile/methylene chloride (7.5/92.5), and those fractions with an $R_f$=0.64 by TLC (acetonitrile/methylene chloride, 20/80) were pooled and concentrated to give (S)-3-[3-fluoro-4-(tetrahydro-1,1-dioxido-2H-thiopyran-4-yl)phenyl]-5-isothiocyanatomethyl-2-oxazolidinone, mp 158–162° C. (dec.).

Step 2: A solution of (S)-3-[3-fluoro-4-(tetrahydro-1,1-dioxido-2H-thiopyran-4-yl)phenyl]-5-isothiocyanatomethyl-2-oxazolidinone (Step 1, 380 mg, 0.988 mmol) in anhydrous tetrahydrofuran (49 mL) at 0° C. under a nitrogen atmosphere was treated (bubbled) with a stream of ammonia gas for 5 minutes. The reaction pot was sealed, and the resulting mixture was stirred at 0° C. for 1 hour. The excess ammonia was then removed under a stream of nitrogen, and the reaction mixture was concentrated in vacuo to give the crude product. Recrystallization from methanol/methylene chloride/diethyl ether gave the title compound, mp 196–198° C. (dec.).

EXAMPLE 13

(S)-N-[[3-[3-Fluoro-4-(4-morpholinyl)phenyl]-2-oxo-5-oxazolidinyl]methyl]-thioformamide (7)

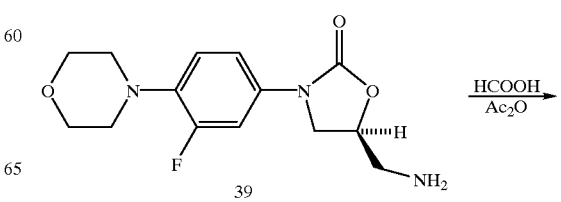

-continued

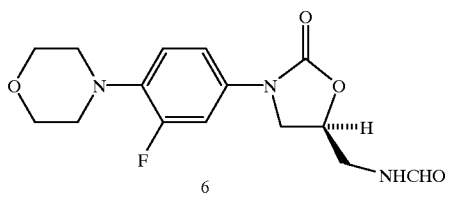

6

A stirred mixture of acetic anhydride (0.23 mL, 0.0024 mol) and 95–97% formic acid (0.10 mL, 0.0027 mL) was warmed, under nitrogen at 50–55° C. for 2 h, cooled to ambient temperature and treated, portionwise during 2 min, with $39^8$ (0.45 g, 0.0015 mol). The suspension was kept at ambient temperature for 4 h and the resulting solution was treated with Et2O (1 mL) and kept at ambient temperature for 18 h. The mixture was diluted with additional $Et_2O$ (10 mL) and the solid was collected by filtration, washed with $Et_2O$ and dried to give 0.38 g of $6^9$: MS (ES) m/z 324 (M+H$^+$), 346 (M+Na$^+$); $^1$H NMR (300 mHz, CDCl$_3$) d 3.08 (m, 4H), 3.72 (m, 2H), 3.77 (d,d, 1H), 3.89 (m, 4H), 4.04 (t, 1H), 4.80 (m, 1H), 6.33 (s, 1H), 7.05 (m, 2H), 7.45 (d,d, 1H), 8.27 (s, 1H).

MS(ES) m/z 340 (M+H$^+$), 362 (M+Na$^+$); $^1$HNMR [300 MHz, (CD$_3$)$_2$SO] d 2.94 (m, 4H), 3.72 (m, 4H), 3.77 (d,d, 1H), 3.94 (t, 2H), 4.12 (t, 1H), 4.93 (m, 1H), 7.05 (t, 1H), 7.16 (d,d, 1H), 7.47 (d,d, 1H), 9.33 (d, 1H), 10.59 (s, 1H). Anal. calcd for C$_{15}$H$_{18}$FN$_3$O$_3$S: C, 53.08; H, 5.35; N, 12.38. Found: C, 53.02; H, 5.44; N, 12.36.

EXAMPLE 14

(S)-N-[[3-[3-Fluoro-4-(4-morpholinyl)phenyl]-2-oxo-5-oxazolidinyl]methyl]thiopropion-amide (9)

1.

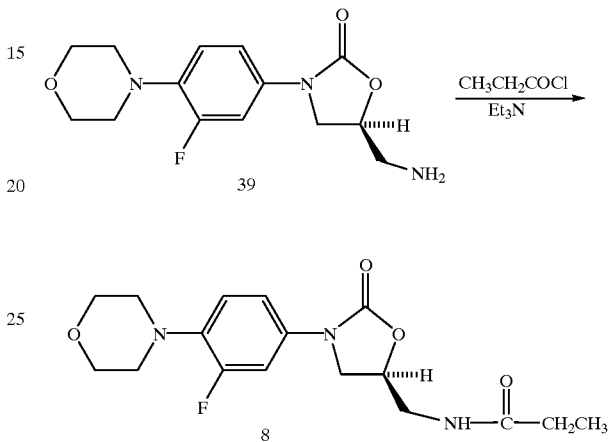

2.

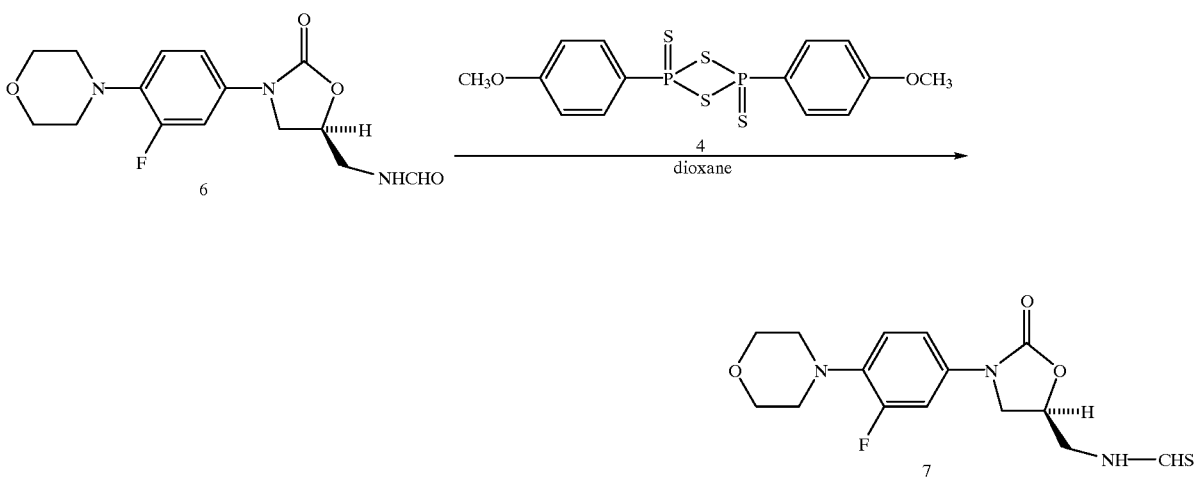

A stirred mixture of 6 (0.38 g, 0.00118 mol) in dioxane (20 mL), under nitrogen was treated with 4 (0.51 g, 0.00126 mol), warmed to reflux during 30 min and kept at this temperature for 90 min. It was then evaporated under a stream of nitrogen. The residue was chromatographed on silica gel with 1.25% MeOH—CH$_2$Cl$_2$ and the slightly impure product was rechromatographed on silica gel with 25% EtOAc—CH$_2$Cl$_2$. The resulting product was crystallized from EtOAc-methyl tert-butyl ether to give 0.114 g of 7: mp 150–155° C. (dec); IR (DRIFT) 3322, 1752 cm$^{-1}$;

An ice cold, stirred solution of 39 (0.395 g, 0.00134 mol) and triethyl amine (0.186 mL, 0.0027 mol) in CH$_2$Cl$_2$ (20 mL), under nitrogen was treated, dropwise during 2 min, with a solution of propionyl chloride (0.128 mL, 0.00147 mol) in CH$_2$Cl$_2$ (3 mL). The mixture was kept in the ice bath for 20 min and at ambient temperature for 1 h. It was then diluted with CH$_2$Cl$_2$, washed with saturated NaHCO$_3$, water and brine, dried (MgSO$_4$) and concentrated. The residue (8) was used without further purification in the next reaction.

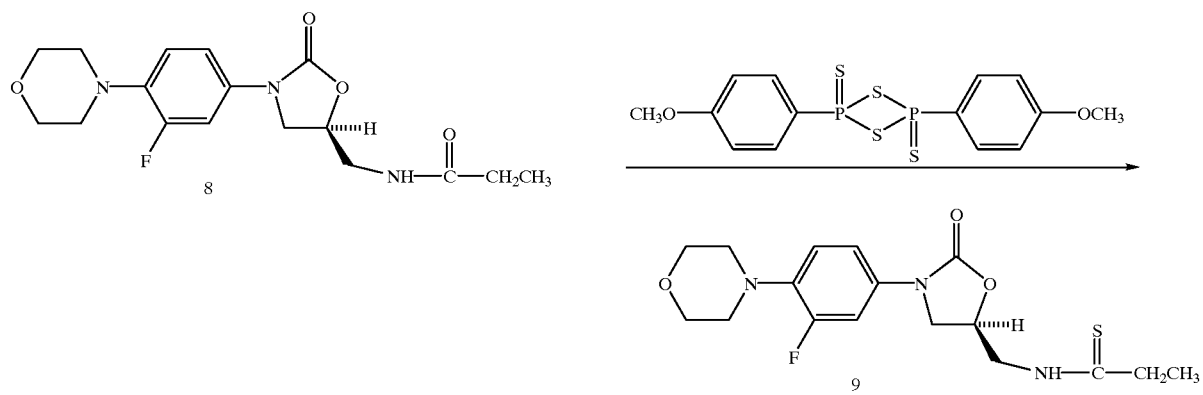

A stirred mixture of the product (8) from the previous reaction and dioxane (20 mL), under nitrogen, was treated, portionwise during 1 min. with Lawesson's reagent (0.58 g, 0.0014 mol) and refluxed for 2 h; it was then concentrated. The residue was chromatographed on silica gel with 2% MeOH—CHCl$_3$ and the product was crystallized from methyl tert-butyl ether to give 0.259 g of 9: mp 138–139° C.; MS(ES) m/z 368 (M+H$^+$), 390 (M+Na$^+$); IR (DRIFT) 3284, 3266, 1748, 1744 cm$^{-1}$; [α]$^{24}_D$+20° (MeOH); 1H NMR[300 MHz, (CD$_3$)$_2$SO] d 1.12 (t, 3H), 2.56 (q, 2H), 2.94 (m, 4H), 3.72 (m, 4H), 3.78 (d,d, 1H), 3.90 (t, 2H), 4.11 (t, 1H), 4.93 (m, 1H), 7.05 (t, 1H), 7.16 (d,d, 1H), 7.47 (d,d, 1H), 10.30 (broad s, 1H). Anal. calcd for C$_{17}$H$_{22}$FN$_3$O$_3$S: C, 55.57; H, 6.03; N, 11.44. Found: C, 55.68; H. 6.21; N, 11.37.

EXAMPLE 15
(S)-N-[[3-[3-Fluoro-4-(4-morpholinyl)phenyl]-2-oxo-5-oxrazolidinyl]methyl]-2-chlorothioacetamide (11)

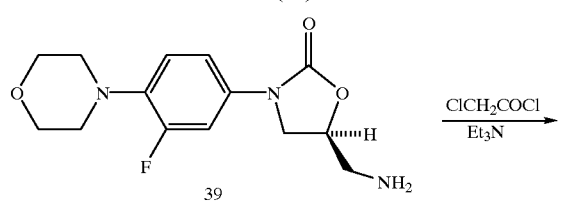

A stirred solution of 39 (1.54 g, 5.2 mmol) and triethylamine (750 mg, 7.5 mmol) in CH$_2$Cl$_2$ (50 mL), urnder nitrogen, was treated, dropwise, during 15 min with a solution of chloroacetyl chloride (465 mL, 5.8 mmol) in CH$_2$Cl$_2$ (30 mL) and kept at ambient temperature for 18 h. It was then washed with saturated NaHCO$_3$ and dilute NaCl, dried (Na$_2$SO$_4$) and concentrated. The residue was flash chromatographed on silica gel with 20–30% acetone-CH$_2$Cl$_2$ to give 1.49 g of 10$^9$ which was used in the next reaction without further purification.

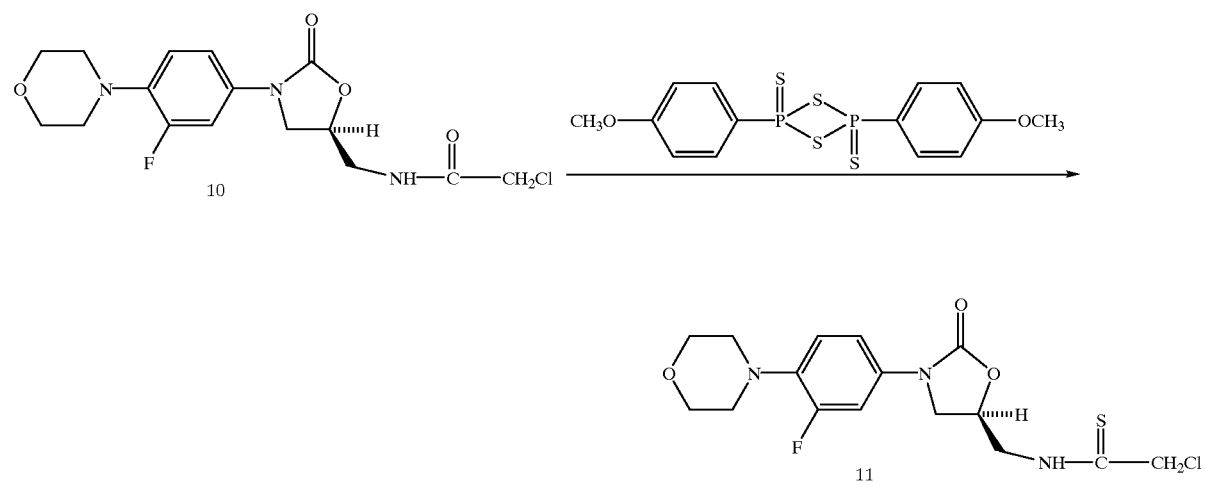

A stirred mixture of 10 (0.371 g, 1.0 mmol) and Lawesson's reagent (0.420 mg, 1.04 mmol) in dioxane (10 mL) was refluxed, under nitrogen for 2 h and concentrated under reduced pressure. The residue was chromatographed on silica gel with 3–10% acetone-$CH_2Cl_2$ to give 0.143 g of 11:

dried ($Na_2SO_4$) and concentrated. The solid residue was recrystallized from acetone-heptane to give 0.566 g of 12: mp 161–164° C. (dec); MS(EI) m/z 391 ($M^+$). Anal. calcd for $C_{16}H_{17}F_4N_3O_4$: C, 49.11; H, 4.38; N, 10.74. Found: C, 48.99; H, 4.56; N, 10.73.

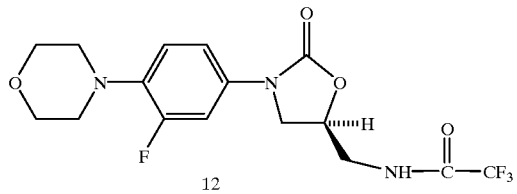

12

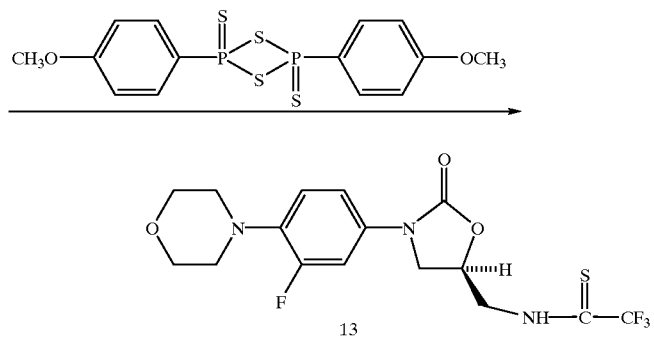

13

MS (CI) m/z 388 ($M+H^+$); $^1H$ NMR (300 MHz, $CDCl_3$) d 3.07 (m, 4H), 3.77 (d,d, 1H), 3.88 (m, 4H), 4.04 (m, 1H), 4.12 (t, 1H), 4.35 (m, 1H), 4.61 (s, 2H), 4.98 (m, 1H), 6.96 (t, 1H), 7.08 (d,d, 1H), 7.44 (d,d, 1H), 8.69 (s, 1H). Anal. calcd for $C_{16}H_{19}ClFN_3O_3S$: C, 49.55; H, 4.94; N, 10.83. Found: C, 49.38; H, 5.20; N, 10.27.

EXAMPLE 16

(S)-N-[[3-[3-Fluoro-4-(4-moropholinyl)phenyl]-2-oxo-5-oxazolidinyl]methyl]-α,α,α-trifluorothioacetamide (13)

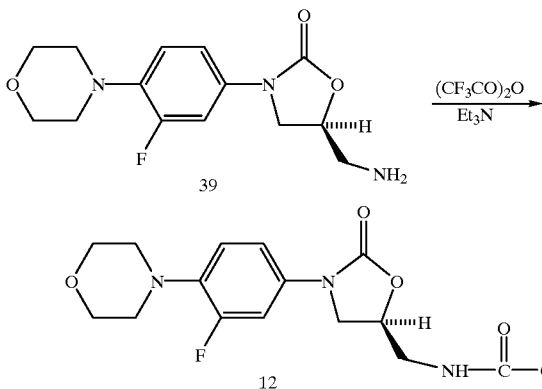

An ice cold stirred solution of 39 (0.590 g, 2.0 mmol) and triethylamine (640 mL, 4.6 mmol) in $CH_2Cl_2$ (10 mL) was treated with trifluoroacetic anhydride (325 mL, 2.3 mmol) and kept in the ice bath for 10 min and then at ambient temperature. The reaction was followed by TLC on silica gel with 30% acetone-$CH_2Cl_2$. Additional trifluoroacetic anhydride and triethylamine were added after 3 d (64 mL/125 mL), 4 d (100 mL/220 mL) and 6 d (325 mL/1.0 mL). The reaction was complete 1 h after the last addition; it was mixed with $CH_2Cl_2$, washed with water and dilute NaCl, A stirred ure of 12 (0.391 g, 1.0 mmol) and Lawesson's reagent (0.422 g, 1.1 mmol) in dioxane (10 mL) was refluxed, under nitrogen for 2 h, cooled slowly to ambient temperature and concentrated in vacuo. The residue was flash chromatographed on silica gel with 5–15% acetone-$CH_2Cl_2$ and the product was crystallized from acetone-heptane to give 0.249 g of 13: mp 151–152° C.; MS(EI) m/z 407 ($M^+$), 363, 209, 151, 95; $^1H$ NMR (300 MHz, $CDCl_3$) d 3.05 (m, 4H), 3.75 (d,d, 1H), 3.87 (m, 4H), 3.95 (m, 1H), 4.14 (t, 1H), 4.32 (m, 1H), 5.01 (m, 1H), 6.92 (t, 1H), 7.05 (d,d, 1H), 7.38 (d,d, 1H), 9.03 (s, 1H). Anal. calcd for $C_{16}H_{17}F_4N_3O_3S$: C, 47.17; H, 4.21; N, 10.31. Found: C, 47.09; H, 4.35; N, 10.27.

EXAMPLE 17

(S)-N-[[3-[3-Fluoro-4-(4-morpholinyl)phenyl]-2-oxo-5-oxazolidinyl]methyl]-α-fluorothioacetamide (15)

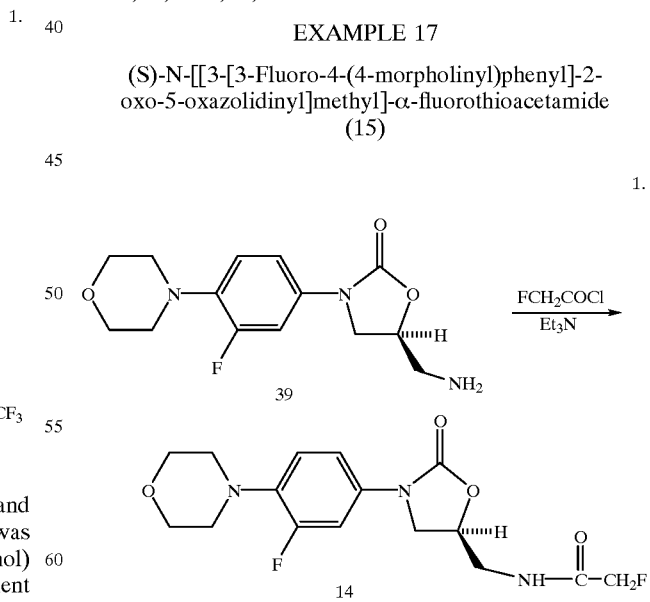

A stirred, ice cold solution of 39 (0.590 g, 2.0 mmol) and triethylarnine (611 mL, 4.4 mmol) in $CH_2Cl_2$ (10 mL), under nitrogen, was treated, dropwise, with a solution of fluoroacetyl chloride (220 mL, 2.2 mmol) in $CH_2Cl_2$ (5 mL), kept in the ice bath for 10 min and at ambient temperature for 2 h. It was then diluted with CH$_2$Cl$_2$, washed with water and dilute NaCl, dried (Na$_2$SO$_4$) and concentrated. The residue was chromatographed on silica gel with 10–30% acetone-CH$_2$Cl$_2$ to give 0.180 g of 14: MS(ES) m/z 356 (M+H$^+$), 378 (M+Na$^+$).

1-hydroxybenzotriazole (0.297 g, 2.2 mmol) in DMF (5 mL) under nitrogen, was treated with 1-(3-dimethylaminopropyl)-3-ethylcarbonde hydrochloride (0.843 g, 4.4 mmol) and kept at ambient temperature for 18 h. It was diluted with CH$_2$Cl$_2$, washed with water and dilute NaCl, dried (Na$_2$SO$_4$) and concentrated. The solid residue

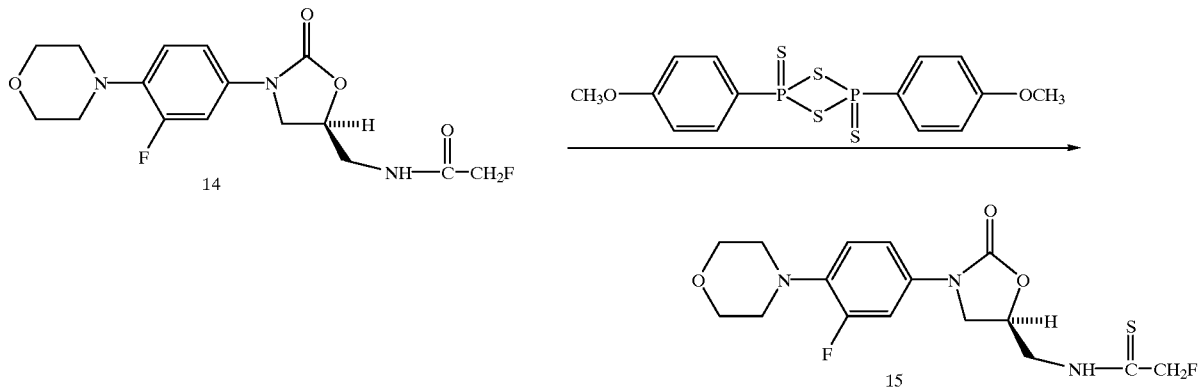

A solution of 14 (0.180 g, 0.507 mmol) in dioxane, under nitrogen, was treated with Lawesson's reagent (0.206 g, 0.51 mmol), warmed at 90–100° C. for 1 h and concentrated in vacuo. The residue was chromatographed on silica gel with 15% acetone-CH$_2$Cl$_2$ to give 0.161 g of 15: MS(EI) m/z 371 (M$^+$); $^1$H NMR (300 MHz, CDCl$_3$) d 3.05 (m, 4H), 3.78 (d,d, 1H), 3.87 (m, 4H), 4.03 (m, 1H), 4.11 (t, 1H), 4.38 (m, 1H), 4.98 (m, 1H), 5.07 (s, 1H), 5.23 (s, 1H), 6.93 (t, 1H), 7.08 (dd, 1H, 7.42 (d,d, 1H), 8.42 (s, 1H). Anal. calcd for C$_{16}$H$_{19}$F$_2$N$_3$O$_3$S: C, 51.74; H, 5.16; N, 11.31. Found: C, 51.79; H, 5.31; N, 11.02.

EXAMPLE 18

(S)-N-[[3-[3-Fluoro-4-(4-morpholinyl)phenyl]-2-oxo-5-oxazolidinyl]methyl]-α,α-difluorothioacetamide (17)

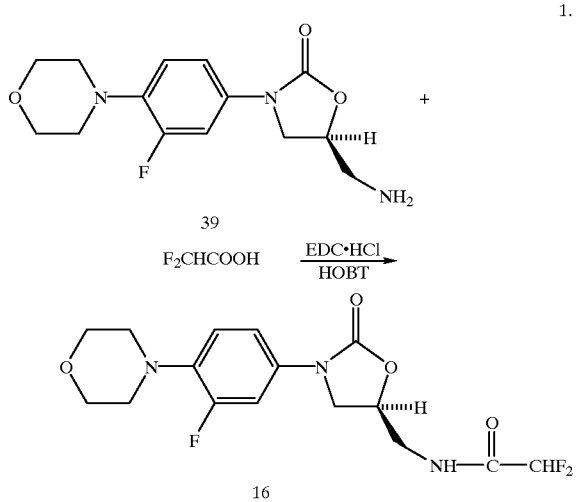

A stirred, ice cold mixture of 39 (0.590 g, 2.0 mmol), difluroacetic acid (190 mL, 2.0 mmol), and was crystallized form EtOAc-heptane to give 0.617 g of 16: mp 149–150° C.; 1H NMR (300 MHz, CDCl3) d 3.05 (m, 4H), 3.66 (m, 2H), 3.85 (m, 5H), 4.08 (t, 1H), 4.80 (m, 1H), 5.93 (t, J=53.9 Hz, 1H), 6.92 (t, 1H), 7.06 (m, 2H), 7.39 (d,d, 1H); MS(EI) m/z 373 (M$^+$). Anal. calcd for C$_{16}$H$_{18}$F$_3$N$_3$O$_4$: C, 51.48; H, 4.86; N, 11.26. Found: C, 51.59; H, 4.91; N, 11.29.

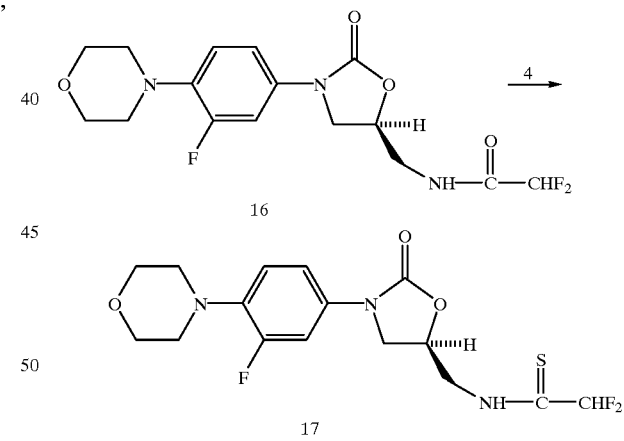

A stirred solution of 16 (0.373 g, 1.00 mmol) in dioxane (10 mL), under nitrogen was treated with Lawesson's reagent (0.404 g, 1.00 mmol), warmed at about 95° C. for 1 h and concentrated in vacuo. Chromatography of the residue on silica gel with 10% acetone-CH$_2$Cl$_2$ and cyrstallization of the product from EtOAc-heptane gave 0.276 g of 17: mp 125–127° C.; MS(EI) m/z 389 (M$^+$), 345, 305, 247, 209, 195, 151, 138, 123, 109, 95; $^1$H NMR (300 MHz, CDCl$_3$) d 3.05 (m, 4H), 3.76 (d,d, 1H), 3.86 (m, 4H), 4.01 (m, 1H), 4.12 (t, 1H), 4.30 (m, 1H), 4.99 (m, 1H), 6.20 (t, J=55.9 Hz, 1H), 6.92 (t, 1H), 7.06 (d,d, 1H), 7.38 (d,d, 1H), 8.78 (broad s, 1H). Anal. calcd for C$_{16}$H$_{18}$F$_3$N$_3$O$_3$S: C, 49.35; H, 4.66; N, 10.79. Found: C, 49.37; H, 4.71; N, 10.83.

EXAMPLE 19

(S)-N-[[3-[3-Fluoro-4-(4-morpholinyl)phenyl]-2-oxo-5-10 oxazolidinyl]methyl]-α-eyanothioacetamnide (19)

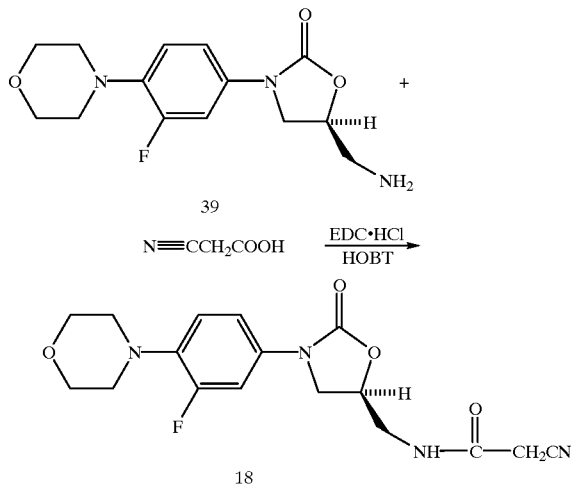

An ice cold, stirred mixture of 39 (0.646 g, 2.19 mmol), cyanoacetic acid (0.179 g, 2.1 mmol) and 1-hydroxybenzotriazole (0.351 g, 2.6 mmol) in DMF (5 mL, under nitrogen, was treated with 1-(3-dimethylaminopropyl)-3-ethylcarbodiimnide hydrochloride (0.997 g, 5.2 mmol) and kept at ambient temperature for 24 h. It was diluted with $CH_2Cl_2$, washed with water and dilute NaCl, dried ($Na_2SO_4$) and concentrated. The solid residue was crystallized from EtOAc-heptane to give 0.546 g of 18: mp 172–174° C.: IR (DRIFT) 3316, 2256, 1754, 1684 cm$^{-1}$; MS(EI) m/z 362 (M$^+$). Anal. calcd for $C_{17}H_{19}FN_4O_4$: C, 56.35; H, 5.28; N. 15.46. Found: C, 56.33; H, 5.30; N, 15.36.

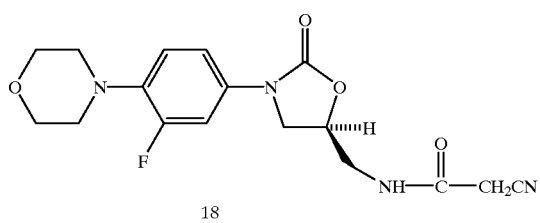

A stirred solution of 18 (0.453 mg, 1.25 mmol) in dioxane (10 mL), under nitrogen, was treated with Lawesson's reagent (0.505 g, 1.25 mmol) and warmed at about 100° C. When the reaction was over (TLC with 30% acetone-$CH_2Cl_2$) the mixture was cooled and concentrated in vacuo. Chromatography of the residue on silica gel with 10–20% acetone-$CH_2Cl_2$ and crystallization of the product from EtOAc-heptane gave 0.110 g of 19: mp 186–187° C. (dec); MS(ES) m/z 379 (M+H$^+$), 401 (M+Na$^+$); $^1$H NMR (300 MHz, CDCl$_3$) d 3.05 (m, 4H), 3.81 (d,d, 1H), 3.86 (m, 4H), 3.89 (s, 2H), 4.09 (t, 1H), 4.14 (m, 2H), 5.01 (m, 1H), 6.92 (t, 1H), 7.05 (d,d, 1H), 7.34 (d,d, 1H), 9.15 (s, 1H); IR (DRIFT) 3244, 2260, 1754 cm$^{-1}$. Anal. calcd for $C_{17}H_{19}FN_4O_3S$: C, 53.96; H, 5.06; N, 14.81. Found: C, 53.88; H, 5.39; N, 14.61.

EXAMPLE 20

(S)-N-[[3-[3-Fluoro-4-(4-morpholinyl)phenyl]-2-oxo-5-oxazolidinyl]methyl]-α,α-dichlorothioacetamide (21)

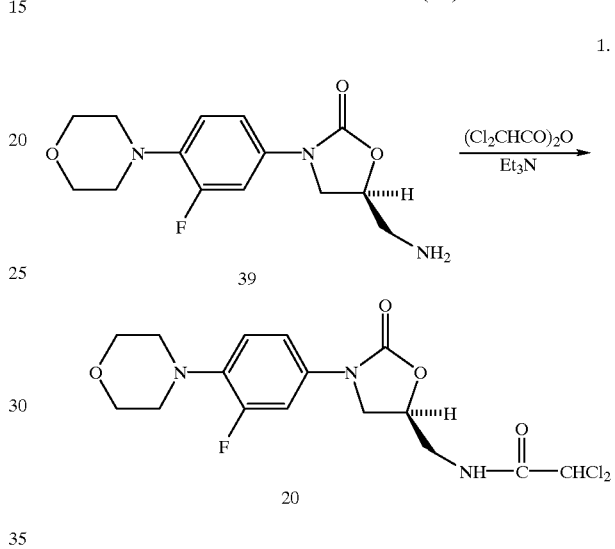

A stirred, ice cold solution of 39 (0.885 g, 3.00 mmol) and triethylamine (975 mL, 7 mmol) in $CH_2Cl_2$ (15 mL), under nitrogen was treated, dropwise with a solution of dichloroacetic anhydride (555 mL, 3.5 mmol) in $CH_2Cl_2$ (5 mL) and kept in the ice bath for 15 min and at ambient temperature for 18 h. It was diluted with $CH_2Cl_2$, washed with water, saturated $NaHCO_3$ and dilute NaCl, dried ($Na_2SO_4$) and concentrated. Chromatography of the residue on silica gel with 10% acetone-$CH_2Cl_2$ and crystallization of the product from acetone-heptane gave 0.463 g of 20: mp 197–198° C.

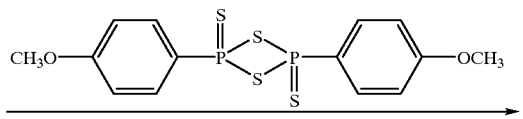

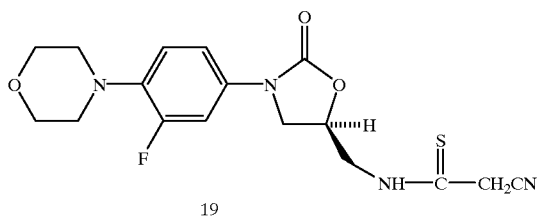

(dec); MS(ES) m/z 406 (M+H$^+$), 428 (M+Na$^+$); $^1$H NMR (300 MHz, CDCl$_3$) d 3.05 (m, 4H), 3.75 (m, 3H), 3.86 (m, 4H), 4.07 (t, 1H), 4.83 (m, 1H), 5.94 (s, 1H), 6.92 (t, 1H), 7.06 (m, 2H), 7.41 (d,d, 1H).

EXAMPLE 21
(S)-N-[[3-[3-Fluoro-4-(4-morpholinyl)phenyl]-2-oxo-5-oxazolidinyl]methyl]-α-(methoxycarbonyl)thioacetamide (23)

1.

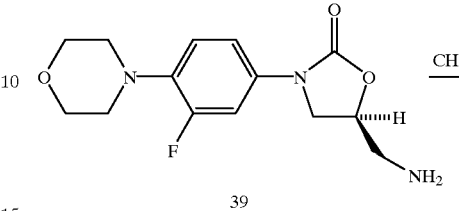

2.

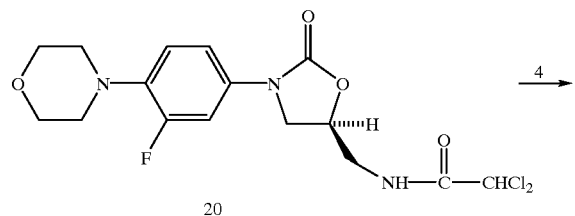

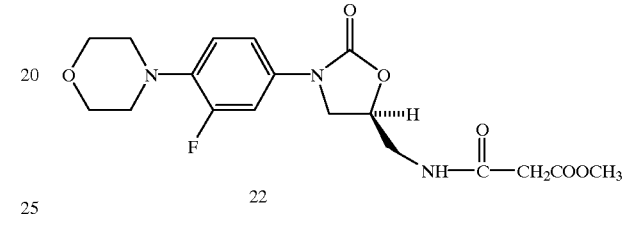

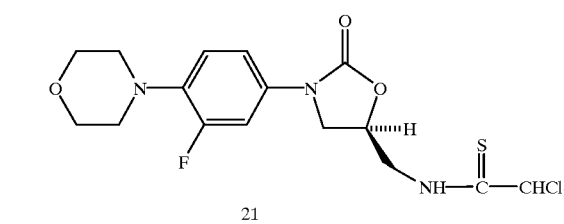

A stirred solution of 20 (0.305g, 0.75 mmol) in dioxane (5 ml), under nitrogen, was treated with Lawesson's reagent (0.202g, 0.5 mmol), warmed at about 90° C. for 1 hour, cooled and concentrated in vacuo. Chromatography of the residue on silica gel first with 30% acetone-heptane and then with 10% acetone-methylene chloride and crystallization of rh product form methylene chloride—heptane gave 0.203 g with 21: mp 143–144° cd.; HR$_{17}$S (EI) calculated for C$_{16}$H$_{18}$cl$_2$ F N$_3$ O$_3$ S(M) 421.0431. Anal. calcd for C$_{16}$H$_{18}$cl$_2$ F N$_3$ O$_3$ S, C, 45.51; H, 4.30; N, 9.95. Found: C, 45.47; H, 4.24; H, 9.88.

A stirred solution of 39 (0.955 g, 3.2 mmol) and triethylamine (650 mL, 4.5 mmol) in CH$_2$Cl$_2$ (50 mL), under nitrogen, was treated, dropwise during 15–20 min with a solution of methyl malonyl chloride (475 mL, 4.3 mmol) in CH$_2$Cl$_2$ (10 mL) and kept at ambient temperature for 3 days. It was then washed with water and dilute NaCl, dried and concentrated. The residue was flash chromatographed on silica gel with 15–30% acetone-CH$_2$Cl$_2$ and the product was crystallized form acetone-hexane to give 0.873 g of 22: mp 150–151° C.; $^1$H NMR (300 MHz, CDCl$_3$) d 3.03 (m, 4H), 3.34 (s, 2H), 3.67 (s, 3H), 3.69 (m, 2H), 3.76 (d,d, 1H), 3.85 (m, 4H), 4.00 (t, 1H), 4.78 (m, 1H), 6.90 (t, 1H), 7.06 (d,d, 1H), 7.41 (d,d, 1H), 7.57 (t, 1H); MS(ES) m/z 396 (M+H$^+$), 418 (M+Na$^+$); HRMS (FAB) calcd for C$_{18}$H$_{23}$FN$_3$O$_6$ (M+H$^+$) 396.1571, found 396.1579. Anal. calcd for C$_{18}$H$_{22}$FN$_3$O$_6$: C, 54.68; H, 5.61; N, 10.63. Found: C, 54.69; H, 5.68; N, 10.58.

2.

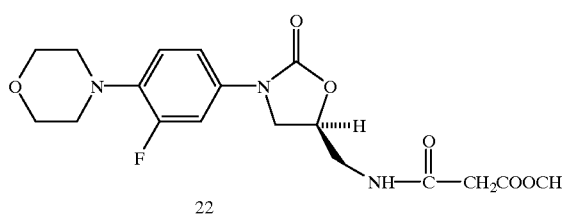

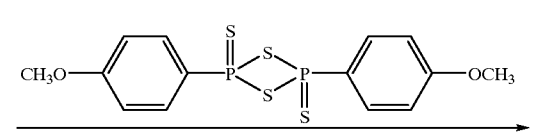

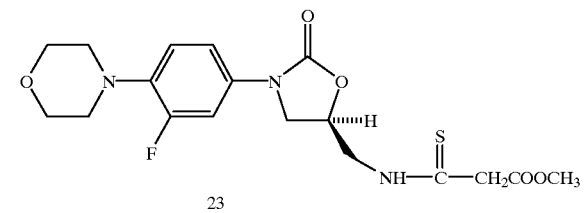

A stirred solution of 22 (0.395 g, 1.0 mmol) in dioxane (10 mL), under nitrogen, was treated with Lawesson's reagent (0.202 g, 0.5 mmol) and kept at ambient temperature for 4 h 10 min and at 80–90° C. for 1.5 h. The reaction was followed by TLC on silica gel with 10% MeOH-CHCl$_3$. At this time a new, less polar product had begun to form. It was kept at ambient temperature for 18 h and at 80° C. for 2 h; additional Laewsson's reagent (40 mg, 0.099 mmol) was added and warming at 80° C. was continued for 2 h; some starting material still remained. The mixture was concentrated and the residue was chromatographed on silica gel with 15% acetone-CH$_2$Cl$_2$ to give 0.348 g of 23: $^1$H NMR (300 MHz, CDCl$_3$) d 3.05 (m, 4H), 3.71 (s, 3H), 3.81 (d,d, 1H), 3.86 (m, 4H), 3.88 (s, 2H), 4.07 (t, 1H), 4.19 (m, 2H), 4.99 (m, 1H), 6.91 (t, 1H), 7.07 (d,d, 1H), 7.42 (d,d, 1H), 9.52 (s, 1H); IR (DRIFT) 3269, 1743 cm$^{-1}$; MS(EI) m/z 411 (M$^+$). Anal. calcd for C$_{18}$H$_{22}$FN$_3$O$_5$S: C, 52.54; H, 5.39; N, 10.21. Found: C, 52.58; H, 5.43; N, 10.14.

EXAMPLE 22

(S)-N-[[3-[4-[1-[1,2,4]Triazolyl]phenyl]-2-oxo-5-oxazolidinyl]methyl]thioacetamide (25)

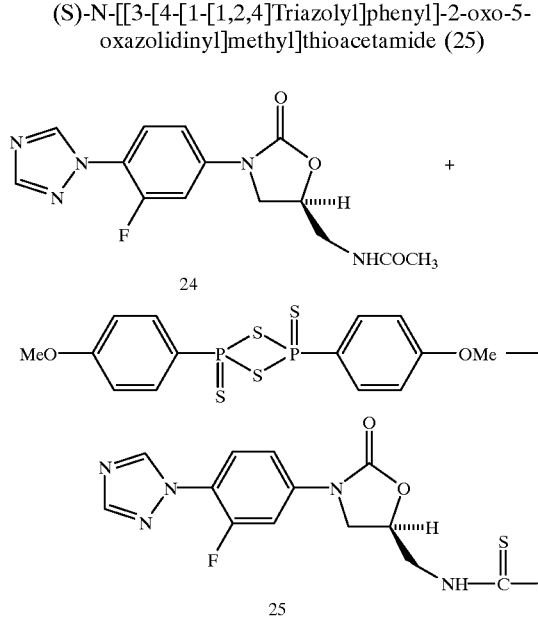

A stirred mixture of 24 (0.150 g, 0.470 mmol) and dioxane (12.5 mL), under nitrogen, was treated with Lawesson's reagent (0.20 g, 0.50 mmol), refluxed for 1.5 h, kept at ambient temperature for 18 h and concentrated in vacuo. Flash chromatography of the residue on silica gel with 5% MeOH-CHCl$_3$ gave the product which was crystallized from MeOH to give 0.100 g (63.4%) of 25: mp 161–163° C.; $^1$H NMR [300 MHz, (CD$_3$)$_2$SO] d 2.43 (s, 3H), 3.87 (m, 3H), 4.22 (t, 1H), 4.99 (m, 1H), 7.51 (d, 1H), 7.77 (m, 2H), 8.26 (s, 1H), 8.97 (d, 1H), 10.35 (broad s, 1H); IR (mull) 3259, 3226, 3044, 1752 cm$^{-1}$; MS(ES) m/z 336 (M+H$^+$), 358 (M+Na$^+$). Anal. calcd for C$_{14}$H$_{14}$FN$_5$O$_2$S: C, 50.14; H, 4.21; N, 20.88. Found: C, 50.18; H, 4.26; N, 20.94.

EXAMPLE 23

(S)-N-[[3-[4-[1-[1,2,4]Triazolyl]phenyl]-2-oxo-5-oxazolidinyl]methyl]thioacetamide (25)

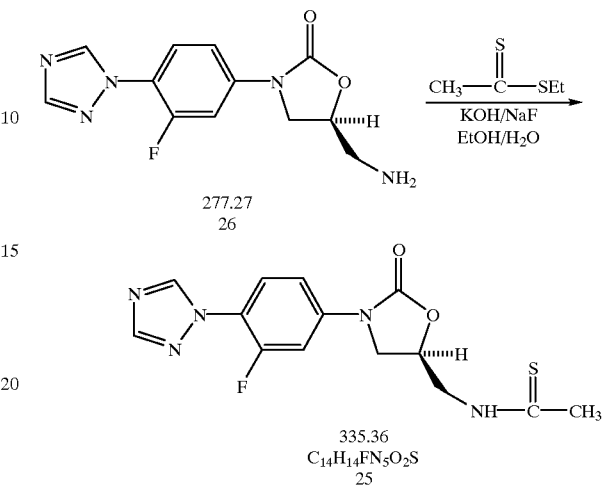

A stirred mixture of 26 (0.26 g, 0.938 mmol), ethyl dithioacetate (0.12 g, 0.998 mmol), sodium fluoride (0.040 g, 0.953 mmol) and absolute EtOH (10 mL), under nitrogen, was treated during 5 min with a solution of 0.97 M KOH (1.03 mL) in EtOH and kept at ambient temperature for 2 h. It was then diluted with CH$_2$CL$_2$ (75 mL), washed with water, 1M KHSO$_4$, water and brine and evaporated. The residue was flash chromatographed on silica gel with 5% MeOH—CHCl$_3$ and the product was crystallized from MeOH to give 0.118 g, mp 164–165° C. (dec) and 0.026 g, mp 162–163° C. (dec) of 25.

EXAMPLE 24

(S)-N-[[3-[1-(Hydroxyacetyl)-5-indolinyl]-2-oxo-5-oxazolidinyl]methyl]thioacetamide (28)

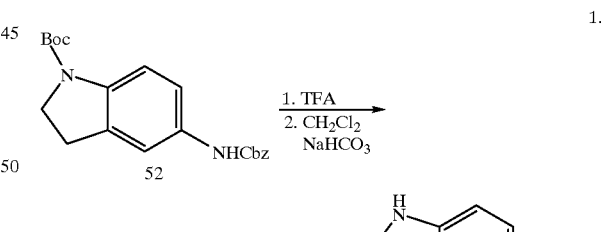

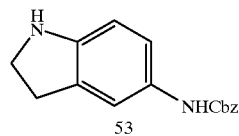

A stirred, ice cold solution of 52 (8.80 g, 0.0240 mol) in CH$_2$Cl$_2$ (25 mL) was treated during 20 min with a solution of trifluoroacetic acid (25 mL) in CH$_2$Cl$_2$ (10 mL). The mixture was kept in the ice bath for 2 h 15 rain and concentrated under reduced pressure. A solution of the residue in CH$_2$Cl$_2$ was washed with saturated NaHCO$_3$ and dilute NaCl, dried (Na$_2$SO$_4$) and concentrated. The residue was used in the next reaction without further purification. A sample of this material (53) had: $^1$H NMR (300 MHz, CDCl$_3$) d 3.00 (t, 2H), 3.54 (t, 2H), 3.85 (broad s, 1H), 5.17 (s, 2H), 6.59 (d, 1H), 6.66 (broad s, 1H), 6.91 (d, 1H), 7.23 (s, 1H), 7.36 (m, 5H); MS m/z 269 (M+H$^+$).

2.

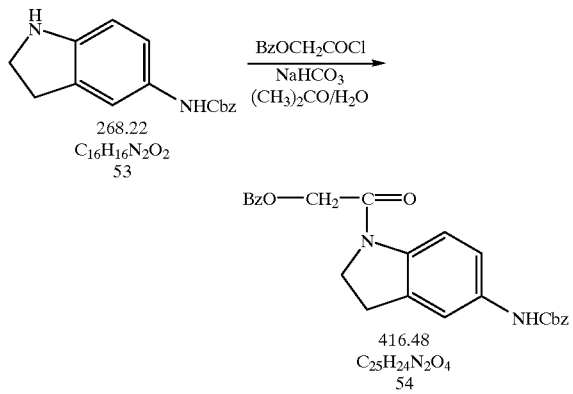

An ice cold, stirred mixture of 53 (crude product from the previous reaction), acetone (200 mL), saturated NaHCO$_3$ (200 mL) and water (30 mL) was treated, dropwise during 20 min, with a solution of benzyloxyacetyl chloride (4.70 mL, 0.030 mol) in acetone (55 mL), warmed slowly to ambient temperature and kept for 18 h. Additional benzyloxytacetyl chloride (1.0 mL) in acetone 35 mL) was added dropwise and the mixture was kept at ambient temperature for an additional 3 h and diluted with EtOAc and water. A solid was collected by filtration and dried to give 4.00 g of crude product. The EtOAc solution was dried (Na$_2$SO$_4$) and concentrated to give 5.36 g of additional crude product. Crystallization of the product from EtOAc gave a total of 6.35 g of 54[14], mp 157–159.5° C. The analytical sample had: mp 158–159.5° C.; $^1$H NMR (300 MHz, CDCl$_3$) δ 3,16 (t,2H), 4.01(t,2H), 4.21 (s, 2H), 4.69 (s, 2H), 5.19 (s, 2H), 6.67 (s, 1H), 6.97 (d, 1H), 7.36 (m, 10H), 7.50 (braod s, 1H), 8.15 (d, 1H); MS(EI) m/z (relative intensity) 416 (M$^+$, 9), 310 (8), 202 (10), 133 (8), 92 (8), 91 (99), 79 (7), 77 (9), 65 (12), 51 (6); IR (mull) 2381, 1722, 1659, 1608, 1558 cm$^{-1}$. Anal. calcd for C$_{25}$H$_{24}$N$_2$O$_4$: C, 72.10; H, 5.81; N, 6.73. Found: C, 72.05; H, 5.86; N, 6.68.

3.

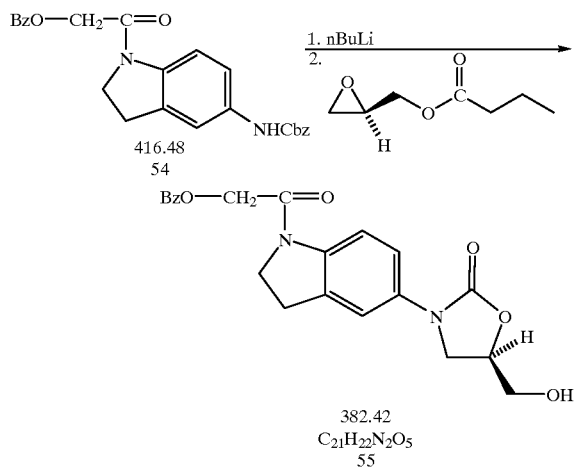

A stirred suspension of 54 (1.16 g, 2.78 mmol) in THF (42 mL) was cooled, under nitrogen, to −78° C. and treated, dropwise, during 5 rnin with 1.6 M n-BuLi in hexane (1.83 mL). It was kept at −78° C. for 50 min, treated, dropwise, during 5 min with a solution of (R)-(−)-glycidyl butyrate (0.500 g, 3.47 mmol) in THF (2 mL), allowed to warm to ambient temperature during 3 h and kpet for 18 h. It was then diluted with EtOAc, washed with saturated NH$_4$Cl, water and brine, dried (MgSO$_4$) and concentrated. Chromatography of the residue on silica gel with 3% MeOH-0.2% NH$_4$OH—CHCl$_3$ gave 0.60 g (56%) of 55[14]: $^1$H NMR [300 MHz, (CD$_3$)$_2$SO] δ 3.14 (t, 2H), 3.59 (m, 2H), 3.79 (d,d, 1H), 4.03 (m, 3H), 4.29 (s, 2H), 4.58 (s, 2H), 4.65 (m, 1H), 5.20 (t, 1H), 7.31 (m, 6H), 7.55 (s, 1H), 8.03 (d, 1H); MS(ES) m/z 383 (M+H$^+$), 405 (M+Na$^+$).

4.

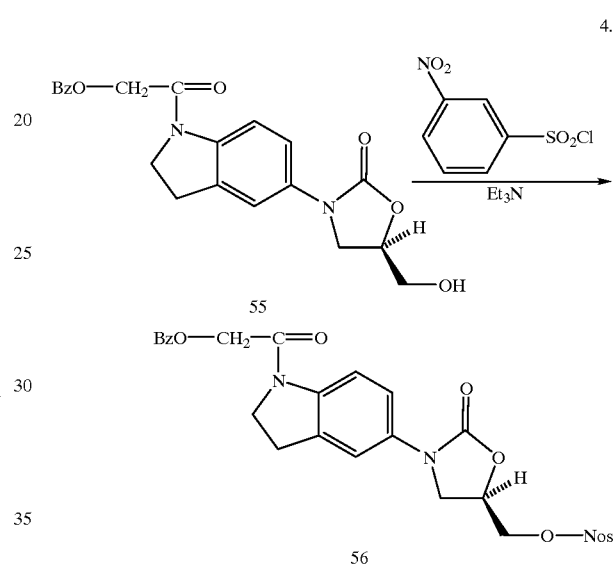

An ice cold, stirred mixture of 55 (0.60 g, 1.57 mmol), triethylamine (2.2 mL), and CH$_2$Cl$_2$ (12 mL), under nitrogen, was treated with 3-nitrobenzenesulfonyl chloride (0.44 g, 1.99 mmol) and kept in the ice bath for 30 min and at ambient temperature for 60 min. It was then diluted with CH$_2$Cl$_2$, washed with water and brine, dried (Na$_2$SO$_4$) and concentrated. Chromatography of the residue on silica gel with 15% CH$_3$CN—CH$_2$Cl$_2$ gave 0.70 g of 56: $^1$H NMR (300 MHz, CDCl$_3$) d 3.19 (t, J=8.3 Hz, 2H), 3.88 (d,d, 1H), 4.04 (t, J=8.4 Hz, 2H), 4.14 (t, 1H), 4.23 (s, 2H), 4.42 (m, 2H), 4.70 (s, 2H), 4.84 (m, 1H), 6.97 (m, 1H), 7.34 (m, 5H), 7.58 (s, 1H), 7.81 (t, 1H), 8.22 (m, 2H), 8.53 (m, 1H), 8.73 (m, 1H); MS(ES) m/z 568 (M+H$^+$), 590 (M+Na$^+$).

5.

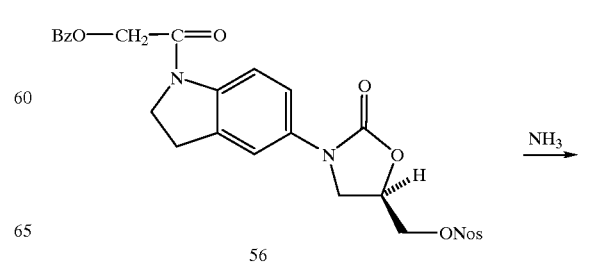

7.

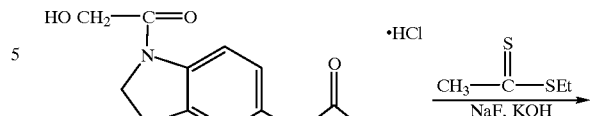

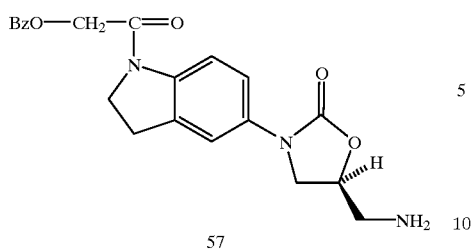

57

A stirred mixture of 56 (crude product from 0.00314 mol of 55), acetonitride (70 mL), isopropanol (70 mL) and 29% ammonium hydroxide (70 mL) was warmed at 40–44° C. for 7 h and kept at ambient temperature for 18 h. It was concentrated in vacuo to an aqueous residue with was extracted with $CH_2Cl_2$. The extract was washed with water and brine, dried ($Na_2SO_4$) and concentrated. Chromatography of the residue on silica gel with 8% MeOH-0.5% $NH_4OH$—$CHCl_3$ gave 1.05 g of 57: $^1H$ NMR [300 MHz, $(CD_3)_2SO$] d 2.78 (m, 2H), 3.13 (t, 2H), 3.82 (d,d, 1H), 4.01 (m, 3H), 4.29 (s, 2H), 4.58 (s, 2H), 4.58 (m, 1H), 7.31 (m, 6H), 7.54 (broad s, 1H), 8.03 (d, 1H); MS(ES) m/z 382 (M+H$^+$), 404 (M+Na$^+$).

6.

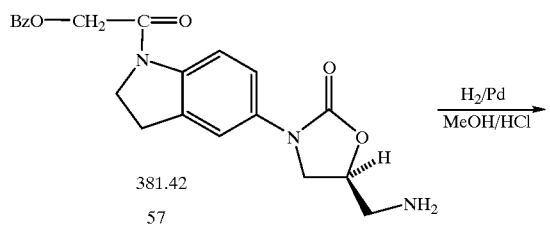

A mixture of 57 (0.46 g, 1.21 mmol), MeOH (150 mL), 1 M HCl (1.2 mL) and 5% palladium-on-carbon catalyst (250 mg) was hydrogenated at an initial pressure of 49 psi for 5 h. Additional 1M HCl (0.5 mL) and catalyst (100 mg) were added and hydrogenation was continued for 18 h. The catalyst was removed by filtration and the filtrate was concentrated to give 0.34 g of 27: $^1H$ NMR [300 MHz, $(CD_3)_2SO$] δ 3.15 (t, 2H), 3.22 (broad s, 2H), 3.84 (d,d, 1H), 4.00 (t, 2H), 4.15 (s, 2H), 4.15 (m, 1H), 4.92 (m, 1H), 7.24 (q, 1H), 7.50 (d, 1H), 8.03 (d, 1H), 8.37 (broad s, 3H); MS(ES) m/z 2.92 (M+H$^+$).

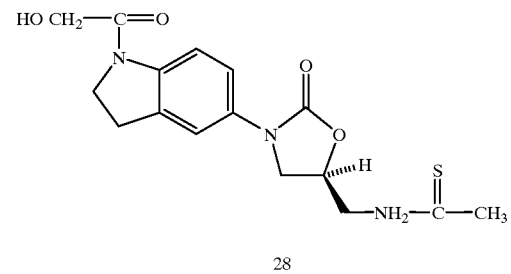

A suspension of 27 (0.10 g, 0.34 mmol) in a mixture of EtOH (15 mL) and 0.97 M KOH (0.7 mL) was added, under nitrogen to a stirred mixture of ethyl dithioacetate (0.0412 g, 0.343 mmol) and sodium fluoride (0.0137 g, 0.326 mmol) in EtOH (5 mL) and the mixture was kept at ambient temperature for 2 h 15 min. Additional 0.97 M KOH (0.2 mL), sodium iodide (6 mg) and ethyl dithioacetate (20 mg) were added and the mixture was stirred for 2 h, mixed with $CH_2Cl_2$ (150 mL), washed with water, 1M KHSO4 and brine, dried ($Na_2SO_4$) and concentrated. The residue was crystallized from acetone to give 0.0404 g of 28: mp 175–176° C. (dec); MS (FAB) m/z 350 (M+H$^+$), 349 (M$^+$), 331, 316, 205, 73; HR MS (FAB) calcd for $C_{16}H_{20}N_3O_4S$ (M+H$^+$) 350.1174, found 350.1183; $^1H$ NMR [300 MHz, $(CD_3)_2SO$] d 2.42 (s, 3H), 3.14 (t, 2H), 3.79 (d,d, 1H), 3.89 (t, 2H), 4.00 (t, 2H), 4.12 (m, 3H), 4.83 (t, 1H), 4.90 (m, 1H), 7.25 (d, 1H), 7.50 (s, 1H), 8.03 (d, 1H), 10.35 (s, 1H); IR (DRIFT) 3255, 3223, 3068, 1747, 1639, 1614 cm$^{-1}$.

EXAMPLE 25

(S)-N-[[3-[3-Fluoro-4-[4-(hydroxyacetyl)-1-piperazinyl]phenyl]-2-oxo-5-oxazolidinyl]methyl]thioacetamide (30)

1.

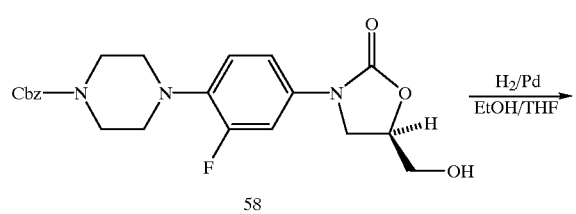

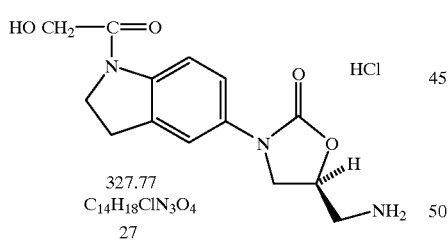

A mixture of 58 (3.00 g, 7.00 mmol), THF (60 mL), absolute EtOH (100 mL) and 10% palladium-on-carbon catalyst (415 mg) was hydrogenated at an initial pressure of 58 psi for 2 h 50 min. The catalyst was removed by filtration and the filtrate was concentrated in vacuo to give 2.67 g of 59 which was used without further purification in the next reaction: $^1$H NMR (300 MHz, CDCl$_3$) d 2.16 (broad s), 3.02 (m, 8H), 3.73 (d,d, J=3.9, 12.6 Hz, 1H), 3.96 (m, 3H), 4.72 (m, 1H), 6.92 (t, J=9.2 Hz, 1H), 7.11 (m, 1H), 7.43 (d,d, J=2.6, 14.3 Hz, 1H); MS(ES) m/z 296 (M+H$^+$).

2.

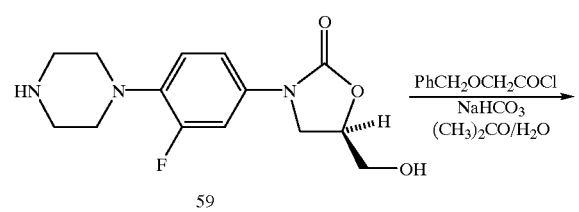

A stirred, ice cold mixture of 59 (2.67 g from the previous reaction), acetone (190 mL) and saturated NaHCO$_3$ (70 mL) was treated, dropwise during 2–3 min with a solution of benzyloxyacetyl chloride (1.34 mL, 8.61 mmol) in acetone (25 mL), kept in the ice bath for 1 h and diluted with EtOAc. The aqueous layer was extracted with EtOAc and the combined organic solution was washed with dilute NaCl, dried and concentrated. Chromatography of the residue on silica gel with 30% acetone-CH$_2$Cl$_2$ gave 2.64 g of 60: $^1$H NMR (300 MHz, CDCl$_3$) d 2.28 (broad s, 1H), 3.00 (m, 4H), 3.66 (m, 2H), 3.77 (m, 3H), 3.96 (m, 3H), 4.22 (s, 2H), 4.61 (s, 2H), 4.74 (m, 1H), 6.88 (t, J=9.2 Hz, 1H), 7.12 (m, 1H), 7.35 (s, 5H), 7.46 (d,d, J=2.6, 14.2 Hz, 1H); IR (mull) 3406, 1748, 1647 cm$^-$; HRMS(EI) calcd for C$_{23}$H$_{26}$FN$_3$O$_5$ (M$^+$) 443.1856, found 443.1842.

3.

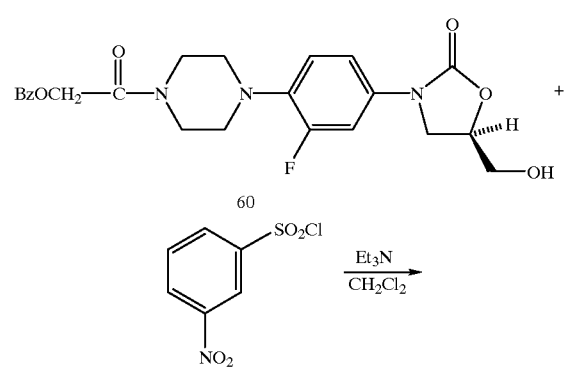

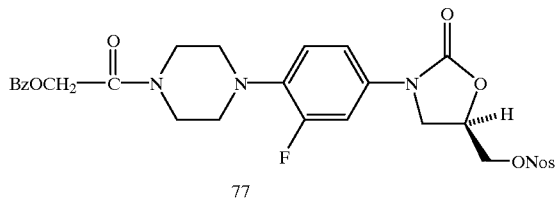

A stirred, ice cold mixture of 60 (2.64 g, 6.00 mmol) and triethylamine (1.14 mL, 8.16 mmol) in CH$_2$Cl$_2$ (200 mL), under nitrogen, was treated with 3-nitrobenzenesulfonyl chloride (1.78 g, 8.04 mmol), warmed to ambient temperature and kept for 5 h 20 min. Additional 3-nitrobenzenesulfonyl chlroide (180 mg) and triethylamine (0.20 mL) were added and the mixture was kept at ambient temperature for 18 h, diluted with CH$_2$Cl$_2$ and washed with water and dilute NaCl, dried (Na$_2$SO$_4$) and concentrated. Chromatography of the residue on silica gel with 40–60% acetone-hexane gave 3.36 g of 77: $^1$H NMR (300 MHz, CDCl$_3$) d 3.02 (broad s, 4H), 3.66 (broad s, 2H), 3.78 (broad s, 2H), 3.87 (d,d, J=5.9, 9.1 Hz, 1H), 4.09 (t, J=9.2 Hz, 1H), 4.22 (s, 2H), 4.41 (m, 2H), 4.61 (s, 2H), 4.84 (m, 1H), 6.88 (t, J=9.1 Hz, 1H), 7.02 (m, 1H), 7.35 (m, 6H), 7.82 (t, J=8.0 Hz, 1H), 8.23 (m, 1H), 8.53 (m, 1H), 8.73 (m, 1H); MS(ES) m/z 629 (M+H$^+$).

4.

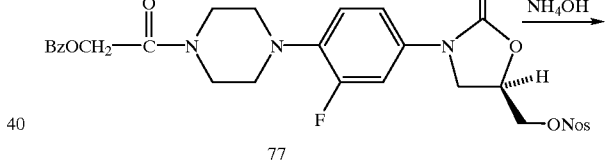

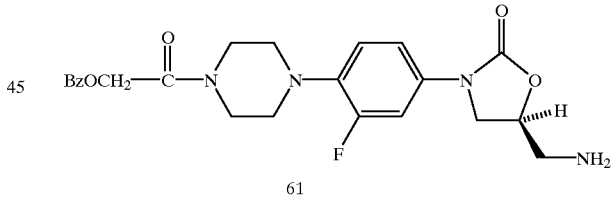

A solution of 77 (3.36 g, 5.34 mmol) in a mixture of acetonitrile (90 mL), isopropanol (90 mL) and concentrated ammonium hydroxide (90 mL) was warmed at 40–45° C. for 18 h, treated with additional ammonium hydroxide (30 mL), warmed at 40–45° C. for 8 h, treated with additional ammonium hydroxide (25 mL) and warmed at 45° C. for 18 h. It was then mixed with water and extracted with CH$_2$Cl$_2$. The extract was washed with dilute NaCl, dried (Na$_2$SO$_4$) and concentrated. Chromatography of the residue on silica gel with 5% MeOH-0.5% NH$_4$OH—CHCl$_3$ gave 2.44 g of 61: $^1$H NMR (300 MHz, CDCl$_3$) d 1.50 (broad s), 3.04 (m, 6H), 3.65 (broad s, 2H), 3.81 (m, 3H), 3.99 (t, 1H), 4.21 (s, 2H), 4.61 (s, 2H), 4.66 (m, 1H), 6.88 (t, 1H), 7.12 (m, 1H), 7.33 (m, 5H), 7.47 (d,d, 1H); MS(ES) m/z 443 (M+H$^+$).

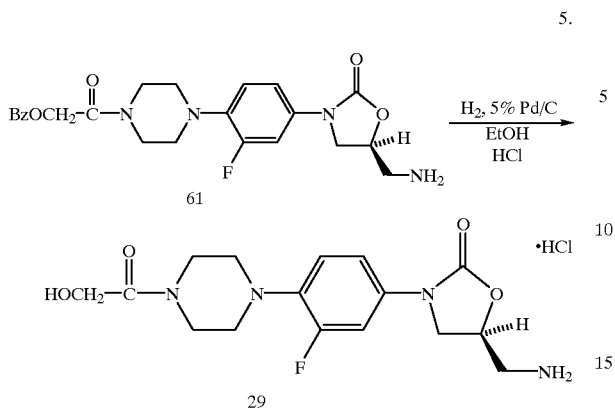

A solution of 61 (1.45 g, 3.3 mmol) and 1.0 N HCl (3.65 mL) in 95% EtOH (150 mL) was treated with 5% palladium-on-carbon catalyst (500 mg) and hydrogenated at an initial pressure of 54 psi for 20 h 15 min. Additional 1.0 N HCl (0.5 mL) and catalyst (100 mg) were added and hydrogenation was continued for 20 h 30 min at an initial pressure of 60 psi. The reaction was compete by TLC; it was neutralized with concentrated NH$_4$OH, filtered and concentrated in vacuo to give 1.18 g of 29: $^1$H NMR [300 MHz, (CD$_3$)$_2$SO] d 2.94 (broad s, 4H), 3.19 (m, 2H), 3.48 (broad s, 2H), 3.60 (broad s, 2H), 3.84 (m, 1H), 4.14 (m, 3H), 4.66 (broad s, 1H), 4.93 (m, 1H), 7.07 (t, 1H), 7.16 (d,d, 1H), 7.48 (d,d, 1H), 8.04 (broad s); IR (mull) 3420, 3099, 3040, 3008, 1755, 1641 cm$^{-1}$; MS(ES) m/z 353 (M+H$^+$). Anal. calcd for C$_{16}$H$_{22}$ClFN$_4$O$_4$: C, 49.42; H, 5.70; Cl, 9.12; N, 14.41. Found: C, 48.16; H, 5.82; Cl, 10.00; N, 14.28.

6.

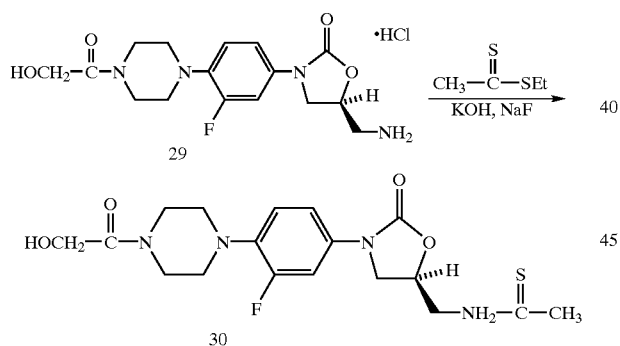

A stirred mixture of ethyl dithioacetate (180 mL, 1.56 mmol), sodium fluoride (72 mg, 1.7 mmol), 29 (500 mg, 1.29 mmol) and EtOH (70 mL) under nitrogen, was treated with 0.97M KOH (1.46 mL, 1.42 mmol) and the resulting solution was kept at ambient temperature for 3 h 35 min, diluted with CHCl$_3$, washed with water and dilute NaCl, dried (Na$_2$SO$_4$) and concentrated. Chromatography of the residue on silica gel with 5% MeOH-0.5% NH$_4$OH—CHCl$_3$ and crystallization of the resulting product from absolute EtOH gave 0.238 mg (44.9%) 30: mp 163–165° C.; $^1$H NMR (300 MHz, CDCl$_3$) d 2.60 (s, 3H), 3.06 (m, 4H), 3.45 (m, 2H), 3.61 (m, 1H), 3.82 (m, 3H), 4.07 (m, 2H), 4.25 (m, 3H), 4.97 (m, 1H), 6.91 (t, 1H), 7.07 (m, 1H), 7.45 (d.d, 1H), 7.91 (broad s, 1H); MS(FAB) m/z (relative intensity) 411 (M+H$^+$, 100), 410 (M$^+$, 66.5), 266 (3.1); IR 3292, 1733, 1653 cm$^{-1}$. Anal. calcd for C$_{18}$H$_{23}$FN$_4$O$_4$S: C, 52.67; H, 5.65; N, 13.65. Found: C, 52.76; H, 5.58; N, 13.64.

EXAMPLE 26

(S)-N-[[3-[3-Fluoro-4-(4-thiomorpholinyl)phenyl]-2-oxo-5-oxazolidinyl]methyl]thio-acetamide (32)

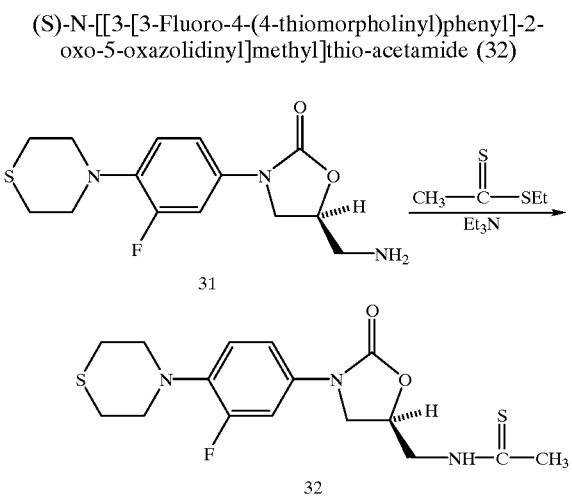

An ice cold, stirred mixture of 31 (0.38 g, 0.0012 mol) and triethylamine (0.38 mL, 0.0027 mol) in THF (12 mL), under nitrogen, was treated with ethyl dithioacetate (0.16 mL, 0.0014 mol) and then kept at ambient temperature for 24.5 h and concentrated in vacuo. A solution of the residue in CH$_2$Cl$_2$ was washed with saturated NaHCO$_3$, water and brine, dried (MgSO$_4$) and concentrated. Crystallization of the residue from EtOAc-hexane gave 0.355 g of 32: mp 155–156° C.; MS(ES) m/z 370 (M+H$^+$), 392 (M+Na$^+$); IR (DRIFT) 3206, 3042, 1759, 1738 cm$^{-1}$; $^1$H NMR (300 MHz, CDCl$_3$) d 2.60 (s, 3H), 2.95 (s, 4H), 3.43 (m, 4H), 3.82 (d, d, 1H), 4.08 (m, 2H), 4.27 (m, 1H), 4.98 (m, 1H), 7.06 (m, 1H), 7.33 (broad s, 1H), 7.51 (d, 1H), 8.03 (broad s, 1H). Anal. calcd for C$_{16}$H$_{20}$FN$_3$O$_2$S$_2$: C, 52.01; H, 5.46; N, 11.37. Found: C, 51.86; H, 5.43; N, 11.20.

EXAMPLE 27

(S)-N-[[3-[3-Fluoro-4-(4-thiomorpholinyl)phenyl]-2-oxo-5-oxazolidinyl]methyl]thio-acetamide, thiomorpholine S-oxide (34)

1.

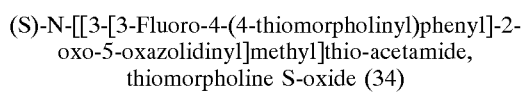

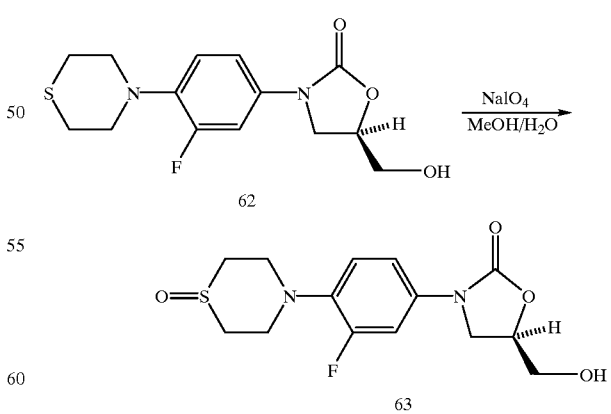

An ice cold, stirred mixture of sodium metaperiodate (1.08 g, 5.05 mmol) and water (12 mL), under nitrogen, was treated with 62 (1.5 g, 4.8 mmol) and MeOH (17 mL) and kept at 6° C. for 18 h and at 4° C. for 3 h. It was then treated with additional sodium metaperiodate (0.1 g), kept at 4° C. for 3 h and extracted with CHCl₃. The extract was dried (MgSO₄) and concentrated to give 1.4 g of 63: ¹H NMR [300 MHz, (CD₃)₂SO] d 2.84 (m, 2H), 3.01 (m, 2H), 3.16 (m, 2H), 3.50 (m, 3H), 3.65 (m, 1H), 3.77 (d,d, 1H), 4.03 (t, 1H), 4.66 (m, 1H), 5.18 (t, 1H), 7.16 (m, 2H), 7.52 (m, 1H); MS(ES) m/z 329 (M+H⁺), 351 (M+Na⁺).

2.

An ice cold, stirred mixture of 63 (1.27 g, 3.87 mmol) and triethylamine (0.732 mL, 5.25 mmol) in CH₂Cl₂ (130 mL), under nitrogen, was treated with m-nitrobenzenesulfonyl chloride (1.15 g, 5.19 mmol) and kept at ambient temperature for about 24 h. It was diluted with CH₂Cl₂, washed with water and brine, dried (Na₂SO₄) and concentrated to give 78 which was used in the next reaction without purification.

3.

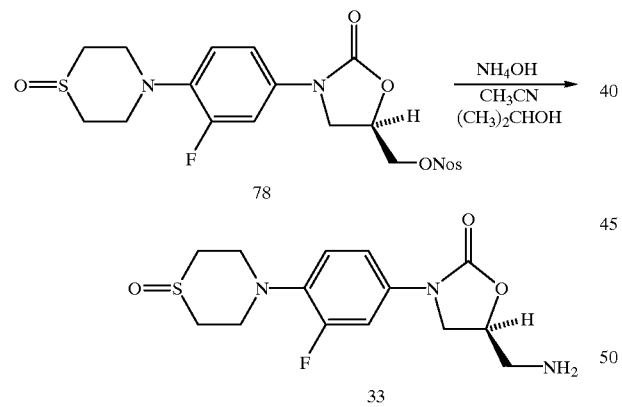

A stirred mixture of the product (78) from the previous reaction, acetonitrile (70 mL) and isopropanol (70 mL) was treated with concentrated ammonium hydroxide (70 mL, 29.9% NH₃) and kept at 40° C. for 2 h, at ambient temperature for 18 h and at 40–45° C. for 4 h; it was concentrated to about 50 mL, diluted with water and extracted with CH₂Cl₂. The extracts were washed with water and brine, dried (MgSO₄) and concentrated. Chromatography of the residue on silica gel with 5% MeOH—CHCl₃ gave 0.58 g of 33: MS(ES) m/z 328 (M+H⁺), 350 (M+Na⁺); ¹H NMR [300 MHz, (CD₃)₂SO] d 2.81 (m, 4H), 3.01 (m, 2H), 3.16 (m, 2H), 3.30 (broad s), 3.49 (m, 2H), 3.80 (d,d, 1H), 4.01 (t, 1H), 4.58 (m, 1H), 7.19 (m, 2H), 7.51 (m, 1H).

4.

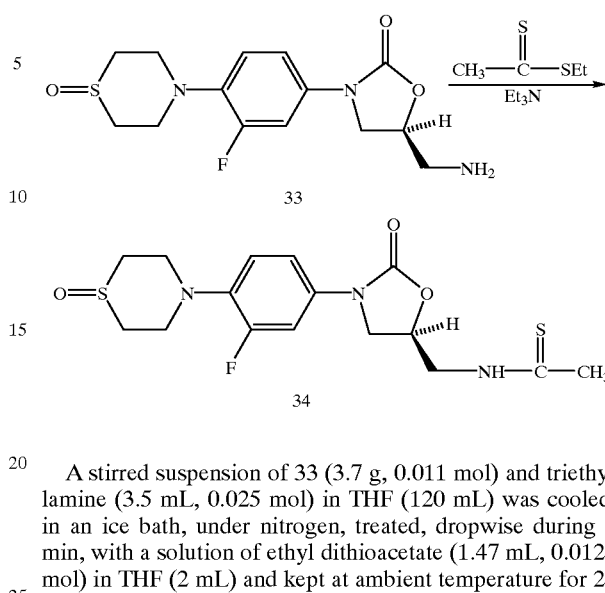

A stirred suspension of 33 (3.7 g, 0.011 mol) and triethylamine (3.5 mL, 0.025 mol) in THF (120 mL) was cooled, in an ice bath, under nitrogen, treated, dropwise during 2 min, with a solution of ethyl dithioacetate (1.47 mL, 0.0128 mol) in THF (2 mL) and kept at ambient temperature for 22 h. The resulting solution was concentrated and the residue crystallized from acetonitrile to give 3.61 g of 34: mp 176–177° C.; ¹H NMR [300 MHz, (CD₃)₂SO] d 2.42 (s, 3H), 2.85 (m, 2H), 3.01 (m, 2H), 3.18 (m, 3H), 3.50 (m, 2H), 3.78 (d,d, 1H), 3.89 (broad s, 2H), 4.12 (t, 1H), 4.92 (m, 1H), 7.18 (m, 2H), 7.49 (m, 1H), 10.33 (s, 1H); IR (DRIFT) 3186, 3102, 1741 cm⁻¹; MS(ES) m/z 386 (M+H⁺), 408 (M+Na⁺). Anal. calcd for C₁₆H₂₀FN₃O₃S₂.0.5 H₂O: C, 48.71; H, 5.37; N, 10.65; S, 16.26; H₂O, 2.38. Found: C, 48.75; H, 5.17; N, 10.72; S, 16.07; H₂O, 1.72.

EXAMPLE 28

(S)-N-[[3-[3-Fluoro-4-(4-thiomorpholinyl)phenyl]-2-oxo-5-oxazolidinyl]methyl]thio-acetamide, thiomorpholine S, S-dioxide (36)

1.

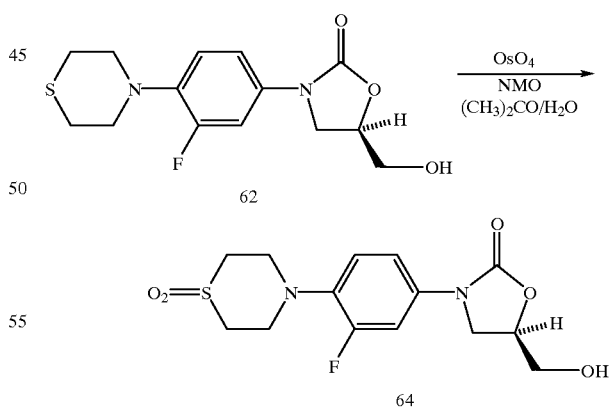

A stirred mixture of 62 (0.399 g, 0.00128 mol) in 25% water/acetone (12 mL), under nitrogen was treated with N-methylmorpholine, N-oxide (0.45 g, 0.00384 mol) and 0.1 mL of a 2.5 wt % solution of osmium tetroxide in tert-butanol. It was kept at ambient temperature for 18 h, mixed with saturated NaHSO₃ (50 mL) and extracted with CH₂Cl₂. The extract was washed with saturated NaHSO₃ and brine, dried (Na$_2$SO$_4$) and concentrated. The residue was mixed with 3.5% MeOH—CH$_2$Cl$_2$ and filtered; the solid was dissolved in 15% MeOH—CH$_2$Cl$_2$ and concentrated to give 0.29 g of 64. The filtrate was chromatographed on silica gel with 3.5% MeOH—CH$_2$Cl$_2$ to give 0.1 of additional 64: MS(ES) m/z 345 (M+H$^+$), 367 (M+Na$^+$); $^1$H NMR [300 MHz, (CD$_3$)$_2$SO] d 3.26 (m, 4H), 3.44 (m, 4H), 3.60 (m, 2H), 3.80 (d,d, 1H), 4.05 (t, 1H), 4.69 (m, 1H), 7.22 (m, 2H), 7.54 (d, 1H).

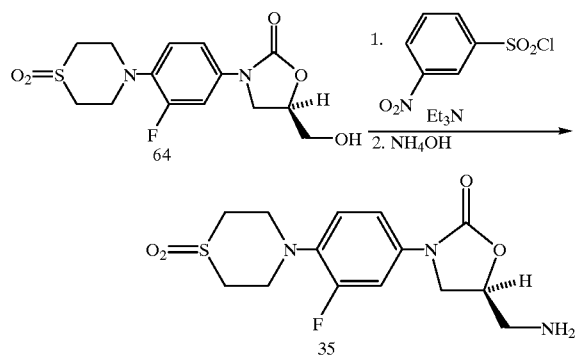

A stirred mixture of 64 (0.39 g, 0.00113 mol) and triethylamine (0.214 mL, 0.00154 mol) in CH$_2$Cl$_2$ (37 mL) was cooled, under nitrogen, in an ice bath and treated, portionwise during 5 min, with 3-nitrobenzenesulfonyl chloride (0.335 g, 0.00151 mol). The mixture was kept in the ice bath for 20 min and at ambient temperature for 18 h and concentrated in vacuo. A stirred solution of the residue in 2-propanol (25 mL) and acetonitrile (25 mL), under nitrogen, was treated with 30% NH$_4$OH (25 mL), warmed at 50–55° C. for 6 h and kept at ambient temperature for 48 h. It was concentrated to remove the organic solvents, diluted with water and extracted with CH$_2$Cl$_2$. The extract was washed with water and brine, dried (MgSO$_4$) and concentrated. Flash chromatography of the residue on silica gel with 6% MeOH-0.4% NH$_4$OH—CHCl$_3$ gave 0.29 g of 35: $^1$H NMR [300 MHz, (CD$_3$)$_2$SO] d 1.59 (broad s, 2H), 2.78 (m, 2H), 3.24 (m, 4H), 3.43 (m, 4H), 3.81 (d,d, 1H), 4.01 (t, 1H), 4.57 (m, 1H), 7.18 (m, 2H), 7.52 (m, 1H); MS(ES) m/z 344 (M+H$^+$), 366 (M+Na$^+$).

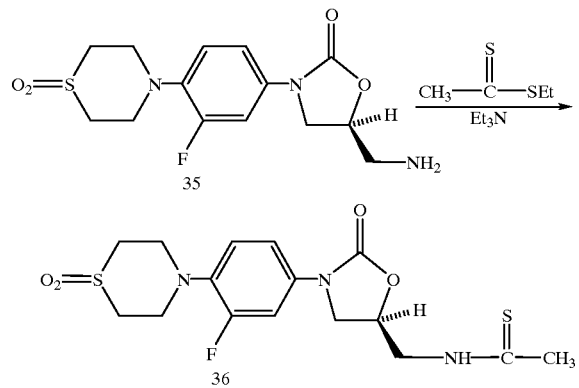

A stirred, ice cold suspension of 35 (0.28 g, 0.85 mmol) in a mixture of Et$_3$N (0.26 mL, 1.9 mmmol) and THF (10 naL) was treated with ethyl dithioacetate (0.11 mL, about 6 drops) and kept in the ice bath for 20 min and then at ambient temperature; the reaction was followed by TLC. After 20 h there was still a suspension and only partial reaction; additional THF (10 mL) and ethyl dithioacetate (3 drops) were added. After an additional 48 h the reaction was still incomplete; the suspension was treated with CH$_2$Cl$_2$ (10 mL) and kept for 72 h. At this time almost complete solution and an almost complete conversion to product had been obtained. An additional drop of ethyl dithioacetate was added and the mixture was kept at ambient temperature for 5 d and concentrated in vacuo. The residue was mixed with EtOAc, washed with saturated NaHCO$_3$, water and brine, dried (MgSO$_4$) and concentrated. Crystallization of the residue from MeOH—EtOAc gave 0.209 g of 36: mp 197–198° C.; $^1$H NMR [300 MHz, (CD$_3$)$_2$SO] d 2.42 (s, 3H), 3.24 (m, 4H), 3.43 (m, 4H), 3.78 (d,d, 1H), 3.88 (m, 2H), 4.12 (t, 1H), 4.92 (m, 1H), 7.18 (m, 2H), 7.50 (m, 1H), 10.37 (broad s, 1H); IR (mull) 3300, 3267, 1743 cm$^{-1}$; MS(ES) m/z 424 (M+Na$^+$). Anal. calcd for C$_{16}$H$_{20}$FN$_3$O$_4$S$_2$: C, 47.87; H, 5.02; N, 10.47. Found: C, 47.84; H, 5.23; N, 10.28.

EXAMPLE 29

(S)-N-[[3-[3,5-Difluoro-4-[4-(hydroxyacetyl)-1-piperazinyl]phenyl]-2-oxo-5-oxazolidinyl]methyl] thioacetamide (38)

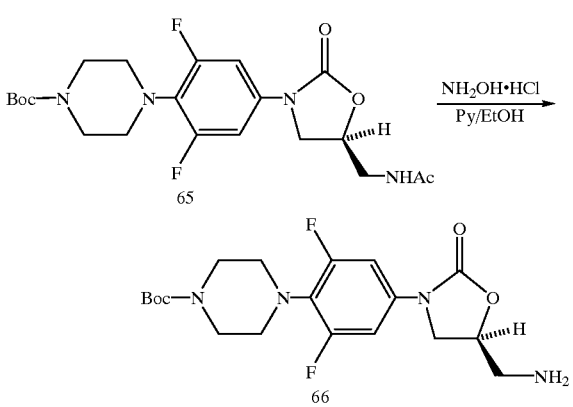

A stirred mixture of 65 (1.8 g, 0.00396 mol), pyridine (30 mL) and absolute EtOH (3 mL), under nitrogen, was treated with hydroxylamine hydrochloride (1.44 g, 0.0207 mol), warmed to the reflux temperature during 2 h, refluxed for 3.5 h, kept at ambient temperature for 18 h and at reflux for 4 h. It was concentrated in vacuo and the residue was mixed with water, adjusted to pH 11 with saturated NaHCO$_3$ and extracted with Et$_2$O. The extracts were washed with brine, dried (Na$_2$SO$_4$) and concentrated. Chromatography of the residue on silica gel with 5% MeOH-0.35% NH$_4$OH—CHCl$_3$ gave 0.75 g of recovered 65 and 0.72 g of 66: $^1$H NMR [300 MHz, (CD$_3$)$_2$SO] d 1.40 (s, 9H), 1.72 (broad s, 2H), 2.78 (m, 2H), 2.97 (m, 4H), 3,40 (m, 4H), 3.80 (d,d, 1H), 4.00 (t, 1H), 4.59 (m, 1H), 7.27 (d, 2H); MS(ES) m/z 413 (M+H$^+$), 435 (M+Na$^+$).

2.

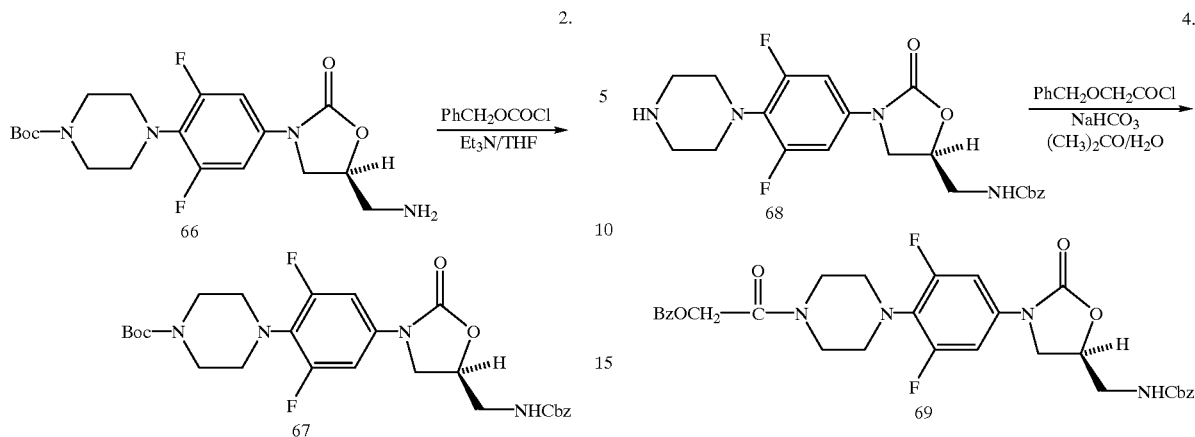

An ice cold, stirred mixture of 66 (0.75 g, 0.0018 mol) and triethylamine (0.315 mL, 0.00225 mol) in THF (12 mL), under nitrogen, was treated, dropwise with benzyl chloroformate (0.29 mL, 0.0020 mol), kept in the ice bath for 15 min and at ambient temperature for 2 h and concentrated in vacuo. The residue was mixed with $CH_2Cl_2$ and washed with saturated $NaHCO_3$, water and brine, dried ($Na_2SO_4$) and concentrated. This residue was mixed with $Et_2O$ and filtered to give 0.939 g of 67: mp 116–118° C.; $^1H$ NMR (300 MHz, $CDCl_3$) d 1.48 (s, 9H), 3.08 (m, 4H), 3.53 (m, 4H), 3.60 (m, 2H), 3.73 (m, 1H), 3.96 (t, 1H), 4.76 (m, 1H), 5.10 (s, 2H), 5.21 (m, 1H), 7.07 (d, 2H), 7.31 (s, 5H); MS(ES) m/z 547 (M+H$^+$), 569 (M+Na$^+$).

3.

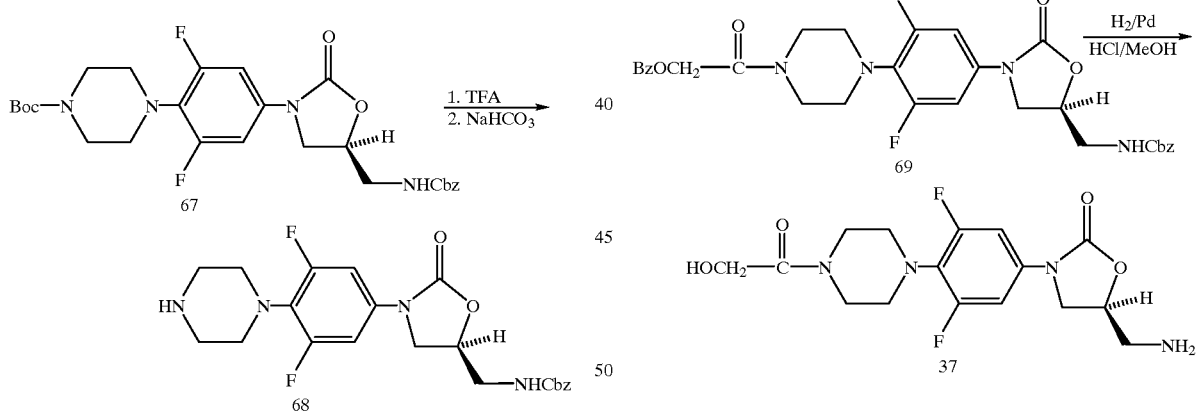

Compound 67 (0.805 g, 0.00147 mol) was added with stirring, portionwise during 5 min, under nitrogen, to ice cold trifluoroacetic acid (9 mL). The resulting solution was kept in the ice bath for 1 h and then concentrated under a stream of nitrogen. The residue was mixed with ice and saturated $NaHCO_3$ and extracted with $CH_2Cl_2$; the extract was washed with water and brine, dried ($Na_2SO_4$) and concentrated to give 0.63 g of product. The combined aqueous layer was reextracted with EtOAc; the extracts were washed with water and brine, dried ($Na_2SO_4$) and concntrated to give additional product. The combined product amounted to 0.68 g of 68 which was used in the next reaction without further purification.

An ice cold, stirred mixture of 68 (0.68 g, 0.00152 mol), saturated $NaHCO_3$ (15.2 mL) and acetone (40 mL), under nitrogen was treated, dropwise during 15 min, with a solution of benzyloxyacetyl chloride (0.29 mL, 0.0019 mol) in acetone (5 mL), kept at ambient temperature for 6 h, diluted with EtOAc and washed with water and brine. The extract was dried ($MgSO_4$) and concentrated in vacuo to give 0.72 g of 69: MS(ES) m/z 395 (M+H$^+$), 617 (M+Na$^+$); $^1H$ NMR (300 MHz, $CDCl_3$) d 3.12 (m, 4H), 3.59 (m, 4H), 3.74 (m, 3H), 3.96 (t, 1H), 4.22 (s, 2H), 4.62 (s, 2H), 4.75 (broad s, 1H), 5.10 (s, 2H), 5.22 (m, 1H), 7.08 (d, 2H), 7.33 (m, 10H).

5.

A mixture of 69 (0.72 g, 0.0012 mol), MeOH and 5% palladium-on-carbon catalyst (0.4 g) was hydrogenated at an initial pressure of 45 psi for 4 h. By TLC (8% MeOH-0.5% $NH_4OH$—$CHCl_3$) the starting material had been reduced and two products formed. 1M Hydrochloric acid (1.34 mL) was added and hydrogenation was continued at an initial pressure of 40 psi for 21 h. By TLC only the more polar product remained. The catalyst was removed by filtration and the filtrate was concentrated to give 0.40 g of 37: MS(ES) m/z 371 (M+H$^+$), 393 (M+Na$^+$); $^1H$ NMR [300 MHz, $(CD_3)_2SO$] d 3.02 (s, 4H), 3.20 (m, 2H), 3.43 (s, 2H), 3.56 (s, 2H), 3.84 (m, 1H), 3.84 (broad s), 4.10 (s, 2H), 4.14 (t, 1H), 4.96 (m, 1H), 7.26 (d, 2H), 8.41 (broad s, 3H).

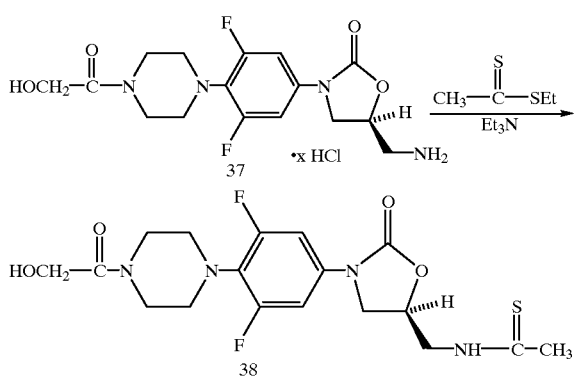

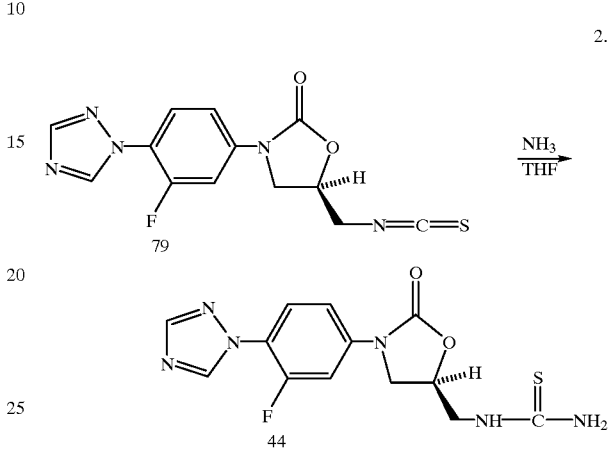

A stirred suspension of 37 (0.38 g) in a solution of Et₃N (0.31 mL) and THF (10 mL), under nitrogen, was treated with ethyl dithioacetate (0.13 mL, about 7 drops) and kept at ambient temperature for 7 d; the reaction was followed by TLC (8% MeOH-0.5% NH₄OH—CHCl₃). Additional ethyl dithioacetate (2 drops) was added after 24 h; after 30 h CH₂Cl₂ (10 mL) and ethyl dithioacetate (3 drops) were added; after 48 h additional triethylamine (0.3 mL) was added. The mixture was concentrated in vacuo and the residue was mixed with ice and saturated NaHCO₃ an extracted with CH₂Cl₂. The extract was washed with water and brine, dried (MgSO₄) and concentrated. The residue was chromatographed on silica gel with 2.5% MeOH—CH₂Cl₂ and the product was crystallized from MeOH to give 0.182 g of 38: mp 110–111° C. (dec); MS(ES) m/z 429 (M+H⁺), 451 (M+Na⁺); HRMS (FAB) calcd for $C_{18}H_{23}F_2N_4O_4S$ (M+H⁺) 429.1408, found 429.1415; IR (DRIFT) 1760, 1652, 1639 cm⁻¹; $[\alpha]^{24}_D 8°$ (MeOH).

EXAMPLE 30

(S)-N-[[3-[4-[1-[1,2,4]Triazolyl]phenyl]-2-oxo-5-oxazolidinyl]methyl]thiourea (44)

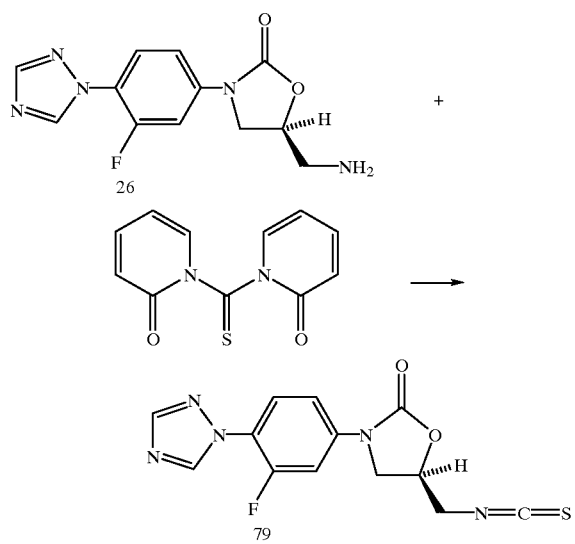

A solution of 26 (0.190 g, 0.685 mmol) in CH₂Cl₂ (20 mL) was added, dropwise during 20 min, under nitrogen, to an ice cold, stirred solution of 1,1¢-thiocarbonyldi-2(1H)-pyridone (0.193 g, 0.831 mmol) in CH₂Cl₂ (7 mL). The mixture was kept in the ice bath for 20 min and at ambient temperature for 2 h, diluted with CH₂Cl₂, washed with water and brine, dried (MgSO₄) and concentrated. Chromatography of the residue on silica gel with 10–15% CH₃CN—CH₂Cl₂ gave 0.11 g of 79 which was used in the next reaction without further purification: MS(ES) m/z 320 (M+H⁺), 342 (M+Na⁺).

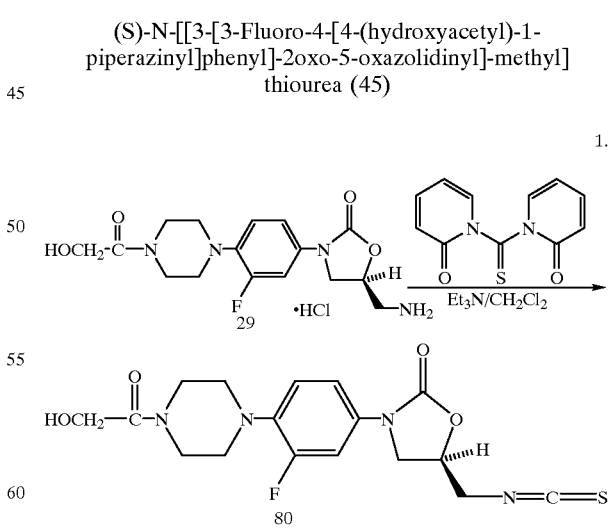

A stirred, ice cold solution of 79 (0.10 g, 0.31 mmol) in THF (15 mL) was treated with excess anhydrous ammonia and kept in the ice bath for 90 min. It was then evaporated under a stream of nitrogen to a volume of about 5 mL to give a solid which was collected by filtration and washed with cold THF to give 0.105 g of 44: mp 214–215° C.; ¹H NMR [300 MHz, (CD₃)₂SO] d 3.82 (m, 3H), 4.18 (t, 1H), 4.89 (broad s, 1H), 7.20 (broad s, 2H), 7.50 (d, 1H), 7.79 (m, 2H), 7.93 (t, 1H), 8.26 (s, 1H), 8.97 (s, 1H); MS(ES) m/z 337 (M+H⁺), 359 (M+Na⁺). Anal. calcd for $C_{13}H_{13}FN_6O_2S$: C, 46.42; H, 3.90; N, 24.99. Found: C, 46.22; H, 3.98; N, 24.55.

EXAMPLE 31

(S)-N-[[3-[3-Fluoro-4-[4-(hydroxyacetyl)-1-piperazinyl]phenyl]-2oxo-5-oxazolidinyl]-methyl]thiourea (45)

An ice cold, stirred solution of 1,1¢-thiocarbonyl-2(1H)-dipyridone (0.123 g, 0.530 mmol) in CH₂Cl₂ (5 mL), under nitrogen, was treated with a suspension of 29 (0.17 g, 0.4 mmol) in CH₂Cl₂ (20 mL) and then during 10 min with a solution of triethylamine (0.111 mL, 0.8 nmmol) in CH$_2$Cl$_2$ (10 mL). It was kept in the ice bath for 30 min, at ambient temperature for 2 h and at <0° C. for 18 h. It was then diluted with CH$_2$Cl$_2$, washed with water and brine, dried (MgSO$_4$) and concentrated. The residue (80) was used without further purification in the next reaction. A sample of 80 that was purified by flash chromatography on silica gel with 10–20% acetonitrile-CH$_2$Cl$_2$ had: $^1$H NMR (300 MHz, CDCl$_3$) d 1.60 (broad s), 3.07 (m, 4H), 3.45 (m, 2H), 3.85 (m, 4H), 3.97 (d,d, 1H), 4.16 (t, 1H), 4.21 (s, 2H), 4.82 (m, 1H), 6.95 (t, 1H), 7.13 (d,d, 1H), 7.47 (d,d, 1H); MS m/z 395 (M+H$^+$); 417 (M+Na$^+$).

2.

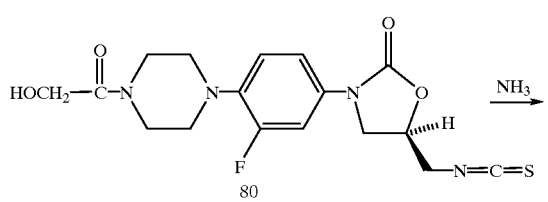
80

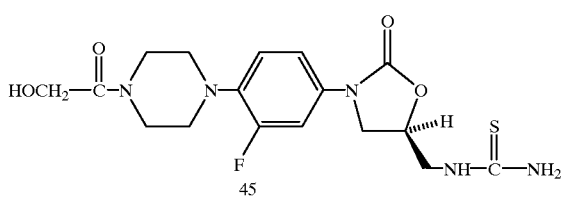
45

Excess anhydrous ammonia was bubbled into a stirred, ice cold solution of 80 (crude product from the previous reaction) in THF (25 mL) and the mixture was kept in the ice bath for 90 min and concentrated under a stream of nitrogen. The residue was chromatographed on silica gel with 5% MeOH-0.4% NH$_4$OH—CHCl$_3$ and the product was crystallized from acetonitrile to give 0.0544 g of 45: mp 209–210° C.; $^1$H NMR [300 MHz, (CD$_3$)$_2$SO] d 294 (broad s, 4H), 3.47 (broad s, 2H), 3.60 (broad s, 2H), 3.78 (broad s, 3H), 4.07 (t, 1H), 4.10 (d, J=5.5 Hz, 2H), 4.63 (t, J=5.5 Hz, 1H), 4.81 (broad s, 1H), 7.05 (t, 1H), 7.16 (d,d, 1H), 7.15 (broad s, 2H), 7.49 (d,d, 1H), 7.91 (t, 1H); IR (mull) 3443, 3403, 3321, 3202, 3081, 1753, 1655, 1648 cm$^{-1}$; HRMS (FAB) calcd for C$_{17}$H$_{23}$FN$_4$O$_4$S (M+H$^+$) 412.1454, found 412.1447. Anal. calcd for C$_{17}$H$_{22}$FN$_5$O$_4$S: C, 49.63; H, 5.39; N, 17.02. Found: C, 49.63; H, 5.48; N, 16.99.

EXAMPLE 32

(S)-N-[[3-[1-(Hydroxyacetyl)-5-indolinyl]-2-oxo-5-5 oxazolidinyl]methyl]thiourea (46)

1.

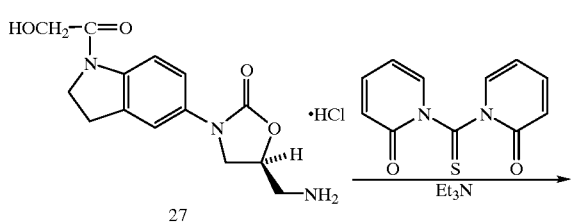
27

-continued

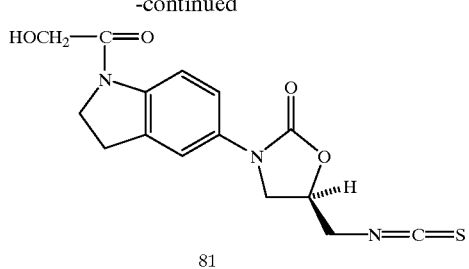
81

An ice cold, stirred solution of 1,1¢-thiocarbonyldi-2(1H)-pyridone (0.096 g, 0.41 mmol) in CH$_2$Cl$_2$ (5 mL) was treated with a suspension of 27 (0.10 g, 0.34 mmol) in CH$_2$Cl$_2$ (15 mL) and then with 0.05 mL (0.36 mmol) of triethylamine. It was kept in the ice bath for 30 min and at ambient temperature for 2 h, diluted with CH$_2$Cl$_2$, washed with water and brine, dried (MgSO$_4$) and concentrated. Chromatography of the residue on silica gel with 20–40% CH$_3$CN—CH$_2$Cl$_2$ gave 0.04 g of 81.

2.

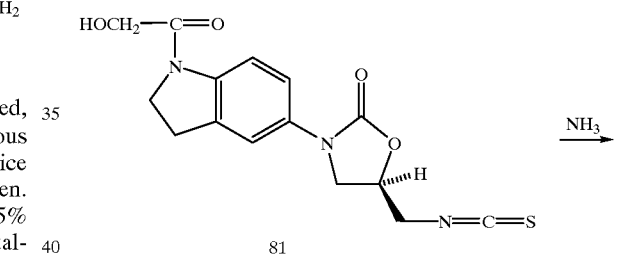
81

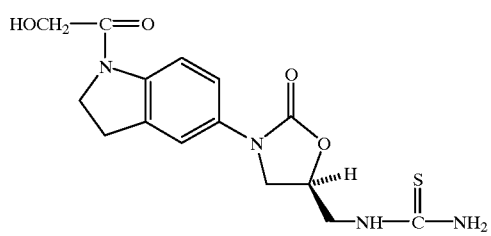
46

Excess anhydrous ammonia was bubbled into an ice cold solution of 81 (0.04 g) in THF (30 mL) and the mixture was kept in the ice bath for 80 min and concentrated under a stream of nitrogen. The residue was crystallized from CH$_3$CN to give 0.0151 g of 46: mp 214–215° C. (dec); MS (FAB) m/z 351 (M+H$^+$), 350 (M$^+$), 319, 304, 147; HRMS (FAB) calcd for C$_{15}$H$_{19}$N$_4$O$_4$S (M+H$^+$) 351.1127, found 351.1130; IR (DRIFT) 3329, 3296, 3196, 1746, 1655, 1626 cm$^{-1}$.

EXAMPLE 33

(S)-N-[[3-[3-Fluoro-4-(4-thiomorpholinyl)phenyl]-2-oxo-5-oxazolidinyl]methyl]thiourea, thiomorpholine S-oxide (47)

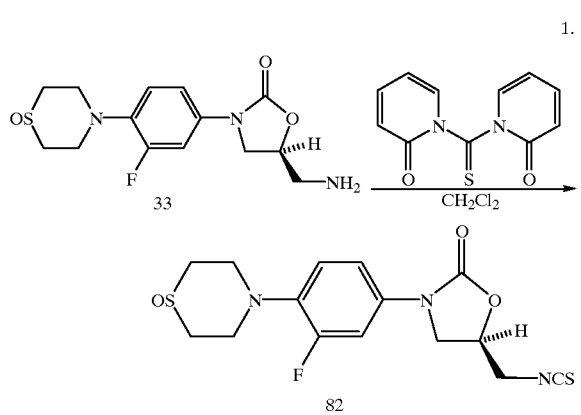

A suspension of 33 (0.30 g, 0.92 mmol) in CH$_2$Cl$_2$ (7 mL) was added, during 20 min, to an ice cold, stirred mixture of 1,1¢-thiocarbonyldi-2(1H)-pyridone (0.258 g, 1.11 mmol) and CH$_2$Cl$_2$ (20 mL). The mixture was kept in the ice bath for 20 min and at ambient temperature for 2 h, mixed with CH$_2$Cl$_2$ (50 mL), washed with water and brine, dried (MgSO$_4$) and concentrated. Chromatography of the product on silica gel with 20–50% CH$_3$CN—CH$_2$Cl$_2$ gave 0.27 g of 82 which was used in the next reaction: MS(ES) m/z 370 (M+H$^+$), 392 (M+Na$^+$).

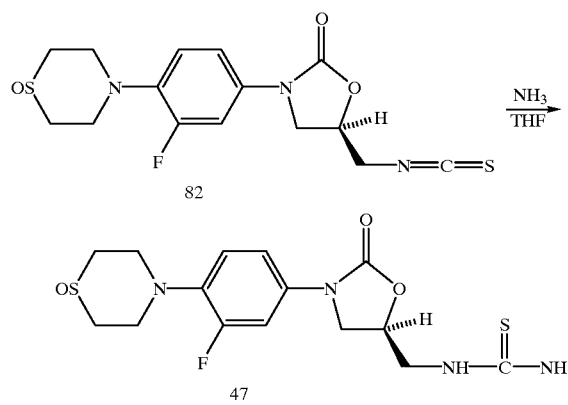

A stirred, ice cold solution of 82 (0.27g, 0.73 mmol) in THF (15 mL), under nitrogen, was treated with excess anhydrous ammonia, kept in the ice bath for 1 h and concentrated; crystallization of the residue from MeOH gave 0.175 g of 47; mp 212–213° C.; $^1$H NMR [300 MHz, (CD$_3$)$_2$SO] d 2.83 (m, 2H), 3.01 (m, 2H), 3.17 (m, 2H), 3.50 (t, 2H), 3.78 (broad s, 3H), 4.08 (t, 1H), 4.80 (broad s, 1H), 7.17 (m, 2H), 7.17 (broad s, 2H), 7.50 (d, 1H), 7.90 (t, 1H); MS(ES) m/z 409 (M+Na$^+$); IR (mull) 3335, 3284, 3211, 3175, 3097, 1750, 1630 cm$^{-1}$. Anal. calcd for C$_{15}$H$_{19}$FN$_4$O$_3$S$_2$: C, 46.62; H, 4.95; N, 14.50. Found: C, 46.50; H, 4.95; N, 14.40.

EXAMPLE 34

(S)-N-[[3-[3-Fluoro-4-(4-morpholinyl)phenyl]-2-oxo-5-oxazolidinyl]methyl-S-methyldithiocarbamate (48)

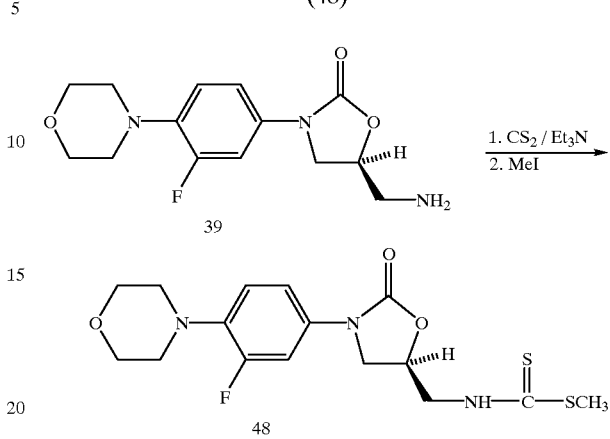

An ice cold, stirred mixture of 39 (0.59 g, 0.0020 mol), EtOH (1.5 mL), water (2 drops) and triethylamine (0.613 mL, 0.00440 mol), under nitrogen, was treated with carbon disulfide (0.066 mL, 0.0011 mol) and kept in the ice bath for 2 h and at ambient temperature for 18 h. (A solution was obtained after the addition of carbon disulfide; a white precipitate began to form soon after the mixture was warmed to ambient temperature.) The thick suspension was treated, dropwise during 2 min, with a solution of methyl iodide (0.137 mL, 0.00220 mol) in EtOH (2 mL) and the mixture was kept at ambient temperature for 1.5 h and concentrated in vacuo. A solution of the residue in EtOAc was washed with saturated NaHCO$_3$, water and brine, dried (MgSO$_4$) and concentrated. The residue was chromatographed on silica gel with 1.8% MeOH—CH$_2$Cl$_2$ and the product was crystallized from EtOAc to give 0.197 g of 48: mp 154–155° C.; IR (mull) 3354, 3346, 1726 cm$^{-1}$. Anal. calcd for C$_{16}$H$_{20}$FN$_3$O$_3$S$_2$: C, 49.85; H, 5.23; N, 10.90. Found: C, 49.73; H, 5.25; N, 10.82.

EXAMPLE 35

(S)-N-[[3-[3-Fluoro-4-(4-morpholinyl)phenyl]-2-oxo-5-oxazolidinyl]methyl-O-methylthiocarbamate (50)

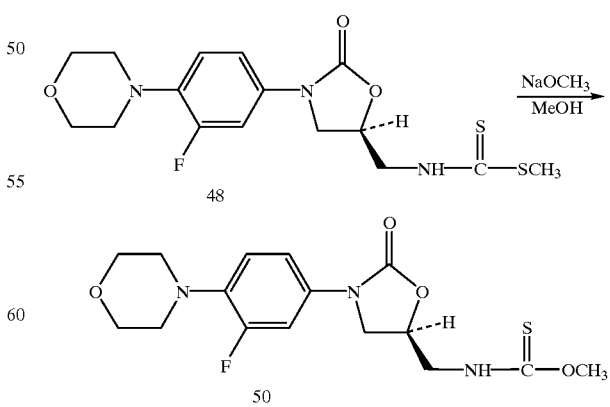

A stirred mixture of 48 (0.200 g, 0.518 mmol), sodium methoxide (0.003 g, 0.06 mmol) and MeOH (5 mL), under nitrogen, was refluxed for 4 h and kept at ambient temperature for 18 h. It was found that the starting material and product had similar mobilities on TLC. the reaction was therefore followed by MS(ES). Starting material was still present. The mixture was refluxed for 3 h, additional sodium methoxide (0.005 g) was added and reflux was continued for 2 h. It was kept at ambient temperature for 18 h, refluxed for 1 h, kept at ambient temperature 1.5 h and concentrated in vacuo. The residue was mixed with ice, the pH was adjusted to 9–10 with 1M KHSO4 and saturated NaHCO$_3$ and the mixture was extracted with CH$_2$Cl$_2$. The extract was washed with water and brine, dried (MgSO$_4$) and concentrated. The residue was chromatographed on silica gel with 5% acetone-CH$_2$Cl$_2$ and the product was crystallized from EtOAc-hexane to give 0.107 g of 50: mp 128–129° C.; MS(ES) m/z 370 (M+H$^+$), 392 (M+Na$^+$); IR (DRIFT) 3282, 3251, 1753, 1735 cm$^{-1}$; $^1$H NMR [300 MHz, (CD$_3$)$_2$SO] d 2.94 (m, 4H), 3.47, 374 (m,m, 7H), 3.86, 3.91 (s,s, 3H), 4.10 (m, 1H), 4.73, 4.86 (m,m, 1H), 7.05 (t, 1H), 7.16 (d,d, 1H), 7.47 (d,d, 1H), 9.41, 9.50 (s,s, 1H). Anal. calcd for C$_{16}$H$_{20}$FN$_3$O$_4$S: C, 52.02; H, 5.46; N, 11.38. Found: C, 51.97; H, 5.49; N, 11.35.

When in the procedure of Example 35 an appropriate amount of sodium ethoxide was substituted for sodium methoxide, the compound of Example 36 below in Table A was obtained.

oxo-5-oxazolidinyl]methyl]isopropylcarboxamide, (S)-N-[[3-[3-fluoro-4-morpholinyl]phenyl]-2-oxo-5-oxazolidinyl] methyl]cyclopropylcarboxamide, or (S)-N-[[3-[3,5-difluoro-4-morpholinyl]phenyl]-2-oxo-5-oxazolidiny] methyl]acetamide was substituted for (S)-N-[[3-[3-fluoro-4-(4-morpholinyl)phenyl]-2-oxo-5-oxazolidinyl]-methyl] acetamide (Compound 11) and the general procedures of Example 1 was followed, the compounds of Examples 37, 38 and 39 respectively as set forth below in Table A were obtained. The isopropylcarboxamide and the cyclopropylcarboxamide are obtained by following the procedure in Example 5 of U.S. Pat. No. 5,688,792 only substituting isobutyric anhydride and cyclopropane carbonyl chloride respectively for acetic anhydride in step 7. The acetamide is obtained as described in U.S. Pat. No. 5,688,792 at Example 4.

When in the procedure of Example 5, step B, an excess amount of dimethylamine in THF is substituted for anhydrous ammonia, the compound of Example 40 set forth below in Table A is obtained.

TABLE A

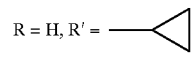

| Example No. | Compound | R, R' |
|---|---|---|
| 36 | (S)-N-[[3-[3-Fluoro-4-(4-morpholinyl)-phenyl]-2-oxo-5-oxazolidinyl]methyl]-O-ethylthiocarbamate; mp 120° C., MS(ES) m/z 384 (M + H$^+$). Anal. calcd for C$_{17}$H$_{22}$FN$_3$O$_4$S: C, 53.25; H, 5.78; N, 10.96. Found: C, 53.23; H, 5.82; N, 10.92. | R = H, R' = OC$_2$H$_5$ |
| 37 | (S)-N-[[3-[3-Fluoro-4-(4-morpholinyl)-phenyl]-2-oxo-5-oxazolidinyl]methyl]-2-methylpropanethioamide; mp 152–153° C. (dec.); Anal. calcd for C$_{18}$H$_{24}$FN$_3$O$_3$S: C, 56.67; H, 6.34; N, 11.02. Found: C, 56.58; H, 6.41; N, 10.81 | R = H, R' = CH(CH$_3$)$_2$ |
| 38 | (S)-N-[[3-[3-Fluoro-4-(4-morpholinyl)-phenyl]-2-oxo-5-oxazolidinyl]methyl]-cyclopropane-carbothioamide; mp 155–156° C.; Anal. calcd for C$_{18}$H$_{22}$FN$_3$O$_3$S: C, 56.98; H, 5.84; N, 11.07. Found: C, 56.98; H, 5.85; N, 10.97 | R = H, R' = ▷ (cyclopropyl) |
| 39 | (S)-N-[[3-[3,5-Difluoro-4-(4-morpholinyl)-phenyl]-2-oxo-5-oxazolidinyl]methyl]-thioacetamide | R = F, R' = CH$_3$ |
| 40 | (S)-N-[[3-[3-Fluoro-4-(4-morpholinyl)-phenyl]-2-oxo-5-oxazolidinyl]methyl]-N',N'-dimethylthiourea | R = H, R' = N(CH$_3$)$_2$ |

PREPARATION Z Methyl Dithiopropionate

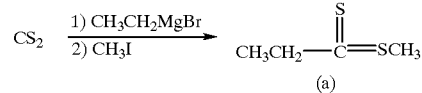

(a)

When in the procedure of Example 1 an appropriate amount of (S)-N-[[3-[3-fluoro-4-morpholinyl]phenyl]-2-

A stirred mixture of magnesium turnings (12.6 g, 0.520 g atom) and THF (100 mL) under nitrogen is treated with a crystal of iodine and about 5% of a solution of bromoethane (30.0 mL, 0.40 mol) in THF (200 mL). When the reaction starts, the remainder of the bromoethane solution is added, dropwise at a rate sufficient to maintain a gentle reflux. After the addition, stirring is continued for 1 hour; the resulting solution is cooled to −20° C. and treated, during 10 minutes with carbon disulfide (24.0 mL, 0.40 mol). The mixture is warmed to 15° C., treated with methyl iodide (28.0 mL, 0.45 mol) and kept at 60° C. for 1 hour. It is then cooled in an ice bath, treated with ice and extracted with $Et_2O$. The extract is washed with brine, dried ($MgSO_4$) and concentrated. Distillation of the residue gives 34.0 g of the titled product, bp 48–52° C. (12 mmHg).

The following methyl dithio compounds were obtained when the appropriate alkyl magnesium bromide was substituted for ethyl magnesium bromide in the above procedure:

The following methyl dithio compounds were obtained when the appropriate alkyl magnesium bromide was substituted for ethyl magnesium bromide in the above procedure:

TABLE B $$Rs-\overset{S}{\underset{\|}{C}}-SCH_3$$

Rs =

| | |
|---|---|
| (b) | $(CH_3)_2CH-$ |
| (c) | cyclopropyl |
| (d) | $CH_3CH_2CH_2-$ |
| (e) | $CH_3\underset{\underset{CH_3}{\|}}{CH}-CH_2-$ |
| (f) | $CH_3CH_2\underset{\underset{CH_3}{\|}}{CH}-$ |
| (g) | $(CH_3)_3C-CH_2-$ |

TABLE B-continued $$Rs-\overset{S}{\underset{\|}{C}}-SCH_3$$

Rs =

| | |
|---|---|
| (h) | cyclobutyl |
| (i) | cyclopentyl |
| (j) | cyclohexyl |
| (k) | cyclopropyl-$CH_2-$ |
| (l) | cyclobutyl-$CH_2-$ |
| (m) | cyclopentyl-$CH_2-$ |

When following the general procedure of Example 27, step 4, an appropriate amount of the amine listed below is reacted with the dithio compound listed below the respective compounds, Examples 41 to 61 of Table C are obtained.

When following the general procedure of Example 25, step 6, an appropriate amount of the amine listed below is reacted with the dithio compound listed below, the respective compounds, Examples 62 to 67, of Table C are obtained.

TABLE C

| Example No. | Compound | Amine | Dithio Compound (from Preparation Z) |
|---|---|---|---|
| 41 | (S)-N-[[3-[3-Fluoro-4-(4-thiomorpholinyl)-phenyl]-2-oxo-5-oxazolidinyl]methyl]-propanethioamide, thiomorpholine S-oxide; mp 196–197° C.; Anal. calcd for $C_{17}H_{22}FN_3O_3S_2$: C, 51.11; H, 5.55; N, 10.52; S, 16.05. Found: C, 50.99; H, 5.60; N, 10.55; S, 15.75 | [structure] | Z (a) |
| 42 | S)-N-[[3-[3-Fluoro-4-(4-thiomorpholinyl)-phenyl]-2-oxo-5-oxazolidinyl]methyl]-2-methylpropanethio-amide, thiomorpholine | Same as above | Z (b) |

TABLE C-continued

| Example No. | Compound | Amine | Dithio Compound (from Preparation Z) |
|---|---|---|---|
|  | S-oxide; mp 195–196° C.; Anal. calcd for $C_{18}H_{24}FN_3O_3S_2$: C, 52.28; H, 5.85; N, 10.16; S, 15.51. Found: C, 52.24; H, 5.97; N, 10.16; S, 15.28 |  |  |
| 43 | (S)-N-[[3-[3-Fluoro-4-(4-thiomorpholinyl)-phenyl]-2-oxo-5-oxazolidinyl]methyl]-cyclopropanecarbothio-amide, thiomorpholine S-oxide; mp 109–110° C.; Anal. calcd for $C_{18}H_{22}FN_3O_3S_2$: C, 52.54; H, 5.39; N, 10.21; S, 15.58. Found: C, 52.48; H, 5.51; N, 10.28; S, 15.29 | Same as above | Z (c) |
| 44 | (S)-N-[[3-[3-Fluoro-4-(4-thiomorpholinyl)-phenyl]-2-oxo-5-oxazolidinyl]methyl]-butanethioamide, thiomorpholine S-oxide | Same as above | Z (d) |
| 45 | (S)-N-[[3-[3-Fluoro-4-(4-thiomorpholinyl)-phenyl]-2-oxo-5-oxazolidinyl]methyl]-3-methylbutanethioamide, thiomorpholine S-oxide | Same as above | Z (e) |
| 46 | (S)-N-[[3-[3-Fluoro-4-(4-thiomorpholinyl)-phenyl]-2-oxo-5-oxazolidinyl]methyl]-2-methylbutanethioamide, thiomorpholine S-oxide | Same as above | Z (f) |
| 47 | (S)-N-[[3-[3-Fluoro-4-(4-thiomorpholinyl)-phenyl]-2-oxo-5-oxazolidinyl]methyl]-3,3-dimethylbutanethio-amide, thiomorpholine S-oxide | Same as above | Z (g) |
| 48 | (S)-N-[[3-[3-Fluoro-4-(4-thiomorpholinyl)-phenyl]-2-oxo-5-oxazolidinyl]methyl]-cyclobutanecarbothio-amide, thiomorpholine S-oxide | Same as above | Z (h) |
| 49 | (S)-N-[[3-[3-Fluoro-4-(4-thiomorpholinyl)-phenyl]-2-oxo-5-oxazolidinyl]methyl]-1-cyclopentanecarbothio-amide, thiomorpholine S-oxide | Same as above | Z (i) |
| 50 | (S)-N-[[3-[3-Fluoro-4-(4-thiomorpholinyl)-phenyl]-2-oxo-5-oxazolidinyl]methyl]-cyclohexanecarbothio-amide, thiomorpholine S-oxide | Same as above | Z (j) |
| 51 | (S)-N-[[3-[3-Fluoro-4-(4-thiomorpholinyl)-phenyl]-2-oxo-5-oxazolidinyl]methyl]-2-cyclopropylethanethio-amide, thiomorpholine S-oxide | Same as above | Z (k) |
| 52 | (S)-N-[[3-[3-Fluoro-4-(4-thiomorpholinyl)-phenyl]-2-oxo-5- | Same as above | Z (l) |

TABLE C-continued

| Example No. | Compound | Amine | Dithio Compound (from Preparation Z) |
|---|---|---|---|
| | oxazolidinyl]methyl]-2-cyclobutylethanethioamide, thiomorpholine S-oxide | | |
| 53 | (S)-N-[[3-[3-Fluoro-4-(4-thiomorpholinyl)-phenyl]-2-oxo-5-oxazolidinyl]methyl]-2-cyclopentylethanethioamide, thiomorpholine S-oxide | Same as above | Z (m) |
| 54 | (S)-N-[[3-[3,5-Difluoro-4-(4-thiomorpholinyl)-phenyl]-2-oxo-5-oxazolidinyl]methyl]-thioacetamide, thiomorpholine S-oxide | 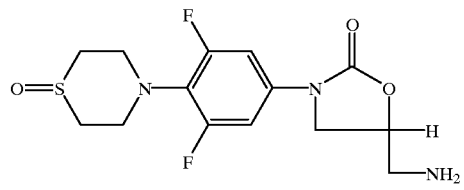 | Ethyl dithioacetate |
| 55 | (S)-N-[[3-[3,5-Difluoro-4-(4-thiomorpholinyl)-phenyl]-2-oxo-5-oxazolidinyl]methyl]-propanethioamide, thiomorpholine S-oxide | Same as above | Z (a) |
| 56 | (S)-N-[[3-[3,5-Difluoro-4-(4-thiomorpholinyl)-phenyl]-2-oxo-5-oxazolidinyl]methyl]-2-methylpropanethioamide, thiomorpholine S-oxide | Same as above | Z (b) |
| 57 | (S)-N-[[3-[3,5-Difluoro-4-(4-thiomorpholinyl)-phenyl]-2-oxo-5-oxazolidinyl]methyl]-cyclopropanecarbothioamide, thiomorpholine S-oxide | Same as above | Z (c) |
| 58 | (S)-N-[[3-[4-(4-thiomorpholinyl)-phenyl]-2-oxo-5-oxazolidinyl]methyl]-thioacetamide, thiomorpholine S-oxide | 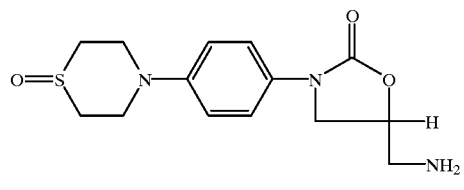 | Ethyl dithioacetate |
| 59 | (S)-N-[[3-[4-(4-thiomorpholinyl)-phenyl]-2-oxo-5-oxazolidinyl]methyl]-propanethioamide, thiomorpholine S-oxide | Same as above | Z (a) |
| 60 | (S)-N-[[3-[4-(4-thiomorpholinyl)-phenyl]-2-oxo-5-oxazolidinyl]methyl]-2-methylpropanethioamide, thiomorpholine S-oxide | Same as above | Z (b) |
| 61 | (S)-N-[[3-[4-(4-thiomorpholinyl)-phenyl]-2-oxo-5-oxazolidinyl]methyl]-cyclopropanecarbothioamide, thiomorpholine S-oxide | Same as above | Z (c) |

TABLE C-continued

| Example No. | Compound | Amine | Dithio Compound (from Preparation Z) |
|---|---|---|---|
| 62 | (S)-N-[[3-[3,5-Difluoro-4-(4-hydroxyacetyl)-1-piperazinyl]phenyl]-2-oxo-5-oxazolidinyl]methyl]propanethioamide | HOCH$_2$-C(=O)-N(piperazinyl)-N-(3,5-difluorophenyl)-oxazolidinone-CH$_2$NH$_2$ | Z (a) |
| 63 | (S)-N-[[3-[3,5-Difluoro-4-(4-hydroxyacetyl)-1-piperazinyl]phenyl]-2-oxo-5-oxazolidinyl]methyl]-2-methyl-propanethioamide | Same as above | Z (b) |
| 64 | (S)-N-[[3-[3,5-Difluoro-4-(4-hydroxyacetyl)-1-piperazinyl]phenyl]-2-oxo-5-oxazolidinyl]methyl]cyclopropane-thioamide | Same as above | Z (c) |
| 65 | (S)-N-[[3-[3-[4-(hydroxyacetyl)-1-piperazinyl]phenyl]-2-oxo-5-oxazolidinyl]methyl]propanethioamide | HOCH$_2$-C(=O)-N(piperazinyl)-N-phenyl-oxazolidinone-CH$_2$NH$_2$ | Z (a) |
| 66 | (S)-N-[[3-[3-[4-(hydroxyacetyl)-1-piperazinyl]phenyl]-2-oxo-5-oxazolidinyl]methyl]-2-methyl-propanethioamide | Same as above | Z (b) |
| 67 | (S)-N-[[3-[3-[4-(hydroxyacetyl)-1-piperazinyl]phenyl]-2-oxo-5-oxazolidinyl]methyl]cyclopropane-carbothioamide | Same as above | Z (c) |

When following the procedure of Example 28, step 3, an appropriate amount of the amine listed below is reacted with the dithio compound listed below, the respective compounds, Examples 68 to 78 of Table D are obtained.

TABLE D

| Example No. | Compound | Amine | Dithio Compound (from Preparation Z) |
|---|---|---|---|
| 68 | (S)-N-[[3-[3-Fluoro-4-(4-thiomorpholinyl)-phenyl]-2-oxo-5-oxazolidinyl]methyl]-propanethioamide, thiomorpholine S,S-dioxide | O$_2$S(thiomorpholinyl)-N-(3-fluorophenyl)-oxazolidinone-CH$_2$NH$_2$ | Z (a) |
| 69 | (S)-N-[[3-[3-Fluoro-4-(4-thiomorpholinyl)-phenyl]-2-oxo-5-oxazolidinyl]methyl]-2-methylpropanethioamide, thiomorpholine S,S-dioxide | Same as above | Z (b) |
| 70 | (S)-N-[[3-[3-Fluoro-4-(4-thiomorpholinyl)-phenyl]-2-oxo-5- | Same as above | Z (c) |

TABLE D-continued

| Example No. | Compound | Amine | Dithio Compound (from Preparation Z) |
|---|---|---|---|
| | oxazolidinyl]methyl]-cyclopropanecarbothioamide, thiomorpholine S,S-dioxide | | |
| 71 | (S)-N-[[3-[3,5-Difluoro-4-(4-thiomorpholinyl)-phenyl]-2-oxo-5-oxazolidinyl]methyl]thioacetamide, thiomorpholine S,S-dioxide | | Ethyl dithioacetate |
| 72 | (S)-N-[[3-[3,5-Difluoro-4-(4-thiomorpholinyl)-phenyl]-2-oxo-5-oxazolidinyl]methyl]-propanethioamide, thiomorpholine S,S-dioxide | Same as above | Z (a) |
| 73 | (S)-N-[[3-[3,5-Difluoro-4-(4-thiomorpholinyl)-phenyl]-2-oxo-5-oxazolidinyl]methyl]-2-methylpropanethioamide, thiomorpholine S,S-dioxide | Same as above | Z (b) |
| 74 | (S)-N-[[3-[3,5-Difluoro-4-(4-thiomorpholinyl)-phenyl]-2-oxo-5-oxazolidinyl]methyl]-cyclopropanecarbothioamide, thiomorpholine S,S-dioxide | Same as above | Z (c) |
| 75 | (S)-N-[[3-[4-(4-thio-morpholinyl)phenyl]-2-oxo-5-oxazolidinyl]-methyl]thioacetamide, thiomorpholine S,S-dioxide | | Ethyl dithioacetate |
| 76 | (S)-N-[[3-[4-(4-thio-morpholinyl)phenyl]-2-oxo-5-oxazolidinyl]-methyl]propanethioamide, thiomorpholine S,S-dioxide | Same as above | Z (a) |
| 77 | (S)-N-[[3-[4-(4-thio-morpholinyl)phenyl]-2-oxo-5-oxazolidinyl]-methyl]-2-methyl-propanethioamide, thiomorpholine S,S-dioxide | Same as above | Z (b) |
| 78 | (S)-N-[[3-[4-(4-thio-morpholinyl)phenyl]-2-oxo-5-oxazolidinyl]-methyl]cyclopropane-carbothioamide, thiomorpholine S,S-dioxide | Same as above | Z (c) |

When following the procedure of Example 26, an appropriate amount of the amine listed below is reacted with the dithio compound listed below the respective compounds, Examples 79 to 99 of Table E are obtained.

TABLE E

| Example No. | Compound | Amine | Dithio Compound (See Preparation Z) |
|---|---|---|---|
| 79 | (S)-N-[[3-[3-Fluoro-4-(4-thiomorpholinyl)-phenyl]-2-oxo-5-oxazolidinyl]methyl]-propanethioamide | [structure: thiomorpholinyl-fluorophenyl-oxazolidinone with CH₂NH₂ group] | Z (a) |
| 80 | (S)-N-[[3-[3-Fluoro-4-(4-thiomorpholinyl)-phenyl]-2-oxo-5-oxazolidinyl]methyl]-2-methylpropanethioamide | Same as above | Z (b) |
| 81 | (S)-N-[[3-[3-Fluoro-4-(4-thiomorpholinyl)-phenyl]-2-oxo-5-oxazolidinyl]methyl] cyclopropanecarbothioamide | Same as above | Z (c) |
| 82 | (S)-N-[[3-[3-Fluoro-4-(4-thiomorpholinyl) phenyl]-2-oxo-5-oxazolidinyl]methyl]-butanethioamide | Same as above | Z (d) |
| 83 | (S)-N-[[3-[3-Fluoro-4-(4-thiomorpholinyl)-phenyl]-2-oxo-5-oxazolidinyl]methyl]-3-methylbutanethioamide | Same as above | Z (e) |
| 84 | (S)-N-[[3-[3-Fluoro-4-(4-thiomorpholinyl)-phenyl]-2-oxo-5-oxazolidinyl]methyl]-2-methylbutanethioamide | Same as above | Z (f) |
| 85 | (S)-N-[[3-[3-Fluoro-4-(4-thiomorpholinyl)-phenyl]-2-oxo-5-oxazolidinyl]methyl]-3,3-dimethylbutanethioamide | Same as above | Z (g) |
| 86 | (S)-N-[[3-[3-Fluoro-4-(4-thiomorpholinyl)-phenyl]-2-oxo-5-oxazolidinyl]methyl]-cyclobutanecarbothioamide | Same as above | Z (h) |
| 87 | (S)-N-[[3-[3-Fluoro-4-(4-thiomorpholinyl)-phenyl]-2-oxo-5-oxazolidinyl]methyl]-cyclopentanecarbothioamide | Same as above | Z (i) |
| 88 | (S)-N-[[3-[3-Fluoro-4-(4-thiomorpholinyl)-phenyl]-2-oxo-5-oxazolidinyl]methyl]-cyclohexanecarbothioamide | Same as above | Z (j) |
| 89 | (S)-N-[[3-[3-5 Fluoro-4-(4-thiomorpholinyl)-phenyl]-2-oxo-5-oxazolidinyl]methyl]-2-cyclopropylethanethioamide | Same as above | Z (k) |
| 90 | (S)-N-[[3-[3-Fluoro-4-(4-thiomorpholinyl)-phenyl]-2-oxo-5-oxazolidinyl]methyl]-2-cyclobutylethanethioamide | Same as above | Z (l) |
| 91 | (S)-N-[[3-[3-Fluoro-4-(4-thiomorpholinyl)-phenyl]-2-oxo-5-oxazolidinyl]methyl]-2-cyclopentylethanethioamide | Same as above | Z (m) |

TABLE E-continued

| Example No. | Compound | Amine | Dithio Compound (See Preparation Z) |
|---|---|---|---|
| 92 | (S)-N-[[3-[3,5-Difluoro-4-(4-thiomorpholinyl)-phenyl]-2-oxo-5-oxazolidinyl]methyl]-thioacetamide | ![structure] | Ethyl dithioacetate |
| 93 | (S)-N-[[3-[3,5-Difluoro-4-(4-thiomorpholinyl)-phenyl]-2-oxo-5-oxazolidinyl]methyl]-propanethioamide | Same as above | Z (a) |
| 94 | (S)-N-[[3-[3,5-Difluoro-4-(4-thiomorpholinyl)-phenyl]-2-oxo-5-oxazolidinyl]methyl]-2-methylpropanethioamide | Same as above | Z (b) |
| 95 | (S)-N-[[3-[3,5-Difluoro-4-(4-thiomorpholinyl)-phenyl]-2-oxo-5-oxazolidinyl]methyl]-cyclopropanecarbothioamide | Same as above | Z (c) |
| 96 | (S)-N-[[3-[4-(4-thio-morpholinyl)phenyl]-2-oxo-5-oxazolidinyl]methyl]thioacetamide | ![structure] | Ethyl dithioacetate |
| 97 | (S)-N-[[3-[4-(4-thio-morpholinyl)phenyl]-2-oxo-5-oxazolidinyl]methyl]propanethioamide | Same as above | Z (a) |
| 98 | (S)-N-[[3-[4-(4-thio-morpholinyl)phenyl]-2-oxo-5-oxazolidinyl]methyl]-2-methyl-propanethioamide | Same as above | Z (b) |
| 99 | (S)-N-[[3-[4-(4-thio-morpholinyl)phenyl]-2-oxo-5-oxazolidinyl]methyl]cyclopropane-carbothioamide | Same as above | Z (c) |

The amine utilized in Examples 41 to 53 is prepared as described in Example 27, step 3. The amine utilized in Examples 54 to 57 is prepared by the procedure of Example 27, steps 1 to 3 by substituting the appropriate (S)-N-[[3-[3,5-difluoro4-(4-thio-morpholinyl)phenyl]-2-oxo-5-oxazolidinyl]methanol for compound 62 in step 1 of Example 27.

The amine utilized in Examples 58 to 61 is prepared by the procedure of Example 27, steps 1 to 3 by substituting the appropriate (S)-N-[[3-[4-(4-thiomorpholinyl)phenyl]-2-oxo-5-oxazolidinyl]methanol for compound 62 in Example 27, step 1. The appropriate oxazolidinyl methanol compound is obtained by following the procedure of Example 1 in U.S. Pat. No. 5,688,792, steps 1 through 3, only substituting 4-fluoronitrobenzene for 3,4-difluoronitrobenzene in step 1 thereof.

The amine utilized in Examples 62 to 64 is prepared as compound 37 in Example 29 from the amide, 65, which is prepared as described in Example 32 of U.S. Pat. No. 5,700,799. The amine utilized in Examples 65 to 67 is prepared by the general procedure of Example 29 from the following amide, the preparation of which is decribed in Example 3 of U.S. Pat. No. 5,700,799:

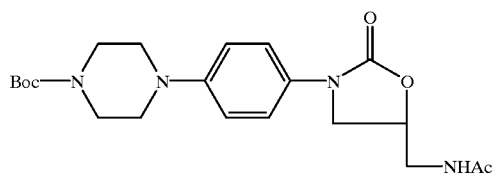

The amine utilized in Examples 68 to 70 is prepared as described in step 2 of Example 28 above.

The amine utilized in Examples 71 to 74 is prepared as described in Example 28 by substituting (S)-N-[[3-[3,5-difluoro-4-(4-thiomorpholinyl)phenyl]-2-oxo-5-oxazolidinyl]methanol for compound 62 in step I and following the procedure of steps 1 and 2. The appropriate oxazolidinyl methanol compound is prepared by following the general procedure of Example 4 of U.S. Pat. No. 5,688,792, steps 1 through 4, only substituting thiomorpholine for morpholine in step 1 thereof.

The amine utilized in Examples 75 to 78 is prepared as described in Example 28, step 1, above by substituting (S)-N-[3-[4-(4-thiomorpholinyl)phenyl]-2-oxo-5-oxazolidinyl]methanol for compound 62 in step 1. The appropriate oxazolidinyl methanol is obtained by following the procedure of Example 1 in U.S. Pat. No. 5,688,792, steps 1 through 3, only substituting 4-fluoronitrobenzene for 3,4-difluoronitrobenzene in step 1 thereof.

The amine utilized in Examples 79 to 91 is prepared as described in Example 1, step 4, of U.S. Pat. No. 5,688,792. The amine utilized in Examples 92 to 95 is prepared as described in Example 4 of U.S. Pat. No. 5,688,792 only substituting thiomorpholine for morpholine in step 1 thereof. The amine utilized in Examples 96 to 99 is prepared by the procedure of Example 1 of U.S. Pat. No. 5,688,792, only substituting 4-fluoronitro-benzene for 3,4-difluoronitrobenzene in step 1 thereof.

EXAMPLE 100
(S)-N-[[3-[3-Fluoro-4-(4-thiomorpholinyl)phenyl]-2-oxo-5-oxazolidinyl]methyl]-O-methylthiocarbamate, thiomorpholine S-oxide

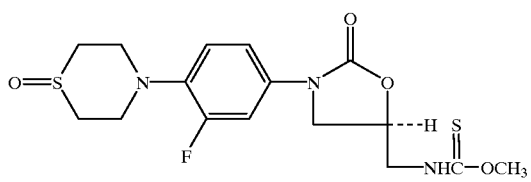

A solution of 201 mg (0.554 mmol) of (S)-N-[[3-[3-fluoro-4-(4-thiomorpholinyl)-phenyl]-2-oxo-5-oxazolidinyl]methyl]isothiocyanate, thiomorpholine s-oxide compound 82 from Example 33, step 1, in methanol (10 mL) is refluxed, under nitrogen for 18 hours and cooled. The solid is collected by filtration to give 0.138 g of the titled product. m.p. 208–209° C.; Anal. calcd for $C_{16}H_{20}FN_3O_4S_2$: C, 47.87; H, 5.02; N, 10.47. Found: C, 47.81; H, 5.04: N, 10.49.

When in the procedure of Example 100 the thioisocyanate listed below is substituted for compound 82 the products listed below as Examples 101 to 109 are obtained.

TABLE F

Isothiocyanate

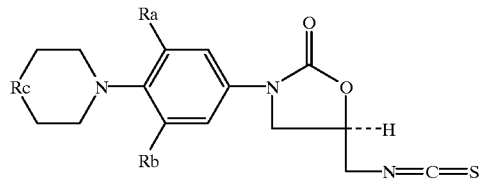

| Rc | Ra | Rb | Example No. | Compound |
|---|---|---|---|---|
| OS | F | F | 101 | (S)-N-[[3-[3,5-Difluoro-4-(4-thiomorpholinyl)-phenyl]-2-oxo-5-oxazolidinyl]methyl]-O-methylthiocarbamate, thiomorpholine S-oxide |
| OS | H | H | 102 | (S)-N-[[3-[4-(4-thiomorpholinyl)phenyl]-2-oxo-5-oxazolidinyl]methyl]-O-methylthiocarbamate, thiomorpholine S-oxide |
| $O_2S$ | H | F | 103 | (S)-N-[[3-[3-Fluoro-4-(4-thiomorpholinyl)phenyl]-2-oxo-5-oxazolidinyl]methyl]-O-methylthiocarbamate, thiomorpholine S,S-dioxide |
| $O_2S$ | F | F | 104 | (S)-N-[[3-[3,5-Difluoro-4-(4-thiomorpholinyl)-phenyl]-2-oxo-5-oxazolidinyl]methyl]-O-methylthiocarbamate, thiomorpholine S,S-dioxide |
| $O_2S$ | H | H | 105 | (S)-N-[[3-[4-(4-thiomorpholinyl)phenyl]-2-oxo-5-oxazolidinyl]methyl]-O-methyithiocarbamate, thiomorpholine S,S-dioxide |
| S | H | F | 106 | (S)-N-[[3-[3-Fluoro-4-(4-thiomorpholinyl)-phenyl]-2-oxo-5-oxazolidinyl]methyl]-O-methyl-thiocarbamate |
| S | F | F | 107 | (S)-N-[[3-[3,5-Difluoro-4-(4-thiomorpholinyl)-phenyl]-2-oxo-5-oxazolidinyl]methyl]-O-methyl-thiocarbamate |
| S | H | H | 108 | (S)-N-[[3-[4-(4-thiomorpholinyl)phenyl]-2-oxo-5-oxazolidinyl]methyl]-O-methylthiocarbamate |
| $HOCH_2\overset{O}{\overset{\|}{C}}N$ | H | H | 109 | (S)-N-[[3-(3-Fluoro-4-(4-(hydroxyacetyl)-1-piperazinyl]phenyl]-2-oxo-5-oxazolidinyl]methyl]-O-methylthiocarbamate |

EXAMPLE 110

(S)-N-[[3-[3-Fluoro-4-(4-thiomorpholinyl)phenyl]-2-oxo-5-oxazolidinyl]methyl]-O-ethylthiocarbamate, thiomorpholine S-oxide. m.p. 198–199° C.; Anal. calcd for $C_{17}H_{22}FN_3O_4S_2$: C, 49.14; H, 5.34; N, 10.11. Found: C, 49.06; H, 5.27; N, 10.10.

EXAMPLE 111

(S)-N-[[3-[3-Fluoro-4-(4-thiomorpholinyl)phenyl]-2-oxo-5-oxazolidinyl]methyl]-O-isopropylthiocarbamate, thiomorpholine S-oxide. m.p. 180–181° C.; Anal. calcd for $C_{18}H_{24}FN_3O_4S_2$: C, 50.33; H, 5.63; N, 9.78. Found: C, 50.29; H, 5.69; N, 9.82.

When in the procedure of Example 114 an appropriate amount of (S)-N-[[3-[3-fluoro-4-(4-thiomorpholinyl)phenyl]-2-oxo-5-oxazolidinyl]isothiocyanate is substituted for compound 82 and ethanol or isopropyl alcohol is substituted for methanol, the following respective products are obtained:

EXAMPLE 112

(S)-N-[[3-[3-Fluoro-4-(4-thiomorpholinyl)phenyl]-2-oxo-5-oxazolidinyl]methyl]-O-ethylthiocarbamate

EXAMPLE 113

(S)-N-[[3-[3-Fluoro-4-(4-thiomorpholinyl)phenyl]-2-oxo-5-oxazolidinyl]methyl]-O-iso-propylthiocarbamate

EXAMPLE 114

(S)-N-[[3-[3-Fluoro-4-(4-thiomorpholinyl)phenyl]-2-oxo-5-oxazolidinyl]methyl]-N-methylthiourea, thiomorpholine S-oxide A stirred suspension of 240 mg (0.650 mmol) of compound 82 from Example 33, step 1 in THF (5 mL) at 0° C. is treated with a 2M solution of methylamine in THF (0.42 mL, 0.845 mmol) and kept at ambient temperature for 18 hours. The solid is collected by filtration to give 0.221 g of the titled product.

Following the procedure of Example 114, only substituting an appropriate amount of dimethylamine and azetidine for methylamine, the following compounds are obtained:

EXAMPLE 115

(S)-N-[[3-[3-Fluoro-4-(4-thiomorpholinyl)phenyl]-2-oxo-5-oxazolidinyl]methyl]-N',N'-dimethylthiourea, thiomorpholine S-oxide; Anal. Calcd for $C_{17}H_{23}FN_4O_3S_2$, C, 49.26; H, 5.59; N, 13.52. Found C, 49.11; H, 5.57; N, 13.40; mp 180–182° C.

EXAMPLE 116

(S)-N-[[3-[3-Fluoro-4-(4-thiomorpholinyl)phenyl]-2-oxo-5-oxazolidinyl]methyl]-1-azetidinecarbothioamide, thiomorpholine S-oxide; Anal. Calcd for $C_{18}H_{23}FN_4O_3S_2$, C, 50.69; H, 5.43; N, 13.14. Found: C, 50.79; H, 5.45; N, 12.82; mp 213–214° C.

When in the procedure of Example 114 an appropriate amount of (S)-N-[[3-[3-fluoro-4-(4-thiomorpholinyl)phenyl]-2-oxo-5-oxazolidinyl]methyl]isothiocyanate is substituted for compound 82, the following compound is obtained:

EXAMPLE 117

(S)-N-[[3-[3-Fluoro-4-(4-thiomorpholinyl)phenyl]-2-oxo-5-oxazolidinyl]methyl]methyl-N'-methylthiourea When in the procedure of Example 117 an appropriate amount of dimethylamine and azetidine are substituted for methylamine, the following respective products are obtained:

EXAMPLE 118

(S)-N-[[3-[3-Fluoro-4-(4-thiomorpholinyl)phenyl]-2-oxo-5-oxazolidinyl]methyl]-N',N'-dimethylthiourea

EXAMPLE 119

(S)-N-[[3-[3-Fluoro-4-(4-thiomorpholinyl)phenyl]-2-oxo-5-oxazolidinyl]methyl]-1-azetidinecarbothioamide When in the procedure of Example 33 an appropriate amount of compound 31 from Example 26 is substituted for compound 33 and the general procedure of steps 1 and 2 of Example 33 are followed, the following compound is obtained.

EXAMPLE 120

(S)-N-[[3-[3-Fluoro-4-(4-thiomorpholinyl)phenyl]-2-oxo-5-oxazolidinyl]methyl]thiourea

EXAMPLE 121

(S)-N-[[3-[3-Fluoro-4-[4-(hydroxyacetyl)-1-piperazinyl]phenyl-2-oxo-5-oxazolidinyl]methyl]propanethioamide

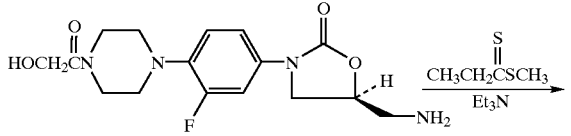

29

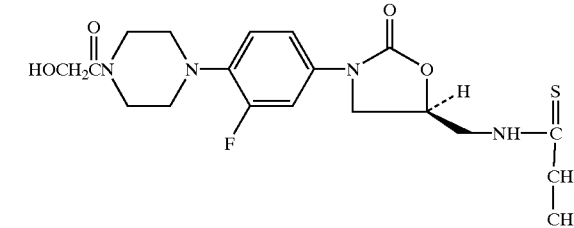

A stirred mixture of 200 mg (0.514 mmol) of 29 methyl dithiopropionate (247 mg, 2.06 mmol), triethylamine (0.58 mL, 4.11 mmol), THF (5.4 mL) and methylene chloride (5.4 mL) is kept, under nitrogen, for 3 days, diluted with water and extracted with methylene chloride. The extracts are dried (MgSO$_4$) and concentrated. Chromatography of the residue on silica gel and crystallization of the product from methanol gives 0.132 g of the titled product. m.p. 190–191°

C.; Anal. calcd for $C_{19}H_{25}FN_4O_4S$: C, 53.76; H, 5.94; N, 13.20; S, 7.55. Found: C, 53.66; H, 5.94; N, 13.20; S, 7.37.

above for methyl dithiopropionate, the following compounds are obtained.

TABLE G

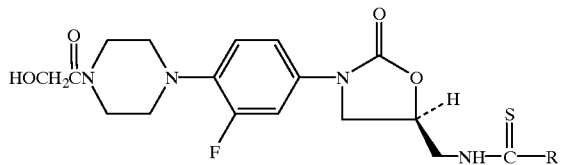

| Example No. | Compound | |
|---|---|---|
| 122 | (S)-N-[[3-[3-fluoro-4-[4-(hydroxyacetyl)-1-piperazinyl)phenyl]-2-oxo-5-oxazolidinyl]-methyl]-2-methylpropanethioamide; Anal. calcd for $C_{20}H_{27}FN_4O_4S$: C, 54.78; H, 6.21; N, 12.78; S, 7.31. Found: C, 54.67; H, 6.34; N, 12.41; S, 7.15 | R = CH(CH₃)₂ |
| 123 | (S)-N-[[3-[3-Fluoro-4-[4-(hydroxyacetyl)-1-piperazinyl]phenyl]-2-oxo-5-oxazolidinyl]-methyl]cyclopropanecarbothioamide; mp 179–181° C.; Anal. calcd for $C_{20}H_{25}FN_4O_4S$: C, 55.03; H, 5.77; N, 12.84; S, 7.34. Found: C, 55.15; H, 5.72; N, 12.76; S, 7.09 | R = cyclopropyl |
| 124 | (S)-N-[[3-[3-Fluoro-4-[4-(hydroxyacetyl)-1-piperazinyl]phenyl]-2-oxo-5-oxazolidinyl]-methyl]butanethioamide | R = CH₂—CH₂—CH₃ |
| 125 | (S)-N-[[3-[3-Fluoro-4-[4-(hydroxyacetyl)-1-piperazinyl]phenyl]-2-oxo-5-oxazolidinyl]-methyl]-3-methylbutanethioamide | R = CH₂—CH(CH₃)—CH₃ |
| 126 | (S)-N-[[3-[3-Fluoro-4-[4-(hydroxyacetyl)-1-piperazinyl]phenyl]-2-oxo-5-oxazolidinyl]-methyl]-2-methylbutanethioamide | R = CH(CH₃)—CH₂—CH₃ |
| 127 | (S)-N-[[3-[3-Fluoro-4-[4-(hydroxyacetyl)-1-piperazinyl]phenyl]-2-oxo-5-oxazolidinyl]-methyl]-3,3-dimethylbutanethioamide | R = CH₂—C(CH₃)₃ |
| 128 | (S)-N-[[3-[3-Fluoro-4-[4-(hydroxyacetyl)-1-piperazinyl]phenyl]-2-oxo-5-oxazolidinyl]-methyl]cyclobutanecarbothioamide | R = cyclobutyl |
| 129 | (S)-N-[[3-[3-Fluoro-4-[4-(hydroxyacetyl)-1-piperazinyl]phenyl]-2-oxo-5-oxazolidinyl]-methyl]cyclopentanecarbothioamide | R = cyclopentyl |
| 130 | (S)-N-[[3-[3-Fluoro-4-[4-(hydroxyacetyl)-1-piperazinyl]phenyl]-2-oxo-5-oxazolidinyl]-methyl]cyclohexanecarbothioamide | R = cyclohexyl |
| 131 | (S)-N-[[3-[3-Fluoro-4-[4-(hydroxyacetyl)-1-piperazinyl]phenyl]-2-oxo-5-oxazolidinyl]-methyl]-2-cyclopropylethanethioamide | R = CH₂—cyclopropyl |
| 132 | (S)-N-[[3-[3-Fluoro-4-[4-(hydroxyacetyl)-1-piperazinyl]phenyl]-2-oxo-5-oxazolidinyl]-methyl]-2-cyclobutylethanethioamide | R = CH₂—cyclobutyl |
| 133 | (S)-N-[[3-[3-Fluoro-4-[4-(hydroxyacetyl)-1-piperazinyl]phenyl]-2-oxo-5-oxazolidinyl]-methyl]-2-cyclopentylethanethioamide | R = CH₂—cyclopentyl |

Following the procedure of Example 121 only substituting dithio compounds Z(b) to Z(m) from Preparation Z When in the procedure of Example 100 an appropriate amount of compound 80 from Example 31 is substituted for compound 82, and ethanol or isopropyl alcohol is substituted for methanol, the following respective compounds are obtained:

EXAMPLE 134

(S)-N-[[3-[3-Fluoro-4-[4-(hydroxyacetyl)-1-piperazinyl]phenyl]-2-oxo-5-oxazolidinyl]methyl]-O-ethylthiocarbamate

EXAMPLE 135

(S)-N-[[3-[3-Fluoro-4-[4-(hydroxyacetyl)-1-piperazinyl]phenyl]-2-oxo-5-oxazolidinyl]methyl]-O-iso-propylthiocarbamate

EXAMPLE 136

(S)-N-[[3-[3-Fluoro-4-[4-(hydroxyacetyl)-1-piperazinyl]phenyl]-2-oxo-5-oxazolidinyl]methyl]-N'-methylthiourea When in the procedure of Example 114 an appropriate amount of compound 80 from Example 31 is substituted for compound 82, the title compound is obtained.

Following the procedure of Example 114 only substituting an appropriate amount of compound 80 from Example 31 for compund 82 and substituting an appropriate amount of dimethylamine and azetidine for methylamnine, the following compounds, Examples 137 and 138, are obtained:

EXAMPLE 137
(S)-N-[[3-[3-Fluoro-4-[4-(hydroxyacetyl)-1-piperazinyl]phenyl]-2-oxo-5-oxazolidinyl]methyl]-N',N'-dimethylthiourea
EXAMPLE 138
(S)-N-[[3-[3-Fluoro-4-[4-(hydroxyacetyl)-1-piperazinyl]phenyl]-2-oxo-5-oxazolidinyl]methyl]-1-azetidinecarbothioamide
EXAMPLE 139
(S)-N-[[3-[3,5-Difluoro-4-[4-(hydroxyacetyl)-1-piperazinyl]phenyl]-2-oxo-5-oxazolidinyl]methyl]-O-methylthiocarbamate
Part A: Following the procedure of Example 33, step 1, only substituting an appropriate amount of compound 37from Example 29, step 5, for compound 33, (S)-N-[[3,5-[3-difluoro-4-[4-(hydroxyacetyl)-1-piperazinyl]phenyl]-2-oxo-5-oxazolidinyl]-methyl]isothiocyanate is obtained.

Part B: Upon substitution of an appropriate amount of (S)-N-[[3-[3,5-difluoro-4-[4-(hydroxyacetyl)-1-piperazinyl]phenyl]-2-oxo-5-oxazolidinyl]methyl]isothiocyanate for compound 82 in the general procedure of Example 100, the title compound is obtained.

EXAMPLE 140

(S)-N-[[3-[4-[4-(hydroxyacetyl)-1-piperazinyl]phenyl]-2-oxo-5-oxazolidinyl]methyl]-O-methylthiocarbamate Part A: Following the procedure of Example 33, step 1, only substituting an appropriate amount of (S)-N-[[3-[4-[4-hydroxyacetyl)-1-piperazinyl]phenyl]-2-oxo-5-oxazolidinyl]methyl]amine for compound 33, (S)-N-[[3-[4-[4(hydroxyacetyl)-1-piperainyl]phenyl]-2-oxo-5-oxazolidinyl]methyl]isothiocyanate is obtained.

Part B: Upon substituting an appropriate amount of (S)-N-[[3-[4-[4-(hydroxy-acetyl)-1-piperazinyl]phenyl]-2-oxo-5-oxazolidinyl]methyl]isothiocyanate for compound 82 in the general procedure of Example 100, the title compound is obtained.

EXAMPLE 141

(S)-N-[[3-Fluoro-4-(4-acetyl-1-piperazinyl)phenyl]-2-oxo-5-oxazolidinyl]methyl]thioacetamide Step 1

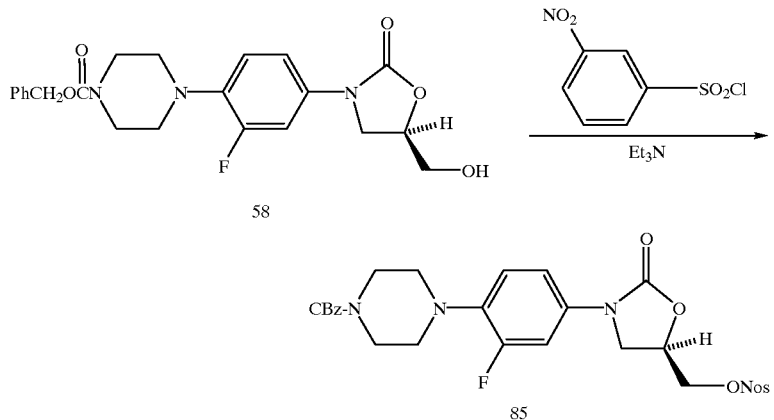

58

85

An ice cold, stirred solution of 30.4 g (70.8 mmol) of starting material 58 from Example 25, step 1), and triethylamine (15.4 mL, 110 mmol) in methylene chloride (2570 mL) is treated with m-nitrobenzenesulfonyl chloride (18.8 g, 84.9 mmol) and kept, under nitrogen, at ambient temperature (24° C.) for 24 hours. Additional m-nitrobenzenesulfonyl chloride (1.88 g) and triethylamine (1.54 mL) are added and the mixture is kept for one additional day at ambient temperature, washed with water, saturated sodium bicarbonate and brine, dried ($Na_2SO_4$) and concentrated to give an oily product, 85. The alcohol, 58 is prepared according to the procedures of Brickner (J. Med. Chem. 1996, 39, 673–679), see compound 5a therein.

Step 2

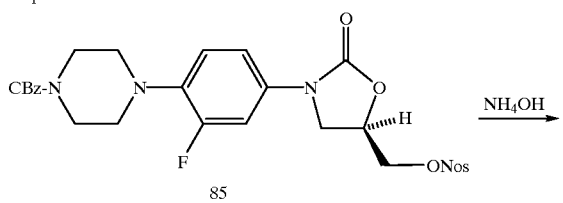

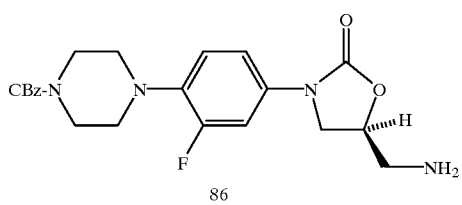

A stirred mixture of 85, acetonitrile (1270 mL), isopropanol (1270 mL) and ammonium hydroxide (1270 mL) is kept at ambient temperature for 3 days and concentrated in vacuo. Chromatography of the residue on silica gel with 0.5% NH$_4$OH-1% MeOH—CH$_2$Cl$_2$ gives 22.4 g of the amine, 86.

Step 3

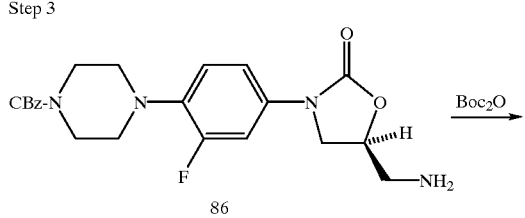

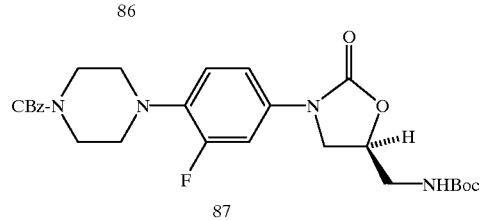

An ice cold, stirred solution of the amine 86 in THF (650 mL) is treated, during 20 mintues with a solution of di-tert-butyl dicarbonate (12.0 g, 55.2 mmol) in THF (90 mL). The mixture is kept at ambient temperature for 18 hours and concentrated in vacuo. The residue, dissolved in methylene chloride, is washed with dilute sodium bicarbonate, dried (MgSO$_4$) and concentrated. Crystallization of the residue from methanol-ethyl acetate gives 20.0 g of the Boc protected amine. Additional product (4.1 g) is obtained by chromatographing the mother liquors on silica gel with 1–2% methanol-methylene chloride.

Step 4

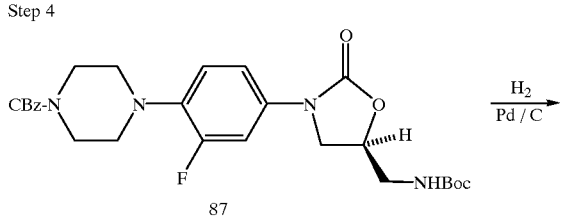

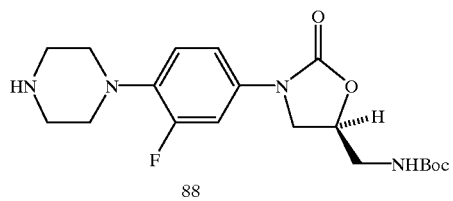

A solution of the protected amine, 87, (5.00 g, 9.46 mmol) in ethanol (150 mL) is treated with 10% palladium-on-carbon catalyst (1.0 g) and hydrogenated at an initial pressure of 30 psi for 3 hours. The catalyst is removed by filtration through Celite and the filtrate was concentrated to give 3.66 g of compound 88.

Step 5

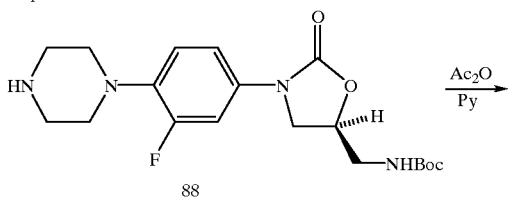

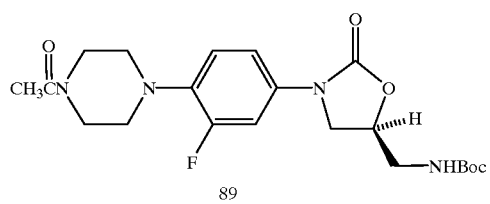

A stirred solution of compound 88 (1.10 g, 2.79 mmol) in pyridine (10 mL) is treated with acetic anhydride (289 µL, 3.07 mmol), kept at ambient temperature for 2 hours and concentrated in vacuo. A solution of the residue in methylene chloride is washed with dilute hydrochloric acid, dried (MgSO$_4$) and concentrated to give 1.23 g of compound 89: MS m/z 436 (M$^+$).

Step 6

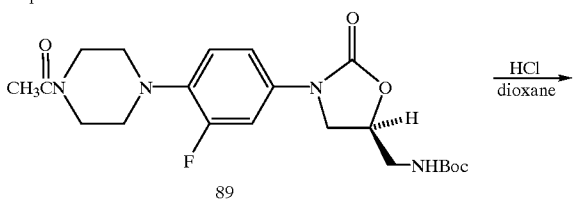

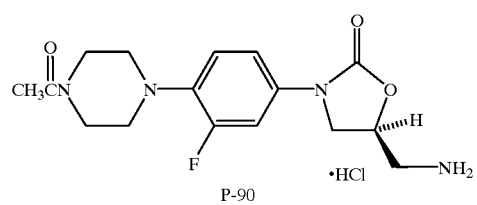

An ice cold, stirred 4N solution of HCl in dioxane (10 mL) is treated with compound 89 (1.10 g, 2.52 mmol). The mixture is kept in the ice bath for 30 minutes and at ambient temperature for 1 hour. It was then mixed with methylene chloride and concentrated. The residue is triturated with methylene chloride to give 1.03 g of the amine hydrochloride.

Step 7

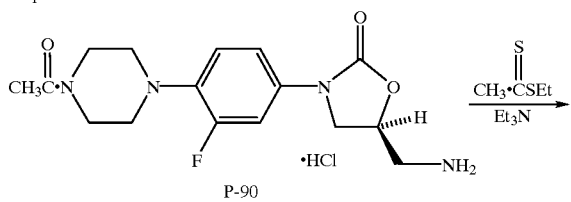

P-90

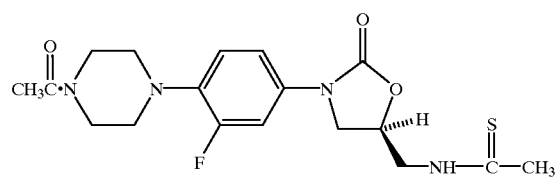

A stirred mixture of compound P-90 (250 mg), triethylamine (0.75 mL, 5.36 mmol), to ethyl dithioacetate (307 μL, 2.68 mmol), methylene chloride (7.4 mL) and THF (7.4 mL) is kept at ambient temperature for 1 day, concentrated and chromatographed on silica gel with mixtures of methanol-methylene chloride containing 1–2% methanol. Crystallization of the product from ethyl acetate-heptane gives 0.160 g of the titled product: Anal. calcd for $C_{18}H_{23}FN_4O_3S$: C, 54.81; H, 5.88; N, 14.20; S, 8.13. Found: C, 54.92; H, 5.95; N, 14.08; S, 7.94; mp 158° C.

When in the general procedure of Example 141 an appropriate amount of x

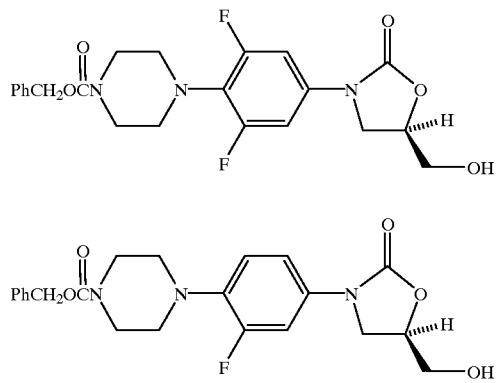

y is substituted for compound 58 and the procedure of steps 1 through 6 are followed, the respective amine compounds P-91 and P-92 listed below are obtained:

P-91

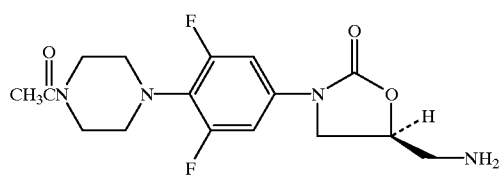

-continued

P-92

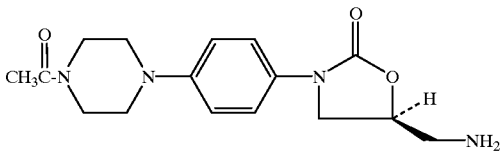

The alcohols above designated as x and y are prepared according to the procedures of Brickner (J. Med. Chem., 1996, 39, 673–679), by substituting an appropriate amount of 2,6-difluoro-4-nitrobenzene (trifluoromethane) sulfonate and 4-fluoronitrobenzene respectively for 3,4-difluoronitrobenzene in the preparation of 2a therein.

When in the procedure of Example 141 an appropriate amount of x or y is substituted for compound 58 and the procedures of steps 1 through 4 are followed, the following Boc protected compounds listed below are obtained.

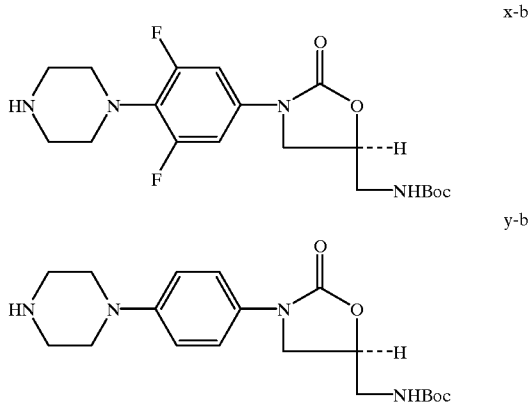

When in the procedure of Example 141, step 5, an appropriate amount of compound 88, compound x-b or compound y-b is treated with the reagent listed below and the general procedures of step 5 and step 6 are followed, the amines listed below as Preparation P-93 through P-128 are obtained.

The amine compound set forth below as P-129 is obtained by refluxing for 6 days a solution of compound 88 (1.00 g, 2.54 mmol), sulfamide (305 mg, 3.18 mmol) and 1,2-dimethyoxyethane (6 mL). The solid which precipitates is collected by filtration and chromatographed on silica gel with 5% methanol-methylene chloride. Crystallization of the product from methanol-methylene chloride gives 0.551 g of the sulfamoyl derivative, which is used in step 6 of Example 141 to give P-129. When compounds x-b and y-b are substituted for compound 88 and this general procedure is followed, Preparations P-130 and P-131 respectively set forth below are obtained.

Following the general procedures of steps 5 and 6 of Example 141 only in step 5 substituting chloroacetonitrile or 2-fluoroethyl bromide respectively for acetic anhydride and using potassium carbonate in acetonitrile, and using either compound 88, compound x-b or compound y-b, the respective amines set forth below as Preparations P-132 to P-137 are obtained.

The amine compound set forth below as Preparation P-138 is obtained by combining compound 88 (1.10 g, 2.75 mmol) set forth in step 5 of Example 141 with N-formylbenzotriazole (493 mg, 3.35 mmol) in THF (30 mL) and the mixture is kept at ambient temperature for 18 hours. The mixture is concentrated and the residue in methylene chloride is washed with 1N sodium hydroxide and dilute sodium chloride, dried (MgSO$_4$), concentrated, and chromatographed on silica gel with mixtures of methanol and methylene chloride containing 1–2% methanol to give 1.09 g of the N-formyl derivative which is utilized in the general procedure of step 6 of Example 141 to give Preparation P-138. When in this foregoing procedure compound x-b or compound y-b is substituted for compound 88, Preparations P-139 and and P-140 as set forth below are obtained.

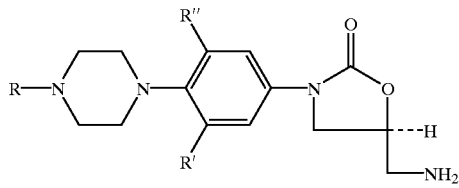

| Reagent | Boc Compound | R | R" | R' | Preparation No. |
|---|---|---|---|---|---|
| methoxyacetylchloride | 88 | CH$_3$OCH$_2$C(O)— | H | F | P-93 |
| | x-b | | F | F | P-94 |
| | y-b | | H | H | P-95 |
| cyanoacetyl chloride | 88 | NCCH$_2$C(O)— | H | F | P-96 |
| | x-b | | F | F | P-97 |
| | y-b | | H | H | P-98 |
| acetoxyacetyl chloride | 88 | CH$_3$C(O)—O—CH$_2$C(O)— | H | F | P-99 |
| | x-b | | F | F | P-100 |
| | y-b | | H | H | P-101 |
| benzyloxyacetyl chloride | 88 | PhCH$_2$OCH$_2$C(O)— | H | F | P-102 |
| | x-b | | F | F | P-103 |
| | y-b | | H | H | P-104 |
| methyl chloroformate | 88 | CH$_3$OC(O)— | H | F | P-105 |
| | x-b | | F | F | P-106 |
| | y-b | | H | H | P-107 |
| methanesulfonyl chloride | 88 | CH$_3$SO$_2$— | H | F | P-108 |
| | x-b | | F | F | P-109 |
| | y-b | | H | H | P-110 |
| ethanesulfonyl chloride | 88 | CH$_3$CH$_2$SO$_2$— | H | F | P-111 |
| | x-b | | F | F | P-112 |
| | y-b | | H | H | P-113 |
| chloromethanesulfonyl chloride | 88 | ClCH$_2$SO$_2$— | H | F | P-114 |
| | x-b | | F | F | P-115 |
| | y-b | | H | H | P-116 |
| cyanomethanesulfonyl chloride | 88 | NCCH$_2$SO$_2$— | H | F | P-117 |
| | x-b | | F | F | P-118 |
| | y-b | | H | H | P-119 |
| N-methylsulfamoyl chloride | 88 | CH$_3$NHSO$_2$— | H | F | P-120 |
| | x-b | | F | F | P-121 |
| | y-b | | H | H | P-122 |
| N,N-dimethylsulfamoyl chloride | 88 | (CH$_3$)$_2$NSO$_2$— | H | F | P-123 |
| | x-b | | F | F | P-124 |
| | y-b | | H | H | P-125 |
| ethyl chloroformate | 88 | CH$_3$CH$_2$OC(O)— | H | F | P-126 |
| | x-b | | F | F | P-127 |
| | y-b | | H | H | P-128 |
| sulfamide | 88 | H$_2$NSO$_2$— | H | F | P-129 |
| | x-b | | F | F | P-130 |
| | y-b | | H | H | P-131 |
| chloroacetonitrile | 88 | NCCH$_2$— | H | F | P-132 |
| | x-b | | F | F | P-133 |
| | y-b | | H | H | P-134 |
| 2-fluoroethyl bromide | 88 | FCH$_2$CH$_2$— | H | F | P-135 |
| | x-b | | F | F | P-136 |
| | y-b | | H | H | P-137 |

-continued

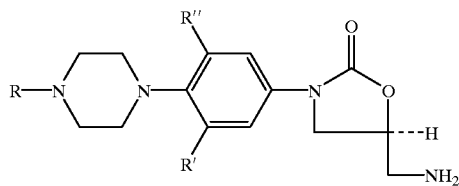

| Reagent | Boc Compound | R | R" | R' | Preparation No. |
|---|---|---|---|---|---|
| N-formylbenzotriazole | 88 | O‖HC— | H | F | P-138 |
|  | x-b |  | F | F | P-139 |
|  | y-b |  | H | H | P-140 |

EXAMPLES 142–161

When following the general procedures of Example 141, step 7, an appropriate amount of the amine listed below and the dithio compound from Preparation Z listed below are utilized, the respective products designated as Examples 142 to 400 in Table H are obtained.

TABLE H

| Example No. | Product | Amine | Dithio Compound |
|---|---|---|---|
| 142 | (S)-N-[[3-[3-Fluoro-4-(4-acetyl-1-piperazinyl)phenyl]-2-oxo-5-oxazolidinyl]methyl]propanethioamide; mp 161–162° C.; Anal. calcd for C$_{19}$H$_{25}$FN$_4$O$_3$S: C, 55.87; H, 6.17; N, 13.72; S, 7.85. Found: C, 55.79; H, 6.26; N, 13.60; S, 7.71 | P-90 | Z (a) |
| 143 | (S)-N-[[3-[3-Fluoro-4-(4-acetyl-1-piperazinyl)phenyl]-2-oxo-5-oxazolidinyl]methyl]-2-methylpropanethioamide | P-90 | Z (b) |
| 144 | (S)-N-[[3-[3-Fluoro-4-(4-acetyl-1-piperazinyl)phenyl]-2-oxo-5-oxazolidinyl]methyl]cyclopropanecarbothioamide; mp 159–160° C.; Anal. calcd for C$_{20}$H$_{25}$FN$_4$O$_3$S: C, 57.13; H, 5.99; N, 13.32; S, 7.62. Found: C, 57.05; H, 6.01; N, 13.15; S, 7.45. | P-90 | Z (c) |
| 145 | (S)-N-[[3-[3-Fluoro-4-(4-acetyl-1-piperazinyl)phenyl]-2-oxo-5-oxazolidinyl]methyl]butanethioamide | P-90 | Z (d) |
| 146 | (S)-N-[[3-[3-Fluoro-4-(4-acetyl-1-piperazinyl)phenyl]-2-oxo-5-oxazolidinyl]methyl]-3-methylbutanethioamide | P-90 | Z (e) |
| 147 | (S)-N-[[3-[3-Fluoro-4-(4-acetyl-1-piperazinyl)phenyl]-2-oxo-5-oxazolidinyl]methyl]-2-methylbutanethioamide | P-90 | Z (f) |
| 148 | (S)-N-[[3-[3-Fluoro-4-(4-acetyl-1-piperazinyl)phenyl]-2-oxo-5-oxazolidinyl]methyl]-3,3-dimethylbutanethioamide | P-90 | Z (g) |
| 149 | (S)-N-[[3-[3-Fluoro-4-(4-acetyl-1-piperazinyl)phenyl]-2-oxo-5-oxazolidinyl]methyl]cyclobutanecarbothioamide | P-90 | Z (h) |
| 150 | (S)-N-[[3-[3-Fluoro-4-(4-acetyl-1-piperazinyl)phenyl]-2-oxo-5-oxazolidinyl]methyl]cyclopentanecarbothioamide | P-90 | Z (i) |
| 151 | (S)-N-[[3-[3-Fluoro-4-(4-acetyl-1-piperazinyl)phenyl]-2-oxo-5-oxazolidinyl]methyl]cyclohexanecarbothioamide | P-90 | Z (j) |
| 152 | (S)-N-[[3-[3-Fluoro-4-(4-acetyl-1-piperazinyl)phenyl]-2-oxo-5-oxazolidinyl]methyl]-2-cyclopropylethanethioamide | P-90 | Z (k) |
| 153 | (S)-N-[[3-[3-Fluoro-4-(4-acetyl-1-piperazinyl)phenyl]-2-oxo-5-oxazolidinyl]methyl]-2-cyclobutylethanethioamide | P-90 | Z (l) |
| 154 | (S)-N-[[3-(3-Fluoro-4-(4-acetyl-1-piperazinyl)phenyl]-2-oxo-5-oxazolidinyl]methyl]-2-cyclopentylethanethioamide | P-90 | Z (m) |
| 155 | (S)-N-[[3-[3,5-Difluoro-4-(4-acetyl-1-piperazinyl)phenyl]-2-oxo-5-oxazolidinyl]methyl]thioacetamide | P-91 | Ethyl dithioacetate |
| 156 | (S)-N-[[3-[3,5-Difluoro-4-(4-acetyl-1-piperazinyl)phenyl]-2-oxo-5-oxazolidinyl]methyl]propanethioamide | P-91 | Z (a) |
| 157 | (S)-N-[[3-[3,5-Difluoro-4-(4-acetyl-1-piperazinyl)phenyl]-2-oxo-5-oxazolidinyl]methyl]-2-methylpropanethioamide | P-91 | Z (b) |
| 158 | (S)-N-[[3-[3,5-Difluoro-4-(4-acetyl-1-piperazinyl)phenyl]-2-oxo-5-oxazolidinyl]methyl]cyclopropanecarbothioamide | P-91 | Z (c) |
| 159 | (S)-N-[[3-[4-(4-Acetyl-1-piperazinyl)phenyl]-2-oxo-5-oxazolidinyl]methyl]thioacetamide | P-92 | Ethyl dithioacetate |
| 160 | (S)-N-[[3-[4-(4-Acetyl-1-piperazinyl)phenyl]-2-oxo-5-oxazolidinyl]methyl]propanethioamide | P-92 | Z (a) |
| 161 | (S)-N-[[3-[4-(4-Acetyl-1-piperazinyl)phenyl]-2-oxo-5-oxazolidinyl]methyl]-2-methylpropanethioamide | P-92 | Z (b) |
| 162 | (S)-N-[[3-[4-(4-Acetyl-1-piperazinyl)phenyl]-2-oxo-5-oxazolidinyl]methyl]cyclopropanecarbothioamide | P-92 | Z (c) |
| 163 | (S)-N-[[3-[3-Fluoro-4-[4-(methoxyacetyl)-1-piperazinyl]-phenyl]-2-oxo-5-oxazolidinyl]-methyl]thioacetamide | P-93 | Ethyl dithioacetate |
| 164 | (S)-N-[[3-[3-Fluoro-4-[4-(methoxyacetyl)-1-piperazinyl]- | P-93 | Z (a) |

TABLE H-continued

| Example No. | Product | Amine | Dithio Compound |
|---|---|---|---|
| | phenyl]-2-oxo-5-oxazolidinyl]-methyl]-propanethioamide | | |
| 165 | (S)-N-[[3-[3-Fluoro-4-[4-(methoxyacetyl)-1-piperazinyl]-phenyl]-2-oxo-5-oxazolidinyl]-methyl]-2-methylpropanethioamide | P-93 | Z (b) |
| 166 | (S)-N-[[3-[3-Fluoro-4-[4-(methoxyacetyl)-1-piperazinyl]-phenyl]-2-oxo-5-oxazolidinyl]-methyl]-cyclopropanecarbothioamide | P-93 | Z (c) |
| 167 | (S)-N-[[3-[3-Fluoro-4-[4-(methoxyacetyl)-1-piperazinyl]-phenyl]-2-oxo-5-oxazolidinyl]-methyl]-butanethioamide | P-93 | Z (d) |
| 168 | (S)-N-[[3-[3-Fluoro-4-[4-(methoxyacetyl)-1-piperazinyl]-phenyl]-2-oxo-5-oxazolidinyl]-methyl]-3-methylbutanethioamide | P-93 | Z (e) |
| 169 | (S)-N-[[3-[3-Fluoro-4-[4-(methoxyacetyl)-1-piperazinyl]-phenyl]-2-oxo-5-oxazolidinyl]-methyl]-2-methylbutanethioamide | P-93 | Z (f) |
| 170 | (S)-N-[[3-[3-Fluoro-4-[4-(methoxyacetyl)-1-piperazinyl]-phenyl]-2-oxo-5-oxazolidinyl]-methyl]-3,3-dimethylbutanethioamide | P-93 | Z (g) |
| 171 | (S)-N-[[3-[3-Fluoro-4-[4-(methoxyacetyl)-1-piperazinyl]-phenyl]-2-oxo-5-oxazolidinyl]-methyl]-cyclobutanecarbothioamide | P-93 | Z (h) |
| 172 | (S)-N-[[3-[3-Fluoro-4-[4-(methoxyacetyl)-1-piperazinyl]-phenyl]-2-oxo-5-oxazolidinyl]-methyl]-cyclopentanecarbothioamide | P-93 | Z (i) |
| 173 | (S)-N-[[3-[3-Fluoro-4-[4-(methoxyacetyl)-1-piperazinyl]-phenyl]-2-oxo-5-oxazolidinyl]-methyl]-cyclohexanecarbothioamide | P-93 | Z (j) |
| 174 | (S)-N-[[3-[3-Fluoro-4-[4-(methoxyacetyl)-1-piperazinyl]-phenyl]-2-oxo-5-oxazolidinyl]-methyl]-2-cyclopropyle-thanethioamide | P-93 | Z (k) |
| 175 | (S)-N-[[3-[3-Fluoro-4-[4-(methoxyacetyl)-1-piperazinyl]-phenyl]-2-oxo-5-oxazolidinyl]-methyl]-2-cyclobutylethanethioamide | P-93 | Z (l) |
| 176 | (S)-N-[[3-[3-Fluoro-4-[4-(methoxyacetyl)-1-piperazinyl]-phenyl]-2-oxo-5-oxazolidinyl]-methyl]-2-cyclopentylethane-thioamide | P-93 | Z (m) |
| 177 | (S)-N-[[3-[3,5-Difluoro-[4-[4-(methoxyacetyl)-1-piperazinyl]-phenyl]-2-oxo-5-oxazolidinyl]-methyl]-thioacetamide | P-94 | Ethyl dithio-acetate |
| 178 | (S)-N-[[3-[3,5-Difluoro-[4-[4-(methoxyacetyl)-1-piperazinyl]-phenyl]-2-oxo-5-oxazolidinyl]-methyl]-propanethioamide | P-94 | Z (a) |
| 179 | (S)-N-[[3-[3,5-Difluoro-[4-[4-(methoxyacetyl)-1-piperazinyl]-phenyl]-2-oxo-5-oxazolidinyl]-methyl]-2-methylpropanethioamide | P-94 | Z (b) |
| 180 | (S)-N-[[3-[3,5-Difluoro-[4-[4-(methoxyacetyl)-1-piperazinyl]-phenyl]-2-oxo-5-oxazolidinyl]-methyl]-cyclopropanecarbothioamide | P-94 | Z (c) |
| 181 | (S)-N-[[3-[4-[4-(methoxyacetyl)-1-piperazinyl]phenyl]-2-oxo-5-oxazo-lidinyl]methyl]thioacetamide | P-95 | Ethel dithio-acetate |
| 182 | (S)-N-[[3-[4-[4-(methoxyacetyl)-1-piperazinyl]phenyl]-2-oxo-5-oxazo-lidinyl]methyl]propanethioamide | P-95 | Z (a) |
| 183 | (S)-N-[[3-[4-[4-(methoxyacetyl)-1-piperazinyl]phenyl]-2-oxo-5-oxazo-lidinyl]methyl]-2-methylpropane-thioamide | P-95 | Z (b) |
| 184 | (S)-N-[[3-[4-[4-(methoxyacetyl)-1-piperazinyl]phenyl]-2-oxo-5-oxazolidinyl]methyl]cyclopropane-carbothioamide | P-95 | Z (c) |
| 185 | (S)-N-[[3-[3-Fluoro-4-[4-(cyano-acetyl)-1-piperazinyl]-phenyl]-2-oxo-5-oxazolidinyl]methyl]thioacetamide | P-96 | Ethel dithio-acetate |
| 186 | (S)-N-[[3-[3-Fluoro-4-[4-(cyano-acetyl)-1-piperazinyl]-phenyl]-2-oxo-5-oxazolidinyl]methyl]propanethio-amide | P-96 | Z (a) |
| 187 | (S)-N-[[3-[3-Fluoro-4-[4-(cyano-acetyl)-1-piperazinyl]-phenyl]-2-oxo-5-oxazolidinyl]methyl]-2-methyl-propanethioamide | P-96 | Z (b) |
| 188 | (S)-N-[[3-[3-Fluoro-4-[4-(cyano-acetyl)-1-piperazinyl]-phenyl]-2-oxo-5-oxazolidinyl]methyl]cyclopropane-carbothioamide | P-96 | Z (c) |
| 189 | (S)-N-[[3-[3,5-Difluoro-4-[4-(cyano-acetyl)-1-piperazinyl]phenyl]-2-oxo-5-oxazolidinyl]-methyl]thioacetamide | P-97 | Ethel dithio-acetate |
| 190 | (S)-N-[[3-[3,5-Difluoro-4-[4-(cyano-acetyl)-1-piperazinyl]phenyl]-2-oxo-5-oxazolidinyl]-methyl]propane-thioamide | P-97 | Z (a) |
| 191 | (S)-N-[[3-[3,5-Difluoro-4-[4-(cyano-acetyl)-1-piperazinyl]phenyl]-2-oxo-5-oxazolidinyl]methyl]-2-methyl-propanethioamide | P-97 | Z (b) |
| 192 | (S)-N-[[3-[3,5-Difluoro-4-[4-(cyano-acetyl)-1-piperazinyl]phenyl]-2-oxo-5-oxazolidinyl]methyl]cyclopropane-carbothioamide | P-97 | Z (c) |
| 193 | (S)-N-[[3-[4-(Cyano-acetyl)-1-piperazinyl]phenyl]-2-oxo-5-oxazolidinyl]methyl]-thioacetamide | P-98 | Ethyl dithio-acetate |
| 194 | (S)-N-[[3-[4-[4-(Cyanoacetyl)-1-piperazinyl]phenyl]-2-oxo-5-oxazo-lidinyl]methyl]propanethioamide | P-98 | Z (a) |
| 195 | (S)-N-[[3-[4-[4-(Cyanoacetyl)-1-piperazinyl]phenyl]-2-oxo-5-oxazoli-dinyl]methyl]-2-methylpropane-thioamide | P-98 | Z (b) |
| 196 | (S)-N-[[3-[4-[4-(Cyanoacetyl)-1-piperazinyl]phenyl]-2-oxo-5-oxazo-lidinyl]methyl]cycopropanecarbothio-amide | P-98 | Z (c) |
| 197 | (S)-N-[[3-[3-Fluoro-4-[4-(acetoxy-acetyl)-1-piperazinyl]phenyl]-2-oxo-5-oxazolidinyl]methyl]-thioacetamide | P-99 | Ethyl dithio-acetate |
| 198 | (S)-N-[[3-[3-Fluoro-4-[4-(acetoxy-acetyl)-1-piperazinyl]phenyl]-2-oxo-5-oxazolidinyl]methyl]-propanethioamide | P-99 | Z (a) |
| 199 | (S)-N-[[3-[3-Fluoro-4-[4-(acetoxy-acetyl)-1-piperazinyl]phenyl]-2-oxo-5-oxazolidinyl]methyl]-2-methylpropanethioamide | P-99 | Z (b) |
| 200 | (S)-N-[[3-[3-Fluoro-4-[4-(acetoxy-acetyl)-1-piperazinyl]phenyl]-2-oxo-5-oxazolidinyl]methyl]-cyclopropanecarbothioamide | P-99 | Z (c) |
| 201 | (S)-N-[[3-[3-Fluoro-4-[4-(acetoxy-acetyl)-1-piperazinyl]phenyl]-2-oxo-5-oxazolidinyl]methyl]-butanethioamide | P-99 | Z (d) |
| 202 | (S)-N-[[3-[3-Fluoro-4-(acetoxy-acetyl)-1-piperazinyl]phenyl]-2-oxo- | P-99 | Z (e) |

TABLE H-continued

| Example No. | Product | Amine | Dithio Compound |
|---|---|---|---|
| | 5-oxazolidinyl]methyl]-3-methylbutanethioamide | | |
| 203 | (S)-N-[[3-[3-Fluoro-4-[4-(acetoxyacetyl)-1-piperazinyl]phenyl]-2-oxo-5-oxazolidinyl]methyl]-2-methylbutanethioamide | P-99 | Z (f) |
| 204 | (S)-N-[[3-[3-Fluoro-4-[4-(acetoxyacetyl)-1-piperazinyl]phenyl]-2-oxo-5-oxazolidinyl]methyl]-3,3-dimethylbutanethioamide | P-99 | Z (g) |
| 205 | (S)-N-[[3-[3-Fluoro-4-[4-(acetoxyacetyl)-1-piperazinyl]phenyl]-2-oxo-5-oxazolidinyl]methyl]-cyclobutanecarbothioamide | P-99 | Z (h) |
| 206 | (S)-N-[[3-[3-Fluoro-4-[4-(acetoxyacetyl)-1-piperazinyl]phenyl]-2-oxo-5-oxazolidinyl]methyl]-cyclopentanecarbothioamide | P-99 | Z (i) |
| 207 | (S)-N-[[3-[3-Fluoro-4-[4-(acetoxyacetyl)-1-piperazinyl]phenyl]-2-oxo-5-oxazolidinyl]methyl]-cyclohexanecarbothioamide | P-99 | Z (j) |
| 208 | (S)-N-[[3-[3-Fluoro-4-[4-(acetoxyacetyl)-1-piperazinyl]phenyl]-2-oxo-5-oxazolidinyl]methyl]-2-cyclopropylethanethioamide | P-99 | Z (k) |
| 209 | (S)-N-[[3-[3-Fluoro-4-[4-(acetoxyacetyl)-1-piperazinyl]phenyl]-2-oxo-5-oxazolidinyl]methyl]-2-cyclobutylethanethioamide | P-99 | Z (l) |
| 210 | (S)-N-[[3-[3-Fluoro-4-[4-(acetoxyacetyl)-1-piperazinyl]phenyl]-2-oxo-5-oxazolidinyl]methyl]-2-cyclopentylethanethioamide | P-99 | Z (m) |
| 211 | (S)-N-[[3-[3,5-Difluoro-4-[4-(acetoxyacetyl)-1-piperazinyl]-phenyl]-2-oxo-5-oxazolidinyl]-methyl]-thioacetamide | P-99 | Ethyl dithio-acetate |
| 212 | (S)-N-[[3-[3,5-Difluoro-4-[4-(acetoxyacetyl)-1-piperazinyl]-phenyl]-2-oxo-5-oxazolidinyl]-methyl]-propanethioamide | P-100 | Z (a) |
| 213 | (S)-N-[[3-[3,5-Difluoro-4-[4-(acetoxyacetyl)-1-piperazinyl]-phenyl]-2-oxo-5-oxazolidinyl]-methyl]-2-methylpropanethioamide | P-100 | Z (b) |
| 214 | (S)-N-[[3-[3,5-Difluoro-4-[4-(acetoxyacetyl)-1-piperazinyl]-phenyl]-2-oxo-5-oxazolidinyl]-methyl]-cyclopropanecarbothioamide | P-100 | Z (c) |
| 215 | (S)-N-[[3-[4-(Acetoxyacetyl)-1-piperazinyl]phenyl]-2-oxo-5-oxazolidinyl]methyl]-thioacetamide | P-100 | Ethyl dithio-acetate |
| 216 | (S)-N-[[3-[4-(Acetoxyacetyl)-1-piperazinyl]phenyl]-2-oxo-5-oxazolidinyl]methyl]-propanethioamide | P-101 | Z (a) |
| 217 | (S)-N-[[3-[4-(Acetoxyacetyl)-1-piperazinyl]phenyl]-2-oxo-5-oxazolidinyl]methyl]-2-methylpropanethioamide | P-101 | Z (b) |
| 218 | (S)-N-[[3-[4-(Acetoxyacetyl)-1-piperazinyl]phenyl]-2-oxo-5-oxazolidinyl]methyl]cyclopropanecarbothioamide | P-101 | Z (c) |
| 219 | (S)-N-[[3-[3-Fluoro-4-(benzyloxyacetyl)-1-piperazinyl]phenyl]-2-oxo-5-oxazolidinyl]methyl]-thioacetamide | P-102 | Ethyl dithio-acetate |
| 220 | (S)-N-[[3-[3-Fluoro-4-(benzyloxyacetyl)-1-piperazinyl]phenyl]-2-oxo-5-oxazolidinyl]methyl]-propanethioamide | P-102 | Z (a) |
| 221 | (S)-N-[[3-[3-Fluoro-4-(benzyloxyacetyl)-1-piperazinyl]phenyl]-2-oxo-5-oxazolidinyl]methyl]-2-methylpropanethioamide | P-102 | Z (b) |
| 222 | (S)-N-[[3-[3-Fluoro-4-(4-benzyloxyacetyl)-1-piperazinyl]phenyl]-2-oxo-5-oxazolidinyl]methyl]-cyclopropanecarbothioamide | P-102 | Z (c) |
| 223 | (S)-N-[[3-[3,5-Difluoro-4-[4-(benzyloxyacetyl)-1-piperazinyl]-phenyl]-2-oxo-5-oxazolidinyl]-methyl]-thioacetamide | P-103 | Ethyl dithio-acetate |
| 224 | (S)-N-[[3-[3,5-Difluoro-4-[4-(benzyloxyacetyl)-1-piperazinyl]-phenyl]-2-oxo-5-oxazolidinyl]-methyl]-propanethioamide | P-103 | Z (a) |
| 225 | (S)-N-[[3-[3,5-Difluoro-4-[4-(benzyloxyacetyl)-1-piperazinyl]-phenyl]-2-oxo-5-oxazolidinyl]-methyl]-2-methylpropanethioamide | P-103 | Z (b) |
| 226 | (S)-N-[[3-[3,5-Difluoro-4-[4-(benzyloxyacetyl)-1-piperazinyl]-phenyl]-2-oxo-5-oxazolidinyl]-methyl]-cyclopropanecarbothioamide | P-103 | Z (c) |
| 227 | (S)-N-[[3-[3-Fluoro-4-[4-(methoxycarbonyl)-1-piperazinyl]-phenyl]-2-oxo-5-oxazolidinyl]-methyl]-thioacetamide | P-105 | Ethyl dithio-acetate |
| 228 | (S)-N-[[3-[3-Fluoro-4-[4-(methoxycarbonyl)-1-piperazinyl]-phenyl]-2-oxo-5-oxazolidinyl]-methyl]-propanethioamide | P-105 | Z (a) |
| 229 | (S)-N-[[3-[3-Fluoro-4-[4-(methoxycarbonyl)-1-piperazinyl]-phenyl]-2-oxo-5-oxazolidinyl]-methyl]-2-methylpropanethioamide | P-105 | Z (b) |
| 230 | (S)-N-[[3-[3-Fluoro-4-[4-(methoxycarbonyl)-1-piperazinyl]-phenyl]-2-oxo-5-oxazolidinyl]-methyl]-cyclopropanecarbothioamide | P-105 | Z (c) |
| 231 | (S)-N-[[3-[3-Fluoro-4-[4-(methoxycarbonyl)-1-piperazinyl]-phenyl]-2-oxo-5-oxazolidinyl]-methyl]-butanethioamide | P-105 | Z (d) |
| 232 | (S)-N-[[3-[3-Fluoro-4-[4-(methoxycarbonyl)-1-piperazinyl]-phenyl]-2-oxo-5-oxazolidinyl]-methyl]-3-methylbutanethioamide | P-105 | Z (e) |
| 233 | (S)-N-[[3-[3-Fluoro-4-[4-(methoxycarbonyl)-1-piperazinyl]-phenyl]-2-oxo-5-oxazolidinyl]-methyl]-2-methylbutanethioamide | P-105 | Z (f) |
| 234 | (S)-N-[[3-[3-Fluoro-4-[4-(methoxycarbonyl)-1-piperazinyl]-phenyl]-2-oxo-5-oxazolidinyl]-methyl]-3,3-dimethylbutanethioamide | P-105 | Z (g) |
| 235 | (S)-N-[[3-[3-Fluoro-4-[4-(methoxycarbonyl)-1-piperazinyl]-phenyl]-2-oxo-5-oxazolidinyl]-methyl]-cyclobutanecarbothioamide | P-105 | Z (h) |
| 236 | (S)-N-[[3-[3-Fluoro-4-[4-(methoxycarbonyl)-1-piperazinyl]-phenyl]-2-oxo-5-oxazolidinyl]-methyl]-cyclopentanecarbothioamide | P-105 | Z (i) |
| 237 | (S)-N-[[3-[3-Fluoro-4-[4-(methoxycarbonyl)-1-piperazinyl]-phenyl]-2-oxo-5-oxazolidinyl]-methyl]-cyclohexanecarbothioamide | P-105 | Z (j) |
| 238 | (S)-N-[[3-[3-Fluoro-4-[4-(methoxycarbonyl)-1-piperazinyl]-phenyl]-2-oxo-5-oxazolidinyl]-methyl]-2-cyclopropylethanethioamide | P-105 | Z (k) |
| 239 | (S)-N-[[3-[3-Fluoro-4-[4-(methoxycarbonyl)-1-piperazinyl]-phenyl]-2-oxo-5-oxazolidinyl]- | P-105 | Z (l) |

TABLE H-continued

| Example No. | Product | Amine | Dithio Compound |
|---|---|---|---|
| | methyl]-2-cyclobutylethane-thioamide | | |
| 240 | (S)-N-[[3-Fluoro-4-[4-(methoxycarbonyl)-1-piperazinyl]phenyl]-2-oxo-5-oxazolidinyl]methyl]-2-cyclopentylethane-thioamide | P-105 | Z (m) |
| 241 | (S)-N-[[3-[3,5-Difluoro-4-[4-(methoxycarbonyl)-1-piperazinyl]phenyl]-2-oxo-5-oxazolidinyl]methyl]-thioacetamide | P106 | Ethyl dithio-acetate |
| 242 | (S)-N-[[3-[3,5-Difluoro-4-[4-(methoxycarbonyl)-1-piperazinyl]phenyl]-2-oxo-5-oxazolidinyl]methyl]-propanethioamide | P106 | Z (a) |
| 243 | (S)-N-[[3-[3,5-Difluoro-4-[4-(methoxycarbonyl)-1-piperazinyl]phenyl]-2-oxo-5-oxazolidinyl]methyl]-methylpropanethioamide | P106 | Z (b) |
| 244 | (S)-N-[[3-[3,5-Difluoro-4-[4-(methoxycarbonyl)-1-piperazinyl]phenyl]-2-oxo-5-oxazolidinyl]methyl]-cyclopropanecarbo-thioamide | P106 | Z (c) |
| 245 | (S)-N-[[3-[4-[4-(methoxycarbonyl)-1-piperazinyl]phenyl]-2-oxo-5-oxazolidinyl]methyl]-thioacetamide | P-107 | Ethyl dithio-acetate |
| 246 | (S)-N-[[3-[4-[4-(methoxycarbonyl)-1-piperazinyl]phenyl]-2-oxo-5-oxazolidinyl]methyl]-propanethioamide | P-107 | Z (a) |
| 247 | (S)-N-[[3-[4-[4-(methoxycarbonyl)-1-piperazinyl]phenyl]-2-oxo-5-oxazolidinyl]methyl]-2-methyl-propanethioamide | P-107 | Z (b) |
| 248 | (S)-N-[[3-[4-[4-(methoxycarbonyl)-1-piperazinyl]phenyl]-2-oxo-5-oxazolidinyl]methyl]-cyclopropanecarbo-thioamide | P-107 | Z (c) |
| 249 | (S)-N-[[3-[3-Fluoro-4-[4-methane-sulfonyl)-1-piperazinyl]phenyl]-2-oxo-5-oxazolidinyl]methyl]-thioacet-amide; mp 197–198° C.; Anal. calcd for $C_{17}H_{23}FN_4O_4S_2$: C, 47.43; H, 5.39; N, 13.01; S, 14.89. Found: C, 47.25; H, 5.40; N, 12.82; S, 14.56. | P-108 | Ethyl dithio-acetate |
| 250 | (S)-N-[[3-[3-Fluoro-4-[4-methane-sulfonyl)-1-piperazinyl]phenyl]-2-oxo-5-oxazolidinyl]methyl]-propane-thioamide; mp 207–208° C.; Anal. calcd for $C_{18}H_{25}FN_4O_4S_2$: C, 48.63; H, 5.67; N, 12.60; S, 14.42. Found: C, 48.51; H, 5.59; N, 12.52; S, 14.09. | P-108 | Z (a) |
| 251 | (S)-N-[[3-[3-Fluoro-4-[4-methane-sulfonyl)-1-piperazinyl]phenyl]-2-oxo-5-oxazolidinyl]methyl]-2-methyl-propanethioamide; mp 204–206° C.; Anal. calcd for $C_{19}H_{27}FN_4O_4S_2$: C, 49.76; H, 5.93; N, 12.22; S, 13.98. Found: C, 49.63; H, 5.92; N, 14.14; S, 13.91. | P-108 | Z (b) |
| 252 | (S)-N-[[3-[3-Fluoro-4-[4-methane-sulfonyl)-1-piperazinyl]phenyl]-2-oxo-5-oxazolidinyl]methyl]-cyclo-propanecarbothioamide; mp 197–198° C.; Anal. calcd for $C_{19}H_{25}FN_4O_4S_2$: C, 49.98; H, 5.52; N, 12.27; S, 14.04. Found: C, 49.42; H, 5.50; N, 12.08; S, 13.80. | P-108 | Z (c) |
| 253 | (S)-N-[[3-[3,5-Difluoro-4-[4-(meth-anesulfonyl)-1-piperazinyl]phenyl]-2-oxo-5-oxazolidinyl]methyl]-thioacetamide | P-109 | Ethyl dithio-acetate |
| 254 | (S)-N-[[3-[3,5-Difluoro-4-[4-(meth-anesulfonyl)-1-piperazinyl]phenyl]-2-oxo-5-oxazolidinyl]methyl]-propanethioamide | P-109 | Z (a) |
| 255 | (S)-N-[[3-[3,5-Difluoro-4-[4-(meth-anesulfonyl)-1-piperazinyl]phenyl]-2-oxo-5-oxazolidinyl]methyl]-2-methylpropanethioamide | P-109 | Z (b) |
| 256 | (S)-N-[[3-[3,5-Difluoro-4-[4-(meth-anesulfonyl)-1-piperazinyl]phenyl]-2-oxo-5-oxazolidinyl]methyl]-cyclopropanecarbothioamide | P-109 | Z (c) |
| 257 | (S)-N-[[3-[4-[4-(methanesulfonyl)-1 piperazinyl]phenyl]-2-oxo-5-oxazoli-dinyl]methyl]-thioacetamide | P-110 | Ethyl dithio-acetate |
| 258 | (S)-N-[[3-[4-[4-(methanesulfonyl)-1 piperazinyl]phenyl]-2-oxo-5-oxazoli-dinyl]methyl]-propanethioamide | P-110 | Z (a) |
| 259 | (S)-N-[[3-[4-[4-(methanesulfonyl)-1 piperazinyl]phenyl]-2-oxo-5-oxazoli-dinyl]methyl]-2-methylpropane-thioamide | P-110 | Z (b) |
| 260 | (S)-N-[[3-[4-[4-(methanesulfonyl)-1 piperazinyl]phenyl]-2-oxo-5-oxazoli-dinyl]methyl]-cyclopropanecarbo-thioamide | P-110 | Z (c) |
| 261 | (S)-N-[[3-[3-Fluoro-4-[4-(ethane-sulfonyl)-1-piperazinyl]phenyl]-2-oxo-5-oxazolidinyl]methyl]-thioacetamide | P-111 | Ethyl dithio-acetate |
| 262 | (S)-N-[[3-[3-Fluoro-4-[4-(ethane-sulfonyl)-1-piperazinyl]phenyl]-2-oxo-5-oxazolidinyl]methyl]-propanethioamide | P-111 | Z (a) |
| 263 | (S)-N-[[3-[3-Fluoro-4-[4-(ethane-sulfonyl)-1-piperazinyl]phenyl]-2-oxo-5-oxazolidinyl]methyl]-2-methylpropanethioamide | P-111 | Z (b) |
| 264 | (S)-N-[[3-[3-Fluoro-4-[4-(ethane-sulfonyl)-1-piperazinyl]phenyl]-2-oxo-5-oxazolidinyl]methyl]-cyclopropanecarbothioamide | P-111 | Z (c) |
| 265 | (S)-N-[[3-[3,5-Difluoro-4-[4-(ethanesulfonyl)-1-piperazinyl]-phenyl]-2-oxo-5-oxazolidinyl]-methyl]-thioacetamide | P-112 | Ethyl dithio-acetate |
| 266 | (S)-N-[[3-[3,5-Difluoro-4-[4-(ethanesulfonyl)-1-piperazinyl]-phenyl]-2-oxo-5-oxazolidinyl]-methyl]-propanethioamide | P-112 | Z (a) |
| 267 | (S)-N-[[3-[3,5-Difluoro-4-[4-(ethanesulfonyl)-1-piperazinyl]-phenyl]-2-oxo-5-oxazolidinyl]-methyl]-2-methylpropanethioamide | P-112 | Z (b) |
| 268 | (S)-N-[[3-[3,5-Difluoro-4-[4-(ethanesulfonyl)-1-piperazinyl]-phenyl]-2-oxo-5-oxazolidinyl]-methyl]-cyclopropanecarbothioamide | P-112 | Z (c) |
| 269 | (S)-N-[[3-[4-[4-(ethanesulfonyl)-1-piperazinyl]phenyl]-2-oxo-5-oxazo-lidinyl]methyl]thioacetamide | P-113 | Ethyl dithio-acetate |
| 270 | (S)-N-[[3-[4-[4-(ethanesulfonyl)-1-piperazinyl]phenyl]-2-oxo-5-oxazo-lidinyl]methyl]propanethioamide | P-113 | Z (a) |
| 271 | (S)-N-[[3-[4-[4-(ethanesulfonyl)-1-piperazinyl]phenyl]-2-oxo-5-oxazo-lidinyl]methyl]-2-methylpropane-thioamide | P-113 | Z (b) |
| 272 | (S)-N-[[3-[4-[4-(ethanesulfonyl)-1-piperazinyl]phenyl]-2-oxo-5-oxazo-lidinyl]methyl]cyclopropanecarbo-thioamide | P-113 | Z (c) |
| 273 | (S)-N-[[3-[3-Fluoro-4-[4-(chloro-methanesulfonyl)-1-piperazinyl]-phenyl]-2-oxo-5-oxazolidinyl]-methyl]-thioacetamide | P-114 | Ethyl dithio-acetate |

TABLE H-continued

| Example No. | Product | Amine | Dithio Compound |
|---|---|---|---|
| 274 | (S)-N-[[3-[3-Fluoro-4-[4-(chloro-methanesulfonyl)-1-piperazinyl]-phenyl]-2-oxo-5-oxazolidinyl]-methyl]-propanethioamide | P-114 | Z (a) |
| 275 | (S)-N-[[3-[3-Fluoro-4-[4-(chloro-methanesulfonyl)-1-piperazinyl]-phenyl]-2-oxo-5-oxazolidinyl]-methyl]-2-methylpropanethioamide | P-114 | Z (b) |
| 276 | (S)-N-[[3-[3-Fluoro-4-[4-(chloro-methanesulfonyl)-1-piperazinyl]-phenyl]-2-oxo-5-oxazolidinyl]-methyl]-cyclopropanecarbothioamide | P-114 | Z (c) |
| 277 | (S)-N-[[3-[3,5-Difluoro-4-[4-(chloro-methanesulfonyl)-1-piperazinyl]-phenyl]-2-oxo-5-oxazolidinyl]-methyl]-thioacetamide | P-115 | Ethyl dithio-acetate |
| 278 | (S)-N-[[3-[3,5-Difluoro-4-[4-(chloro-methanesulfonyl)-1-piperazinyl]-phenyl]-2-oxo-5-oxazolidinyl]-methyl]-propanethioamide | P-115 | Z (a) |
| 279 | (S)-N-[[3-[3,5-Difluoro-4-[4-(chloro-methanesulfonyl)-1-piperazinyl]-phenyl]-2-oxo-5-oxazolidinyl]-methyl]-2-methylpropanethioamide | P-115 | Z (b) |
| 280 | (S)-N-[[3-[3,5-Difluoro-4-[4-(chloro-methanesulfonyl)-1-piperazinyl]-phenyl]-2-oxo-5-oxazolidinyl]-methyl]-cyclopropanecarbothioamide | P-115 | Z (c) |
| 281 | (S)-N-[[3-[4-[4-(chloromethanesul-fonyl)-1-piperazinyl]phenyl]-2-oxo-5-oxazolidinyl]methyl]-thioacetamide | P-116 | Ethyl dithio-acetate |
| 282 | (S)-N-[[3-[4-[4-(chloromethanesul-fonyl)-1-piperazinyl]phenyl]-2-oxo-5-oxazolidinyl]methyl]-propanethioamide | P-116 | Z (a) |
| 283 | (S)-N-[[3-[4-[4-(chloromethanesul-fonyl)-1-piperazinyl]phenyl]-2-oxo-5-oxazolidinyl]methyl]-2-methylpropanethioamide | P-116 | Z (b) |
| 284 | (S)-N-[[3-[4-[4-(chloromethanesul-fonyl)-1-piperazinyl]phenyl]-2-oxo-5-oxazolidinyl]methyl]-cyclopropanecarbothioamide | P-116 | Z (c) |
| 285 | (S)-N-[[3-[3-Fluoro-4-[4-(cyano-methane-sulfonyl)-1-piperazinyl]-phenyl]-2-oxo-5-oxazolidinyl]-methyl]-thioacetamide | P-117 | Ethyl dithio-acetate |
| 286 | (S)-N-[[3-[3-Fluoro-4-[4-(cyano-methane-sulfonyl)-1-piperazinyl]-phenyl]-2-oxo-5-oxazolidinyl]-methyl]-propanethioamide | P-117 | Z (a) |
| 287 | (S)-N-[[3-[3-Fluoro-4-[4-(cyano-methane-sulfonyl)-1-piperazinyl]-phenyl]-2-oxo-5-oxazolidinyl]-methyl]-2-methylpropanethioamide | P-117 | Z (b) |
| 288 | (S)-N-[[3-[3-Fluoro-4-[4-(cyano-methane-sulfonyl)-1-piperazinyl]-phenyl]-2-oxo-5-oxazolidinyl]-methyl]-cyclopropanecarbothioamide | P-117 | Z (c) |
| 289 | (S)-N-[[3-[3,5-Difluoro-4-[4-(cyano-methane-sulfonyl)-1-piperazinyl]-phenyl]-2-oxo-5-oxazolidinyl]-methyl]thioacetamide | P-118 | Ethyl dithio-acetate |
| 290 | (S)-N-[[3-[3,5-Difluoro-4-[4-(cyano-methane-sulfonyl)-1-piperazinyl]-phenyl]-2-oxo-5-oxazolidinyl]-methyl]propanethioamide | P-118 | Z (a) |
| 291 | (S)-N-[[3-[3,5-Difluoro-4-[4-(cyano-methane-sulfonyl)-1-piperazinyl]-phenyl]-2-oxo-5-oxazolidinyl]-methyl]-2-methylpropanethioamide | P-118 | Z (b) |
| 292 | (S)-N-[[3-[3,5-Difluoro-4-[4-(cyano-methane-sulfonyl)-1-piperazinyl]-phenyl]-2-oxo-5-oxazolidinyl]-methyl]cyclopropanecarbothioamide | P-118 | Z (c) |
| 293 | (S)-N-[[3-[4-[4-(Cyanomethane-sulfonyl)-1-piperazinyl]phenyl]-2-oxo-5-oxazolidinyl]methyl]-thioacetamide | P-119 | Ethyl dithio-acetate |
| 294 | (S)-N-[[3-[4-[4-(Cyanomethane-sulfonyl)-1-piperazinyl]phenyl]-2-oxo-5-oxazolidinyl]methyl]-propanethioamide | P-119 | Z (a) |
| 295 | (S)-N-[[3-[4-[4-(Cyanomethane-sulfonyl)-1-piperazinyl]phenyl]-2-oxo-5-oxazolidinyl]methyl]-2-methylpropanethioamide | P-119 | Z (b) |
| 296 | (S)-N-[[3-[4-[4-(Cyanomethane-sulfonyl)-1-piperazinyl]phenyl]-2-oxo-5-oxazolidinyl]methyl]-cyclopropanecarbothioamide | P-119 | Z (c) |
| 297 | (S)-N-[[3-[3-Fluoro-4-[4-(N-methyl-sulfamoyl)-1-piperazinyl]phenyl]-2-oxo-5-oxazolidinyl]methyl]-thioacetamide | P-120 | Ethyl dithio-acetate |
| 298 | (S)-N-[[3-[3-Fluoro-4-[4-(N-methyl-sulfamoyl)-1-piperazinyl]phenyl]-2-oxo-5-oxazolidinyl]methyl]-propanethioamide | P-120 | Z (a) |
| 299 | (S)-N-[[3-[3-Fluoro-4-[4-(N-methyl-sulfamoyl)-1-piperazinyl]phenyl]-2-oxo-5-oxazolidinyl]methyl]-2-methylpropanethioamide | P-120 | Z (b) |
| 300 | (S)-N-[[3-[3-Fluoro-4-[4-(N-methyl-sulfamoyl)-1-piperazinyl]phenyl]-2-oxo-5-oxazolidinyl]methyl]-cyclopropanecarbothioamide | P-120 | Z (c) |
| 301 | (S)-N-[[3-[3,5-Difluoro-4-[4-(N-methylsulfamoyl)-1-piperazinyl]-phenyl]-2-oxo-5-oxazolidinyl]-methyl]thioacetamide | P-121 | Ethyl dithio-acetate |
| 302 | (S)-N-[[3-[3,5-Difluoro-4-[4-(N-methylsulfamoyl)-1-piperazinyl]-phenyl]-2-oxo-5-oxazolidinyl]-methyl]propanethioamide | P-121 | Z (a) |
| 303 | (S)-N-[[3-[3,5-Difluoro-4-[4-(N-methylsulfamoyl)-1-piperazinyl]-phenyl]-2-oxo-5-oxazolidinyl]-methyl]-2-methylpropanethioamide | P-121 | Z (b) |
| 304 | (S)-N-[[3-[3,5-Difluoro-4-[4-(N-methylsulfamoyl)-1-piperazinyl]-phenyl]-2-oxo-5-oxazolidinyl]-methyl]cyclopropanecarbothioamide | P-121 | Z (c) |
| 305 | (S)-N-[[3-[4-[4-(N-methylsulfamoyl)-1-piperazinyl]phenyl]-2-oxo-5-oxazo-lidinyl]methyl]-thioacetamide | P-122 | Ethyl dithio-acetate |
| 306 | (S)-N-[[3-[4-[4-(N-methylsulfamoyl)-1-piperazinyl]phenyl]-2-oxo-5-oxazo-lidinyl]methyl]-propanethioamide | P-122 | Z (a) |
| 307 | (S)-N-[[3-[4-[4-(N-methylsulfamoyl)-1-piperazinyl]phenyl]-2-oxo-5-oxazo-lidinyl]methyl]-2-methyl-propanethioamide | P-122 | Z (b) |
| 308 | (S)-N-[[3-[4-[4-(N-methylsulfamoyl)-1-piperazinyl]phenyl]-2-oxo-5-oxazo-lidinyl]methyl]-cyclopropane-carbothioamide | P-122 | Z (c) |
| 309 | (S)-N-[[3-[3-Fluoro-4-[4-(N,N-dimethylsulfamoyl)-1-piperazinyl]-phenyl]-2-oxo-5-oxazolidinyl]-methyl]-thioacetamide | P-123 | Ethyl dithio-acetate |
| 310 | (S)-N-[[3-[3-Fluoro-4-[4-(N,N-dimethylsulfamoyl)-1-piperazinyl]-phenyl]-2-oxo-5-oxazolidinyl]-methyl]-propanethioamide | P-123 | Z (a) |
| 311 | (S)-N-[[3-[3-Fluoro-4-[4-(N,N-dimethylsulfamoyl)-1-piperazinyl]-phenyl]-2-oxo-5-oxazolidinyl]-methyl]-2-methylpropanethioamide | P-123 | Z (b) |
| 312 | (S)-N-[[3-[3-Fluoro-4-[4-(N,N-dimethylsulfamoyl)-1-piperazinyl]- | P-123 | Z (c) |

TABLE H-continued

| Example No. | Product | Amine | Dithio Compound |
|---|---|---|---|
| | phenyl]-2-oxo-5-oxazolidinyl]-methyl]-cyclopropanecarbothioamide | | |
| 313 | (S)-N-[[3-[3,5-Difluoro-4-[4-(N,N-dimethylsulfamoyl)-1-piperazinyl]-phenyl]-2-oxo-5-oxazolidinyl]-methyl]-thioacetamide | P-124 | Ethyl dithio-acetate |
| 314 | (S)-N-[[3-[3,5-Difluoro-4-[4-(N,N-dimethylsulfamoyl)-1-piperazinyl]-phenyl]-2-oxo-5-oxazolidinyl]-methyl]-propanethioamide | P-124 | Z (a) |
| 315 | (S)-N-[[3-[3,5-Difluoro-4-[4-(N,N-dimethylsulfamoyl)-1-piperazinyl]-phenyl]-2-oxo-5-oxazolidinyl]-methyl]-2-methylpropanethioamide | P-124 | Z (b) |
| 316 | (S)-N-[[3-[3,5-Difluoro-4-[4-(N,N-dimethylsulfamoyl)-1-piperazinyl]-phenyl]-2-oxo-5-oxazolidinyl]-methyl]-cyclopropanecarbothioamide | P-124 | Z (c) |
| 317 | (S)-N-[[3-[4-[4-(N,N-dimethylsulfamoyl)-1-piperazinyl]phenyl]-2-oxo-5-oxazolidinyl]methyl]-thioacetamide | P-125 | Ethyl dithio-acetate |
| 318 | (S)-N-[[3-[4-[4-(N,N-dimethylsulfamoyl)-1-piperazinyl]phenyl]-2-oxo-5-oxazolidinyl]methyl]-propanethioamide | P-125 | Z (a) |
| 319 | (S)-N-[[3-[4-[4-(N,N-dimethylsulfamoyl)-1-piperazinyl]phenyl]-2-oxo-5-oxazolidinyl]methyl]-2-methylpropanethioamide | P-125 | Z (b) |
| 320 | (S)-N-[[3-[4-[4-(N,N-dimethylsulfamoyl)-1-piperazinyl]phenyl]-2-oxo-5-oxazolidinyl]methyl]-cyclopropanecarbothioamide | P-125 | Z (c) |
| 321 | (S)-N-[[3-[3-Fluoro-4-[4-(ethoxycarbonyl)-1-piperazinyl]phenyl]-2-oxo-5-oxazolidinyl]methyl]-thioacetamide | P-126 | Ethyl dithio-acetate |
| 322 | (S)-N-[[3-[3-Fluoro-4-[4-(ethoxycarbonyl)-1-piperazinyl]phenyl]-2-oxo-5-oxazolidinyl]methyl]-propanethioamide | P-126 | Z (a) |
| 323 | (S)-N-[[3-[3-Fluoro-4-[4-(ethoxycarbonyl)-1-piperazinyl]phenyl]-2-oxo-5-oxazolidinyl]methyl]-2-methylpropanethioamide | P-126 | Z (b) |
| 324 | (S)-N-[[3-[3-Fluoro-4-[4-(ethoxycarbonyl)-1-piperazinyl]phenyl]-2-oxo-5-oxazolidinyl]methyl]-cyclopropanecarbothioamide | P-126 | Z (c) |
| 325 | (S)-N-[[3-[3-Fluoro-4-[4-(ethoxycarbonyl)-1-piperazinyl]phenyl]-2-oxo-5-oxazolidinyl]methyl]-butanethioamide | P-126 | Z (d) |
| 326 | (S)-N-[[3-[3-Fluoro-4-[4-(ethoxycarbonyl)-1-piperazinyl]phenyl]-2-oxo-5-oxazolidinyl]methyl]-3-methylbutanethioamide | P-126 | Z (e) |
| 327 | (S)-N-[[3-[3-Fluoro-4-[4-(ethoxycarbonyl)-1-piperazinyl]phenyl]-2-oxo-5-oxazolidinyl]methyl]-methylbutanethioamide | P-126 | Z (f) |
| 328 | (S)-N-[[3-[3-Fluoro-4-[4-(ethoxycarbonyl)-1-piperazinyl]phenyl]-2-oxo-5-oxazolidinyl]methyl]-dimethylbutanethioamide | P-126 | Z (g) |
| 329 | (S)-N-[[3-[3-Fluoro-4-[4-(ethoxycarbonyl)-1-piperazinyl]phenyl]-2-oxo-5-oxazolidinyl]methyl]-cyclobutanecarbothioamide | P-126 | Z (h) |
| 330 | (S)-N-[[3-[3-Fluoro-4-[4-(ethoxycarbonyl)-1-piperazinyl]phenyl]-2-oxo-5-oxazolidinyl]methyl]-cyclopentanecarbothioamide | P-126 | Z (i) |
| 331 | (S)-N-[[3-[3-Fluoro-4-[4-(ethoxycarbonyl)-1-piperazinyl]phenyl]-2-oxo-5-oxazolidinyl]methyl]-cyclohexanecarbothioamide | P-126 | Z (j) |
| 332 | (S)-N-[[3-[3-Fluoro-4-[4-(ethoxycarbonyl)-1-piperazinyl]phenyl]-2-oxo-5-oxazolidinyl]methyl]-2-cyclopropylethanethioamide | P-126 | Z (k) |
| 333 | (S)-N-[[3-[3-Fluoro-4-[4-(ethoxycarbonyl)-1-piperazinyl]phenyl]-2-oxo-5-oxazolidinyl]methyl]-2-cyclobutylethanethioamide | P-126 | Z (l) |
| 334 | (S)-N-[[3-[3-Fluoro-4-[4-(ethoxycarbonyl)-1-piperazinyl]phenyl]-2-oxo-5-oxazolidinyl]methyl]-2-cyclopentylethanethioamide | P-126 | Z (m) |
| 335 | (S)-N-[[3-[3,5-Difluoro-4-[4-(ethoxycarbonyl)-1-piperazinyl]phenyl]-2-oxo-5-oxazolidinyl]methyl]-thioacetamide | P-127 | Ethyl dithio-acetate |
| 336 | (S)-N-[[3-[3,5-Difluoro-4-[4-(ethoxycarbonyl)-1-piperazinyl]phenyl]-2-oxo-5-oxazolidinyl]methyl]-propanethioamide | P-127 | Z (a) |
| 337 | (S)-N-[[3-[3,5-Difluoro-4-[4-(ethoxycarbonyl)-1-piperazinyl]phenyl]-2-oxo-5-oxazolidinyl]methyl]-2-methylpropanethioamide | P-127 | Z (b) |
| 338 | (S)-N-[[3-[3,5-Difluoro-4-[4-(ethoxycarbonyl)-1-piperazinyl]phenyl]-2-oxo-5-oxazolidinyl]methyl]-cyclopropanecarbothioamide | P-127 | Z (c) |
| 339 | (S)-N-[[3-[4-[4-(ethoxycarbonyl)-1-piperazinyl]-phenyl]-2-oxo-5-oxazolidinyl]methyl]thioacetamide | P-128 | Ethyl dithio-acetate |
| 340 | (S)-N-[[3-[4-[4-(ethoxycarbonyl)-1-piperazinyl]-phenyl]-2-oxo-5-oxazolidinyl]methyl]propane-thioamide | P-128 | Z (a) |
| 341 | (S)-N-[[3-[4-[4-(ethoxycarbonyl)-1-piperazinyl]-phenyl]-2-oxo-5-oxazolidinyl]methyl]2-methylpropanethioamide | P-128 | Z (b) |
| 342 | (S)-N-[[3-[4-[4-(ethoxycarbonyl)-1-piperazinyl]-phenyl]-2-oxo-5-oxazolidinyl]methyl]cyclopropanecarbothioamide | P-128 | Z (c) |
| 343 | (S)-N-[[3-[3-Fluoro-4-(4-sulfamoyl-1-piperazinyl)-phenyl]-2-oxo-5-oxaxolidinyl]methyl]-thioacetamide | P-129 | Ethyl dithio-acetate |
| 344 | (S)-N-[[3-[3-Fluoro-4-(4-sulfamoyl-1-piperazinyl)-phenyl]-2-oxo-5-oxaxolidinyl]methyl]propane-thioamide | P-129 | Z (a) |
| 345 | (S)-N-[[3-[3-Fluoro-4-(4-sulfamoyl-1-piperazinyl)-phenyl]-2-oxo-5-oxazolidinyl]methyl]-2-methyl-propanethioamide | P-129 | Z (b) |
| 346 | (S)-N-[[3-[3-Fluoro-4-(4-sulfamoyl-1-piperazinyl)-phenyl]-2-oxo-5-oxazolidinyl]methyl]-cyclo-propanecarbothioamide | P-129 | Z (c) |
| 347 | (S)-N-[[3-[3-Fluoro-4-(4-sulfamoyl-1-piperazinyl)-phenyl]-2-oxo-5-oxazolidinyl]methyl]butane-thioamide | P-129 | Z (d) |
| 348 | (S)-N-[[3-[3-Fluoro-4-(4-sulfamoyl-1-piperazinyl)-phenyl]-2-oxo-5-oxazolidinyl]methyl]-3-methyl-butanethioamide | P-129 | Z (e) |
| 349 | (S)-N-[[3-[3-Fluoro-4-(4-sulfamoyl-1-piperazinyl)-phenyl]-2-oxo-5-oxazolidinyl]methyl]-2-methyl-butanethioamide | P-129 | Z (f) |

TABLE H-continued

| Example No. | Product | Amine | Dithio Compound |
|---|---|---|---|
| 350 | (S)-N-[[3-[3-Fluoro-4-(4-sulfamoyl-1-piperazinyl)-phenyl]-2-oxo-5-oxazolidinyl]methyl]-3,3-dimethyl-butanethioamide | P-129 | Z (g) |
| 351 | (S)-N-[[3-[3-Fluoro-4-(4-sulfamoyl-1-piperazinyl)-phenyl]-2-oxo-5-oxazolidinyl]methyl]cyclo-butanecarbothioamide | P-129 | Z (h) |
| 352 | (S)-N-[[3-[3-Fluoro-4-(4-sulfamoyl-1-piperazinyl)-phenyl]-2-oxo-5-oxazolidinyl]methyl]cyclo-pentanecarbothioamide | P-129 | Z (i) |
| 353 | (S)-N-[[3-[3-Fluoro-4-(4-sulfamoyl-1-piperazinyl)-phenyl]-2-oxo-5-oxazolidinyl]methyl]cyclo-hexanecarbothioamide | P-129 | Z (j) |
| 354 | (S)-N-[[3-[3-Fluoro-4-(4-sulfamoyl-1-piperazinyl)-phenyl]-2-oxo-5-oxazolidinyl]methyl]-2-cyclo-propylethanethioamide | P-129 | Z (k) |
| 355 | (S)-N-[[3-[3-Fluoro-4-(4-sulfamoyl-1-piperazinyl)-phenyl]-2-oxo-5-oxazolidinyl]methyl]-2-cyclo-butylethanethioamide | P-129 | Z (l) |
| 356 | (S)-N-[[3-[3-Fluoro-4-(4-sulfamoyl-1-piperazinyl)-phenyl]-2-oxo-5-oxazolidinyl]methyl]-2-cyclo-pentylethanethioamide | P-129 | Z (m) |
| 357 | (S)-N-[[3-[3,5-Difluoro-4-(4-sulfamoyl-1-piperazinyl)phenyl]-2-oxo-5-oxazolidinyl]methyl]-thioacetamide | P-130 | Ethyl dithio-acetate |
| 358 | (S)-N-[[3-[3,5-Difluoro-4-(4-sulfamoyl-1-piperazinyl)phenyl]-2-oxo-5-oxazolidinyl]methyl]propane-thioamide | P-130 | Z (a) |
| 359 | (S)-N-[[3-[3,5-Difluoro-4-(4-sulfamoyl-1-piperazinyl)phenyl]-2-oxo-5-oxazolidinyl]methyl]-2-methylpropanethioamide | P-130 | Z (b) |
| 360 | (S)-N-[[3-[3,5-Difluoro-4-(4-sulfamoyl-1-piperazinyl)phenyl]-2-oxo-5-oxazolidinyl]methyl]cyclopropane-carbothioamide | P-130 | Z (c) |
| 361 | (S)-N-[[3-[4-(4-sulfamoyl-1-piperazinyl)phenyl]-2-oxo-5-oxazolidinyl]methyl]-thioacetamide | P-131 | Ethyl dithio-acetate |
| 362 | (S)-N-[[3-[4-(4-sulfamoyl-1-piperazinyl)phenyl]-2-oxo-5-oxazolidinyl]methyl]-propanethioamide | P-131 | Z (a) |
| 363 | (S)-N-[[3-[4-(4-sulfamoyl-1-piperazinyl)phenyl]-2-oxo-5-oxazolidinyl]methyl]-2-methylpropanethioamide | P-131 | Z (b) |
| 364 | (S)-N-[[3-[4-(4-sulfamoyl-1-piperazinyl)phenyl]-2-oxo-5-oxazolidinyl]methyl]-cyclopropanecarbothioamide | P-131 | Z (c) |
| 365 | (S)-N-[[3-[3-Fluoro-4-[4-(cyano-methyl)-1-piperazinyl]phenyl]-2-oxo-5-oxazolidinyl]methyl]-thioacetamide | P-132 | Ethyl dithio-acetate |
| 366 | (S)-N-[[3-[3-Fluoro-4-[4-(cyano-methyl)-1-piperazinyl]phenyl]-2-oxo-5-oxazolidinyl]methyl]-propanethioamide | P-132 | Z (a) |
| 367 | (S)-N-[[3-[3-Fluoro-4-[4-(cyano-methyl)-1-piperazinyl]phenyl]-2-oxo-5-oxazolidinyl]methyl]-2-methylpropanethioamide | P-132 | Z (b) |
| 368 | (S)-N-[[3-[3-Fluoro-4-[4-(cyano-methyl)-1-piperazinyl]phenyl]-2-oxo-5-oxazolidinyl]methyl]-cyclopropanecarbothioamide | P-132 | Z (c) |
| 369 | (S)-N-[[3-[3,5-Difluoro-4-[4-(cyanomethyl)-1-piperazinyl]phenyl]-2-oxo-5-oxazolidinyl]methyl]-thioacetamide | P-133 | Ethyl dithio-acetate |
| 370 | (S)-N-[[3-[3,5-Difluoro-4-[4-(cyanomethyl)-1-piperazinyl]phenyl]-2-oxo-5-oxazolidinyl]methyl]-propanethioamide | P-133 | Z (a) |
| 371 | (S)-N-[[3-[3,5-Difluoro-4-[4-(cyanomethyl)-1-piperazinyl]phenyl]-2-oxo-5-oxazolidinyl]methyl]-2-methylpropanethioamide | P-133 | Z (b) |
| 372 | (S)-N-[[3-[3,5-Difluoro-4-[4-(cyanomethyl)-1-piperazinyl]phenyl]-2-oxo-5-oxazolidinyl]methyl]-cyclopropanecarbothioamide | P-133 | Z (c) |
| 373 | (S)-N-[[3-[4-[4-(cyanomethyl)-1-piperazinyl]phenyl]-2-oxo-5-oxazo-lidinyl]methyl]thioacetamide | P-134 | Ethyl dithio-acetate |
| 374 | (S)-N-[[3-[4-[4-(cyanomethyl)-1-piperazinyl]phenyl]-2-oxo-5-oxazo-lidinyl]methyl]propanethioamide | P-134 | Z (a) |
| 375 | (S)-N-[[3-[4-[4-(cyanomethyl)-1-piperazinyl]phenyl]-2-oxo-5-oxazo-lidinyl]methyl]-2-methylpropane-thioamide | P-134 | Z (b) |
| 376 | (S)-N-[[3-[4-[4-(cyanomethyl)-1-piperazinyl]phenyl]-2-oxo-5-oxazo-lidinyl]methyl]cyclopropane-carbothioamide | P-134 | Z (c) |
| 377 | (S)-N-[[3-[3-Fluoro-4-[4-(2-fluoro-ethyl)-1-piperazinyl]phenyl]-2-oxo-5-oxazolidinyl]methyl]-thioacetamide | P-135 | Ethyl dithio-acetate |
| 378 | (S)-N-[[3-[3-Fluoro-4-[4-(2-fluoro-ethyl)-1-piperazinyl]phenyl]-2-oxo-5-oxazolidinyl]methyl]-propanethioamide | P-135 | Z (a) |
| 379 | (S)-N-[[3-[3-Fluoro-4-[4-(2-fluoro-ethyl)-1-piperazinyl]phenyl]-2-oxo-5-oxazolidinyl]methyl]-2-methylpropanethioamide | P-135 | Z (b) |
| 380 | (S)-N-[[3-[3-Fluoro-4-[4-(2-fluoro-ethyl)-1-piperazinyl]phenyl]-2-oxo-5-oxazolidinyl]methyl]-cyclopropanecarbothioamide | P-135 | Z (c) |
| 381 | (S)-N-[[3-[3,5-Difluoro-4-[4-(2-fluoroethyl)-1-piperazinyl]phenyl]-2-oxo-5-oxazolidinyl]methyl]-thioacetamide | P-136 | Ethyl dithio-acetate |
| 382 | (S)-N-[[3-[3,5-Difluoro-4-[4-(2-fluoroethyl)-1-piperazinyl]phenyl]-2-oxo-5-oxazolidinyl]methyl]-propanethioamide | P-136 | Z (a) |
| 383 | (S)-N-[[3-[3,5-Difluoro-4-[4-(2-fluoroethyl)-1-piperazinyl]phenyl]-2-oxo-5-oxazolidinyl]methyl]-2-methylpropanethioamide | P-136 | Z (b) |
| 384 | (S)-N-[[3-[3,5-Difluoro-4-[4-(2-fluoroethyl)-1-piperazinyl]phenyl]-2-oxo-5-oxazolidinyl]methyl]-cyclopropanecarbothioamide | P-136 | Z (c) |
| 385 | (S)-N-[[3-[4-[4-(2-fluoroethyl)-1-piperazinyl]phenyl]-2-oxo-5-oxazo-lidinyl]methyl]thioacetamide | P-137 | Ethyl dithio-acetate |
| 386 | (S)-N-[[3-[4-[4-(2-fluoroethyl)-1-piperazinyl]phenyl]-2-oxo-5-oxazo-lidinyl]methyl]propane-thioamide | P-137 | Z (a) |
| 387 | (S)-N-[[3-[4-[4-(2-fluoroethyl)-1-piperazinyl]phenyl]-2-oxo-5-oxazo-lidinyl]methyl]-2-methylpropane-thioamide | P-137 | Z (b) |
| 388 | (S)-N-[[3-[4-[4-(2-fluoroethyl)-1-piperazinyl]phenyl]-2-oxo-5-oxazo-lidinyl] | P-137 | Z (c) |

TABLE H-continued

| Example No. | Product | Amine | Dithio Compound |
|---|---|---|---|
| | lidinyl]methyl]cyclopropane-carbothioamide | | |
| 389 | (S)-N-[[3-[3-Fluoro-4-(4-formyl-1-piperazinyl)phenyl]-2-oxo-5-oxazo-lidinyl]methyl]-thioacetamide; Anal calcd for $C_{17}H_{21}FN_4O_3S$: C, 53.67; H, 5.56; N, 14.73; S, 8.43. Found: C, 53.14; H, 5.42; N, 14.25; S, 8.18. | P-138 | Ethyl dithio-acetate |
| 390 | (S)-N-[[3-[3-Fluoro-4-(4-formyl-1-piperazinyl)phenyl]-2-oxo-5-oxazo-lidinyl]methyl]-propanethioamide; mp 166–167° C.; Anal. calcd for $C_{18}H_{23}FN_4O_3S$: C, 54.81; H, 5.88; N, 14.20; S, 8.13. Found: C, 54.83; H, 6.00; N, 14.12; S, 7.96. | P-138 | Z (a) |
| 391 | (S)-N-[[3-[3-Fluoro-4-(4-formyl-1-piperazinyl)phenyl]-2-oxo-5-oxazo-lidinyl]methyl]-2-methyl-propanethioamide; mp 157–158° C.; Anal. calcd for $C_{19}H_{25}FN_4O_3S$: C, 55.87; H, 6.17; N, 13.72; S, 7.85. Found: C, 55.67; H, 6.19; N, 13.50; S, 7.70. | P-138 | Z (b) |
| 392 | (S)-N-[[3-[3-Fluoro-4-(4-formyl-1-piperazinyl)phenyl]-2-oxo-5-oxazo-lidinyl]methyl]-cyclopropanecarbothioamide; mp 178–179° C.; Anal. calcd for $C_{19}H_{23}FN_4O_3S$: C, 56.14; H, 5.70; N, 13.78; S, 7.89. Found: C, 56.13; H, 5.64; N, 13.64; S, 7.75. | P-138 | Z (c) |
| 393 | (S)-N-[[3-[3,5-Difluro-4-(4-formyl-1-piperazinyl)-phenyl]-2-oxo-5-oxazolidinyl]methyl]-thioacetamide | P-139 | Ethyl dithio-acetate |
| 394 | (S)-N-[[3-[3,5-Difluro-4-(4-formyl-1-piperazinyl)-phenyl]-2-oxo-5-oxazolidinyl]methyl]propane-thioamide | P-139 | Z (a) |
| 395 | (S)-N-[[3-[3,5-Difluro-4-(4-formyl-1-piperazinyl)-phenyl]-2-oxo-5-oxazolidinyl]methyl]-2-methyl-propanethioamide | P-139 | Z (b) |
| 396 | (S)-N-[[3-[3,5-Difluro-4-(4-formyl-1-piperazinyl)-phenyl]-2-oxo-5-oxazolidinyl]methyl]cyclo-propanecarbothioamide | P-139 | Z (c) |
| 397 | (S)-N-[[3-[4-(4-formyl-1-piperazinyl)phenyl]-2-oxo-5-oxazolidinyl]methyl]-thioacetamide | P-140 | Ethyl dithio-acetate |
| 398 | (S)-N-[[3-[4-(4-formyl-1-piperazinyl)phenyl]-2-oxo-5-oxazo-lidinyl]methyl]propanethioamide | P-140 | Z (a) |
| 399 | (S)-N-[[3-[4-(4-formyl-1-piperazinyl)phenyl]-2-oxo-5-oxazo-lidinyl]methyl]-2-methylpro-panethioamide | P-140 | Z (b) |
| 400 | (S)-N-[[3-[4-(4-formyl-1-piperazinyl)phenyl]-2-oxo-5-oxazo-lidinyl]methyl]cyclopropane-carbothioamide | P-140 | Z (c) |

When in the general procedure of Example 31, step 1, an appropriate amount of the amine listed below is substituted for compound 33, the isothiocyanate corresponding to the amines P-90, P-93, P-99, P-105, P-126 and P-129 are obtained.

When in the general procedure of Example 114 an appropriate amount of the isothiocyanate and the amine listed below are substituted for compound 82 and methylamine, the respective products listed below are obtained.

TABLE I

| Example No. | Product | Isothiocyanate Corresponding to Amine No. | Amine |
|---|---|---|---|
| 401 | (S)-N-[[3-[3-Fluoro-4-(4-acetyl-1-piperazinyl)phenyl]-2-oxo-5-oxazolidinyl]-methyl]-N'-methylthiourea | P-90 | methylamine |
| 402 | (S)-N-[[3-[3-Fluoro-4-(4-acetyl-1-piperazinyl)phenyl]-2-oxo-5-oxazolidinyl]-methyl]-N',N'-dimethylthiourea | P-90 | dimethylamine |
| 403 | (S)-N-[[3-[3-Fluoro-4-(4-acetyl-1-piperazinyl)phenyl]-2-oxo-5-oxazolidinyl]-methyl]-1-azetidinecarbothioamide | P-90 | azetidine |
| 404 | (S)-N-[[3-[3-Fluoro-4-(4-thiomorpholinyl)-phenyl]-2-oxo-5-oxazolidinyl]-methyl]-thiourea | P-90 | anhydrous ammonia |
| 405 | (S)-N-[[3-[3-Fluoro-4-[4-(methoxyacetyl)-1-piperazinyl]phenyl]-2-oxo-5-oxazolidinyl]-methyl]-N'-methylthiourea | P-93 | methylamine |
| 406 | (S)-N-[[3-[3-Fluoro-4-[4-(methoxyacetyl)-1-piperazinyl]phenyl]-2-oxo-5-oxazolidinyl]-methyl]-N',N'-dimethylthiourea | P-93 | dimethylamine |
| 407 | (S)-N-[[3-[3-Fluoro-4-[4-(methoxyacetyl)-1-piperazinyl]phenyl]-2-oxo-5-oxazolidinyl]methyl]-1-azetidine-carbothioamide | P-93 | azetidine |
| 408 | (S)-N-[[3-[3-Fluoro-4-[4-(acetoxyacetyl)-1-piperazinyl]phenyl]-2-oxo-5-oxazolidinyl]-methyl]-N'-methylthiourea | P-99 | methylamine |
| 409 | (S)-N-[[3-[3-Fluoro-4-[4-(acetoxyacetyl)-1-piperazinyl]phenyl]-2-oxo-5-oxazolidinyl]-methyl]-N',N'-dimethylthiourea | P-99 | dimethylamine |
| 410 | (S)-N-[[3-[3-Fluoro-4-[4-(acetoxyacetyl)-1-piperazinyl]phenyl]-2-oxo-5-oxazolidinyl]-methyl]-1-azetidine-carbothioamide | P-99 | azetidine |
| 411 | (S)-N-[[3-[3-Fluoro-4-[4-(methoxycarbonyl)-1-piperazinyl]phenyl]-2-oxo-5-oxazolidinyl]-methyl]-N'-methylthiourea | P-105 | methylamine |
| 412 | (S)-N-[[3-[3-Fluoro-4-[4-(methoxycarbonyl)-1-piperazinyl]phenyl]-2-oxo-5-oxazolidinyl]-methyl]-N',N'-dimethylthiourea | P-105 | dimethylamine |
| 413 | (S)-N-[[3-[3-Fluoro-4-[4-(methoxycarbonyl)- | P-105 | azetidine |

TABLE I-continued

| Example No. | Product | Isothiocyanate Corresponding to Amine No. | Amine |
|---|---|---|---|
| | 1-piperazinyl]phenyl]-2-oxo-5-oxazolidinyl]-methyl]-1-azetidine-carbothioamide | | |
| 414 | (S)-N-[[3-[3-Fluoro-4-[4-(ethoxycarbonyl)-1-piperazinyl]phenyl]-2-oxo-5-oxazolidinyl]-methyl]-N'-methylthiourea | P-126 | methylamine |
| 415 | (S)-N-[[3-[3-Fluoro-4-[4-(ethoxycarbonyl)-1-piperazinyl]phenyl]-2-oxo-5-oxazolidinyl]-methyl]-N',N'-dimethylthiourea | P-126 | dimethylamine |
| 416 | (S)-N-[[3-[3-Fluoro-4-[4-(ethoxycarbonyl)-1-piperazinyl]phenyl]-2-oxo-5-oxazolidinyl]-methyl]-1-azetidine-carbothioamide | P-126 | azetidine |
| 417 | (S)-N-[[3-[3-Fluoro-4-(4-sulfamoyl-1-piperazinyl)phenyl]-2-oxo-5-oxazolidinyl]-methyl]-N'-methylthiourea | P-129 | methylamine |
| 418 | (S)-N-[[3-[3-Fluoro-4-(4-sulfamoyl-1-piperazinyl)phenyl]-2-oxo-5-oxazolidinyl]-methyl]-N'-N'-dimethylthiourea | P-129 | dimethylamine |
| 419 | (S)-N-[[3-[3-Fluoro-4-(4-sulfamoyl-1-piperazinyl)phenyl]-2-oxo-5-oxazolidinyl]-methyl]-N'-azetidine-carbothioamide | P-129 | azetidine |

When in the general procedure of Example 100 an appropriate amount of the isothiocyanate and alcohol listed below are utilized in the same manner as Compound 82 and methanol are utilized, the respective products listed below are obtained.

TABLE J

| Example No. | Product | Isothiocyanate Corresponding to Amine No. | Amine |
|---|---|---|---|
| 420 | (S)-N-[[3-[3-Fluoro-4-(4-acetyl-1-piperazinyl)phenyl]-2-oxo-5-oxazolidinyl]-methyl]-O-methyl-thiocarbamate | P-90 | methanol |
| 421 | (S)-N-[[3-[3-Fluoro-4-(4-acetyl-1-piperazinyl)phenyl]-2-oxo-5-oxazolidinyl]-methyl]-O-ethyl-thiocarbamate | P-90 | ethanol |
| 422 | (S)-N-[[3-[3-Fluoro-4-(4-acetyl-1-piperazinyl)phenyl]-2-oxo-5-oxazolidinyl]-methyl]-O-iso-propylthiocarbamate | P-90 | isopropyl alcohol |
| 423 | (S)-N-[[3-[3-Difluoro-4-(4-acetyl-1-piperazinyl)phenyl]-2-oxo-5-oxazolidinyl]-methyl]-O-methyl-thiocarbamate | P-91 | methanol |
| 424 | (S)-N-[[3-[4-(4-Acetyl-1-piperazinyl)phenyl]-2-oxo-5-oxazolidinyl]-methyl]-O-methyl-thiocarbamate | P-92 | methanol |
| 425 | (S)-N-[[3-[3-Fluoro-4-[4-(methoxyacetyl)-1-piperazinyl)phenyl]-2-oxo-5-oxazolidinyl]-methyl]-O-methyl-thiocarbamate | P-93 | methanol |
| 426 | (S)-N-[[3-[3-Fluoro-4-[4-(methoxyacetyl)-1-piperazinyl)phenyl]-2-oxo-5-oxazolidinyl]-methyl]-O-ethylthiocarbamate | P-93 | ethanol |
| 427 | (S)-N-[[3-[3-Fluoro-4-[4-(methoxyacetyl)-1-piperazinyl)phenyl]-2-oxo-5-oxazolidinyl]-methyl]-O-iso-propylthiocarbamate | P-93 | isopropyl alcohol |
| 428 | (S)-N-[[3-[3,5-Difluoro-[4-[4-(methoxy-acetyl)-1-piperazinyl]phenyl]-2-oxo-5-oxazolidinyl]methyl]-O-methylthiocarbamate | P-94 | methylaminel |
| 429 | (S)-N-[[3-[4-[4-(methoxyacetyl)-1-piperazinyl]phenyl]-2-oxo-5-oxazolidinyl]methyl]-O-methyl-thiocarbamate | P-95 | methylamine |
| 430 | (S)-N-[3-[3-Fluoro-4-[4-(cyanoacetyl)-1-piperazinyl]phenyl]-2-oxo-5-oxazolidinyl]-methyl]-O-methylthiocarbamate | P-96 | methanol |
| 431 | (S)-N-[[3-[3,5-Difluoro-4-[4-(cyanoacetyl)-1-piperazinyl]phenyl]-2-oxo-5-oxazolidinyl]-methyl]-O-methylthiocarbamate | P-97 | methanol |
| 432 | (S)-N-[[3-[4-[4-(Cyanoacetyl)-1-piperazinyl]phenyl]-2-oxo-5-oxazolidinyl]-methyl]-O-methylthiocarbamate | P-98 | methanol |
| 433 | (S)-N-[[3-[3-Fluoro-4-[4-(acetoxyacetyl)-1-piperazinyl]phenyl]-2-oxo-5-oxazolidinyl]-methyl]-O-methylthiocarbamate | P-99 | methanol |
| 434 | (S)-N-[[3-[3-Fluoro-4-[4-(acetoxyacetyl)-1-piperazinyl]phenyl]-2-oxo-5-oxazolidinyl]-methyl]-O-ethylthiocarbamate | P-99 | ethanol |
| 435 | (S)-N-[[3-[3-Fluoro-4-[4-(acetoxyacetyl)-1-piperazinyl]phenyl]-2-oxo-5-oxazolidinyl]- | P-99 | isopropyl alcohol |

TABLE J-continued

| Example No. | Product | Isothiocyanate Corresponding to Amine No. | Amine |
|---|---|---|---|
| 436 | methyl]-O-iso-propylthiocarbamate (S)-N-[[3-[3,5-Difluoro-4-[4-(acetoxyacetyl)-1-piperazinyl]phenyl]-2-oxo-5-oxazolidinyl]-methyl]-O-methyl-thiocarbamate | P-100 | methanol |
| 437 | (S)-N-[[3-[4-[4-(Acetoxyacetyl)-1-piperazinyl]phenyl]-2-oxo-5-oxazolidinyl]-methyl]-O-methyl-thiocarbamate | P-101 | methanol |
| 438 | (S)-N-[[3-[3-Fluoro-4-[4-(benzyloxyacetyl)-1-piperazinyl]phenyl]-2-oxo-5-oxazolidinyl]-methyl]-O-methyl-thiocarbamate | P-102 | methanol |
| 439 | (S)-N-[[3-[3,5-Difluoro-4-[4-(benzyloxy-acetyl)-1-piperazinyl]phenyl]-2-oxo-5-oxazolidinyl]methyl]-O-methylthiocarbamate | P-103 | methanol |
| 440 | (S)-N-[[3-[3-Fluoro-4-[4-(methoxycarbonyl)-1-piperazinyl]phenyl]-2-oxo-5-oxazolidinyl]-methyl]-O-methylthiocarbamate | P-105 | methanol |
| 441 | (S)-N-[[3-[3-Fluoro-4-[4-(methoxycarbonyl)-1-piperazinyl]phenyl]-2-oxo-5-oxazolidinyl]-methyl]-O-ethylthiocarbamate | P-105 | ethanol |
| 442 | (S)-N-[[3-[3-Fluoro-4-[4-(methoxycarbonyl)-1-piperazinyl]phenyl]-2-oxo-5-oxazolidinyl]-methyl]-O-iso-propylthiocarbamate | P-105 | isopropyl alcohol |
| 443 | (S)-N-[[3-[3,5-Difluoro-4-[4-(methoxycarbonyl)-1-piperazinyl]phenyl]-2-oxo-5-oxazolidinyl]methyl]-O-methylthiocarbamate | P-106 | methanol |
| 444 | (S)-N-[[3-[4-[4-(methoxycarbonyl)-1-piperazinyl]phenyl]-2-oxo-5-oxazolidinyl]-methyl]-O-methyl-thiocarbamate | P-107 | methanol |
| 445 | (S)-N-[[3-[3-Fluoro-4-[4-(methanesulfonyl)-1-piperazinyl]phenyl]-2-oxo-5-oxazolidinyl]-methyl]-O-methylthiocarbamate | P-108 | methanol |
| 446 | (S)-N-[[3-[3,5-Difluoro-4-[4-(methanesulfonyl)-1-piperazinyl]phenyl]-2-oxo-5-oxazolidinyl]methyl]-O-methylthiocarbamate | P-109 | methanol |
| 447 | (S)-N-[[3-[4-[4-(methanesulfonyl)-1-piperazinyl]phenyl]-2-oxo-5-oxazolidinyl]-methyl]-O-methyl-thiocarbamate | P-110 | methanol |
| 448 | (S)-N-[[3-[3-Fluoro-4-[4-(ethanesulfonyl)-1-piperazinyl]phenyl]-2-oxo-5-oxazolidinyl]-methyl]-O-methyl-thiocarbamate | P-111 | methanol |
| 449 | (S)-N-[[3-[3,5-Difluoro-4-[4-(ethanesulfonyl)-1-piperazinyl]phenyl]-2-oxo-5-oxazolidinyl]methyl]cyclopropane-carbothioamide | P-112 | methanol |
| 450 | (S)-N-[[3-[4-[4-(ethanesulfonyl)-1-piperazinyl]phenyl]-2-oxo-5-oxazolidinyl]methyl]-O-methylthiocarbamate | P-113 | methanol |
| 451 | (S)-N-[[3-[3-Fluoro-4-[4-(chloromethane-sulfonyl)-1-piperazinyl]phenyl]-2-oxo-5-oxazolidinyl]methyl]-O-methylthiocarbamate | P-114 | methanol |
| 452 | (S)-N-[[3-[3,5-Difluoro-4-[4-(chloromethane-sulfonyl)-1-piperazinyl]phenyl]-2-oxo-5-oxazolidinyl]methyl]-O-methyl-thiocarbamate | P-115 | methanol |
| 453 | (S)-N-[[3-[4-[4-(chloromethanesulfonyl)-1-piperazinyl]phenyl]-2-oxo-5-oxazolidinyl]methyl]-O-methylthiocarbamate | P-116 | methanol |
| 454 | (S)-N-[[3-[3-Fluoro-4-[4-(cyanomethane-sulfonyl)-1-piperazinyl]phenyl]-2-oxo-5-oxazolidinyl]methyl]-O-methylthiocarbamate | P-117 | methanol |
| 455 | (S)-N-[[3-[3,5-Difluoro-4-[4-(cyanomethane-sulfonyl)-1-piperazinyl]phenyl]-2-oxo-5-oxazolidinyl]methyl]-O-methylthiocarbamate | P-118 | methanol |
| 456 | (S)-N-[[3-[4-[4-(Cyanomethanesulfonyl)-1-piperazinyl]phenyl]-2-oxo-5-oxazolidinyl]-methyl]-O-methylthiocarbamate | P-119 | methanol |
| 457 | (S)-N-[[3-[3-Fluoro-4-[4-(N-methylsulfa-moyl)-1-piperazinyl]phenyl]-2-oxo-5-oxazoli-dinyl]methyl]-O-methylthiocarbamate | P-120 | methanol |
| 458 | (S)-N-[[3-[3,5-Difluoro-4-[4-(N-methylsulfa-moyl)-1-piperazinyl]phenyl]-2-oxo-5-oxazoli-dinyl]methyl]-O-methylthiocarbamate | P-121 | methanol |
| 459 | (S)-N-[[3-[4-[4-(N-methylsulfamoyl)-1-piperazinyl]phenyl]-2-oxo-5-oxazolidinyl]-methyl]-O-methylthiocarbamate | P-122 | methanol |
| 460 | (S)-N-[[3-[3-Fluoro-4-[4-(N,N-dimethylsulfa-moyl)-1-piperazinyl] | P-123 | methanol |

TABLE J-continued

| Example No. | Product | Isothiocyanate Corresponding to Amine No. | Amine |
|---|---|---|---|
| | phenyl]-2-oxo-5-oxazolidinyl]methyl]-O-methylthiocarbamate | | |
| 461 | (S)-N-[[3-[3,5-Difluoro-4-[4-(N,N-dimethylsulfamoyl)-1-piperazinyl]phenyl]-2-oxo-5-oxazolidinyl]methyl]-O-methylthiocarbamate | P-124 | methanol |
| 462 | (S)-N-[[3-[4-[4-(N,N-dimethylsulfamoyl)-1-piperazinyl]phenyl]-2-oxo-5-oxazolidinyl]methyl]-O-methylthiocarbamate | P-125 | methanol |
| 463 | (S)-N-[[3-[3-Fluoro-4-[4-(ethoxycarbonyl)-1-piperazinyl]phenyl]-2-oxo-5-oxazolidinyl]-methyl]-O-methylthiocarbamate | P-126 | methanol |
| 464 | (S)-N-[[3-[3-Fluoro-4-[4-(ethoxycarbonyl)-1-piperazinyl]phenyl]-2-oxo-5-oxazolidinyl]-methyl]-O-ethylthiocarbamate | P-126 | ethanol |
| 465 | (S)-N-[[3-[3-Fluoro-4-[4-(ethoxycarbonyl)-1-piperazinyl]phenyl]-2-oxo-5-oxazolidinyl]-methyl]-O-isopropylthiocarbamate | P-126 | isopropyl alcohol |
| 466 | (S)-N-[[3-[3,5-Difluoro-4-[4-(ethoxycarbonyl)-1-piperazinyl]phenyl]-2-oxo-5-oxazolidinyl]methyl]-O-methylthiocarbamate | P-127 | methanol |
| 467 | (S)-N-[[3-[4-[4-(ethoxycarbonyl)-1-piperazinyl]phenyl]-2-oxo-5-oxazolidinyl]methyl]-O-methylthiocarbamate | P-128 | methanol |
| 468 | (S)-N-[[3-[3-Fluoro-4-(4-sulfamoyl-1-piperazinyl)phenyl]-2-oxo-5-oxazolidinyl]-methyl]-O-methylthiocarbamate, | P-129 | methanol |
| 469 | (S)-N-[[3-[3-Fluoro-4-(4-sulfamoyl-1-piperazinyl)phenyl]-2-oxo-5-oxazolidinyl]methyl]-O-ethylthiocarbamate | P-129 | ethanol |
| 470 | (S)-N-[[3-[3-Fluoro-4-(4-sulfamoyl-1-piperazinyl)phenyl]-2-oxo-5-oxazolidinyl]-methyl]-O-isopropylthiocarbamate | P-129 | isopropyl alcohol |
| 471 | (S)-N-[[3-[3,5-Difluoro-4-(4-sulfamoyl-1-piperazinyl)phenyl]-2-oxo-5-oxazolidinyl]methyl]-O-methylthiocarbamate | P-130 | methanol |
| 472 | (S)-N-[[3-[4-(4-sulfamoyl-1-piperazinyl)-phenyl]-2-oxo-5-oxazolidinyl]methyl]-O-methylthiocarbamate | P-131 | methanol |
| 473 | (S)-N-[[3-[3-Fluoro-4-[4-(cyanomethyl)-1-piperazinyl]phenyl]-2-oxo-5-oxazolidinyl]-methyl]-O-methylthiocarbamate | P-132 | methanol |
| 474 | (S)-N-[[3-[3,5-Difluoro-4-[4-(cyanomethyl)-1-piperazinyl]phenyl]-2-oxo-5-oxazolidinyl]-methyl]-O-methylthiocarbamate | P-133 | methanol |
| 475 | (S)-N-[[3-[4-[4-(cyanomethyl)-1-piperazinyl]phenyl]-2-oxo-5-oxazolidinyl]-methyl]-O-methylthiocarbamate | P-134 | methanoll |
| 476 | (S)-N-[[3-[3-Fluoro-4-[4-(2-fluoroethyl)-1-piperazinyl]phenyl]-2-oxo-5-oxazolidinyl]-methyl]-O-methylthiocarbamate | P-135 | methanol |
| 477 | (S)-N-[[3-[3,5-Difluoro-4-[4-(2-fluoroethyl)-1-piperazinyl]phenyl]-2-oxo-5-oxazolidinyl]-methyl]-O-methylthiocarbamate | P-136 | methanol |
| 478 | (S)-N-[[3-[4-[4-(2-fluoroethyl)-1-piperazinyl]phenyl]-2-oxo-5-oxazolidinyl]-methyl]-O-methylthiocarbamate | P-137 | methanol |
| 479 | (S)-N-[[3-[3-Fluoro-4-(4-formyl-1-piperazinyl)phenyl]-2-oxo-5-oxazolidinyl]-methyl]-O-methylthiocarbamate | P-138 | methanol |
| 480 | (S)-N-[[3-[3,5-Difluro-4-(4-formyl-1-piperazinyl)phenyl]-2-oxo-5-oxazolidinyl]-methyl]-O-methylthiocarbamate | P-139 | methanol |
| 481 | (S)-N-[[3-[4-(4-formyl-1-piperazinyl)-phenyl]-2-oxo-5-oxazolidinyl]methyl]-O-methylthiocarbamate | P-140 | methanol |

EXAMPLE 482

(5S)-N-[[3-[3-Fluoro-4-(tetrahydro-1,4-tiazepin-4(5H)-yl)phenyl]-2-oxo-5-oxazolidinyl]methyl]thioacetamide, thiazepine S-oxide

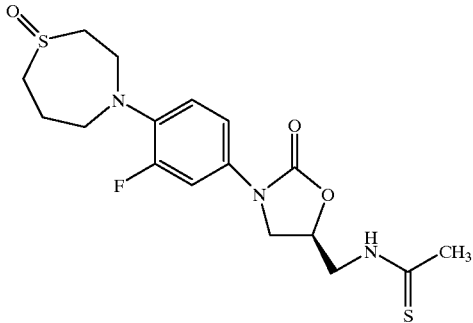

Step 1. Rexahydro-5-oxo-1,4-thiazepine is prepared according to the procedure described by Gallego (*J. Org. Chem.* 1993, 58, 3905–3911).

Step 2. Lithium aluminum hydride (5.5 mL of a 1M solution in THF) is added dropwise to a stirred solution of hexahydro-5-oxo-1,4-thiazepine (721.5 mg) in dry THF (21 mL) cooled to 0° C. The reaction mixture is stirred at 0° C. for 10 min, then at room temperature for 4 h. The reaction mixture is quenched by careful successive addition of water (0.2 mL), 5 N aqueous NaOH (0.2 mL) and water (0.74 mL). The reaction mixture becomes very thick and gel-like. The reaction mixture is diluted with ether (50 mL) and filtered through a pad of celite. The filter cake is washed with ether (100 mL). The filtrate is concentrated to afford 616.6 mg of 1,4-hexahydrothiazepine which is used immediately in the next step.

Step 3. To a stirred solution of 1,4-hexahydrothiazepine (596.0 mg) and 3,4-difluoronitrobenzene (0.51 mL) in acetonitrile (14 mL) is added diisopropylethylamine (1.0 mL). The yellow solution is heated at reflux for 18 h, then cooled and concentrated. The residue is diluted with $CH_2Cl_2$ (100 mL) and washed with saturated aqueous $NH_4Cl$ (35 mL). The phases are separated and the organics are dried ($MgSO_4$), filtered and concentrated. The residue is purified by flash chromatography using 20% EtOAc in hexane as the eluent to afford 830.2 mg of the nitrobenzene. Mp 115–116° C.; Anal. Calcd for $C_{11}H_{13}FN_2O_2S$: C, 51.55; H, 5.11; N, 10.93; S, 12.51. Found: C, 51.47; H, 5.12; N, 10.79; S, 12.42.

Step 4. To a stirred suspension of the nitrobenzene prepared in Step 3 (5.5 g) in EtOH (260 mL) is added a solution of 2 M aqueous $CuSO_4$ (11.9 mL). The mixture is cooled to 0° C. and $NABH_4$ (4.1 g) is added in portions. The reaction mixture turns very dark and is stirred at 0° C. for 10 min, at room temperature for 30 min, and then heated at reflux for 3 h. The cooled reaction mixture is diluted with EtOAc (500 ml) and washed with water (200 mL). The aqueous mixture is extracted with EtOAc (3×200 mL). The combined organics are dried ($MgSO_4$), filtered and concentrated to afford the aniline intermediate.

Step 5. The dark residue from Step 4 is dissolved in 2:1 acetone/water (255 mL) and cooled to 0° C. To this stirred mixture is added solid $NaHCO_3$ (5.4 g) followed by benzylchloroformate (7.7 mL). The reaction mixture is stirred at 0° C. for 10 min, then at room temperature for 24 h. The reaction mixture is quenched with 10% aqueous $NaHSO_4$ (200 mL) and then poured into EtOAc (300 mL). The phases are separated and the aqueous phase is extracted with EtOAc (2×250 mL). The combined organics are dried ($MgSO_4$), filtered and concentrated. The residue is purified by MPLC using 20% EtOAc in hexane to afford 6.03 g of the benzylcarbamate as a yellow solid. mp 72–74° C.; Anal. Calcd for $C_{19}H_{21}FN_2O_2S$: C, 63.3 1; H, 5.87; N, 7.77; S, 8.89. Found: C, 63.31; H, 5.97; N, 7.69; S, 8.79.

Step 6. To a stirred solution of the carbamate from Step 5 (3.0 g) in dry THF (33 mL) under $N_2$ cooled to −78° C., is added dropwise via syringe a 1.6 M solution of nBuLi in hexane (5.4 mL). The reaction mixture was stirred at −78° C. for 35 min, then R-glycidyl butyrate (1.2 mL) is added. The reaction mixture is stirred at −78° C. for 30 min, then at room temperature overnight during which time a precipitate forms. The reaction mixture is quenched with saturated aqueous $NH_4Cl$ (33 mL) and poured into EtOAc (100 mL). The phases are separated. The organic phase is washed with saturated aqueous $NaHCO_3$ (50 mL), brine (50 mL), dried ($MgSO_4$), filtered and concentrated. The residue is purified by flash chromatography using EtOAc as the eluent to afford 2.5 g of a hydroxymethyl oxazolidinone. Mp 100–102° C. Anal. Calcd for $C_{15}H_{19}FN_2O_3S$: C, 55.20; H, 5.87; N, 8.58; S, 9.82. Found: C, 55.09; H, 5.91; N, 8.36; S, 9.57.

Step 7. To a stirred solution of the alcohol prepared in Step 6 (1.7 g) in $CH_2Cl_2$ (35 mL) cooled to 0° C., is added triethylamine (1.1 mL) followed by methanesulfonyl chloride (0.5 mL). The reaction mixture is stirred at 0° C. for 10 min, then at room temperature for 1 h. The reaction mixture is treated with water (35 mL). The phases are separated and the aqueous phase is extracted with $CH_2Cl_2$ (35 mL). The combined organic phases are dried ($MgSO_4$), filtered and concentrated. The residue is purified by flash chromatography using 80% EtOAc in hexane as the eluent to afford 2.1 g of the mesylate. Mp 132–142° C. Anal. Calcd for $C_{16}H_{21}FN_2O_5S_2$: C, 47.51; H, 5.23; N, 6.93; S. 15.85. Found: C, 47.18; H, 5.28; N, 6.84; S, 15.60.

Step 8. Ammonia gas is bubbled into a stirred suspension of the mesylate prepared in Step 7 (941.7 mg) in 1:1 THF/$CH_3OH$ (40 mL) until saturated (approx. 5 min). The reaction mixture is heated in a sealed tube at 100° C. for 72 h. The cooled reaction mixture is concentrated to give the crude amine, which is immediately suspended in $CH_2Cl_2$ (35 mL) and cooled to 0° C. To this stirred suspension is added triethylamine (0.97 mL, 6.9 mmol) followed by di-tert-butyl dicarbonate (759.5 mg, 3.5 mmol). The reaction mixture becomes homogeneous and is stirred at RT for 18 h. The reaction mixture is poured into $CH_2Cl_2$ (75 mL) and washed with $H_2O$ (1×50 mL). The organic phase is dried ($MgSO_4$), filtered and concentrated. The resulting residue is purified on a Biotage 40 S column using 30–35% ethyl acetate in $CH_3OH$ as the eluent to afford 867.4 mg of the protected amine. mp 74–75° C. Anal Cald: C, 56.45; H, 6.63; N, 9.88. Found: C, 56.95; H, 6.85; N, 9.55.

Step 9. To a stirred suspension of the protected amine prepared in Step 8 (205.2 mg) in 1:1 $CH_3OH/H_2O$ (6 mL) cooled to 0° C. is added sodium meta periodate (113.5 mg). The resulting suspension is stirred at RT for 18 h. The reaction mixture is filtered and the solid is washed with $CH_2Cl_2$ (2×20 mL). The filtrate is extracted with $H_2O$ (1×10 mL). The phases are separated. The aqueous phase is extracted with $CH_2Cl_2$ (1×25 mL). The combined organic phases are dried ($MgSO_4$), filtered and concentrated. The white solid residue is purified on a Biotage 12 M column using 5% $CH_3OH$ in $CH_2Cl_2$ as the eluent to afford 187.3 mg of the sulfoxide. mp 78–81° C.

Step 10. Dry HCl gas is passed over the surface of a stirred solution of the sulfoxide prepared in Step 9 (179.3 mg) in CH₃OH (2 mL) cooled to 0° C. for 1 minute. The reaction mixture is stirred at 0° C. for 10 min, then at room temperature for 15 min, then concentrated. The resulting yellow residue is suspended in THF (5 mL) and CH₂Cl₂ (5 mL) and cooled to 0° C. To this stirred suspension is added triethylamine (0.46 mL) followed by ethyldithioacetate (0.18 mL). The dark reaction mixture is stirred at RT overnight then concentrated. The dark residue is diluted with CH₂Cl₂ (30 mL) and washed with H₂O (2×15 mL). The organic phases are dried (MgSO₄), filtered and concentrated. The dark residue is purified on a Biotage 12 M column using 5% CH₃OH in CH₂Cl₂ as the eluent to afford 71.5 mg of the title compound as a tan solid. mp 85–89° C.

Following the general procedure outlined in Step 10 of Example 482, but substituting the dithioesters listed below, the compounds of Examples 483 to 495 of Table K can be obtained.

TABLE K

| Example No. | Compound | Amine | Dithioester (from Preparation Z) |
|---|---|---|---|
| 483 | (5S)-N-[[3-[3-Fluoro-4-(tetrahydro-1,4-thiazepin-4(5H)-yl))-phenyl]-2-oxo-5-oxazolidinyl]methyl]-propanethioamide, thiazepine S-oxide | [Structure: 3-fluoro-4-(1,4-thiazepan-4-yl S-oxide)phenyl connected to oxazolidinone with CH₂NH₂ substituent] | Z (a) |
| 484 | (5S)-N-[[3-[3-Fluoro-4-(tetrahydro-1,4-thiazepin-4(5H)-yl))-phenyl]-2-oxo-5-oxazolidinyl]methyl]-2-methylpropanethioamide, thiazepine S-oxide. | Same as above | Z (b) |
| 485 | (5S)-N-[[3-[3-Fluoro-4-(tetrahydro-1,4-thiazepin-4(5H)-yl))-phenyl]-2-oxo-5-oxazolidinyl]methyl]-cyclopropanecarbothioamide, thiazepine S-oxide. | Same as above | Z (c) |
| 486 | (5S)-N-[[3-[3-Fluoro-4-(tetrahydro-1,4-thiazepin-4(5H)-yl))-phenyl]-2-oxo-5-oxazolidinyl]methyl]-butanethioamide, thiazepine S-oxide | Same as above | Z (d) |
| 487 | (5S)-N-[[3-[3-Fluoro-4-(tetrahydro-1,4-thiazepin-4(5H)-yl))-phenyl]-2-oxo-5-oxazolidinyl]methyl]-3-methylbutanethioamide, thiazepine S-oxide | Same as above | Z (e) |
| 488 | (5S)-N-[[3-[3-Fluoro-4-(tetrahydro-1,4-thiazepin-4(5H)-yl))-phenyl]-2-oxo-5-oxazolidinyl]methyl]-2-methylbutanethioamide, thiazepine S-oxide | Same as above | Z (f) |

TABLE K-continued

| Example No. | Compound | Amine | Dithioester (from Preparation Z) |
|---|---|---|---|
| 489 | (5S)-N-[[3-[3-Fluoro-4-(tetrahydro-1,4-thiazepin-4(5H)-yl))-phenyl]-2-oxo-5-oxazolidinyl]methyl]-3,3-dimethylbutanethio-amide, thiazepine S-oxide | Same as above | Z (g) |
| 490 | (5S)-N-[[3-[3-Fluoro-4-(tetrahydro-1,4-thiazepin-4(5H)-yl))-phenyl]-2-oxo-5-oxazolidinyl]methyl]-cyclobutanecarbothio-amide, thiazepine S-oxide | Same as above | Z (h) |
| 491 | (5S)-N-[[3-[3-Fluoro-4-(tetrahydro-1,4-thiazepin-4(5H)-yl))-phenyl]-2-oxo-5-oxazolidinyl]methyl]-1-cyclopentanecarbothio-amide, thiazepine S-oxide | Same as above | Z (i) |
| 492 | (5S)-N-[[3-[3-Fluoro-4-(tetrahydro-1,4-thiazepin-4(5H)-yl))-phenyl]-2-oxo-5-oxazolidinyl]methyl]-cyclohexanecarbothio-amide, thiazepine S-oxide | Same as above | Z (j) |
| 493 | (5S)-N-[[3-[3-Fluoro-4-(tetrahydro-1,4-thiazepin-4(5H)-yl))-phenyl]-2-oxo-5-oxazolidinyl]methyl]-2-cyclopropylethanethio-amide, thiazepine S-oxide | Same as above | Z (k) |
| 494 | (5S)-N-[[3-[3-Fluoro-4-(tetrahydro-1,4-thiazepin-4(5H)-yl))-phenyl]-2-oxo-5-oxazolidinyl]methyl]-2-cyclobutylethanethio-amide, thiazepine S-oxide | Same as above | Z (l) |
| 495 | (5S)-N-[[3-[3-Fluoro-4-(tetrahydro-1,4-thiazepin-4(5H)-yl))-phenyl]-2-oxo-5-oxazolidinyl]methyl]-2-cyclopentylethanethio-amide, thiazepine S-oxide | Same as above | Z (m) |

EXAMPLE 496

(5S)-N-[[3-[3,5-Difluoro-4-(tetrahydro-1,4-thiazepin-4(5H)-yl)phenyl]-2-oxo-5-oxazolidinyl]methyl]thioacetamide, thiazepine S-oxide

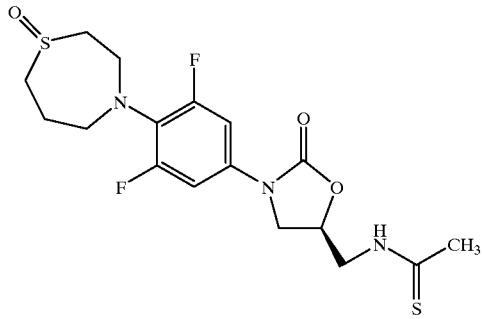

The title compound can be prepared by the procedure of Example 482, by substituting an appropriate quantity of 2,6-difluoro-4-nitrobenzene (trifluoromethane) sulfonate for 3,4-difluoronitrobenzene in Step 1.

Utilizing the amine prepared in Example 496, but substituting the dithioester listed below for ethyl dithioacetate in the final step, the compounds of Examples 497 to 499 of Table L are obtained.

EXAMPLE 500

(5S)-N-[[3-[4-(Tetrahydro-1,4-thiazepin-4(5H)-yl)phenyl]-2-oxo-5-oxazolidinyl]methyl]thioacetamide, thiazepine S-oxide

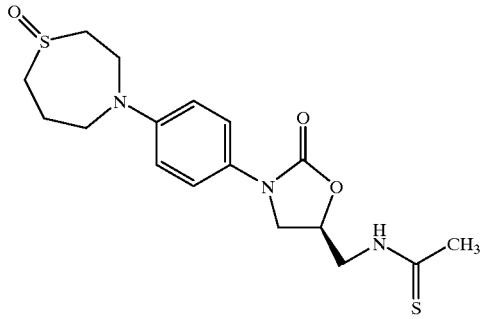

The title compound can be prepared by the procedure of Example 482, by substituting an appropriate quantity of 4-fluoronitrobenzene for 3,4-difluoronitro-benzene in Step 1.

Utilizing the amine prepared in Example 500, but substituting the dithioester listed below for ethyl dithioacetate in the final step, the compounds of Examples 501 to 503 of Table M are obtained

TABLE L

| Example No. | Compound | Amine | Dithioester (from Preparation Z) |
|---|---|---|---|
| 497 | (5S)-N-[[3-[3,5-Difluoro-4-(tetrahydro-1,4-thiazepin-4(5H)-yl))-phenyl]-2-oxo-5-oxazolidinyl]methyl]-propanethioamide, thiazepine S-oxide | (structure shown) | Z (a) |
| 498 | (5S)-N-[[3-[3,5-Difluoro-4-(tetrahydro-1,4-thiazepin-4(5H)-yl))-phenyl]-2-oxo-5-oxazolidinyl]methyl]-2-methylpropanethio-amide, thiazepine S-oxide | Same as above | Z (b) |
| 499 | (5S)-N-[[3-[3,5-Difluoro-4-(tetrahydro-1,4-thiazepin-4(5H)-yl))-phenyl]-2-oxo-5-oxazolidinyl]methyl]-cyclopropanecarbothio-amide, thiazepine S-oxide | Same as above | Z (c) |

TABLE M

| Example No. | Compound | Amine | Dithioester (from Preparation Z) |
|---|---|---|---|
| 501 | (5S)-N-[[3-[4-(Tetrahydro-1,4-thiazepin-4(5H)-yl))-phenyl]-2-oxo-5-oxazolidinyl]methyl]-propanethioamide, thiazepine S-oxide | 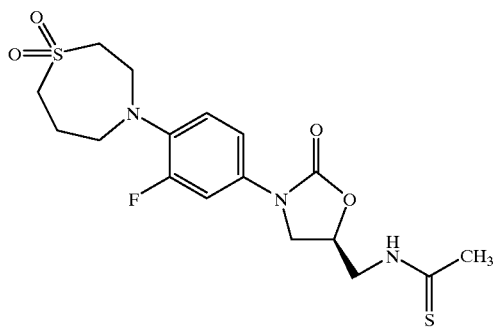 | Z (a) |
| 502 | (5S)-N-[[3-[4-(Tetrahydro-1,4-thiazepin-4(5H)-yl))-phenyl]-2-oxo-5-oxazolidinyl]methyl]-2-methylpropanethio-amide, thiazepine S-oxide | Same as above | Z (b) |
| 503 | (5S)-N-[[3-[4-(Tetrahydro-1,4-thiazepin-4(5H)-yl))-phenyl]-2-oxo-5-oxazolidinyl]methyl]-cyclopropanecarbothio-amide, thiazepine S-oxide | Same as above | Z (c) |

EXAMPLE 504

(5S)-N-[[3-[3-Fluoro-4-(tetrahydro-1,4-thiazepin-4(5H)-yl)phenyl]-2-oxo-5-oxazolidinyl]methyl] thioacetamnide, thiazepine S,S-dioxide Step 1. To a stirred solution of the thiazepine prepared in Step 8 of Example 482 (243.7 mg) in 25% H$_2$O/acetone (8 mL) is added 4-methylmorpholine N-oxide (201.5 mg) followed by a solution of osmium tetroxide in 2-methyl-2-propanol (2.5 wt %, 30 µL). The reaction mixture is stirred at room temperature for 18 h. The reaction mixture is treated with saturated sodium bisulfate (8 mL), then poured into CH$_2$Cl$_2$ (50 mL). The phases are separated. The aqueous phase is extracted with CH$_2$Cl$_2$ (2×25 mL). The combined organic phases are washed with brine (1×25 mL), dried (MgSO$_4$), filtered and concentrated. The residue is purified on a Biotage 40 S column using 1% CH$_3$OH in CH$_2$Cl$_2$ as the eluent to afford 216.1 mg (0.47 mmol, 83%) of the thiazepine S,S-dioxide as a white solid. mp 144–146° C.

Step 2. Dry HCl gas is passed over the surface of a stirred solution of the thiazepine S,S-dioxide prepared in Step 1 (108.2 mg) in CH$_3$OH(3 mL) at 0° C. for 1 minute. The reaction mixture is stirred at 0° C. for 10 min and then at room temperature for 15 min. The reaction is concentrated and the yellow residue is suspended in CH$_2$Cl$_2$ (2 mL) and THF (2 mL). This stirred suspension is cooled to 0° C. and triethylamine (0.27 mL) is added followed by a solution of ethyldithioacetate (0.11 mL) in THF (0.5 mL) with 0.25 mL rinse. The yellowish-green solution is stirred at 0° C. for 10 min then at room temperature for 18 h. The reaction mixture is poured into CH$_2$Cl$_2$ (20 mL) and washed with H$_2$O (2×10 mL). The organic phase was dried (MgSO$_4$), filtered and concentrated. The residue is purified on a Biotage 12 M column using 2% CH$_3$OH in CH$_2$Cl$_2$ as the eluent to afford 77.3 mg of the title compound as a white solid. mp 88–90° C.

Following the general procedure outlined in Step 2 of Example 504, but substituting the dithioester listed below for ethyl dithioacetate, the compounds of Examples 505 to 507 of Table N are obtained.

TABLE N

| Example No. | Compound | Amine | Dithioester (from Preparation Z) |
|---|---|---|---|
| 505 | (5S)-N-[[3-[3-Fluoro-4-(4-thiomorpholinyl)-phenyl]-2-oxo-5-oxazolidinyl]methyl]-propanethioamide, thiazepine S,S-dioxide | (structure shown) | Z (a) |
| 506 | (5S)-N-[[3-[3-Fluoro-4-(4-thiomorpholinyl)-phenyl]-2-oxo-5-oxazolidinyl]methyl]-2-methylpropanethio-amide, thiazepine S,S-dioxide | Same as above | Z (b) |
| 507 | (5S)-N-[[3-[3-Fluoro-4-(4-thiomorpholinyl)-phenyl]-2-oxo-5-oxazolidinyl]methyl]-cyclopropanecarbothio-amide, thiazepine S,S-dioxide | Same as above | Z (c) |

EXAMPLE 508

(5S)-N-[[3-[3,5-Difluoro-4-(tetrahydro-1,4-thiazepin-4(5H)-yl)phenyl]-2-oxo-5-oxazolidinyl]methyl]thioacetamide, thiazepine S,S-dioxide

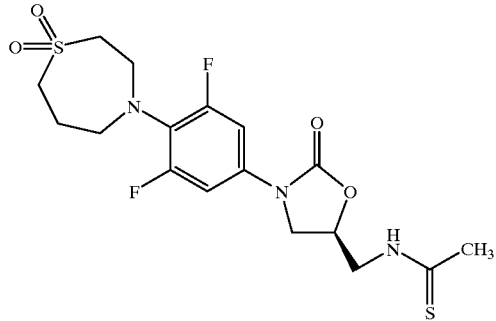

The title compound can be prepared by the procedures of Examples 504 and 482, by substituting an appropriate quantity of 2,6-difluoro-4-nitrobenzene (trifluoromethane) sulfonate for 3,4-difluoronitrobenzene in Step 1 of Example 482.

Utilizing the amine prepared in Example 508, but substituting the dithioester listed below for ethyl dithioacetate in the final step, the compounds of Examples 509 to 511 of Table O are obtained.

TABLE O

| Example No. | Compound | Amine | Dithioester (from Preparation Z) |
|---|---|---|---|
| 509 | (5S)-N-[[3-[3,5-Difluoro-4-(4-thiomorpholinyl)-phenyl]-2-oxo-5-oxazolidinyl]methyl]-propanethioamide, thiazepine S,S-dioxide | (structure shown) | Z (a) |

TABLE O-continued

| Example No. | Compound | Amine | Dithioester (from Preparation Z) |
|---|---|---|---|
| 510 | (5S)-N-[[3-[3,5-Difluoro-4-(4-thiomorpholinyl)-phenyl]-2-oxo-5-oxazolidinyl]methyl]-2-methylpropanethio-amide, thiazepine S,S-dioxide | Same as above | Z (b) |
| 511 | (5S)-N-[[3-[3,5-Difluoro-4-(4-thiomorpholinyl)-phenyl]-2-oxo-5-oxazolidinyl]methyl]-cyclopropanecarbothio-amide, thiazepine S,S-dioxide | Same as above | Z (c) |

EXAMPLE 512

(5S)-N-[[3-[4-(Tetrahydro-1,4-thiazepin-4(5H)-yl)phenyl]-2-oxo-5-oxazolidinyl]methyl]thioacetamide, thiazepine S,S-dioxide

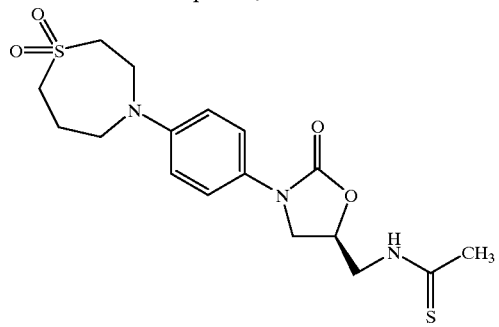

The title compound can be prepared by the procedure of Examples 504 and 482, by substituting an appropriate quantity of 4-fluoronitrobenzene for 3,4-difluoronitro-benzene in Step 1 of Example 482.

Utilizing the amine prepared in Example 512, but substituting the dithioester listed below for ethyl dithioacetate in the final step, the compounds of Examples 513 to 515 of Table P are obtained.

TABLE P

| Example No. | Compound | Amine | Dithioester (From Preparation Z) |
|---|---|---|---|
| 513 | (5S)-N-[[3-[4-(tetrahydro-1,4-thiazepin-4(5H)-yl))phenyl]-2-oxo-5-oxazolidinyl]-methyl]propanethio-amide, thiazepine S,S-dioxide | | Z (a) |
| 514 | (5S)-N-[[3-[4-(tetrahydro-1,4-thiazepin-4(5H)-yl))phenyl]-2-oxo-5-oxazolidinyl]methyl]-2-methylpropanethio-amide, thiazepine S,S-dioxide | Same as above | Z (b) |
| 515 | (5S)-N-[[3-[4-(tetrahydro-1,4-thiazepin-4(5H)-yl))phenyl]-2-oxo-5-oxazolidinyl]- | Same as above | Z (c) |

TABLE P-continued

| Example No. | Compound | Amine | Dithioester (From Preparation Z) |
|---|---|---|---|
| | methyl]cyclopropane-carbothioamide, thiazepine S,S-dioxide | | |

EXAMPLE 516

(5S)-N-[[3-[3-Fluoro-4-(tetrahydro-1,4-thiazepin-4 (5H)-yl)phenyl]-2-oxo-5-oxazolidinyl]methyl] thioacetamide

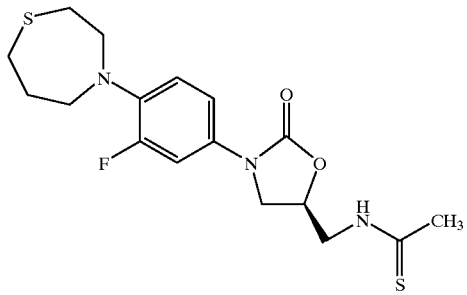

This compound is prepared according to the procedure of Step 8 in Example 482, but stubstituting an appropriate quantity of ethyl dithioacetate for di-tert-butyl dicarbonate; mp 129–131° C.

Utilizing the amine prepared in Step 8 of Example 482, but substituting an appropriate quantity of the dithioester listed below for di-tert-butyl dicarbonate, the compounds of Examples 517 to 529 of Table Q are obtained.

TABLE Q

| Example No. | Compound | Amine | Dithioester (From Preparation Z) |
|---|---|---|---|
| 517 | (5S)-N-[[3-[3-Fluoro-4-(tetrahydro-1,4-thiazepin-4(5H)-yl))-phenyl]-2-oxo-5-oxazolidinyl]methyl]-propanethioamide | | Z (a) |
| 518 | (5S)-N-[[3-[3-Fluoro-4-(tetrahydro-1,4-thiazepin-4(5H)-yl))-phenyl]-2-oxo-5-oxazolidinyl]methyl]-2-methylpropanethioamide | Same as above | Z (b) |
| 519 | (5S)-N-[[3-[3-Fluoro-4-(tetrahydro-1,4-thiazepin-4(5H)-yl))-phenyl]-2-oxo-5-oxazolidinyl]methyl]-cyclopropanecarbothio-amide | Same as above | Z (c) |
| 520 | (5S)-N-[[3-[3-Fluoro-4-(tetrahydro-1,4-thiazepin-4(5H)-yl))-phenyl]-2-oxo-5-oxazolidinyl]methyl]-butanethioamide | Same as above | Z (d) |
| 521 | (5S)-N-[[3-[3-Fluoro-4-(tetrahydro-1,4-thiazepin-4(5H)-yl))-phenyl]-2-oxo-5-oxazolidinyl]methyl]-3-methylbutanethioamide | Same as above | Z (e) |
| 522 | (5S)-N-[[3-[3-Fluoro-4-(tetrahydro-1,4-thiazepin-4(5H)-yl))- | Same as above | Z (f) |

TABLE Q-continued

| Example No. | Compound | Amine | Dithioester (From Preparation Z) |
|---|---|---|---|
| | phenyl]-2-oxo-5-oxazolidinyl]methyl]-2-methylbutanethioamide | | |
| 523 | (5S)-N-[[3-[3-Fluoro-4-(tetrahydro-1,4-thiazepin-4(5H)-yl))-phenyl]-2-oxo-5-oxazolidinyl]methyl]-3,3-dimethylbutanethio-amide | Same as above | Z (g) |
| 524 | (5S)-N-[[3-[3-Fluoro-4-(tetrahydro-1,4-thiazepin-4(5H)-yl))-phenyl]-2-oxo-5-oxazolidinyl]methyl]-cyclobutanecarbothio-amide | Same as above | Z (h) |
| 525 | (5S)-N-[[3-[3-Fluoro-4-(tetrahydro-1,4-thiazepin-4(5H)-yl))-phenyl]-2-oxo-5-oxazolidinyl]methyl]-cyclopentanecarbothio-amide | Same as above | Z (i) |
| 526 | (5S)-N-[[3-[3-Fluoro-4-(tetrahydro-1,4-thiazepin-4(5H)-yl))-phenyl]-2-oxo-5-oxazolidinyl]methyl]-cyclohexanecarbothio-amide | Same as above | Z (j) |
| 527 | (5S)-N-[[3-[3-5 Fluoro-4-(tetrahydro-1,4-thiazepin-4(5H)-yl))-phenyl]-2-oxo-5-oxazolidinyl]methyl]-2-cyclopropylethanethio-amide | Same as above | Z (k) |
| 528 | (5S)-N-[[3-[3-Fluoro-4-(tetrahydro-1,4-thiazepin-4(5H)-yl))-phenyl]-2-oxo-5-oxazolidinyl]methyl]-2-cyclobutylethanethio-amide | Same as above | Z (l) |
| 529 | (5S)-N-[[3-[3-Fluoro-4-(tetrahydro-1,4-thiazepin-4(5H)-yl))-phenyl]-2-oxo-5-oxazolidinyl]methyl]-2-cyclopentylethanethio-amide | Same as above | Z (m) |

EXAMPLE 530

(5S)-N-[[3-[3,5-Difluoro-4-(tetrahydro-1,4-thiazepin-4(5H)-yl)phenyl]-2-oxo-5-oxazolidinyl]methyl]thioacetamide

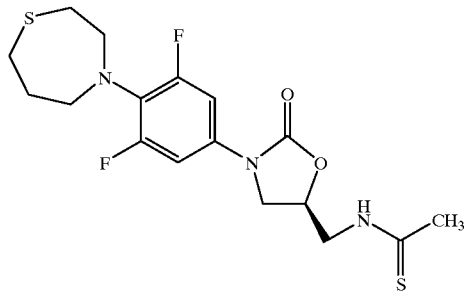

This compound can be prepared according to the procedures of Example 482 and Example 516, but substituting an appropriate quantity of 2,6-difluoro-4-nitrophenyl trifluoromethane sulfonate for 3,4-difluoronitrobenzene in Step 1 of Example 482.

Utilizing the amine prepared in Example 530, but substituting an appropriate quantity of the dithioester listed below for di-tert-butyl dicarbonate, the compounds of Examples 531 to 533 of Table R can be prepared.

EXAMPLE 534

(5S)-N-[[3-[4-(Tetrahydro-1,4-thiazepin-4(5H)-yl)phenyl]-2-oxo-5-oxazolidinyl]methyl]thioacetamide; mp 129–131° C.

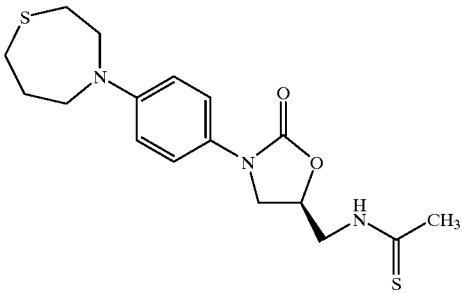

This compound can be prepared according to the procedures of Example 482 and Example 516, but substituting an appropriate quantity of 4-fluoronitrobenzene for 3,4-difluoronitrobenzene in Step 1 of Example 482.

Utilizing the amine prepared in Example 534, but substituting an appropriate quantity of the dithioester listed below for di-tert-butyl dicarbonate, the compounds of Examples 535 to 537 of Table S can be prepared.

TABLE R

| Example No. | Compound | Amine | Dithio Compound (from Preparation Z) |
|---|---|---|---|
| 531 | (5S)-N-[[3-[3,5-Difluoro-4-(tetrahydro-1,4-thiazepin-4(5H)-yl))-phenyl]-2-oxo-5-oxazolidinyl]methyl]-propanethioamide | | Z (a) |
| 532 | (5S)-N-[[3-[3,5-Difluoro-4-(tetrahydro-1,4-thiazepin-4(5H)-yl))-phenyl]-2-oxo-5-oxazolidinyl]methyl]-2-methylpropanethioamide | Same as above | Z (b) |
| 533 | (5S)-N-[[3-[3,5-Difluoro-4-(tetrahydro-1,4-thiazepin-4(5H)-yl))-phenyl]-2-oxo-5-oxazolidinyl]methyl]-cyclopropanecarbothioamide | Same as above | Z (c) |

TABLE S

| Example No. | Compound | Amine | Dithio Compound (from Preparation Z) |
|---|---|---|---|
| 535 | (5S)-N-[[3-[4-(Tetrahydro-1,4-thiazepin-4(5H)-yl))-phenyl]-2-oxo-5-oxazolidinyl]-methyl]propanethioamide | ![structure] | Z (a) |
| 536 | (5S)-N-[[3-[4-(Tetrahydro-1,4-thiazepin-4(5H)-yl))-phenyl]-2-oxo-5-oxazolidinyl]methyl]-2-methylpropanethioamide | Same as above | Z (b) |
| 537 | (5S)-N-[[3-[4-(Tetrahydro-1,4-thiazepin-4(5H)-yl))-phenyl]-2-oxo-5-oxazolidinyl]-methyl]cyclopropane-carbothioamide | Same as above | Z (c) |

EXAMPLE 538

(5S)-N-[[3-[3-Fluoro-4-(tetrahydro-1,4-thiazepin-4(5H)-yl)phenyl]-2-oxo-5-oxazolidinyl]methyl] thiourea, thiazepine S-oxide

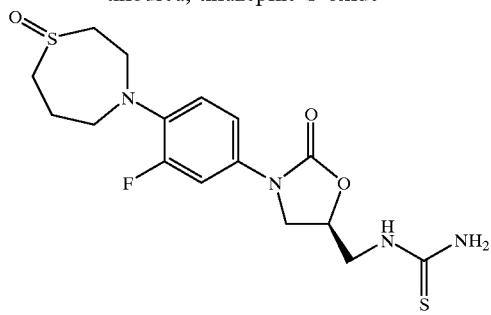

This compound can be prepared by the procedure described in Example 33, but substituting the amine prepared in Example 482 for the amine 33.

By reaction of the isothiocyanate prepared in Example 538 with the amines and alcohols listed in Table T, the compounds of Examples 539 to 544 can be prepared.

TABLE T

| Example No. | Compound | Isothiocyanate | Amine or Alcohol |
|---|---|---|---|
| 539 | (5S)-N-[[3-[3-Fluoro-4-(tetrahydro-1,4-thiazepin-4(5H)-yl)phenyl]-2-oxo-5-oxazolidinyl]methyl]-N'-methylthiourea, thiazepine S-oxide | ![structure] | CH₃NH₂ |
| 540 | (5S)-N-[[3-[3-Fluoro-4-(tetrahydro-1,4-thiazepin-4(5H)- | Same as above | (CH₃)₂NH |

TABLE T-continued

| Example No. | Compound | Isothiocyanate | Amine or Alcohol |
|---|---|---|---|
|  | yl)phenyl]-2-oxo-5-oxazolidinyl]methyl]-N',N'-dimethylthiourea, thiazepine S-oxide |  |  |
| 541 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide, thiazepine S-oxide | Same as above | Azetidine |
| 542 | (5S)-N-[[3-[3-Fluoro-4-(tetrahydro-1,4-thiazepin-4(5H)-yl)phenyl]-2-oxo-5-oxazolidinyl]methyl]-O-methylthiocarbamate, thiazepine S-oxide | Same as above | $CH_3OH$ |
| 543 | (5S)-N-[[3-[3-Fluoro-4-(tetrahydro-1,4-thiazepin-4(5H)-yl)phenyl]-2-oxo-5-oxazolidinyl]methyl]-O-ethylthiocarbamate, thiazepine S-oxide | Same as above | $CH_3CH_2OH$ |
| 544 | (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate, thiazepine S-oxide | Same as above | $(CH_3)_2CHOH$ |

EXAMPLE 545
(5S)-N-[[3-[3,5-Difluoro-4-(tetrahydro-1,4-thiazepin-4(5H)-yl)phenyl]-2-oxo-5-oxazolidinyl]methyl]thiourea, thiazepine S-oxide

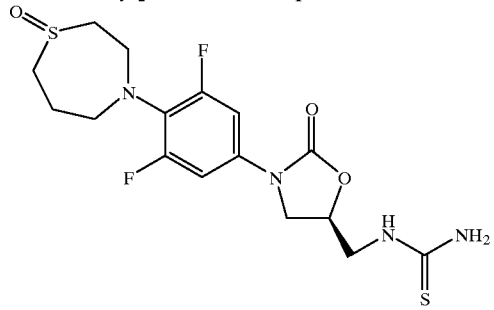

This compound can be prepared by the procedure described in Example 33, but substituting the amine prepared in Example 496 for the amine 33.

By reaction of the isothiocyanate prepared in Example 545 with the amines and alcohols listed in Table U, the compounds of Examples 546 to 551 can be prepared.

TABLE U

| Example No. | Compound | Isothiocyanate | Amine or Alcohol |
|---|---|---|---|
| 546 | (5S)-N-[[3-[3,5-Difluoro-4-(tetrahydro-1,4-thiazepin-4(5H)-yl)phenyl]-2-oxo-5-oxazolidinyl]methyl]-N'-methylthiourea, thiazepine S-oxide |  | $CH_3NH_2$ |

TABLE U-continued

| Example No. | Compound | Isothiocyanate | Amine or Alcohol |
|---|---|---|---|
| 547 | (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea, thiazepine S-oxide | Same as above | $(CH_3)_2NH$ |
| 548 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S-oxide | Same as above | Azetidine |
| 549 | (5S)-N-[[3-[3,5-Difluoro-4-(tetrahydro-1,4-thiazepin-4(5H)-yl)phenyl]-2-oxo-5-oxazolidinyl]methyl]-O-methylthiocarbamate, thiazepine S-oxide | Same as above | $CH_3OH$ |
| 550 | (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate, thiazepine S-oxide | Same as above | $CH_3CH_2OH$ |
| 551 | (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate, thiazepine S-oxide | Same as above | $(CH_3)_2CHOH$ |

EXAMPLE 552
(5S)-N-[[3-[4-(Tetrahydro-1,4-thiazepin-4(5H)-yl)phenyl]-2-oxo-5-oxazolidinyl]methyl]thiourea, thiazepine S-oxide

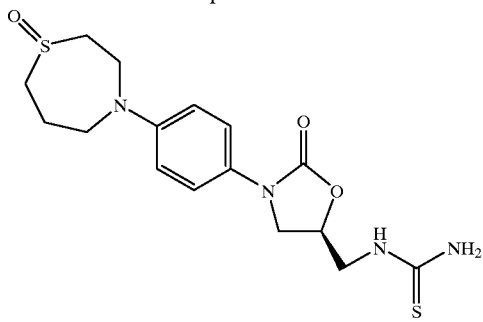

This compound can be prepared by the procedure described in Example 33, but substituting the amine prepared in Example 500 for the amine 33.

By reaction of the isothiocyanate prepared in Example 552 with the amines and alcohols listed in Table V, the compounds of Examples 553 to 558 can be prepared.

TABLE V

| Example No. | Compound | Isothiocyanate | Amine or Alcohol |
|---|---|---|---|
| 553 | (5S)-N-[[3-[4-(Tetrahydro-1,4-thiazepin-4(5H)-yl)phenyl]-2-oxo-5-oxazolidinyl]methyl]-N'-methylthiourea, thiazepine S-oxide | (structure shown) | $CH_3NH_2$ |
| 554 | (5S)-N-[[3-[4-(Tetrahydro-1,4-thiazepin-4(5H)-yl)phenyl]-2-oxo-5-oxazolidinyl]methyl]-N',N'-dimethylthiourea, thiazepine S-oxide | Same as above | $(CH_3)_2NH$ |
| 555 | (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S-oxide | Same as above | Azetidine |
| 556 | (5S)-N-[[3-[4-(Tetrahydro-1,4-thiazepin-4(5H)-yl)phenyl]-2-oxo-5-oxazolidinyl]methyl]-O-methylthiocarbamate, thiazepine S-oxide | Same as above | $CH_3OH$ |
| 557 | (5S)-N-[[3-[4-(Tetrahydro-1,4-thiazepin-4(5H)-yl)phenyl]-2-oxo-5-oxazolidinyl]methyl]-O-ethylthiocarbamate, thiazepine S-oxide | Same as above | $CH_3CH_2OH$ |
| 558 | (5S)-N-[[3-[4-(Tetrahydro-1,4-thiazepin-4(5H)-yl)phenyl]-2-oxo-5-oxazolidinyl]methyl]-O-isopropylthiocarbamate, thiazepine S-oxide | Same as above | $(CH_3)_2CHOH$ |

EXAMPLE 559

(5S)-N-[[3-[3-Fluoro-4-(tetrahydro-1,4-thiazepin-4(5H)-yl)phenyl]-2-oxo-5-oxazolidinyl]rmethyl] thiourea, thiazepine S,S-dioxide

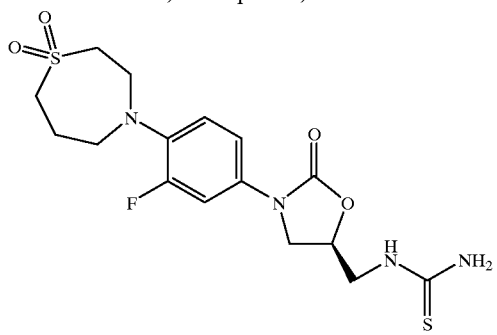

This compound can be prepared by the procedure described in Example 33, but substituting the amine prepared in Example 504 for the amine 33.

By reaction of the isothiocyanate prepared in Example 559 with the amines and alcohols listed in Table W, the compounds of Examples 560 to 565 can be prepared.

TABLE W

| Example No. | Compound | Isothiocyanate | Amine or Alcohol |
|---|---|---|---|
| 560 | (5S)-N-[[3-[3-Fluoro-4-(tetrahydro-1,4-thiazepin-4(5H)-yl)phenyl]-2-oxo-5-oxazolidinyl]methyl]-N'-methylthiourea, thiazepine S,S-dioxide | (structure shown) | $CH_3NH_2$ |
| 561 | (5S)-N-[[3-[3-Fluoro-4-(tetrahydro-1,4-thiazepin-4(5H)-yl)phenyl]-2-oxo-5-oxazolidinyl]methyl]-N',N'-dimethylthiourea, thiazepine S,S-dioxide | Same as above | $(CH_3)_2NH$ |
| 562 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide, thiazepine S,S-dioxide | Same as above | Azetidine |
| 563 | (5S)-N-[[3-[3-Fluoro-4-(tetrahydro-1,4-thiazepin-4(5H)-yl)phenyl]-2-oxo-5-oxazolidinyl]methyl]-O-methylthiocarbamate, thiazepine S,S-dioxide | Same as above | $CH_3OH$ |
| 564 | (5S)-N-[[3-[3-Fluoro-4-(tetrahydro-1,4-thiazepin-4(5H)-yl)phenyl]-2-oxo-5-oxazolidinyl]methyl]-O-ethylthiocarbamate, thiazepine S,S-dioxide | Same as above | $CH_3CH_2OH$ |
| 565 | (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate, thiazepine S,S-dioxide | Same as above | $(CH_3)_2CHOH$ |

EXAMPLE 566
(5S)-N-[[3-[3,5-Difluoro-4-(tetrahydro-1,4-thiazepin-4(5H)-yl)phenyl]-2-oxo-5-oxazolidinyl]methyl]thiourea, thiazepine S,S-dioxide

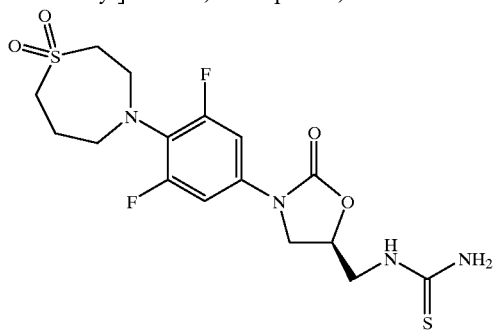

This compound can be prepared by the procedure described in Example 33, but substituting the amine prepared in Example 508 for the amine 33.

By reaction of the isothiocyanate prepared in Example 566 with the amines and alcohols listed in Table X, the compounds of Examples 561 to 572 can be prepared.

TABLE X

| Example No. | Compound | Isothiocyanate | Amine or Alcohol |
|---|---|---|---|
| 567 | (5S)-N-[[3-[3,5-Difluoro-4-(tetrahydro-1,4-thiazepin-4(5H)-yl)phenyl]-2-oxo-5-oxazolidinyl]methyl]-N'-methylthiourea, thiazepine S,S-dioxide | (structure shown) | $CH_3NH_2$ |
| 568 | (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea, thiazepine S,S-dioxide | Same as above | $(CH_3)_2NH$ |
| 569 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S,S-dioxide | Same as above | Azetidine |
| 570 | (5S)-N-[[3-[3,5-Difluoro-4-(tetrahydro-1,4-thiazepin-4(5H)-yl)phenyl]-2-oxo-5-oxazolidinyl]methyl]-O-methylthiocarbamate, thiazepine S,S-dioxide | Same as above | $CH_3OH$ |
| 571 | (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate, thiazepine S,S-dioxide | Same as above | $CH_3CH_2OH$ |
| 572 | (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate, thiazepine S,S-dioxide | Same as above | $(CH_3)_2CHOH$ |

EXAMPLE 573

(5S)-N-[[3-[4-(Tetrahydro-1,4-thiazepin-4(5H)-yl)phenyl]-2-oxo-5-oxazolidinyl]methyl]thiourea, thiazepine S,S-dioxide

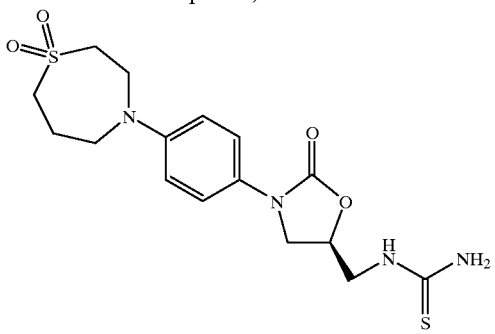

This compound can be prepared by the procedure described in Example 33, but substituting the amine prepared in Example 512 for the amine 33.

By reaction of the isothiocyanate prepared in Example 573 with the amines and alcohols listed in Table Y, the compounds of Examples 574 to 579 can be prepared.

TABLE Y

| Example No. | Compound | Isothiocyanate | Amine or Alcohol |
|---|---|---|---|
| 574 | (5S)-N-[[3-[4-(Tetrahydro-1,4-thiazepin-4(5H)-yl)phenyl]-2-oxo-5-oxazolidinyl]methyl]-N'-methylthiourea, thiazepine S,S-dioxide | (structure shown) | CH₃NH₂ |
| 575 | (5S)-N-[[3-[4-(Tetrahydro-1,4-thiazepin-4(5H)-yl)phenyl]-2-oxo-5-oxazolidinyl]methyl]-N',N'-dimethylthiourea, thiazepine S,S-dioxide | Same as above | (CH₃)₂NH |
| 576 | (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S,S-dioxide | Same as above | Azetidine |
| 577 | (5S)-N-[[3-[4-(Tetrahydro-1,4-thiazepin-4(5H)-yl)phenyl]-2-oxo-5-oxazolidinyl]methyl]-O-methylthiocarbamate, thiazepine S,S-dioxide | Same as above | CH₃OH |
| 578 | (5S)-N-[[3-[4-(Tetrahydro-1,4-thiazepin-4(5H)-yl)phenyl]-2-oxo-5-oxazolidinyl]methyl]-O-ethylthiocarbamate, thiazepine S,S-dioxide | Same as above | CH₃CH₂OH |
| 579 | (5S)-N-[[3-[4-(Tetrahydro-1,4-thiazepin-4(5H)-yl)phenyl]-2-oxo-5-oxazolidinyl]methyl]-O-isopropylthiocarbamate, thiazepine S,S-dioxide | Same as above | (CH₃)₂CHOH |

EXAMPLE 580

(5S)-N-[[3-[3-Fluoro-4-(tetrahydro-1,4-thiazepin-4(5H)-yl)phenyl]-2-oxo-5-oxazolidinyl]methyl]thiourea

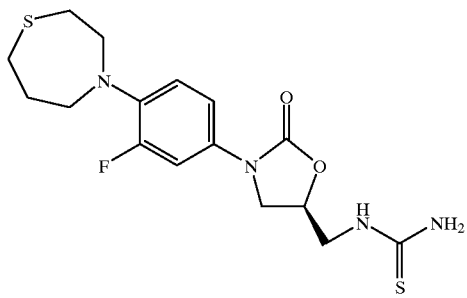

This compound can be prepared by the procedure described in Example 33, but substituting the amine prepared in Step 8 of Example 482 for the amine 33.

By reaction of the isothiocyanate prepared in Example 580 with the amines and alcohols listed in Table Z, the compounds of Examples 581 to 586 can be prepared.

TABLE Z

| Example No. | Compound | Isothiocyanate | Amine or Alcohol |
|---|---|---|---|
| 581 | (5S)-N-[[3-[3-Fluoro-4-(tetrahydro-1,4-thiazepin-4(5H)-yl)phenyl]-2-oxo-5-oxazolidinyl]methyl]-N'-methylthiourea | (structure shown) | CH₃NH₂ |
| 582 | (5S)-N-[[3-[3-Fluoro-4-(tetrahydro-1,4-thiazepin-4(5H)-yl)phenyl]-2-oxo-5-oxazolidinyl]methyl]-N',N'-dimethylthiourea | Same as above | (CH₃)₂NH |
| 583 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide | Same as above | Azetidine |
| 584 | (5S)-N-[[3-[3-Fluoro-4-(tetrahydro-1,4-thiazepin-4(5H)-yl)phenyl]-2-oxo-5-oxazolidinyl]methyl]-O-methylthiocarbamate | Same as above | CH₃OH |
| 585 | (5S)-N-[[3-[3-Fluoro-4-(tetrahydro-1,4-thiazepin-4(5H)-yl)phenyl]-2-oxo-5-oxazolidinyl]methyl]-O-ethylthiocarbamate | Same as above | CH₃CH₂OH |
| 586 | (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate | Same as above | (CH₃)₂CHOH |

EXAMPLE 587

(5S)-N-[[3-[3,5-Difluoro-4-(tetrahydro-1,4-thiazepin-4(5H)-yl)phenyl]-2-oxo-5-oxazolidinyl]methyl]thiourea

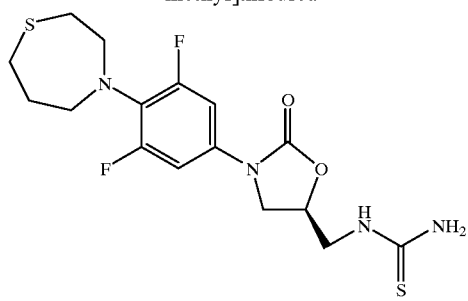

This compound can be prepared by the procedure described in Example 33, but substituting the amine prepared in Example 530 for the amine 33.

By reaction of the isothiocyanate prepared in Example 587 with the amines and alcohols listed in Table AA, the compounds of Examples 588 to 593 can be prepared.

TABLE AA

| Example No. | Compound | Isothiocyanate | Amine or Alcohol |
|---|---|---|---|
| 588 | (5S)-N-[[3-[3,5-Difluoro-4-(tetrahydro-1,4-thiazepin-4(5H)-yl)phenyl]-2-oxo-5-oxazolidinyl]methyl]-N'-methylthiourea | [structure shown] | CH$_3$NH$_2$ |
| 589 | (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea | Same as above | (CH$_3$)$_2$NH |
| 590 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide | Same as above | Azetidine |
| 591 | (5S)-N-[[3-[3,5-Difluoro-4-(tetrahydro-1,4-thiazepin-4(5H)-yl)phenyl]-2-oxo-5-oxazolidinyl]methyl]-O-methylthiocarbamate | Same as above | CH$_3$OH |
| 592 | (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate | Same as above | CH$_3$CH$_2$OH |
| 593 | (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate | Same as above | (CH$_3$)$_2$CHOH |

EXAMPLE 594

(5S)-N-[[3-[4-(Tetrahydro-1,4-thiazepin-4(5H)-yl)phenyl]-2-oxo-5-oxazolidinyl]methyl]thiourea

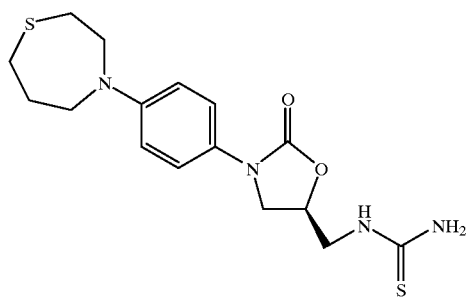

This compound can be prepared by the procedure described in Example 33, but substituting the amine prepared in Example 534 for the amine 33.

By reaction of the isothiocyanate prepared in Example 594 with the amines and alcohols listed in Table BB, the compounds of Examples 595 to 600 can be prepared.

TABLE BB

| Example No. | Compound | Isothiocyanate | Amine or Alcohol |
|---|---|---|---|
| 595 | (5S)-N-[[3-[4-(Tetrahydro-1,4-thiazepin-4(5H)-yl)phenyl]-2-oxo-5-oxazolidinyl]methyl]-N'-methylthiourea | 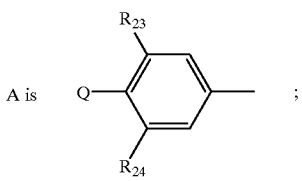 | $CH_3NH_2$ |
| 596 | (5S)-N-[[3-[4-(Tetrahydro-1,4-thiazepin-4(5H)-yl)phenyl]-2-oxo-5-oxazolidinyl]methyl]-N',N'-dimethylthiourea | Same as above | $(CH_3)_2NH$ |
| 597 | (5S)-N-[[3-[4-(Tetrahydro-1,4-thiazepin-4(5H)-yl)phenyl]-2-oxo-5-oxazolidinyl]methyl]-1-azetidinecarbothioamide | Same as above | Azetidine |
| 598 | (5S)-N-[[3-[4-(Tetrahydro-1,4-thiazepin-4(5H)-yl)phenyl]-2-oxo-5-oxazolidinyl]methyl]-O-methylthiocarbamate | Same as above | $CH_3OH$ |
| 599 | (5S)-N-[[3-[4-(Tetrahydro-1,4-thiazepin-4(5H)-yl)phenyl]-2-oxo-5-oxazolidinyl]methyl]-O-ethylthiocarbamate | Same as above | $CH_3CH_2OH$ |
| 600 | (5S)-N-[[3-[4-(Tetrahydro-1,4-thiazepin-4(5H)-yl)phenyl]-2-oxo-5-oxazolidinyl]methyl]-O-isopropylthiocarbamate | Same as above | $(CH_3)_2CHOH$ |

What is claimed:
1. A compound of the formula I

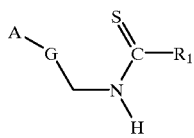

or a pharmaceutical acceptable salt thereof wherein:

G is 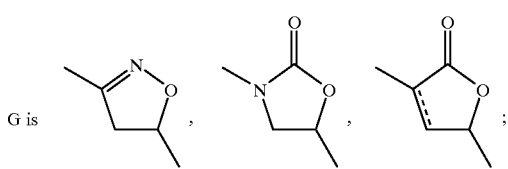 ;

$R_1$ is
 a) H,
 b) $NH_2$,
 c) $NHC_{1-4}$alkyl,
 d) $C_{1-4}$ alkyl,
 e) —$OC_{1-4}$ alkyl,
 f) —$SC_{1-4}$ alkyl,
 g) $C_{1-4}$ alkyl substituted with one to three fluoro, one to two chloro, CN or —$COOC_{1-4}$ alkyl,
 h) $C_{3-6}$cycloalkyl,
 i) $N(C_{1-4}alkyl)_2$, or
 j) $N(CH_2)_{2-5}$;

A is $R_{23}$ and $R_{24}$ are independently
 a) H,
 b) F,
 c) Cl,
 d) $C_{1-2}$alkyl,
 e) CN,
 f) OH,
 g) $C_{1-2}$alkoxy, h) nitro, or
i) amino;

Q is 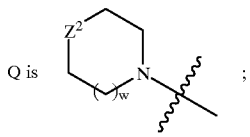 ;

$Z^2$ is
a) —$O_2S$—,
b) —O—,
c) —OS—, or
d) —S—;
and w is 2.

2. A compound of formula I as shown in claim 1 which is

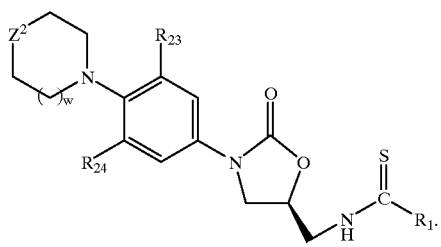

3. A compound of claim 2 wherein $R_{23}$ is H and $R_{24}$ is F.
4. A compound of claim 2 wherein $Z^2$ is —$SO_2$—, —SO—, or —S—.
5. A compound of claim 2 wherein $Z^2$ is —O—.
6. A compound of claim 4 or 5 wherein $R_1$ is $C_1$–$C_4$alkyl, $NH_2$, $C_3$–$C_4$cycloalkyl, $OC_1$–$C_4$alkyl, $NHC_1$–$C_4$alkyl, or $N(C_1$–$C_4)$alkyl.
7. A compound of claim 1 which is
1) (5S)-N-[[3-[3-Fluoro-4-(tetrahydro-1,4-thiazepin-4(5H)-yl)phenyl]-2-oxo-5-oxazolidinyl]methyl]thioacetamide, thiazepine S-oxide;
2) (5S)-N-[[3-[3-Fluoro-4-(tetrahydro-1,4-thiazepin-4(5H)-yl))phenyl]-2-oxo-5-oxazolidinyl]methyl]propanethioamide, thiazepine S-oxide;
3) (S)-N-[[3-[3-Fluoro-4-(tetrahydro-1,4-thiazepin-4(5H)-yl))phenyl]-2-oxo-5-oxazolidinyl]-methyl]-2-methylpropanethioamide, thiazepine S-oxide;
4) (5S)-N-[[3-[3-Fluoro-4-(tetrahydro-1,4-thiazepin-4(5H)-yl))phenyl]-2-oxo-5-oxazolidinyl]methyl]cyclopropanecarbothio-amide, thiazepine S-oxide;
5) (5S)-N-[[3-[3-Fluoro-4-(tetrahydro-1,4-thiazepin-4(5H)-yl))phenyl]-2-oxo-5-oxazolidinyl]methyl]butanethioamide, thiazepine S-oxide;
6) (5S)-N-[[3-[3-Fluoro-4-(tetrahydro-1,4-thiazepin-4(5H)-yl))phenyl]-2-oxo-5-oxazolidinyl]methyl]butanethioamide, thiazepine S-oxide;
7) (5S)-N-[[3-[3-Fluoro-4-(tetrahydro-1,4-thiazepin-4(5H)-yl))phenyl]-2-oxo-5-oxazolidinyl]methyl]-2-methylbutanethioamide, thiazepine S-oxide;
8) (5S)-N-[[3-[3-Fluoro-4-(tetrahydro-1,4-thiazepin-4(5H)-yl))phenyl]-2-oxo-5-oxazolidinyl]methyl]-3,3-dimethylbutanethioamide, thiazepine S-oxide;
9) (5S)-N-[[3-[3-Fluoro-4-(tetrahydro-1,4-thiazepin-4(5H)-yl))phenyl]-2-oxo-5-oxazolidinyl]methyl]cyclobutanecarbothioamide, thiazepine S-oxide;
10) 10) (5S)-N-[[3-[3-Fluoro-4-(tetrahydro-1,4-thiazepin-4(5H)-yl))phenyl]-2-oxo-5-oxazolidinyl]methyl]-1-cyclopentanecarbothioamide, thiazepine S-oxide;
11) (5S)-N-[[3-[3-Fluoro-4-(tetrahydro-1,4-thiazepin-4(5H)-yl))phenyl]-2-oxo-5-oxazolidinyl]methyl]cyclohexanecarbothioamide, thiazepine S-oxide;
12) (5S)-N-[[3-[3-Fluoro-4-(tetrahydro-1,4-thiazepin-4(5H)-yl))phenyl]-2-oxo-5-oxazolidinyl]methyl]-2-cyclopropylethanethioamide, thiazepine S-oxide;
13) (5S)-N-[[3-[3-Fluoro-4-(tetrahydro-1,4-thiazepin-4(5H)-yl))phenyl]-2-oxo-5-oxazolidinyl]methyl]-2-cyclobutylethanethioamide, thiazepine S-oxide;
14) (5S)-N-[[3-[3-Fluoro-4-(tetrahydro-1,4-thiazepin-4(5H)-yl))phenyl]-2-oxo-5-oxazolidinyl]methyl]-2-cyclopentylethanethioamide, thiazepine S-oxide;
15) (5S)-N-[[3-[3,5-Difluoro-4-(tetrahydro-1,4-thiazepin-4(5H)-yl)phenyl]-2-oxo-5-oxazolidinyl]methyl]thioacetamide, thiazepine S-oxide;
16) (5S)-N-[[3-[3,5-Difluoro-4-(tetrahydro-1,4-thiazepin-4(5H)-yl)phenyl]-2-oxo-5-oxazolidinyl]methyl]propanethioamide, thiazepine S-oxide;
17) (5S)-N-[[3-[3,5-Difluoro-4-(tetrahydro-1,4-thiazepin-4(5H)-yl))phenyl]-2-oxo-5-oxazolidinyl]methyl]-2-methylpropanethioamide, thiazepine S-oxide;
18) (5S)-N-[[3-[3,5-Difluoro-4-(tetrahydro-1,4-thiazepin-4(5H)-yl))phenyl]-2-oxo-5-oxazolidinyl]methyl]cyclopropanecaibothioamide, thiazepine S-oxide;
19) (5S)-N-[[3-[4-(Tetrahydro-1,4-thiazepin-4(5H)-yl)phenyl]-2-oxo-5-oxazolidinyl]methyl]thioacetamide, thiazepine S-oxide;
20) (5S)-N-[[3-[4-(Tetrahydro-1,4-thiazepin-4(5H)-yl))phenyl]-2-oxo-5-oxazolidinyl]methyl]propanethioamide, thiazepine S-oxide;
21) (5S)-N-[[3-[4-(Tetrahydro-1,4-thiazcpin-4(5H)-yl))phenyl]-2-oxo-5-oxazolidinyl]methyl]-2-methylpropanethioamide, thiazepine S-oxide;
22) (5S)-N-[[3-[4-(Tetrahydro-1,4-thiazepin-4(5H)-yl))phenyl]-2-oxo-5-oxazolidinyl]methyl]cyclopropanecarbothioamide, thiazepine S-oxide;
23) (5S)-N-[[3-[3-Fluoro-4-(tetrahydro-1,4-thiazepin-4(5H)-yl)phenyl]-2-oxo-5-oxazolidinyl]methyl]thioacetamide, thiazepine S,S-dioxide;
24) (5S)-N-[[3-[3-Fluoro-4-(4-thiomorpholinyl)phenyl]-2-oxo-5-oxazolidinyl]methyl]-propanethioamide, thiazepine S,S-dioxide;
25) (5S)-N-[[3-[3-Fluoro-4-(4-thiomorpholinyl]phenyl]-2-oxo-5-oxazolidinyl]methyl]-2-methylpropanethioamide, thiazepine S,S-dioxide;
26) (5S)-N-[[3-[3-Fluoro-4-(4-thiomorpholinyl]phenyl]-2-oxo-5-oxazolidinyl]methyl]-cyclopropanecarbothioamide, thiazepine S,S-dioxide;
27) (5S)-N-[[3-[3,5-Difluoro-4-(tetrahydro-1,4-thiazepin-4(5H)-yl)phenyl]-2-oxo-5-oxazolidinyl]methyl]thioacetamide, thiazepine S,S-dioxide;
28) (5S)-N-[[3-[3,5-Difluoro-4-(4-thiomorpholinyl)phenyl]-2-oxo-5-oxazolidinyl]methyl]-propanethioamide, thiazepine S,S-dioxide;
29) (5S)-N-[[3-[3,5-Difluoro-4-(4-thiomorpholinyl)phenyl]-2-oxo-5-oxazolidinyl]-methyl]-2-methylpropanethioamide, thiazcpine S,S-dioxide;
30) (5S)-N-[[3-[3,5-Difluoro-4-(4-thiomorpholinyl)phenyl]-2-oxo-5-oxazolidinyl]methyl]-cyclopropanecarbothioamide, thiazepine S,S-dioxide;
31) (5S)-N-[[3-[4-(Tetrahydro-1,4-thiazepin-4(5H)-yl)phenyl]-2-oxo-5-oxazolidinyl]methyl]thioacetamide, thiazepine S,S-dioxide;

32) (5S)-N-[[3-[4-(tetrahydro-1,4-thiazepin-4(5H)-yl))phenyl]-2-oxo-5-oxazolidinyl]methyl]propanethioamide, thiazepine S,S-dioxide;
33) (5S)-N-[[3-[4-(tetrahydro-1,4-thiazepin-4(5H)-yl))phenyl]-2-oxo-5-oxazolidinyl]methyl]-2-methylpropanethioamide, thiazepine S,S-dioxide;
34) (5S)-N-[[3-[4-(tetrahydro-1,4-thiazepin-4(5H)-yl))phenyl]-2-oxo-5-oxazolidinyl]-methyl]cyclopropanecarbothioamide, thiazepine S,S-dioxide;
35) (5S)-N-[[3-[3-Fluoro-4-(tetrahydro-1,4-thiazepin-4(5H)-yl)phenyl]-2-oxo-5-oxazolidinyl]methyl]thioacetamide;
36) (5S)-N-[[3-[3-Fluoro-4-(tetrahydro-1,4-thiazepin-4(5H)-yl))phenyl]-2-oxo-5-oxazolidinyl]methyl]propanethioamide;
37) (5S)-N-[[3-[3-Fluoro-4-(tetrahydro-1,4-thiazepin-4(5H)-yl))phenyl]-2-oxo-5-oxazolidinyl]methyl]-2-methylpropanethioamide:
38) (5S)-N-[[3-[3-Fluoro-4-(tetrahydro-1,4-thiazepin-4(5H)-yl))phenyl]-2-oxo-5-oxazolidinyl]methyl]cyclopropanecarbothioamide;
39) (5S)-N-[[3-[3-Fluoro-4-(tetrahydro-1,4-thiazepin-4(5H)-yl))phenyl]-2-oxo-5-oxazolidinyl]methyl]butanethioamide;
40) (5S)-N-[[3-[3-Fluoro-4-(tetrahydro-1,4-thiazepin-4(5H)-yl ) )phenyl]-2-oxo-5-oxazolidinyl]methyl]-3-methylbutanethioamide;
41) (5S)-N-[[3-[3-Fluoro-4-(tetrahydro-1,4-thiazepin-4(5H)-yl))phenyl]-2-oxo-5-oxazolidinyl]methyl]-2-methylbutanethioamide;
42) (5S)-N-[[3-[3-Fluoro-4-(tetrahydro-1,4-thiazepin-4(5H)-yl))phenyl]-2-oxo-5-oxazolidinyl]methyl]-3,3-dimethylbutanethioamide;
43) (5S)-N-[[3-[3-Fluoro-4-(tetrahydro-1,4-thiazepin-4(5H)-yl))phenyl]-2-oxo-5-oxazolidinyl]methyl]cyclobutanecarbothioamide;
44) (5S)-N-[[3-[3-Fluoro-4-(tetrahydro-1,4-thiazepin-4(5H)-yl))phenyl]-2-oxo-5-oxazolidinyl]methyl]cyclopentanecarbothioamide;
45) (5S)-N-[[3-[3-Fluoro-4-(tetrahydro-1,4-thiazepin-4(5H)-yl))phenyl]-2-oxo-5-oxazolidinyl]methyl]cyclohexanecarbothioamide;
46) (5S)-N-[[3-[3–5 Fluoro-4-(tetrahydro-1,4-thiazepin-4(5H )-yl))phenyl]-2-oxo-5-oxazolidinyl]methyl]-2-cyclopropylethanethioamide,
47) (5S)-N-[[3-[3-Fluoro-4-(tetrahydro-1,4-thiazepin-4(5H)-yl))phenyl]-2-oxo-5-oxazolidinyl]methyl]-2-cyclobutylethanethioamide,
48) (5S)-N-[[3-[3-Fluoro-4-(tetrahydro-1,4-thiazepin-4(5H)-yl))phenyl]-2-oxo-5-oxazolidinyl]methyl]-2-cyclopentylethanethioamide;
49) (5S)-N-[[3-[3,5-Difluoro-4-(tetrahydro-1,4-thiazepin-4(5H)-yl)phenyl]-2-oxo-5-oxazolidinyl]methyl]thioacetamide;
50) (5S)-N-[[3-[3,5-Difluoro-4-(tetrahydro-1,4-thiazepin-4(5H)-yl))phenyl]-2-oxo-5-oxazolidinyl]methyl]propanethioamide;
51) (5S)-N-[[3-[3,5-Difluoro-4-(tetrahydro-1,4-thiazepin-4(5H)-yl))phenyl]-2-oxo-5-oxazolidinyl]methyl]-2-methylpropanethioamide;
52) (5S)-N-[[3-[3,5-Difluoro-4-(tetrahydro-1,4-thiazepin-4(5H)-yl))phenyl]-2-oxo-5-oxazolidinyl]methyl]cyclopropanecarbothioamide;
53) (5S)-N-[[3-[4-(Tetrahydro-1,4-thiazepin-4(5H)-yl))phenyl]-2-oxo-5-oxazolidinyl]methyl]thioacetamide;
54) (5S)-N-[[3-[4-(Tetrahydro-1,4-thiazepin-4(5H)-yl))phenyl]-2-oxo-5-oxazolidinyl]-methyl]propanethioamide;
55) (5S)-N-[[3-[4-(Tetrahydro-1,4-thiazepin-4(5H)-yl))phenyl]-2-oxo-5-oxazolidinyl]-methyl]-2-methylpropanethioamide;
56) (5S)-N-[[3-[4-(Tetrahydro-1,4-thiazepin-4(5H)-yl))phenyl]-2-oxo-5-oxazolidinyl]-methyl]cyclopropanecarbothioamide;
57) (SS)-N-[[3-[3-Fluoro-4-(tetrahydro-1,4-thiazepin-4(5H)-yl)phenyl]-2-oxo-5-oxazolidinyl]methyl]thiourea, thiazepine S-oxide;
58) SS)-N-[[3-[3-Fluoro-4-(tetrahydro-1,4-thiazepin-4(5H)-yl)phenyl]-2-oxo-5-oxazolidinyl]methyl]-N'-methylthiourea, thiazepine S-oxide;
59) (5S)-N-[[3-[3-Fluoro-4-(tetrahydro-1,4-thiazepin-4(5H)-yl)phenyl]-2-oxo-5-oxazolidinyl]methyl]-N',N'-dimethylthiourea, thiazepine S-oxide;
60) (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide, thiazepine S-oxide;
61) (5S)-N-[[3-[3-Fluoro-4-(tetrahydro-1,4-thiazepin-4(5H)-yl)phenyl]-2-oxo-5-oxazolidinyl]methyl]-O-methylthiocarbamate, thiazepine S-oxide;
62) (5S)-N-[[3-[3-Fluoro-4-(tetrahydro-1,4-thiazepin-4(5H)-yl)phenyl]-2-oxo-5-oxazolidinyl]methyl]-O-ethylthiocarbamate, thiazepine S-oxide;
63) (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate, thiazepine S-oxide;
64) (5S)-N-[[3-[3,5-Difluoro-4-(tetrahydro-1,4-thiazepin-4(5H)-yl)phenyl]-2-oxo-5-oxazolidinyl]methyl]thiourea, thiazepine S-oxide;
65) (5S)-N-[[3-[3,5-Difluoro-4-(tetrahydro-1,4-thiazepin-4(5H)-yl)phenyl]-2-oxo-5-oxazolidinyl]methyl]-N'-methylthiourea, thiazepine S-oxide;
66) (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea, thiazepine S-oxide;
67) (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S-oxide;
68) (5S)-N-[[3-[3,5-Di fluoro-4-(tetrahydro-1,4-thiazepin-4(5H)-yl)phenyl]-2-oxo-5-oxazolidinyl]methyl]-O-methylthiocarbamate, thiazepine S-oxide;
69) (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate, thiazepine S-oxide;
70) (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate, thiazepine S-oxide;
71) (5S)-N-[[3-[4-(Tetrahydro-1,4-thiazepin-4(5H)-yl)phenyl]-2-oxo-5-oxazolidinyl]methyl]thiourea, thiazepine S-oxide;
72) (5S)-N-[[3-[4-(Tetrahydro-1,4-thiazepin-4(5H)-yl)phenyl]-2-oxo-5-oxazolidinyl]methyl]-N'-methylthiourea, thiazepine S-oxide;
73) (5S)-N-[[3-[4-(Tetrahydro-1,4-thiazepin-4(5H)-yl)phenyl]-2-oxo-5-oxazolidinyl]methyl]-N',N'-dimethylthiourea, thiazepine S-oxide;

74) (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S-oxide;

75) (5S)-N-[[3-[4-(Tetrahydro-1,4-thiazepin-4(5H)-yl)phenyl]-2-oxo-5-oxazolidinyl]methyl]-O-methylthiocarbamate, thiazepine S-oxide;

76) (5S)-N-[[3-[4-(Tetrahydro-1,4-thiazepin-4(5H)-yl)phenyl]-2-oxo-5-oxazolidinyl]methyl]-O-methylthiocarbamate, thiazcpine S-oxide;

77) (5S)-N-[[3-[4-(Tetrahydro-1,4-thiazcpin-4(5H)-yl)phenyl]-2-oxo-5-oxazolidinyl]methyl]-O-isopropylthiocarbamate, thiazepine S-oxide;

78) (5S)-N-[[3-[3-Fluoro-4-(tetrahydro-1,4-thiazepin-4(5H)-yl)phenyl]-2-oxo-5-oxazolidinyl]methyl]thiourea, thiazepine S,S-dioxide;

79) (5S)-N-[[3-[ 3-Fluoro-4-(tetrahydro-1,4-thiazepin-4(5H)-yl)phenyl]-2-oxo-5-oxazolidinyl]methyl]-N'-methylthiourea, thiazepine S,S-dioxide;

80) (5S)-N-[[3-[3-Fluoro-4-(tetrahydro-1,4-thiazepin-4(5H)-yl)phenyl]-2-oxo-5-oxazolidinyl]methyl]-N',N'-dimethylthiourea, thiazcpine S,S-dioxide;

81) (5S)-N-[[3-[3-Fluoro-4-(tetrahydro-1,4-thiazcpin-4(5H)-yl)phenyl]-2-oxo-5-oxazolidinyl]methyl]-1-azetidinecarbothioamide, thiazepine S,S-dioxide;

82) (5S)-N-[[3-[3-Fluoro-4-(tetrahydro-1,4-thiazepin-4(5H)-yl)phenyl]-2-oxo-5-oxazolidinyl]methyl]-O-methylthiocarbamate, thiazepine S,S-dioxide;

83) (5S)-N-[[3-[3-Fluoro-4-(tetrahydro-1,4-thiazepin-4(5H)-yl)phenyl]-2-oxo-5-oxazolidinyl]methyl]-O-ethylthiocarbamate, thiazepine S,S-dioxide;

84) (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate, thiazcpine S,S-dioxide;

85) (5S)-N-[[3-[3,5-Difluoro-4-(tetrahydro-1,4-thiazepin-4(5H)-yl)phenyl]-2-oxo-5-oxazolidinyl]methyl]thiourea, thiazepine S,S-dioxide;

86) (5S)-N-[[3-[3,5-Difluoro-4-(tetrahydro-1,4-thiazepin-4(5H)-yl)phenyl]-2-oxo-5-oxazolidinyl]methyl]-N'-methylthiourea, thiazepine S,S-dioxide;

87) (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea, thiazepine S,S-dioxide;

88) (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S,S-dioxide;

89) (5S)-N-[[3-[3,5-Difluoro-4-(tetrahydro-1,4-thiazcpin-4(5H)-yl)phenyl]-2-oxo-5-oxazolidinyl]methyl]-O-methylthiocarbamate, thiazepine S,S-dioxide;

90) (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate, thiazepine S,S-dioxide;

91) (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate, thiazepine S,S-dioxide;

92) (5S)-N-[[3-[4-(Tetrahydro-1,4-thiazepin-4(5H)-yl)phenyl]-2-oxo-5-oxazolidinyl]methyl]thiourea, thiazepine S,S-dioxide;

93) (5S)-N-[[3-[4-(Tetrahydro-1,4-thiazepln-4(5H)-yl)phenyl]-2-oxo-5-oxazolidinyl]methyl]-N'-methylthiourea, thiazepine S,S-dioxide;

94) (5S)-N-[[3-[4-(Tetrahydro-1,4-thiazepin-4(5H)-yl)phenyl]-2-oxo-5-oxazolidinyl]methyl]-N',N'-dimethylthiourea, thiazepine S,S-dioxide;

95) (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S,S-dioxide;

96) (5S)-N-[[3-[4-(Tetrahydro-1,4-thiazepin-4(5H)-yl)phenyl]-2-oxo-5-oxazolidinyl]methyl]-O-methylthiocarbamate, thiazepine S,S-dioxide;

97) (5S)-N-[[3-[4-(Tetrahydro-1,4-thiazepin-4(5H)-yl)phenyl]-2-oxo-5-oxazolidinyl]methyl]-O-ethylthiocarbamate, thiazepine S,S-dioxide;

98) (5S)-N-[[3-[4-(Tetrahydro-1,4-thiazepin-4(5H)-yl)phenyl]-2-oxo-5-oxazolidinyl]methyl]-O-isopropylthiocarbamate, thiazepine S,S-dioxide;

99) (5S)-N-[[3-[3-Fluoro-4-(tetrahydro-1,4-thiazepin-4(5H)-yl)phenyl]-2-oxo-5-oxazolidinyl]methyl]thiourea;

100) (5S)-N-[[3-[3-Fluoro-4-(tetrahydro-1,4-thiazepin-4(5H)-yl)phenyl]-2-oxo-5-oxazolidinyl]methyl]-N'-methylthiourea;

101) (5S)-N-[[3-[3-Fluoro-4-(tetrahydro-1,4-thiazepin-4(5H)-yl)phenyl]-2-oxo-5-oxazolidinyl]methyl]-N',N'-dimethylthiourea;

102) (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide;

103) (5S)-N-[[3-[3-Fluoro-4-(tetrahydro-1,4-thiazepin-4(5H)-yl)phenyl]-2-oxo-5-oxazolidinyl]methyl]-O-methylthiocarbamate;

104) (5S)-N-[[3-[3-Fluoro-4-(tetrahydro-1,4-thiazepin-4(5H)-yl)phenyl]-2-oxo-5-oxazolidinyl]methyl]-O-ethylthiocarbamate;

105) (5S)-N-[[3-[3-Fluoro-4-(tetrahydro-1,4-thiazepin-4(5H)-yl)phenyl]-2-oxo-5-oxazolidinyl]methyl]-O-isopropylthiocarbamate;

106) (5S)-N-[[3-[3,5-Difluoro-4-(tetrahydro-1,4-thiazepin-4(5H)-yl)phenyl]-2-oxo-5-oxazolidinyl]methyl]thiourea;

107) (5S)-N-[[3-[3,5-Difluoro-4-(tetrahydro-1,4-thiazepin-4(5H)-yl)phenyl]-2-oxo-5-oxazolidinyl]methyl]-N'-methylthiourea;

108) (5S)-N-[[3-[3,5-Difluoro-4-(tetrahydro-1,4-thiazepin-4(5H)-yl)phenyl]-2-oxo-5-oxazolidinyl]methyl]-N',N'-dimethylthiourea;

109) (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide;

110) (5S)-N-[[3-[3,5-Difluoro-4-(tetrahydro-1,4-thiazepin-4(5H)-yl)phenyl]-2-oxo-5-oxazolidinyl]methyl]-O-methylthiocarbamate;

111) (5S)-N-[[3-[3,5-Difluoro-4-(tetrahydro-1,4-thiazepin-4(5H)-yl)phenyl]-2-oxo-5-oxazolidinyl]methyl]-O-ethylthiocarbamate;

112) (5S)-N-[[3-[3,5-Difluoro-4-(tetrahydro-1,4-thiazepin-4(5H)-yl)phenyl]-2-oxo-5-oxazolidinyl]methyl]-O-isopropylthiocarbamate;

113) (5S)-N-[[3-[4-(Tetrahydro-1,4-thiazepin-4(5H)-yl)phenyl]-2-oxo-5-oxazolidinyl]methyl]thiourea;

114) (5S)-N-[[3-[4-(Tetrahydro-1,4-thiazepin-4(5H)-yl)phenyl]-2-oxo-5-oxazolidinyl]methyl]-N'-methylthiourea;

115) (5S)-N-[[3-[4-(Tetrahydro-1,4-thiazepin-4(5H)-yl)phenyl]-2-oxo-5-oxazolidinyl]methyl]-N',N'-dimethylthiourea;

116) (5S)-N-[[3-[4-(Tetrahydro-1,4-thiazepin-4(5H)-yl)phenyl]-2-oxo-5-oxazolidinyl]methyl]-1-azetidinccarbothioamide;
117) (5S)-N-[[3-[4-(Tetrahydro-1,4-thiazepin-4(5H)-yl)phenyl]-2-oxo-5-oxazolidinyl]methyl]-O-methylthiocarbamate;
118) (5S)-N-[[3-[4-(Tetrahydro-1,4-thiazepin-4(5H)-yl)phenyl]-2-oxo-5-oxazolidinyl]methyl]-O-ethylthiocarbamate;
119) (5S)-N-[[3-[4-(Tetrahydro-1,4-thiazepin-4(5H)-yl)phenyl]-2-oxo-5-oxazolidinyl]methyl]-O-isopropylthiocarbamate.

8. A method for treating microbial infections in patients comprising administering to a patient in need thereof an effective amount of a compound of formula I as shown in claim 1.

9. The method of claim 8 wherein said compound of formula I is administered, orally, parenterally, or topically.

10. The method of claim 8 wherein said compound is administered in an amount of from about 0.1 to about 100 mg/kg of body weight/day.

11. A pharmaceutical composition comprising a compound of claim 1 and pharmaceutically acceptable carrier.

* * * * *